US007982109B2

(12) United States Patent
Komori

(10) Patent No.: US 7,982,109 B2
(45) Date of Patent: Jul. 19, 2011

(54) METHOD FOR IMPROVING FERTILITY OF HYBRID PLANTS COMPRISING PLACING FERTILITY RESTORER GENES INTO MULTIPLE GENE LOCI

(75) Inventor: Toshiyuki Komori, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 1078 days.

(21) Appl. No.: 10/560,736

(22) PCT Filed: Jun. 9, 2004

(86) PCT No.: PCT/JP2004/008025

§ 371 (c)(1),
(2), (4) Date: Mar. 22, 2007

(87) PCT Pub. No.: WO2004/113537

PCT Pub. Date: Dec. 29, 2004

(65) Prior Publication Data

US 2007/0277255 A1 Nov. 29, 2007

(30) Foreign Application Priority Data

Jun. 18, 2003 (JP) ................................ 2003-173927
Oct. 20, 2003 (JP) ................................ 2003-359158

(51) Int. Cl.
*A01H 1/02* (2006.01)
*A01H 5/00* (2006.01)
*C12N 15/29* (2006.01)
*C12N 15/82* (2006.01)

(52) U.S. Cl. ..................... 800/320.2; 800/274; 800/275; 800/278; 800/303

(58) Field of Classification Search ........................ None
See application file for complete search history.

(56) References Cited

U.S. PATENT DOCUMENTS

| | | | | |
|---|---|---|---|---|
| 6,046,382 | A * | 4/2000 | Mariani et al. | 800/274 |
| 7,164,058 | B2 * | 1/2007 | Hanson et al. | 800/298 |
| 7,314,971 | B2 * | 1/2008 | Brown et al. | 800/278 |
| 2003/0177535 | A1 | 9/2003 | Hanson et al. | |
| 2005/0048482 | A1 | 3/2005 | Komori et al. | |
| 2006/0179517 | A1 | 8/2006 | Komori et al. | |
| 2006/0253931 | A1 | 11/2006 | Komori et al. | |

FOREIGN PATENT DOCUMENTS

| | | | |
|---|---|---|---|
| EP | 1310553 | A1 | 5/2003 |
| EP | 1316252 | | 6/2003 |
| JP | 2002-345485 | A | 12/2002 |
| JP | 2004-24126 | A | 1/2004 |
| WO | WO-02/14506 | A1 | 2/2002 |
| WO | WO-02/19803 | A1 | 3/2002 |
| WO | WO-03/27290 | A1 | 4/2003 |
| WO | WO-03/057859 | A2 | 7/2003 |
| WO | WO-2004/005515 | A1 | 1/2004 |

OTHER PUBLICATIONS

Tang et al. Genetics 150(1): 383-391 (Sep. 1998).*
Schoffl et al. Transgenic Research 2: 93-100 (1993).*
Mariani et al. Nature 357: 384-387 (Jun. 1992).*
Hanson et al (2007a). SEQ ID No. 35 from US Patent 7,164,058, issued Jan. 2007.*
Kazama et al. Accession No. RF1_ORSYI (Mar. 2005).*
Hanson et al (2007b). SEQ ID No. 23 from US Patent 7,164,058, issued Jan. 2007.*
Akagi et al. Current Genetics 25(1): 52-58 (Jan. 1994).*
Komori et al., Euphytica, vol. 129, pp. 241-247 (2003).
Ahmed et al., Hybrid Cultivar Development, pp. 221-256, 1998.
B.S. Dhillon., Hybrid Cultivar Development, pp. 282-315, 1998.
Wen et al., Curr Genet, vol. 35, pp. 521-526, 1999.
Fukuta et al., Japanese Journal of Breed, vol. 42, Supplemental No. 1, pp. 164-165, 1992.
Hiei et al., The Plant Journal, vol. 6, No. 2, pp. 271-282, 1994.
Komari et al., The Plant Journal, vol. 10, No. 1, pp. 165-174. 1996.
Ditta et al., Proc. Natl. Acad. Sci. USA, Genetics, vol. 77, No. 12, pp. 7347-7351, Dec. 1980.
Lemos et al., Plasmid vol. 27, pp. 161-163, 1992.
Cui et al., The rf2 Nuclear Restorer Gene of Male- Sterile T-Cytoplasm Maize, Science, vol. 272, pp. 1334-1336, May 31, 1996.
Liu et al., The Plant Cell, vol. 13, pp. 1063-1078, May 2001.
Michaels et al., The Plant Journal, vol. 14, No. 3, pp. 381-385, 1998.
Neff et al., The Plant Journal, vol. 14, No. 3, pp. 387-392, 1998.
Komari et al., Theoretical and Applied Genetics, vol. 77, pp. 547-552, 1989.
Altschul et al., J. Mol. Biol, vol. 215, pp. 403-410, 1990.
Komori et al., Fine mapping of a restorer gene, Rf-1, that restores the BT-type cytoplasmic male Sterility, Breed. Res., vol. 4, Suppl. 2, p. 243, 2002.
Harushima et al., A High-Density Rice Genetic Linkage Map with 2275 Markers Using a Single F2 Population, Genetics, vol. 148, pp. 479-494, Jan. 1998.
Kunio Kariya., Japanese Journal of Crop Science, vol. 58, No. 1, pp. 96-102, 1989.
Kazama et al., A pentatricopeptide repeat-containing gene that promotes the processing of aberrant atp6 RNA of cytoplasmic male-sterile rice, vol. 544, pp. 99-102, 2003.*
Amitahb Mohanty et al., Plant Science (1999), vol. 147, pp. 127 to 137.

* cited by examiner

*Primary Examiner* — David T Fox
(74) *Attorney, Agent, or Firm* — Birch, Stewart, Kolasch & Birch, LLP.

(57) ABSTRACT

An object of the present invention to provide a hybrid plant having a high fertility and a method for producing such a hybrid plant. The hybrid plant of the present invention is characterized by having two or more copies of a fertility restorer gene at two or more gene loci which do not have a complete linkage relationship. Further, the method of the present invention comprises introducing a fertility restorer gene by genetic engineering and placing two or more copies of a fertility restorer gene at two or more gene loci which do not have a complete linkage relationship.

8 Claims, 10 Drawing Sheets

Figure 9. Primers used for verifying the site of Rf-1 insertion

SEQUENCE LISTING

```
<160> NUMBER OF SEQ ID NOS: 72

<210> SEQ ID NO 1
<211> LENGTH: 76363
<212> TYPE: DNA
<213> ORGANISM: Orza sativa IR24

<400> SEQUENCE: 1

gatcaactaa caacctcttt gcagcaaaaa agcatacaca caagtgtttg tcttggcctg     60
gggctctgca gatggactga tactctgacc tgcagtgggc ttgggagcta acaatggttt    120
cattcttttt ttttttatgt tttcccctgt tgtttttgct catgttttgt gtaatttttt    180
cttctcatct agcgatgtta tttttcttag catgatggga gtagccctcc ttttttttttc    240
tctaattaag tgtaaagtag caacagcata gggatgaatg ttcagtgtag tgtgtggtgt    300
ttcagttatt cagagacgtc catacagttt gtaccttgtg accacacgtc ttaatctgat    360
gaagcttaga ataaatcaca tgttagcaat gcaatatcat ctgcgtcttc tctcactttg    420
gtggccatca aattctgtgt agaagtgtat ggttggtgtg ctgttgcaaa tgccgtattc    480
cgctctgttt tgtggaagtt aagaagtccc tagttgaaat accgattttt catgatctcg    540
gagattgatg caactctgat tgcagcattt ctttttatta gaatgtacac tccatgctat    600
catgatgttt attgtttagt actacaagat ttggttaacc attattttaa tatcataata    660
attttataaa atcttggagt aacaagttca taatacatga tagcataact ttttgaggct    720
agtctatgta tattgtctcc tttgttttta aactaagcac tcaataaatt attgatggct    780
gtaattttct gaaggtttca ccggtttcgg cccgtgcttt ataaatagct tcggcacaaa    840
agacaaaacg gtccctccaa cacataaatg gttgagttta cgttttcatt atctttggta    900
aaatcaagtc caccacgtag acactcataa caaaagtttg aatatcctca gaaattttga    960
cttgagtcta tcttaccttt gatatcggac atccaaccct ccctccctcc ctgaacttta   1020
tattattcat attacacctg aactttatat tattcatatt acaccctgaa gtggttttca   1080
tttaattgca tacatgctga aatagtttga caacgtgaga tgcactaaaa atctacacgt   1140
tcgtcttaag ttgcaattca ttttatccct tttctttttc tctcttacat aggaatatca   1200
atagtactaa ttcacattac aatatagtat aaattggtaa tcgattattg gcaatatact   1260
atattaaata ttcaaaacta gtcatttaag ctgccaaata agtaaaccac tatcgaaaac   1320
cacaatataa atggcattac aaaacttagg gggttgaata tccaatttta aagttcatga   1380
```

```
tgctagagga atttctatca aaagtttatg ggtacatatg gactttttcc tttttaaaag   1440
aagctattct tgtcgtaaac gttaaatatt ttttgtactt tattttttat gattgaaaaa   1500
aaaacttagt tttcaaaatg attggtctgt atacaagcat caattagact taataaattc   1560
atctaacagt ttcctggcag aaactgtaat ttgtttttgt tattagacta cgtttattat   1620
ttcaaatatg tgtacgtata tctgatgtga caaccaaacc caaaaatttt ccctaactcc   1680
atgaggcctt acagatatat ttgatgggtg taaagttttt taagttcttt gggtgcaaag   1740
tttttaaagt atacggacac acatttgaag tattaaatat agacaaataa caaaacatat   1800
tacatattct gcctgtaaac aacgagacaa atttattaag cctaattaat ctgtcattag   1860
caaacgttta ctgcagcatc acattgtcaa atcatagcgt aattaggctc aaaaatattc   1920
gtctcgtaat ttacatgcaa actgtgtaat tggttttttt ttcgtcaaca tttaatactc   1980
catgcatgtc caaatatttg atgcgatctt tttggccaaa ttttgttgga atctaaacaa   2040
ggatcaaatt tgctgaattt ttccagacgt cacggcttgt tcatccatcg ttcgcatcgc   2100
gattcgccac cgacgccttg gtttccaacg aattttatca tccgcttaaa tacatccaaa   2160
gctctccatc gccatcggcg gccaacggcg accgctccgc tctacccaat ccacccatcc   2220
actcgccgcc gccccctgat ccaaagcctc cgccgcgccg ccgtcgagag gaggaggagg   2280
aggaggagga ggaggcgtga gcccctatgg ggaccctcct ccggccgcgt ccgcttgccc   2340
acgccgccgg cgccggcgac gccacgccgt cgaccgcgca cggtagccac gcgcctctcg   2400
agaggccccc cccccccgcc gctcgctgat ctctcttctc atcctgtttg ggtttgggtt   2460
tgtgatttgg gtgttttttt tttttccgca gcggtggtgg tgagcggtgg ccgcggccgt   2520
ggcgtggagt gccagccgca tcgggtgcgc cgccgcccgg gtccgcaggt tgcggtggcg   2580
acggcgagct ggaggaggcg gagggagacc gtggtgagat cggatttcgc cgctggtggt   2640
gccgctacca tgggggattc gccgcaggcg ctctcaggtt tgcagcctcc tccactctct   2700
tctcgcaaaa tgtgttgcta tgttcctctc gctgggctgg cctcatagcc attaatgtag   2760
tttgctggaa cattacattc ggaacgttgt tggcaattgc ttgacaaaat gtggaattgt   2820
ggaggggaga aaaatcgttt gaacctgcag tgacaaaatt gccatctata attttaaaac   2880
tgaaggtgtg gaaatcaaac ataatcattg ccagcacatc attcttgtta accaccttga   2940
catattgttg gcttataaca gttagctcca caccaacttg gaaggtgtca atggaatgta   3000
agtataaatt gaggataact ggcagttgtt aagactttct acagaacttg tagcagctaa   3060
aactagctat tgtgcattta tgtttcatgg aatttgagcg gcaatggata tttcttacta   3120
agacgtataa tgcaaaaaaa aaaaaaaaac tatgtctatg cagtttacat gtaatgtgcg   3180
gatgcaaata aaatcatgtt catggacaaa ctaatgggat tcataccaaa ttccagaatt   3240
gcatttctta tgtggttact tttgtttgtt gatttggtta ccagacatcg atgtggtttc   3300
aagggtcaga ggggtttgct tctacgcggt gactgcagtt gcagcaatct ttttgtttgt   3360
cgccatggtt gtggttcatc cacttgtgct cctatttgac cgataccgga ggagagctca   3420
gcactacatt gcaaagattt gggcaactct gacaatttcc atgttctaca agcttgacgt   3480
cgagggaatg gagaacctgc caccgaatag tagccctgct gtctatgttg cgaaccatca   3540
gagtttcttg gatatctata cccttctaac tctaggaagg tgtttcaagt ttataagcaa   3600
gacaagtata tttatgttcc caattattgg atgggcaatg tatctcttag gagtaattcc   3660
tttgcggcgt atggacagca ggagccagct ggtatggctg tagtctcatc cctgctttct   3720
taagtagaca tatatacatt tacagtattt ggtaaataaa caagatttta tgaatcatat   3780
```

-continued atgattttgg ggaaaacaca aaactctctt tgttggctgc cttgaacata gttctgttca 3840
cacagttata gcaccttctt taaaatgaag aactttgttg catacacata aggccaaacc 3900
acataatgaa ttttgtttat ttctatcttt gaatgttagc atcgtttttg tttaatgcat 3960
gatcgccttc ctatatattt gtagtatgtc aacattgtat tccatgctga gcataacaaa 4020
tggtttgtta aaattcagga ctgtcttaaa cggtgtgtgg atttggtgaa aaaaggagca 4080
tctgtatttt tctttccaga ggggactaga agcaaagatg gaaagctagg tgcatttaag 4140
gttcagtaac caaacttagg ttacattaca tctaatgaga tttttatatt cagtatataa 4200
tgttaacctt ctcatggtgt actgacgtgg ttataaatgt ccccagagag gtgcattcag 4260
tgtggctaca aagaccggtg ctcctgtgat acctattact cttctcggga cagggaaact 4320
gatgccttct ggaatggaag gcatccttaa ttcaggttca gtaaagctca ttattcacca 4380
tccaattgaa gggaatgatg ctgagaaatt atgttctgaa gcaaggaagg tgatagctga 4440
cactcttatt ctaaacggtt atggagtgca ctaaagaaag atggtgtttt tttttattat 4500
atggaaccta ttcaaaggca cagacaggct ttcaaggcta agcttgttac aggtactgat 4560
actagttact aattactttc gtaatcagta taaataagct tgtgtagtgt aatggcattg 4620
tacatttctg cacttggtaa atttacagaa gaggcaagta atattttaga ggattgagtt 4680
tattcaccca gtcatatagt tgaagaggca agtaacctgt aagagaggac tgaacattaa 4740
cacctcttgt tcgattaaaa atgaccaaag agcatcaaac atgtattcga ggctgttact 4800
ttagatatgg cccattaatt tgtttagttg tctatgtaca tcctagttgg tgtaaatgcc 4860
agttaccatt tctatgatct aaaacaatca actcttttag tatattttca aaaacgaaat 4920
tcagtacaca tgtatgaatc ttaatattct tctctagctc gttacaaaag caacaaaggc 4980
accgtgtcag ctggttcaca ttagctagtt tgtacttagc attatccact agcaccttat 5040
tttcatgcat atcatgctaa tttgcttgcc cacgttgagt gggaattttt ttcatgtttt 5100
ataatttata tatgttttag acttctagtc cacaatttat gtacttcatg ttcctgagcc 5160
tctagtatgg ctgatagcag actaggtgct gagtgctgtc ctttttttgca gactgaagag 5220
agaagaaata caagactgtc cattgttagt cagatttgta aaaatagact ctgatgtagt 5280
ttacttttgc ccctatttta tttttaacaa tacaaatata taacagatcc taagaactta 5340
tcttaattta ggagaagttg ctcgtttcat taaattaaat tgtgaagtaa aaatgtgtgc 5400
tcgagtctgt caatgcaatc ctgtgttctt gtttgaagat atggtgtagg gcaggccagg 5460
attgaacact gaatggtaag actgcttctg ccttcagacg ttattgctaa atttttagct 5520
acttgcagtt agtgctgcca cgccgattaa gcagtagaac aaagtagttt tgtcgtgcac 5580
aaatgagtta tatttcattg gaaatcgaag cgaaaacgaa tcaaaagtta gaagaaaagg 5640
ggaaacttgg taattactcc ataaagagag tgcattttat tggtaagatg gtatccggaa 5700
gctgtgagct ccgggctgta tgtattctgg caaatttgat atgagatgct cgattattgg 5760
cttaagttag cgatatcaaa tttggggaag caccaaagga attattgtga aggagttatg 5820
ggtgcgtgac gttatctgct aggttcaaat ccttgtggct atgaatattt atctgctagg 5880
ttcaaatcct agtgactatg aatattaatg ggtaaggtaa gggatttatt gttaatttta 5940
gtttctttaa gattgtgcca tcggacgcca ttcggtaact gtaataatgc tttgtattgg 6000
attcacttgt gttacatgca cgcactaaac atgtgcttta ccttttcatc tgtttttgcg 6060
ttctgggcta gaaactcaaa cgttgaattt tccatggtct gctcaacttg acaattactg 6120
cgtgtcaagc gatcttatac gcatactatg cgcacaagtg attgtatacg gatatgatga 6180

```
cagtataacg tgtgatattg attttttttaa taaaaaaatg atgttcattt ccttgatgaa   6240
ggaacaaaga cttttttaa aagaagggta ttactaaaaa caaaaatgac aaaaacaaaa   6300
tatcagtgca catggcaagt gtgctcggca attttttctc tgtactttaa acaaaaatac   6360
ttctatatgt tctttttat aagggtggca caaatctttt aaatgagcca aatatctaca   6420
ttggatttat taaaaactgt ataaattata atttatactc tgaaaggttg tgtgcatctc   6480
tcttggagaa aatgtataag ttgcaaacaa acattaatcc acgttatgta actttttttc   6540
gccggaaagg ccgaaggagg cctgacggag cgtggggctc ctcaccggga gaccgcgcag   6600
gcccccttt gccggttcgg ccggggactc agggtgaaat tctaagctct ctgtatgtgg   6660
aaggttcgcg accgtcgaaa gagcataaga cacgggcgat gtatacaggt tcgggccgct   6720
gagaagcgta ataccctact cctgtgtttt gggggatctg tgtatgaagg agctacaaag   6780
tatgagccag cctctccctt gttctgggtt ccgaatctgg aaaagtccag tccagtcccc   6840
ccctctaagt gggcaaggtc ctccttttat atcttaaggg gataccacat gcaccatctc   6900
cctcctttct gtggagactt accctacctt ttcataaatg gacggagatt tgtatagttg   6960
ccgtccgaat gaccttctga taggacggcc catacctacc tccacttccg ccgaaagcag   7020
gtgcgacgtg ggattatggc tgtctgctga cgacatgacc agtgtcagac tggtcacaaa   7080
ttgctcattc ctgtccacca cgcgtcagtt tagcaatcta catgttggcc cttcttcaca   7140
caacatcttg cctgtaatgg ttaggatgaa gcctggcata tatctaacca ggactaacgt   7200
gccatctcta ggaggtaaca cgctagctcc agctggggac gagcgcctag aagccctcgt   7260
cctgacggga tggggcgagg cgtgcgtcag atcgcctgtc gccacctaac ctgcgatctg   7320
accggtctgt gactggtcac agaccggata aacgagtgca ctgcacttcg ttacatgcag   7380
cgtgacacgc tcagccaaac cgcaataaat gtggttaggt gagccccgct gtgctcacct   7440
aacccataca cgcggagcaa aaacccacga ggggtcgggg cgcctcggcc ctcggggccg   7500
aggcgggtgc ggtccgaccc cctcgggggg actaagagga gggcgaacac atcaccctcg   7560
ggcccgacgt cccccgaggg tgccaggcca cgtgggcgat tgtgtctgcc tcaaacctct   7620
agtcatgata ctcctgatcc catgtcaccg acagtagccc ccggcgttat gccagggcga   7680
tcgccctctt taagggaagc ggtcgggcgt gacgccactc ctaaggcctg gtgacaggtg   7740
ggaccggtct ccacaattgg gcagaaaccc aacggtcaca aatcacgcac atcggcaatg   7800
gtaactctac tatcaataat gagcggtctc ttcaagactg ccacattact cgagtagcac   7860
acgaatctgg acatggcgat tcgtttcgtc tggagatatg gtaacgtcgc tttggtcggc   7920
gagcgtaatt aacgcgcgca cgatatgatc tatctcgact gccacaaccg catatccacc   7980
tcatgcgccg caagcgggcg aatgggatta gtggaagcgt gggcgcgaga aacgaggggg   8040
cgaaatagtg ggcgcgagaa gcgaggagcc gggcacagcg ttggcaagag tataaaggca   8100
ctgaggaaag gatctgtttc cttcctttcg ccatcatttc ccttgtcttc gccgcttgcg   8160
ccctaactcc ttctttcctg tgctctactt tcgccacacg cgctcgctct caatcttctc   8220
ttcctccggc gccatggcac ggggctccgc tctgctcgat ggtagcgtgc tgccgccttc   8280
ccgcatcgtg agcgagaggc aggctgggct gccgcgccgc ttcatgccgg aatctgccac   8340
cggccgggag atagtcacgc tgggcgaggg acgcccggcg ccagactacc cggggcggtc   8400
cgtcttcttt ctccccttttg caatggcagg gctggttccg ccattttctt ctttcttcat   8460
ggatgttctg aagttctacg atctccagat ggcgcacctc acccccaacg cggtgatgac   8520
attggccatc ttcgcgcatc tgtgcgagat gttcattggg gtgcgcccat ctcttcggct   8580
```

-continued

```
gttccggtgg ttcttcaccg tgcagtcggt gtcgccgcca tcggtagttg gtggctgcta   8640
cttccagcca cgggggccgg tgctgaatcg ctacatcccc tgcgccctcc gcaagaagtg   8700
ggacgactgg aagagcgact ggttctacac ccccctcgcc gacgaagcgc gcctccgact   8760
tccgagccag cccccggcgc aggcctccag ctggcgggcg ccggtagatc tgggggatgg   8820
ctatgacgcc gtcctcgacc gcctggcggg cctacgatcc caggggctca cagggaccat   8880
ggtgtacggc gactacctcc gtcgtcggat tgcgccgctc cagcggcgcg ctcggggcgc   8940
ctgggagtac accgggtccg aagactacat gaggacccac cagggagtca gatgggactg   9000
ggctcctgag gatttcaaga tagtggtcca acgggtgctg aatctcaact ccatggaggc   9060
gtccctcatt ccccaaggaa tcctccctct ctgcagcgat ccagaccgcg cctccatcct   9120
gaccattatg acggcggtcg gggcctcaga ggagtgagct ccaaagggcc acgacggcgc   9180
aggcgggagc cgtagggggg atcaatctac ccggggaggg ggtcgtgctt ctgggtctcg   9240
cgacggaggc ccgaggagca gccgccctgc cgacgcccgg gggaagagga agcagggagg   9300
aacacctccc ccatctcctc cccgaggggg cggggcggtg cgtgccagca gcaggcgccc   9360
ggagggggcc gcgccgacat cgcagcccga gggggagcgc aagaagaagc ggctccgcaa   9420
gatgggggag acagaaccat ctcagggaaa ccttatttcc cctctaaagt ggtcgtttaa   9480
ccgacccccct cgcaggttcg tctctcaccc atcgtggctg tattcattct ctcaacgcga   9540
gttttcactc acccatcttg ttcgtcttct ggtcttttct tctgtttcag cgagatcccg   9600
tcgcgtccct cccgccattc caagtccggc cagtctgagg ccgaggatcc ggcggccgca   9660
gaggcccgga ggcgggaatc tgaccggcga gaggccgcgg atcgcctacg ggaagccgag   9720
gaggccgccc aggaggccgc ccgggctcgc caggtcgagg aaaccgctcg ggaggaggcc   9780
gcccgggccc gccaggccga ggaagccgct cgggaggagg ccgcccgagc ccaccaggcc   9840
gaggaagccg ctcgggagaa agccggattt cgccaggacg aggcaatggc gacttccgag   9900
gcagctcgcg atgaggtcgc gggcgcgtcg cttgagccca cttcctcggg cgacgctcag   9960
gcgacaactt ccggggcagc tggcgacgag gctgcgggcg cgtcgcttgg gcccactccc  10020
tcaggcgacg cccaggacca accaggtccg agggacatcc ctgagtccgg cacttccatc  10080
ggcggcccga gccgcgtggc atcctctcca aggcggctct tccccacgcc ttctatcgcc  10140
ccactgagcg cagagcccct tctgcaggcc ttggccgccg caaacaccgc ggtgttggac  10200
gggcttagtg cccaggtgga ggccctgcaa gcagagtggg cggagctcga cgccgcgtgg  10260
gcgcatgtcg aggaggggcg gcgctcagtg gaggccatgg tggaggtggg ccgcaaggca  10320
caccgccggc atgtctcgga gcttgaagcc cgtaagaagg tgttggcgga aatcgccaag  10380
gaagtggagg aggagcgggg ggctgccctc attgccacca gcgtgatgaa cgaggcgcag  10440
gacaccctcc gccttcaata cgggagctgg gaggcggagc tagggaaaaa gctcgacacc  10500
gcccaggggg tgcttgacgc tgccgctgcc cgagaacagc gggcggggga gaccgaagcg  10560
gcgtcccgac ggcgcgaaga gacccttgag gcgcgcgcca tggcgctgga agagcgcgcc  10620
tgcgtcgtgg agagggatct ggcggaccgc gaggccgccg tcactatccg ggaggcaaca  10680
ctggcggcgc acgagtccgc ctgtgccgaa gaggagtccg cactccgcct ccacgaggac  10740
gcgctcaccg agcgggagcg agctctcgag gaggccgagg ccgcggcgca acggctggcg  10800
gacagcctgt ccctccgcga ggcagcgcag gaggagcagg cgcgccgcac tctggaatgt  10860
gtccgcgccg agaggaccgc actgaaccag caggccgctg acctcgaggc gcgggagaag  10920
gagctggacg cgagggcgcg cagcgacggg gcggctgcgg gcgaaaacga cttagccgcc  10980
```

cgcctcgctg ctgccgaaca taccatcgcc gatctgcagg gcgcgctaaa ctcgtccgcc 11040
ggggaggtcg aggccctccg cttggcaggc gaggtagggc ccggcatgct ttgggacgcc 11100
gtctcccgcc tagatcgcgc cggtcggcag gtgggcctct ggagagggcg gaccgtaaag 11160
tacgccgcca accatggagg cctcgcccag cgcctctcga agatggccag ggctctccaa 11220
cggctccccg aggagctcga gaagacaatt aagtcatcct cgagggacct cgcccaagga 11280
gcggtggagc tcgtactggc gagttaccag gccagggacc ccaatttctc tccatggatg 11340
gcgctggatg agttccctcc tgggaccgag gacagcgcgc gcgcaggtcc gggatgccgc 11400
cgaccatatc gtccacagct tcgagggctc agcccctcgg ctcgcgttcg cccccaactc 11460
cgacgaggag gacaatgccg gtggtgcaga cgacagtgac gatgaggccg gcgacccggg 11520
cgtatcggat tgatccccca agcccccgcc attctttagt tttttcttct tttccttctt 11580
ctaaggcctt cgggcctctt ttttgtatag atcaacttaa tctgtaatca aaaatgaaga 11640
aatttttgtg tcaatttcat cttgctgtgt gtatgagatg aggatgatct gtgacgtggt 11700
ccttttgcgt cttagcttga ttaagggctc gtgcccaggt cccagtcctc aaaaggcgtg 11760
ggtcggggct agtgcctggg gagatccaca tgtcgagact ggccaggccg ggaacgtggt 11820
gaccgagggt tatgggtgac ccgattgtgg gtttttgccg attccccccc ggagttcacc 11880
acgccccggg gcacggctcg gttctgggcc ccgtttggcg attttagccg acccgagccc 11940
ccgagggcag gattgagcac gagtgaccta tttcaagtca agattcttca aaaggaaaaa 12000
aaaacacaga tacagccttt aggaaattga aactgctttt attgaaatac tgaaataaga 12060
gaaataagaa tgtgcatgtg tggcagcccc cggccaacgc tgcacgcccg agggggtgcg 12120
gggttggccc gagcccgaaa cctgacaccc gacccccccc tcaggggtag aagcgacgaa 12180
ggtgttcgat gttccacggg ttaggcagct caatgccgtc gcccgtggcc agccgtatgg 12240
agcccggccg ggggacgccg accactcgat acggaccctc ccacattggt gagagcttgc 12300
tcaatccagc acgcgtttgg acgcggcgta ggacgaggtc gtcgacgcag agtgatcggg 12360
cccggacgtg acgctgatgg tagcgccgca ggctctgctg gtagcgcgcg gctctgaggg 12420
ccgcgcgccg ccttcgctct tccaagtagt cgaggtcatc tctgcgaagt tgatcttgat 12480
cagcctcgca gtacatggtg gcccgaggag acctcagggt gagctcggat gggagaaccg 12540
cttccgcgcc gtagacgagg aagaaaggcg tttccccggt tgctcggctt ggtgtagttc 12600
ggtttgccca gagcaccgct agcaactcct cgatccatga atcgtcgtgc ttcttgagta 12660
tgttgaaggt cttggtttta aggcctttga ggatttctga attggcgcgc tccacttggc 12720
cattgcttct ggggtgggca ggtgaggcga agcagagctt gatgcccatg tcttcgcagt 12780
agtcgccgaa gagttcacta gtgaattggg tgccattatc cgtaataata cggttaggca 12840
ctccaaaccg ggccgtgatg cccttaatga atttaagtgc ggagtgctta tcgatcttga 12900
cgaccggata agcctcgggc cacttagtga acttgtcgat cgcgacatac agatactcaa 12960
acccgcccgg ggcccgccta aacggtccca ggatatcgag cccctagaca gcaaatggcc 13020
acgaaagtgg tatggtctgc agggcctggg ccggctgatg gatttgcttg gcgtggaatt 13080
gacacgctct acatcgccgg accaggtcga ccgcatcatt gagagctgtc ggccaataga 13140
aaccctggcg aaaagcttta ccaaccaagg tgcgcgaggc ggagtgggct ccgcattcgc 13200
cttcatggat atcggcaaga agcacaacgc cttgttcccg aggaatgcac ttcaggagga 13260
ttccattagc cgcgcgccga tagagggtcc cttctaccag cacgtagcgt ttggagatgc 13320
gatggacgcg ttcactccct tcgcggtcct cgggtaaagt cttatctgtg aggtatgctt 13380

-continued ggatctcggc aatccaagca atcaatctaa gggagctggg agcgctcccc tcgggtcccg 13440
aggcctggac ttcgacgggc ctcgggggcc ggtcaggcgc gtccgtctcc cctaaggggt 13500
cgggtcgcgc cgacggctgg gcaagccttt cttcaaaggc gcccggtggg gtctgggctc 13560
gcgtggacgc gagccgtgag agttcgtcgg caatcatgtt atcccgtctg ggcacatgcc 13620
gaagctcaat cccgtcaaaa tggcgctcca tacgccgtac ttggcgcacg taggcgtcca 13680
tctgcgggtc agagcaccgg tactccttac agacttggtt aacgaccagc tgggagtcgc 13740
ctaacaccag gaggcggcgg atccccagtc cagctgccac tctgagtccg gcaaggagtc 13800
cctcgtactc tgccatattg ttagtcgctc gaaagtcgag gcggaccaag tatctgagga 13860
cgtctccgct cggagaggtc aacgtgaccc ccgcaccggc gccctgaaga gacagggagc 13920
cgtcgaactg cattacccag tgggcggtgt gaggcagctg cgaggggtcc gtgctggcct 13980
cggggattga gacgggctcg ggagccgggg tccactctgc cacaaaatcg gcgagagcct 14040
ggctcttgat agcgtgacgt ggttcaaagt gcaaatcgaa ctcagaaagt tcgattgccc 14100
atttcaccac ccgtcctgta ccctctcgat tatgcaagat ttgaccgagg gggtaagacg 14160
taaccacagt gacccgatgc gcctggaaat aatggcgcag tttcctcgag gccatcagaa 14220
tagcgtaaag catcttctgg gcctgagggt atcgggtttt ggcgtcccgg agggcctcac 14280
taacaaagta gacgggccgc tgcacctttc ggtggggccg atcctcttcg ctagggggccg 14340
catccctggg gcactcttcg tccaagcagc ctcgcggggc gcacttgtct tctgtgctga 14400
tgacctcggg gtcggaggat aacaggggcg gccttcccac agtggctttg gggccgtcct 14460
gggggtcagg ggctcctggc gtcgtcggac aagcgggcaa agggccaact ccggtcgtca 14520
ggggccttag gcctccgttc ggctcggggg cctcttctcc ctgctctttc ccgggtcgag 14580
tcagcacagg gttagcctcg gggtcaaagg gcgataggtg cggccttccc acagtggcct 14640
cagggccttc ctgggggtcg ggggctccta gcaccgtctg acaagcgggc agagggccaa 14700
ctccggtcgt cgggggcctc aggccaccgt tcggctcggg ggcctctcct ccctgctctc 14760
tcccgggcca agtcggcaca gggtggggaa gcgcgaaatg agaattatcc tcatcgcgct 14820
ccacaaccaa tgccgcacta actacttgcg gggtcgccgc taagtagagt agcaagggct 14880
cgtctggctc cggggcgacc ataactgggg gagagcttag atacgccttc aactgggtga 14940
gggcattttc agcttccttc gtccaggtaa acggtccgga gcgtttgaga agcttaaata 15000
agggtaacgc cttctctccc agcctcgata tgaaccgact tagggcggcc atgcaaccgg 15060
tgacgtattg cacatcccta agtttgctgg ggggcgcatc cgctctatag cccgtatctt 15120
ctcggggttg gcctcaatgc cccgggcaga gaccaagaac ccgagaagct tgcccgcagg 15180
tacaccgaac acacacttat cggggtttaa ttttatgcgg gcggagcgga gactctcaaa 15240
agtttccgct agatctatga gtaacgtttc ctggttgcgc gtctttacaa ccaagtcatc 15300
gacataagcc tcaatattac gtcctaattg gctaccgaaa gaaattcgag tagtacgttg 15360
aaaagtagga cctgcattct ttaacccgaa gggcattgtc gtataacaat aggttcctat 15420
gggggtaatg aacgcagttt tttcctcatc ctccctagcc atgcgaatct gatggtaacc 15480
agagtatgca tctagaaaac acaaaaggtc gcaccccgca gtggagtcga caatctgatc 15540
tatgcgaggc agggggtaag gatccttagg acatgccttg ttaaggtcgg tgtagtcgat 15600
gcacatccga agcttgccgt tcgccttggg aacgaccacc gggttcgcca gccactcggc 15660
ggggttgacg ctgccatcat atttttcggc gatggtgggc cggaaccttg ggggccaacg 15720
gacattccga agactcgcca caaaggctct acagccgaca ccaccaaccg ggggcacgga 15780

-continued gggctgattc ccgcgtccgt gttgaggtga cactctggac gaggaagcgc cctccgttgc 15840
gtgggcagca cttcggtcat tacgccggcg ctcgatgctg gtgcgggcgt ccggcccccc 15900
acgcagatct ttctgggtcg aaggagtcga cgaaggagtg gcggccgaat ggcgaacagc 15960
ggctgccgct cgtcgtgccc tccgtcttga cgacgcggag ccggtggtag cagcaccaga 16020
ggccttggtg gcggaggacc gcccaccagc atctaggcgc tgccgtgccg tcatgactaa 16080
tttggccacg tcgtccagcc atcgttgggc tggagactcc gggtcaggga cgacaggcgg 16140
gtgacgtaag agcgcgcccg cagcttggag cgcgccctgg ggcgtgctgc cgtcgccgta 16200
gacgaggagg cgacgctccc catctcgccg ttcttctcca tcgcccgcga tcggtgaagt 16260
cgcggatctt tcgaccctct cgagcgcctc cccccgctta ggactttggc atggagggag 16320
cggtggagta cgagctcgac ggcgtgggtt cggctccccg tcgtcgccac tcacactcgg 16380
agagaggtcg tgcgcctttg cttgctcggc catcaggctg aacaggaaaa gcttggcgca 16440
cacggaagag tacgagagct cagaaaaaca cacactgagt cccctacctg gcgcgccaga 16500
tgacggagcg tggggctcct caccgggaga ccgcgcaggc ccccctttgc cggttcggcc 16560
ggggactcaa ggtgaaattc taagctctct gtatgtggaa ggtttgcgac cgtcgaaaga 16620
gcataagaca cgggcgatgt atacaggttc gggccgctga gaagcgtaat accctactcc 16680
tgtgttttgg gggatctgtg tatgaaggag ctacaaagta tgagccagcc tctcccttgt 16740
tctgggttcc gaatctggaa aagtccagtc cagtccagtc ccccctcta agtgggcaag 16800
gtcctccttt tatatcttaa ggggatacca catgcaccat ctccctcctt tctgtggaga 16860
cttaccctat cttttcataa atggacggag atttgtatag ttgccgtccg aatgaccttc 16920
tgataggacg gcccatacct acctccactt ccgccgaaag caggtgcgac gtgggattat 16980
ggctgtctgc tgacgacatg accagtgtca gactggtcac aaattgctca ttcctgtcca 17040
ccacgcgtca gtttagcaat ctacatgttg gcccttcttc acacaacatc ttgcctgtaa 17100
tggttaggat gaagcctggc atatatctaa ccaggactaa cgtgccatct ctaggaggta 17160
acacgctagc tccagctggg gacgagcgcc tagaaaccct cgtcctgacg ggatggggcg 17220
aggcgtgcgt cagatcgcct gtcgccacct aacccgcgat ctgaccggtc tgtgactggt 17280
cacagaccgg ataaacgagt gcactgcact tcgttacatg cggcgtgaca cgctcagcca 17340
aaccacaata aatgtggtta ggtgagcccc gctgtgctca cctaacccat acacgcggag 17400
caaaaaccca cgaggggtcg gggcgcctcg gccctcgggg ccgaggcggg tgcggtccga 17460
ccccctcggg gggactaaga ggagggcgaa cacatcaccc tcgggcccga cgtcccccga 17520
gggtgccagg ccacgtgggc gattgtgtct gcctcaaacc tctagtcatg atactcctga 17580
tcccatgtca ccgacaaggc catccgaatg tattaaggag taaaagttac aagaaaaaac 17640
accataatgc accaatgtgc atgaccacac accatacact acccccaagc acaaaccact 17700
gagggtgaag cctagcacca aacgaccgcc actaagtgtg accaaacgcc gctaggccta 17760
cggcagcaac acatagatga gacttcgaaa acgatgccac caaggtggtc acgacatcta 17820
ggatgctgcc atcgtccatc taaaaagatg tggttttcac ccagagaaac tcatcaagaa 17880
ggggagaggg taacccttga cagcgcccca aggaggttac gacgcccgaa ggcgtagccg 17940
ctgccggtcc ggtgaaccac cggactaggc ttccgcctag gaccctatag ccttgatcgc 18000
agatcaccgt ccaccactca gaaccaccac acagacaaaa ggtagcacgt agcttccacc 18060
acaccgcacc gacgcccctt cgtcggccga ctccatcgaa ccaccatccc tgagagctgg 18120
cccaggaccc ctccgttcca ccacccgccg gccgccttgc cagttttggc caaaggagaa 18180

-continued cccgggactg ggtgacattg cttcggcagc ctgagcttcc cccgctggcg agctgctgtc 18240
tcaatccaac ctagaaactc cccgcaaaag aaggggatga gctctaggaa gggcgagggt 18300
gccgaccggc aacgaggaag acaacccatc gactccagct ccctttgcac taccatctgg 18360
ccctgcgcca atgccggata cgctgtcgct ccggctccgg cgccacccac ctgcaccccc 18420
tttgcctggt ctccgcgccc ctcctggctg cgtcgcgccg cccagctggc cgctaagggc 18480
accgcgacgg ccgcccggct accgaggcct ggccgcgcca tgggacagct cgcgctggca 18540
ccagcgagcc acggccgtcg cgctgttgcc ggcgccagcg agcacaaccg ccagctccaa 18600
gggccgagca tgccactgag ccgccgccgc tgccgcccgg gccggctgca cgtcaccggc 18660
gcacacgacc gcacgccgcc acgctccgcc tccgcgcccg aggcagcccc atgccattgc 18720
cgcgcacctc gcccgcccgc tgccgagccg ccaccgcgca ccttgctgag ccgccaccgc 18780
cgtccctagc cgcctcgtgc cgccgccacg ccagatccag gcgcgggatg gccggatccg 18840
gccttggggg cgccggatcc accgcctccc cacaccgcca cggcgtcacc acctccgacc 18900
gcagtgaggg cttcgtcgtt tgccccatcc tcatcgcgtc gaggaggaag acgccaagaa 18960
aaaagggcct cgccgctgcc ttccttgctc gctgccggct tcgccgccgg cgagctccgg 19020
cggcggcgag gtgggggaga agaagtgggg agtgggcagc tagggttttt tcgcccccca 19080
agccgcccgt gcgagagcga cggtgggggg ggggggggact ttccaacctc ttccagtgtt 19140
ctagttctcc acgttatgta actcaatttg tttaaccata gaaagtaaga aacctaccag 19200
cgtgttaagc tctctttcat tccctttctt cttcctggtt ttgcttccat cacatgtcaa 19260
gtgaagggtt cttaactacc attactccta cacatctaat ttttttctca gatctttcgc 19320
aggtatatat tgatgctaca ttttatgatc ttaagataat ctccttcaca ttaccctctg 19380
ctgaaacttt agcttgaacc gtcatcttca ccacaatttg agcccaattt gcacagagca 19440
caacgagcaa tagcttgccc ttacgttcat tatttagcat gaactactac taactaccca 19500
agaatcaata caccggttta ataacgccat tttatcacgt taatatatgt ttcattcaac 19560
acaccggttt tggcacagtt gcaaacttgc aataaattct ttcctacttc tccatcccat 19620
aatataacaa attggtatgt ctcgtctggt actaagttac tatattatga gatggaggga 19680
gcacttcttt tcttccaaaa tataagaata tagtattgga ttagatatta tctagattca 19740
cgaattcgat taggttgtct agatttatag ttgtatgtaa tgtataattc ggtaataggt 19800
tattacctct caggatggag ggagtagttt tgactttttt tttcttataa atcgctttga 19860
tttttatatt agtcaaattt tatcgagttt aactaagttt atagaaaaaa attagcaaca 19920
tttaagcacc acactagttt cattaaattt agcatggaat atattttgat aatatatttg 19980
ttctgtgtta aaaatgctgc tatatttttc tataaacgta gtcaaattta aataagttag 20040
actaaaaaaa atcaaaacga cttataatat gaaatggagg aagtagtaga ctataacaaa 20100
tttaaaccgt gctttgattt tagagcatca ctaatatgtt agcaataatc tatccctaaa 20160
atttattttt tttcctaaac tgaaaatagg aagtggaaat actcctccat ctaagagaga 20220
gcctaaattc aataaaaaac taaaaaacta aaggtggatc cctctattaa actaccgcaa 20280
aaaatttatg tttttttctt cttccacgcg cgcagaacag atatctcgat caagttagca 20340
tgtaaaattt ttaaagagat accttatacg actccttccg tatttccaaa agcaaacgga 20400
tttaaaatct gactcaaata aagatctata tatccaattt acatgacaca tgtttcgccg 20460
aatttttata ttaataataa ttaatatttt taaaattaaa ttattagcaa tttgtttgga 20520
ggatttatca aaacaggatg gacgttgttt ataacagcgt ctagacctag acgcgcttgc 20580

-continued aaactgcggc caccctttta tcacacaaat ttttgacaat ttgacacttt ccaaaaatta 20640
attttataaa ttaaccgtga ccaaaactta tttaaaaatg atctttttgt tgagcgcaaa 20700
atcgtatact tcagcgccaa atagcacggc gccgacctcc cccttcccct cccctctatc 20760
ctccactgct gccgcccacc tctccgtatc agctgcgtcg cgttggtttc cgccggcgct 20820
gctgctgctg caccagtccg ctagggcggg cgggcatggc gcgccgcgcc gcttcccgcg 20880
tccgcgccgg cgctgttggc gcccttcgct cggagggctc gacccaaggg cgagggggcc 20940
gcacgggggg cagtggcgcc gaggacgcac gccacgtgtt cgacgaattg ctccggcgtg 21000
gcaggggcgc ctcgatctac ggcttgaact gcgccctcgc cgacgtcgcg cgtcacagcc 21060
ccgcggccgc cgtgtcccgc tacaaccgca tggcccgagc cggcgccgac gaggtaactc 21120
ccaacttgtg cacctacggc attctcatcg gttcctgctg ctgcgcgggc cgcttggacc 21180
tcggtttcgc ggccttgggc aatgtcatta agaagggatt tagagtggat gccatcgcct 21240
tcactcctct gctcaagggc ctctgtgctg acaagaggac gagcgacgca atggacatag 21300
tgctccgcag aatgacccag cttggctgca taccaaatgt cttctcctac aatattcttc 21360
tcaaggggct gtgtgatgag aacagaagcc aagaagctct cgagctgctc caaatgatgc 21420
ctgatgatgg aggtgactgc ccacctgatg tggtgtcgta taccactgtc atcaatggct 21480
tcttcaagga gggggatctg gacaaagctt acggtacata ccatgaaatg ctggaccggg 21540
ggattttacc aaatgttgtt acctacaact ctattattgc tgcgttatgc aaggctcaag 21600
ctatggacaa agccatggag gtacttacca gcatggttaa gaatggtgtc atgcctaatt 21660
gcaggacgta taatagtatc gtgcatgggt attgctcttc agggcagccg aaagaggcta 21720
ttggatttct caaaaagatg cacagtgatg gtgtcgaacc agatgttgtt acttataact 21780
cgctcatgga ttatctttgc aagaacggaa gatgcacgga agctagaaag atgttcgatt 21840
ctatgaccaa gaggggccta aagcctgaaa ttactaccta tggtaccctg cttcaggggt 21900
atgctaccaa aggagccctt gttgagatgc atggtctctt ggatttgatg gtacgaaacg 21960
gtatccaccc taatcattat gttttcagca ttctaatatg tgcatacgct aaacaaggga 22020
aagtagatca ggcaatgctt gtgttcagca aaatgaggca gcaaggattg aatccggata 22080
cagtgaccta tggaacagtt ataggcatac tttgcaagtc aggcagagta gaagatgcta 22140
tgcgttattt tgagcagatg atcgatgaaa gactaagccc tggcaacatt gtttataact 22200
ccctaattca tagtctctgt atctttgaca aatgggacaa ggctaaagag ttaattcttg 22260
aaatgttgga tcgaggcatc tgtctggaca ctattttctt taattcaata attgacagtc 22320
attgcaaaga agggagggtt atagaatctg aaaaactctt tgacctgatg gtacgtattg 22380
gtgtgaagcc caatatcatt acgtacagta ctctcatcga tggatattgc ttggcaggta 22440
agatggatga agcaacgaag ttacttgcca gcatggtctc agttggaatg aaacctgatt 22500
gtgttacata taatactttg attaatggct actgtaaaat tagcaggatg gaagatgcgt 22560
tagttctttt tagggagatg gagagcagtg gtgttagtcc tgatattatt acgtataata 22620
taattctgca aggtttattt caaaccagaa gaactgctgc tgcaaaagaa ctctatgtcg 22680
ggattaccga aagtggaacg cagcttgaac ttagcacata caacataatc cttcatgggc 22740
tttgcaaaaa caatctcact gacgaggcac ttcgaatgtt tcagaaccta tgtttgacgg 22800
atttacagct ggagactagg acttttaaca ttatgattgg tgcattgctt aaagttggca 22860
gaaatgatga agccaaggat ttgtttgcag ctctctcggc taacggttta gtgccagatg 22920
ttaggaccta cagtttaatg gcagaaaatc ttatagagca ggggttgcta gaagaattgg 22980
atgatctatt tctttcaatg gaggagaatg gctgtactgc caactcccgc atgctaaatt 23040
ccattgttag gaaactgtta cagaggggtg atataaccag ggctggcact tacctgttca 23100
tgattgatga gaagcacttc tccctcgaag catccactgc ttccttgttt ttagatcttt 23160
tgtctggggg aaaatatcaa gaatatcata ggtttctccc tgaaaaatat aagtccttta 23220
tagaatcttt gagctgctga agccttttgc agctttgaaa ttctgtgttg gagttctttt 23280
ctcctacagt cgtattagag gagggatctt ctctttatgt gtaaatagcg aggtatgtat 23340
gtcacctctc cgaattattt ttactctggt tcctagacgg taaacaagca attatgttct 23400
gcctttgatg ccagaaaaaa cacaaaagtt tgtcgttatc tctactaacg gatcataaag 23460
gaatttgtaa ctggagtttc aaacttaatt tgtctaggca gtagttttgg cattagatcc 23520
aacattgtgt aggattcatt tgtgtgtatc aatctatagg gtttcattaa atttcgttta 23580
tgtgtactgt ttaggtgttg aatagtttga cttgtttttt aactgaacaa aagatactga 23640
aatcgttcca ttcaacaaac acatgttccg ttaatgaaat tattgtacgt taccttttgt 23700
tttcttactc acaagtgtcc tcttttctta tatcctatag attggtacaa caaattattg 23760
attcaatttt ggttttgaac attgatgatc ctccctgcac tattggtgca gctgctcttc 23820
tattcatttt gtgaagtgat gtgagtacct ctcaatccca tccttatgct tctgtgcatg 23880
cttcattcca atttttacg catatcgatt gttttctttt atataacagt ccataaagat 23940
aatcacatca tgacaaagtt atttatttct acagtatagt tatataagta ttcaccagtt 24000
ttccatgaat attttggcat gtgattacaa agaagattat ttgagaaaat ccatgctttt 24060
atttcatcat tttgtttgaa gttgaacttt aatttatggt gtaaatttca gttattattg 24120
ctagcagctc gtactcttta atggtataac ttcacttgtg cttattctcc aatatctccc 24180
ttcttgttgt tcaggttcaa gaaaatcatt tgttggattc agaatctggt gtccattttc 24240
ttcttaaatt attaaatcct ccagtgaatc ttgttgattc caaagcacca tcgataggtt 24300
ccaaacttct tggaatcagt aaagttcaaa tgcttaatgg atcaaataag gattctgact 24360
gcatttcaga ggaaatcctt tcaaaagttg aagagattct cttaagctgt caagtgatca 24420
agtcgctcga caaagatgac aagaaaacaa caaggccaga actgtgtcca aagtggcttg 24480
ctttgttgac aatggaaaat gcatgcttgt ctgctgtttc agtagagggt aagttttaat 24540
caaatttctt ggtcatgatt tccctttatg accattatat ttatttatat gagccaaata 24600
agcagttgtc aacttgtcat aagttacata gcacctattt gcaatattca tgggtggttt 24660
gcttagccct tttcttcacc tgcttttgat tgatgacttc catctgtgtt gcagaattga 24720
attggagtag tggactgcac tagaagcacc tatggccatt gtcatactag gaaggttttc 24780
ccttatcaaa tatttgattg ttacagagac ttctgacaca gtgtccagag ttggaggaaa 24840
ttttaaagag acattaaggg agatgggagg tcttgatagt atttttgacg ttatggtgga 24900
ttttcattca acattggaga tgagatctcg ctaacatcgc atattttaca tttcctttgt 24960
tcaactctaa tagattgtgc aggcttgttc cttttcgcca ttttagcttt aatgcgcttg 25020
aagccacatg aaagtaatgc ttgtccagat acatagccaa aggttgttat attttggggc 25080
atggaaaatg cttgaggtag taactatttt catcaggaca tggaaaattg gctgcaacac 25140
aaattatgtt gttttatgtt gcaaaaatag tttttttaata ctttttttatt ctgcatgtgg 25200
tgttagtatc ttacagttcc tctgatgatt atatccccca cgataataac acttgaaacg 25260
ataataacac ttgacatatc tacaccaagt gaacattatt catttggatg ttacttttcc 25320
agctatactt gctgttcttg catgtgtaag caagtttgga gtaaattgcg cattaattta 25380

-continued

```
aatgcttggt gttcctatct gtgtactttt tattccccaa ctaataatgc aatcatatta  25440
cgctgataaa ctgaataaat aaattaacaa tatacttctg gtggcaaacc ttgtgtatca  25500
gaatctcata aaggatacat ccacttcagc tttggaccga aatgaaggaa catctttgca  25560
aagtgctgct ctcctcttga aatgtttgaa aatattggaa aatgccatat ttctaagcga  25620
tgataacaag gtaatgctcc ttatatgttc tgtttcagtt tagtacccat ttccttcttc  25680
tgtactatct tctctcctga tttgttctgt gcaaaatgtg caaacagtgc gactttgtat  25740
gtctgcttaa caattttctt ttcttcctga aaaagcaata tgaactctta cattcatttt  25800
gcttcttgca gacccatttg cttaatatga gtagaaaatt gaacccgaaa cgctccttgc  25860
tttcttttgt tggtgtcatt atcaatacta ttgagttatt atcaggtatt tttcttaata  25920
atacaatgtg ttcgctaaca caataaaatg ttttaaacat ccagtatgtt aaagttgcag  25980
tctgacgcct attttgtttt gctgcagctc tttcaatact tcagaattct tctgttgttt  26040
ccagctctac atatccgaaa tcgtctaaag tctctcaaca gagttactct ggtaataaca  26100
aacaccaatt ttgtttgatc agttgatctc gttggctttt ctatgcactg tctcaatata  26160
gtttggtcgc cattcaagtc tcactacaga tgttgaactt ggcctgacac caaatattta  26220
taaaatgcta cctgatattt ttaatatttc atgtttcctg acccagatta tcttgttggt  26280
tcctcgtata agtttaatta gtgacattct tgaagctttg ttatgcagca gatgtcatgg  26340
ggggaacttc atttaatgat ggaaagagca agaactcgaa aaaaaaaaac ttttgtcgaa  26400
ccagacacgt cattgttgct tatcttcaaa atcagaagtt tctcatatta ctatatcttc  26460
tggtagtgat gctggtctgt cacagaaggc attcaattgt tctccattta tatcaagcaa  26520
tggggcatca agtggttcat taggcgagag gcacagcaat ggtagtggtt tgaagttgaa  26580
tataaaaaag gatcgtggca atgcaaatcc aattagaggc tcaactggat ggatttcaat  26640
aagagcgcac agttctgatg ggaactccag agaaatggca aaaagactcc gtctatctta  26700
aaatgtaatc accgacagtg gtggtggtga tgaccctttt gcatttgacc gccgcgtcgg  26760
cgtcgccacc acgtaatcgc ccacgtcgct gcccccgctg ccacgtcgtc gaccgcgcac  26820
ggtaatcaca cgcatctcga ggccgccgct agctgatatc ttctcatccg gttgatttgt  26880
gattttggcg tttttgcagt ggtgatggcg gggggcgacc gtggccgagg cgtggagtgc  26940
catccgcatc agggtgtatc ggccgcgctg ctccgccctg gtccgcaggc tttggcggcg  27000
agctggcggc ggagggagac tgtggtgaga tcggatttcg ccgctggtgg tgtcgctacc  27060
atgggggatt cgccgcaggc gctctcaggt ttgcagcctc ctccactctc ttccctttt   27120
tatttttttt tctcgcaaaa tgtgttgtga tgttcgtctc gctgggctgg cctcatagcc  27180
attaatgtag tttgctggaa catttacatt tggaacgttg ttggcaattg ctttacaaaa  27240
tgtggaattg tggaggggag aaaaatcatt tgaacctgca gtgacaaaat tgccatctct  27300
aattttaaaa ctgaaggtgt ggaaatcaaa cataatcatt gccagcgcat cattcttgtt  27360
aaccaccatg atatattgtt ggttataaca gttagctcca caccaacctt gaaggtgtca  27420
atagaatgtt tagtataaat tgaggagaac aggcagttgt taagactttc taaagaactt  27480
gtagcagcta atactagcta ttgtgcattt gtgtttcatg gaatttgagc agcaatggat  27540
atttcttact aagatgtatg atgcaaaaca aaaaactatg tctatacagt ttacatgtaa  27600
tgtgcggatg caaataaaat catgtacatg gacaaactca tgggattcat accgaattcc  27660
agaattgcat ttcttatgtg gttacttttg ttgttgattt ggttaccaga catcgatgtg  27720
atttcaaggg tcagaggggt ttgcttctac gcggtggctg cagttgcagc aatctttttg  27780
```

-continued

```
tttgtcgcca tggttgtggt tcatccactt gtgctcctat ttgaccgata ccggaggaga  27840
gttcaggaaa aaaatttgaa aatacccatt ttttgaaaaa gatttacgtt tatatacact  27900
agtatgaaga atttgcgaaa atataactaa tccgcagatc ggttatgcgg gagcgcaaca  27960
aaagtatggc gtggcggcgc ggagtggacg gccgaggcgt tcgcgcggaa tggggctgcg  28020
ggaccgagcc agtctcgctt gccggtaacg cggaaccggt acgctcccgc agcgccagtg  28080
tgcggaaccg cggcgccaac attttttttac tgcatggcac tgtgtttaat actgtttgac  28140
actgtttctg gtactgtttt acacagttcc cgggtcagtt ccgcacaatg gaggcgcggc  28200
accgaccatg aacaatgtgt gaacagtgct gcacagggtt aaaacagtgt ataaactgcg  28260
ctgcacagtg ctggagtcgc tggccactgc ggttccgcgt tttggaaccg cgggaccgtc  28320
gcgattccgc gttttggagc tgccggacca tgacggttcc gcgcaggatc gtcggtcccg  28380
tattttgaat ctgcggaacc gtcgctgtcc cgcgtttcca tttcgcggga tgcgtatatt  28440
tttataaaac ctctccatgc atgtatataa acataaatta ttgaaaaaat aagtatattt  28500
gcaaattttt ttcgagagct cagcactaca ttgcaaagat ttgggcaact ctgacaattt  28560
ccatgttcta caagcttgac gtcgagggaa tggagaacct gccaccgaat agtagccctg  28620
ctatctatgt tgcgaaccat cagagttttt tggatatcta taccttcta actctaggaa  28680
ggtgtttcaa gtttataagc aagacaagta tatttatgtt ccgaattatt tgatgggcaa  28740
tgtatctctt aggagtaatt cctttgcggc gtatggacag caggagccag ctggtatggc  28800
tgtagtctca tccctgcttt cttaagtaga catatatgca attacagaat ttggtaaaca  28860
aacaagattt tatgaatcat atatgatttt ggggaaaaca ccaaactctc tttggtggct  28920
gccttgaaca tagttctatt cacacagtta tagcaccttc tttaaaatga agaactttgt  28980
tgcatacaca tatggccaaa ccacataatg aattttgttt atttctatct ttgaatgtta  29040
gcaccttatt ttcatgcata tcatgctaat ttgcttgccc acgttgagtg ggaatttttt  29100
tccatgtttt ataatttata tatgttctag acttctagtc cacaatttat ctacttcatg  29160
ttcctgagcc tctagtatgg ctggtagcag actaggtgct gagtgctgtc catttttgca  29220
gactgaagag aggagaaata caggactgtc cgttgttagt cagatttgta aaaatagact  29280
ctgatgtagt ttattttagc ccctatttta tatttaacaa tacaaatata taacgtatcc  29340
taagaactta tcgtaattta ggagaagttg ctcgtttcat taaattaaac tgtgaagtaa  29400
aaatgtgtgc tcgagtctgt caatgcaatc ctgtgttctt gtttgaagat atggtgtagg  29460
gcaggctagg atcgaacact gaatggtaag actgcttctg ccttcatttg tgcacttggt  29520
gctgccacgc cgattaagca gtagaacaaa gtaattttgt cgtgcacaaa tgagttatat  29580
ttcattgaaa atcgaagtga aaatgaacca aaagatagaa gaaaagggga aacttggtaa  29640
ttatatactc cacaaattta ttggtaagat ttgatattag acgctcgatt acttggctta  29700
agttaaggat atcaaatttg gggaagcacc aaaggaatta ttgtgaagga gttgtgggtg  29760
cataacgtta tctactagtt caaatcctag tgactatgaa tattaatgag taaggtaagg  29820
gatttattgt taattttagt ttctttaaga ttgtgtccga gtacaccatt cggtaagtgt  29880
aataatgttt tgtattggat tcacttgtgt tacgtgcatg tgcttttacc ttttcatttg  29940
tttctgcgtt ctgggtatga atttgacgag attccatggt cagctcaaca tatcagttac  30000
tgcgtgtcaa gcgatcttat atggtatgcg cacaagcgat tgtatacgga tatgacagta  30060
taatgtgtga tattgatacg atgttccttt cctttataaa ggaacaaaga cttttttttaa  30120
aaaaagaagg ggtattacta aaaaccaaaa tgtcaaaaac aaaatatcag tgcacatggc  30180
```

-continued

```
aagtgtgcac gagcaatagc ttgcccttac gttcattatt tagcatgtac tactactaac  30240
tacgcaaaaa tcaattcacc gattattaaa ctgttaacat cattttagca cgttaacata  30300
tgtttcattc aacacaccgg ttttggcaca tttacaaact tgcaaagttg caatactccc  30360
ttcgttacat agcataagag attttaggtg aatgtgacac atctatccaa attcattata  30420
ctagaatgta tcaccgcctc cacgccggga gggagagcgc cgccggtgga gaaaggggga  30480
gggagtggtc gaggggaacc agtagggtgc cctccccgtc gccgcctccc cgtggccgcg  30540
ccggcgagac aggaggaaga gggggagatg gagcggcgcc gccggtgagg gcgcgcgtgc  30600
gcgggggggg gggggggga gcggcgacgc cggtgaggaa gggaagggga gtggtggctt  30660
tgagagagat aggggagagg gaaaatgatt ttagagttag ggtttgggct gctgagtttt  30720
tatatagatc gggatcaatc aggaccgtcc atcagatcgg acaactacgg tttctcccgc  30780
gttgggccgg gtgccactcc taggttgccc acactattgg gccacatgta cgctccgcgt  30840
gaaataagtt cactttaggt cctttaagtt gcctctgaat tgttcccagg ccggccgcac  30900
tattgggcca ccccataggc catgtgtacg ctccgcacag aataatttcg ctttagctcc  30960
cttaatttgt cccctcaaac ttctaaaacc agtgcaaatc tttaattttt agttcaccca  31020
ttgcaactca cgggcatatt tgctagtgac atataatatg aaacgaagga tgtagcagac  31080
tatagaattt aaactgtgct ttcattttag agcatcacta actgttattt agatttttat  31140
ttaaataaat gcagaaatga tgtttttatt atgaaaatta gcaataaagc tcccaaaatt  31200
tcaaaaaaaa attaaaagag atttattaat catggttaat ttaattaaaa attaaatcta  31260
accatatcat attatttcac ggtccgtgat gaggaaatgg cagctgctat cacttatggt  31320
gggagagaag gggcattgtt tatttttata actatctctt ataactccca tgaaactata  31380
aaataaatat aatcattatc ataacattag tttttttcca ttgcaacgca agggtaattt  31440
ttcagtacaa taaaaaaata aaagtgggcc attctgaacg gaaatttctg gttttttttc  31500
ccaagagcgc cgcacacaac tgcgcaagag atcgatcgcg atcaccctgc tcgtcgccga  31560
tctcctacac catccctgcc atctccttcc cctccactgg ctgctgctgc acctgtcagc  31620
tagggcgggc atggcgcgcc gcgccgcttc ccgcgctgct ggcgcccttc gctcggaggg  31680
ctcgatccaa gggcgagggg gccgcgcggg gggcagtggc ggtggcgcgg aggacgcacg  31740
ccacgtgttc gacgaattgc tccgtcgtgg cataccagat gtcttctcct acaatattct  31800
tctcaacggg ctgtgtgatg agaacagaag ccaagaagct ctcgagctac tgcacataat  31860
ggctgatgat ggaggtgact gcccacctga tgtggtgtcg tacagcaccg tcatcaatgg  31920
cttcttcaag gagggggatc tggacaaaac ttacagtaca tacaatgaaa tgcttgacca  31980
gaggatttcg ccaaatgttg tgacctacaa ctctattatt gctgcgctat gcaaggctca  32040
aactgtggac aaggccatgg aggtacttac caccatggtt aagagtggtg tcatgcctga  32100
ttgcatgaca tataatagta ttgtgcatgg gttttgctct tcagggcagc cgaaagaggc  32160
tattgtattt ctcaaaaaga tgcgcagtga tggtgtcgaa ccagatgttg ttacttataa  32220
ctcgctcatg gattatcttt gcaagaacgg aagatgcacg gaagcaagaa agatttttga  32280
ttctatgacc aagaggggcc taaagcctga aattactacc tatggtaccc tgcttcaggg  32340
gtatgctacc aaaggagccc ttgttgagat gcatggtctc ttggatttga tggtacgaaa  32400
cggtatccac cctaatcatt atgttttcag cattctagta tgtgcatacg ctaaacaaga  32460
gaaagtagaa gaggcaatgc ttgtgttcag caaaatgagg cagcaaggat tgaatccgaa  32520
tgcagtgacg tatggagcag ttataggcat actttgcaag tcaggcagag tagaagatgc  32580
```

-continued

```
tatgctttat tttgagcaga tgatcgatga aggactaagc cctggcaaca ttgtttataa  32640
ctccctaatt catggtttgt gcacctgtaa caaatgggag agagctgaag agttaattct  32700
tgaaatgttg gatcgaggca tctgtctgaa cactattttc tttaattcaa taattgacag  32760
tcattgcaaa gaagggaggg ttatagaatc tgaaaaactc tttgacctga tggtacgtat  32820
tggtgtgaag cccgatatca ttacgtacag tactctcatc gatggatatt gcttggcagg  32880
taagatggat gaagcaacga agttacttgc cagcatggtc tcagttggaa tgaaacctga  32940
ttgtgttaca tatagtactt tgattaatgg ctactgtaaa attagcagga tgaaagatgc  33000
gttagttctt tttagggaga tggagagcag tggtgttagt cctgatatta ttacgtataa  33060
tataattctg caaggtttat ttcaaaccag aagaactgct gctgcaaaag aactctatgt  33120
cgggattacc aaaagtggaa ggcagcttga acttagcaca tacaacataa tccttcatgg  33180
actttgcaaa aacaaactca ctgatgatgc acttcggatg tttcagaacc tatgtttgat  33240
ggatttgaag cttgaggcta ggactttcaa cattatgatt gatgcattgc ttaaagttgg  33300
cagaaatgat gaagccaagg atttgtttgt tgctttctcg tctaacggtt tagtgccgaa  33360
ttattggacg tacaggttga tggctgaaaa tattatagga caggggttgc tagaagaatt  33420
ggatcaactc tttctttcaa tggaggacaa tggctgtact gttgactctg gcatgctaaa  33480
tttcattgtt agggaactgt tgcagagagg tgagataacc agggctggca cttacctttc  33540
catgattgat gagaagcact ttccctcga agcatccact gcttccttgt ttatagatct  33600
tttgtctggg ggaaaatatc aagaatatca tagatttctc cctgaaaaat acaagtcctt  33660
tatagaatct ttgagctgct gaagcatttt gcagctttga aattctgtgt tggaattctt  33720
ttctcctaca gtccgattag aggagggatc ttctctgtat gtgtaaatag cgaggtatgt  33780
atgtcacctc tccgaattat tttgactgtg gttcctggac tgtaaacaag ctattatctt  33840
ctggtgttga tgccagaaaa aacacaaaag tttgtcgtta tctctactaa cggatcataa  33900
aggggtttgt aactggagtt tcaaacttaa ggtatctagg cagtaggtat atattgatcc  33960
tacatcttat gatcttaaga tgatatcctt ctcattatcc tctgctgaaa ctttagcttg  34020
aaccgtcatc tacaccacaa tttgagcccc ttagcacaga gcacaacgag caatagcttg  34080
cccttacgtt cattatttag catgcactac tactaactac ccaataatca atacatcggt  34140
tattaaactg tttgtacagt ttaataatgt cattttatca cgttaacata tgtttcattc  34200
aacaccacac cggttttggc acagttgcaa acttgcaata acatttttac tacttctccg  34260
ccccataata taacaatctc gttccatact atattgctat attacaggat ggatgaagta  34320
cttcttttct tccaaaatat aagaatctag tactagatta gatattattt ggattcacga  34380
atttgattag gctgtctaga tttgtagtcg tatgtaatgt ctaattcggt aataggttat  34440
tacctctttg gatggaggga gtagttttta tttcgtactc cctccgtttc atattataag  34500
ttgttttgac ttttttctta gtcaaatttt attgagtttg attaaattta tagaaaaaaa  34560
ttagcaacat ttaagcacca cattagtttc attaaatgta gcatggaata tatttttata  34620
atatgtttgt tttttattaa aatgctacta tatttttcta taaatgtagt caaatttaaa  34680
gaagtttgat tatgaaaaaa tcaaaatgac atataatatg aaactgagga tgtagcagac  34740
tatagcaaat ttaaactatg cttttatttt agagcatcac caaaagatta gcaataattt  34800
atccctaaaa ttcaagtttt gggtttctta aactgaaaat aggaagtgaa aaatcttttc  34860
cgtccaagag atagcctaaa tcttatctta actaattaaa atattcataa ttttcctttc  34920
gtcacattaa attttcgtcc gtaaatctga ttgaaatcca attggacaat ccaaaaaata  34980
```

```
gagaaaaaga acagaaaaaa taataaaaag cacacaaatc ttatctcaat cccgcgggaa  35040
gctgccgacg ccgccgaatc cgctcgagcg ccgccgccgc cgctcacggg gaacgatgtc  35100
gctgctgtcg cacgcggtat gggagggcgc cgctgccact gcttgggaga taggatatgg  35160
agagagaagg aaatgtgagg gttagggtta ggtttttccc cgtccgtatc ttcagcgaca  35220
cggaggcgat ccaagctgtc catcagatcg gacggctcag aatgcctcca tcgtcgggcc  35280
gcgcatgctt gatgggccga gggaaggccg gagggtcgaa caaacgcaat caaaggagga  35340
gttggaggag gtaaattaga atttatttgc gggctgagat agtaaatgga ctgaaaatgg  35400
cccatagaga aattgggaat tttatttaaa taaatgttga aaaggtgttt atattatcaa  35460
aattaaaaat taagctccga aaattctaaa aaatattcaa agagcattat taatcatggt  35520
taatttaata aaaattaaat ccaaccatat catattattt cacggcgcgc ggtaggaaaa  35580
tgcgcagctg ttgtcgttta cggtgggaga gaagggacat tgtttatttc cagaactatc  35640
ttttataact cccatggaac tttaaaataa atataatcat tattatagca ttagtttttt  35700
tctgtctttt ttttccccaa gagcgccgcg cagaagagat cgatcgcgat ctccctgccc  35760
cgacgtcgcc ggccgatctc tcattctctc cacgccctgc tcgtcgccga tctcctacac  35820
catccctgcc atctcctcct tcccctcccc tctatcctcc actggtgccg cccacctctc  35880
cgtataagac aaactgcgtt gcggcgttgg tttccgccgg cgctgctgct gcacctgtca  35940
gctagggcag gcatggcgcg ccgcgccgct tcccgcgctg ttggcgccct tcgctcggac  36000
ggctcgatcc aagggcgagg aggccgcgcg gggggcagtg gcgccgagga cgcacgccac  36060
gtgttcgagg aattgctccg gcgtggcagg ggcgcctcga tctacggctt gaaccgcgcc  36120
ctcgccgacg tcgcgcgtca cagccccgcg gccgccgtgt cccgctacaa ccgcatggcc  36180
cgagccggcg ccggcaaggt aactcccacc gtgcacacct atggcattct catcggttgc  36240
tgctgccgcg cgggccgctt ggacctcggt ttcgcggcct tgggcaatgt cgtcaagaag  36300
ggatttagag tggaagccat caccttcact cctctgctca agggcctctg tgccgacaag  36360
aggacgagcg acgcaatgga catagtgctc cgcagaatga ccgagctcag ctgcatgcca  36420
gatgttttct cctgcaccat tcttctcaag ggtctgtgtg atgagaacag aagccaagaa  36480
gctctcgagc tgctgcacat gatggctgat gatcgaggag gaggtagcgc acctgatgtg  36540
gtgtcgtata ccactgtcat caatggcttc ttcaaagagg gggattcaga caaagcttac  36600
agtacatacc atgaaatgct tgatcggagg atttcaccag atgttgtgac ttacagctct  36660
attattgctg cgttatgcaa gggtcaagct atggacaaag ccatggaggt acttaccacg  36720
atggttaaga atggtgtcat gcctaattgc atgacatata atagtattct gcatggatat  36780
tgctcttcag agcagccgaa agaggctatt ggatttctca aaaagatgcg cagtgatggt  36840
gtcgaaccag atgttgttac ttataactcg ctcatggatt atctttgcaa gaacggaaga  36900
tccaccgaag ctagaaagat ttttgattct atgaccaaga ggggcctaga gcctgatatt  36960
gctacctatt gtaccctgct tcaggggtat gctaccaaag gagcccttgt tgagatgcat  37020
gctctcttgg atttgatggt acgaaacggc atccaccctg atcatcatgt attcaacatt  37080
ctaatatgtg catacgctaa acaagagaaa gtagatgagg caatgcttgt attcagcaaa  37140
atgaggcagc atggattgaa tccgaatgta gtgacgtatg gagcagttat aggcatactt  37200
tgcaagtcag gcagtgtaga cgatgctatg ctttattttg agcagatgat cgatgaagga  37260
ctaaccccta acattattgt gtatacctcc ctaattcata gtctctgtat ctttgacaaa  37320
tgggacaagg ctgaagagtt aattcttgaa atgttggatc gaggcatctg tctgaacact  37380
```

```
attttcttta attcaataat tcacagtcat tgcaaagaag ggagggttat agaatctgaa  37440
aaactctttg acctgatggt acgtattggt gtgaagccca atgtcattac gtacagtact  37500
ctcatcgatg gatattgctt ggcaggtaag atggatgaag caacgaagtt actctccagc  37560
atgttctcag ttggaatgaa acctgattgt gttacatata atactttgat taatggctac  37620
tgtagagtta gcaggatgga tgacgcatta gctcttttca aagagatggt gagcagtggt  37680
gttagtccta atattattac gtataacata attctgcaag gtttatttca taccagaaga  37740
actgctgctg caaaagaact ctatgtcggg attaccaaaa gtggaacgca gcttgaactt  37800
agcacataca acataatcct tcatgggctt tgcaaaaaca atctcactga cgaggcactt  37860
cgaatgtttc agaacctatg tttgacggat ttacagctgg agactaggac ttttaacatt  37920
atgattggtg cattgcttaa agttggcaga aatgatgaag ccaaggattt gtttgcagct  37980
ctctcggcta acggtttagt gccagatgtt aggacctaca gtttaatggc agaaaatctt  38040
atagagcagg ggttgctaga agaattggat gatctatttc tttcaatgga ggagaatggc  38100
tgtactgcca actcccgcat gctaaattcc attgttagga aactgttaca gaggggtgat  38160
ataaccaggg ctggcactta cctttccatg attgatgaga agcacttttc cctcgaagca  38220
tccactgctt ccttgttata gatcttttgt ctgggggaaa atatcaagaa tatcatagat  38280
ttctccctga aaaatacaag tcctttatag aatctttgag ctgctgaagc attttgcagc  38340
tttgaaattc tgtgttggaa ttcttttctc ctacagtccg attagaggag ggatcttctc  38400
tgtatgtgta aatagcgagg tatgtatgtc acctctccga attattttga ctgtggttcc  38460
tggactgtaa acaagctatt atcttctggt gttgatgcca gaaaaaacac aaaagtttgt  38520
cgttatctct actaacggat cataaagggg tttgtaactg gagtttcaaa cttaaggtat  38580
ctaggcagta gttttgacat tagatccaac attgtgtagt attcatttgt gtgtatcaat  38640
ctatagggtt tcattaaatt tcatttgtgt actgtttagg tgttgaatat attgttttac  38700
ttgtttttta actgaacaaa agatagctga agctttgttc tttaccaaat gcagtagtga  38760
tcatcacaat atattttttt acggaacagg agattgtata aaatggtttc catcggcggc  38820
caacggcgac cgctctgctc tgacccacca cccaatccat ccatccactc gccgccgccc  38880
ctgatccaag cctccgccgc gcgacagcga cgcaccgccg tcgagaggag gaggcgtgag  38940
ccccatgggg accctcctcc ggccgcgtaa tgccgctgca cggtaaccac gcgcctctcg  39000
aggcctccgc cgctagctga tctcttctca tcctgtttgg gtttgggttt gtgatttggg  39060
tgtttttttcc gcagcggtgg tggtggtggt ggttgcggcg ggaggggggcg gtggccgcgg  39120
ccgtggcgtg gagtgccagc tgcatcgggt gcaccgccgc cggggtccgc aggttgtggt  39180
ggcgacggcg agctgaggag gcggagggag actggtgagg gacacaggca ggcaggctct  39240
caaggctaag cttgttacag gtactgagac tagttactaa ttactttgat aatcagtata  39300
aataagcttg tgtagtgtaa tggcattgtg catttctgca cttgtaaatt ttacagaaga  39360
tggtcattca atttgaacct gcatctaata ttttagtggt ttgagtttat tctcccagtc  39420
acagagttga agaggcaagt aacctgtaag agaggactga acattaacac ctcttgttcg  39480
attaaaaatg accaaagagc atcaaacatg tattcgaggc tgttacttta atatggccca  39540
ttaatttgtt tagttggcta tgtacatcct agttggtgca gtgttgtgga aaacggaata  39600
cgggtgtcgg atggacgagg tgccgtcaag cgattaatcg taatacggat gattaaacgg  39660
aattatatgg atttttggcg ttcgcactaa gatgtacata attgatgtta atggcaatgg  39720
tggagacaaa atgcatcatc ttaataaaaa atatttgtat aaatctctaa ctatattatg  39780
```

aaaatgccat ttattagttc aatagatatc aacactgatg gttagtagcg caatagcatt 39840
gggcttgtta gtcaaaatag tgcagctggg ctgcaagttg caagtttatg ttagtttcat 39900
aaacagacat ctgatttgtc gataaataac cgactaatcg tgccatacaa ctgtataatt 39960
actctgaaat agtaatgttg ctccgacttg atgatacggt acggtctggc taccgtttcc 40020
gttttgacag acgattaaac ggctgtgccg gtcgacttcc acaacactga gttggtgtaa 40080
atgccagtta ccatttctat gatctaaaat aatcaactct tttagtatat tttcaaaaac 40140
gaaaattcag tacacatgca tgaatcttaa tcttcatatc tagctcgtta caaaatcaac 40200
aaaggcaccg tgtcagctgg tgcacattag ctagttcgta cttagcatta tccactagca 40260 ccttatttc atgcatatca tgctaatttg cttgcccacg ttgagtggga attttttcc 40320 atgttttata atttatatat gttctagact tctacttcat gttcctgagc ctctagtatg 40380
gctggtagca gactaggtgc tgaatgctgt cctttttgc agactgaaga gaggagaaat 40440
acaagactgt ccgttgttag tcagatttgt aaaaatagac actgatgtag tttattttg 40500 cccctatttt atatttaaca atacaaatat ataacgtatc ctaagaattt atcgtaattt 40560
aggagaagtt gctcgtttca ttaaattaaa ttgggaagta aaaatgtgtg ctcgagtatg 40620
tcaatgcaat cctgtgttct tgtttgaaga tatggtgtag ggcaggccag gattgaacac 40680
tgaatggtaa gactgcttct gctttcagac gttattgcta aatttttagc tagttgcaat 40740
tagtgctgtc acgccgatta agcagtagaa caaagtaatt ttgtcgtgac aaatgagtta 40800
tatttctttg aaaatcgaag cgaaaacgaa ccaaaagata gaagaaaagg gaaacttggt 40860
aattactcca caaagagaac aaatttattg gtaagatttg atatgagatg ctcgattact 40920
tggcttaagt taacaatatc aaatttgggg aagcaccaaa agaattattg tgacttaagt 40980
taaagatatc aaatttgggg aagcaccaaa ggaattattg tgatggagtt gtgggtgcat 41040
aacgttattt gctttgttca aatcctagtg actatgaata tgaatattaa tgcgtaaggt 41100
aaggaattta ttgttaattt taggttcttt acgattgtgt ccggggacgc cattcggtaa 41160
ctgtaataat gttttgtatt ggattcactt gtgttacatg cacgcactaa acatgtgctt 41220
taccttttca tttgtttgtg cgttctgcgt ttgaatttga cgagattcca tggtcagctc 41280
aacatgtcag ttactgcgtg tcaagcagtt actgcgtgtc aagcgatctt atatggtatg 41340
cgcacaagcg attgtatacg gatatgacag tataacgtgt gatattgatt tttttatata 41400
aaaaaatacg atgttacttt ccttcataaa ggaacaaaga cttttttttt aaaaaaaaga 41460
aggggtatta ctaaaaacaa aaatgtcaaa aacaaaatat cagtgcacat ggcaagtgtg 41520
ctcggcaatt ttttgtctgt actttaaaca aaaatatttc tatatggtat tttttacaag 41580
ggtgtcacaa atattttaaa ttagccaaac atctgcattt tattaaaaac tgtataaatt 41640
ataatttata ctctaaaagg ttgtgtacat ctctcttgga gaaaatgtat aagttgcgaa 41700
caaacattaa tccacgttat ataagtcaat ctgttattta accatagaaa gtaagaaacc 41760
tactagcgtg ttaagctaag ctctctttca ttctctttct tcttcctggt tttgcttcaa 41820
tcacttgtca agtgaagggt tcttaactac cattactcct actcaccaaa ttttttctc 41880 agatctttcg taggtatata ttgatcctac atcttatgat cttaagatga tatccttctc 41940
attatcctct gctgaaactt tagcttgaac cgtcatctac accacaattt gagcccctta 42000
gcacagagca caacgagcaa tagcttgccc ttacgttcat tatttagcat gcactactac 42060
taactaccca ataatcaata catcggttat taaactgttt gtacagttta ataatgtcat 42120
tttatcacgt taacatatgt ttcattcaac accacaccgg ttttggcaca gttgcaaact 42180
tgcaataaca tttttactac ttctccaccc cataatataa caatctcgtt ccatactaga 42240
ttgctatatt acgggacgga tgaagtactt ctttccttcc aaaatataag aatatagtac 42300
tagattagat attatttgga ttcacgaatt tgattaggct atctagattt gtagtcgtac 42360
gtaatgtcta attcggtaat aggttattac ctctttggat ggagggagta gtttttattt 42420
cgtactccct ccgtttcata ttataagttg ttttgacttt tttcttagtc aaattttatt 42480
gagtttgact aaatttatag aaaaaaatta gcaacattta agcaccacat tagtttcatt 42540
aaatgtagca tggaatatat ttttataata tgtttgtttt tttattaaaa tgctactata 42600
tttttctata aatgtagcca aatttaaaga agtttgatta cgaaaaaaaa tcaaaatgac 42660
atataatatg aaactgagga tgtagcagac tatagcaaat ttaaactatg cttttatttt 42720
agagcatcac caaaagatta gcaataattt atccctaaaa ttcaagtttt gggtttctta 42780
aactgaaaat aggaagtgaa aaatcttttc cgtccaagag atagcctaaa tcttatctta 42840
actaattaaa atattcataa ttttcctttc gtcacattaa attttcgtcc gtaaatccga 42900
ttgaaatcca attggacaat ccaaaaaata gagaaaaaga acagaaaaaa taataaaaag 42960
cacacaaatc ttatctcaat cccgcgggaa gctgccgacg ccgccgaatc cgctcgagcg 43020
ccgccgccgc cgccgccgct cacggggaac gatgtcgctg ctgtcgcacg cggtatggga 43080
gggcgccgcc gccgctgctt gggagatagg atatggagag agaaggaaat gtgagggagg 43140
gttaggtttt tccccatccg tatcttcagc gacacggagg cgatccaagc tgtccatcag 43200
atcggacggc tcagaacgcc tccatcgtca ggccgcgcat gcttgatggg ccgagggaag 43260
gccggagggt cgaacaaacg cagtcagagg aggagttgga ggaggtaaag tagaatttat 43320
ttgcgggctg agatagtaaa tggactgaaa atggcccata gagaaattgg gaattttatt 43380
taaataaatg ttgaaaaggt gtttatatta tcaaaattag aaattaagct ccgaaaattt 43440
taaaaaatat tcaaagagca ttattaatca tgattaattt aataaaaatt aaatccaacc 43500
atatcatatt atttcacggc gcacggtagg aaaatgcgca gctgttgtcg ctgacggtgg 43560
gagagaaggg acattgttta tttccagaac tatcttttat aactcccatg gaactttaaa 43620
ataaatataa tcattattat agcattagtt tttttctgtc ttttttttcc ccaagagcgc 43680
cgcgcagaag agatcgatcg cgatctccct gccccgacgt cgccggccga tctctcattc 43740
tctccacgcc ctgctcgtcg ccgatctcct acaccatccc tgccatctcc tccttcccct 43800
cccctctatc ctccactggt gccgcccacc tctccgtata agacaaactg cgttgcggcg 43860
ttggtttccg ccggcgctgc tgctgcacct gtcagctagg gcgggcatgg cgcgccgcgc 43920
cgcttcccgc gctgttggcg cccttcgctc ggacggctcg atccaagggc gaggaggccg 43980
cgcggggggc agtggcgccg aggacgcacg ccacgtgttc gacgaattgc tccgccgtgg 44040
caggggcgcc tcgatctacg gcttgaaccg cgccctcgcc gacgtcgcgc gtgacagccc 44100
cgcggccgcc gtgtcccgct acaaccgcat ggcccgagcc ggcgccgacg aggtaactcc 44160
cgacttgtgc acctacggca ttctcatcgg ttgctgctgc cgcgcgggcc gcttggacct 44220
cggtttcgcg gccttgggca atgtcattaa gaagggattt agagtggacg ccatcgcctt 44280
cactcctctg ctcaagggcc tctgtgccga caagaggacg agcgacgcaa tggacatagt 44340
gctccgcaga atgaccgagc tcggctgcat accaaatgtc ttctcctaca atattcttct 44400
caaggggctg tgtgatgaga acagaagcca agaagctctc gagctgctgc acatgatggc 44460
tgatgatcga ggaggaggta gcccacctga tgtggtgtcg tataccactg tcatcaatgg 44520
cttcttcaaa gagggggatt cagacaaagc ttacagtaca taccatgaaa tgctggaccg 44580

```
ggggatttta cctgatgttg tgacctacaa ctctattatt gctgcgttat gcaaggctca  44640
agctatggac aaagccatgg aggtacttaa caccatggtt aagaatggtg tcatgcctga  44700
ttgcatgaca tataatagta ttctgcatgg atattgctct tcagggcagc cgaaagaggc  44760
tattggattt ctcaaaaaga tgcgcagtga tggtgtcgaa ccagatgttg ttacttatag  44820
cttgctcatg gattatcttt gcaagaacgg aagatgcatg gaagctagaa agattttcga  44880
ttctatgacc aagaggggcc taaagcctga aattactacc tatggtaccc tgcttcaggg  44940
gtatgctacc aaaggagccc ttgttgagat gcatggtctc ttggatttga tggtacgaaa  45000
cggtatccac cctgatcatt atgttttcag cattctaata tgtgcatacg ctaaacaagg  45060
gaaagtagat caggcaatgc ttgtgttcag caaaatgagg cagcaaggat tgaatccgaa  45120
tgcagtgacg tatggagcag ttataggcat actttgcaag tcaggcagag tagaagatgc  45180
tatgctttat tttgagcaga tgatcgatga aggactaagc cctggcaaca ttgtttataa  45240
ctccctaatt catggtttgt gcacctgtaa caaatgggag agggctgaag agttaattct  45300
tgaaatgttg gatcgaggca tctgtctgaa cactattttc tttaattcaa taattgacag  45360
tcattgcaaa gaagggaggg ttatagaatc tgaaaaactc tttgagctga tggtacgtat  45420
tggtgtgaag cccaatgtca ttacctacaa tactcttatc aatggatatt gcttggcagg  45480
taagatggat gaagcaatga agttactttc tggcatggtc tcagttgggt tgaaacctaa  45540
tactgttact tatagcactt tgattaatgg ctactgcaaa attagtagga tggaagacgc  45600
gttagttctt tttaaggaga tggagagcag tggtgttagt cctgatatta ttacgtataa  45660
cataattctg caaggtttat ttcaaaccag aagaactgct gctgcaaaag aactctatgt  45720
taggattacc gaaagtggaa cgcagattga acttagcaca tacaacataa tccttcatgg  45780
actttgcaaa aacaaactca ctgatgatgc acttcagatg tttcagaacc tatgtttgat  45840
ggatttgaag cttgaggcta ggactttcaa cattatgatt gatgcattgc ttaaagttgg  45900
cagaaatgat gaagccaagg atttgtttgt tgctttctcg tctaacggtt tagtgccgaa  45960
ttattggacg tacaggttga tggctgaaaa tattatagga caggggttgc tagaagaatt  46020
ggatcaactc tttctttcaa tggaggacaa tggctgtact gttgactctg gcatgctaaa  46080
tttcattgtt agggaactgt tgcagagagg tgagataacc agggctggca cttacctttc  46140
catgattgat gagaagcact ttccctcgaa agcatccact gcttccttgt ttatagatct  46200
tttgtctggg ggaaaatatc aagaatatta taggtttctc cctgaaaaat acaagtcctt  46260
tatagaatct ttgagctgct gaagcatttt gcagctttga aattctgtgt tggaattctt  46320
ttctcctaca gtcctattag aggagggatc ttctctgtat gtgtaaatag cgaggtatgt  46380
atgccacctc tccgaattat ttttactgtg gttcctagac tgtaaacaag caattatgtt  46440
atgctgttga tgccagaaaa aacataaaag tttgtcgtta tctctactaa cggatcataa  46500
agggatttgt gactggagtt tcaaacttaa tgtgtctagg cagtaatttt gacattagat  46560
ccaaaacaat tttatagggtt tcattaaatt tcatctatgt gtactgttta ggtgttgaat  46620
agtttgactt gtttttaac tgaacaaaag atatgtctga agctttgttc tttaccaaat  46680
gcagtactga tcatcacaat atatttttta tggaacaaga ttggattgta tagaatggtt  46740
tctgatctga ttatcttatc tcaacgtatt attatgcaca tgtactaatc atgaaatatc  46800
tgatggaatg atgtttctat ttacctgtgt gaggcagcaa ggagtgagat ggataacacc  46860
acatactccc tctgtcccag aatataagaa gttttagagt tggacacgat tattaagaaa  46920
gtaggtagaa gtgagtagtg gagggttgtg attgcatgag tagtggaggt aggtgggaaa  46980
```

-continued

```
agtgaatggt ggagggttgt gattggttgg gaagagaatg ttggtagaga agttgttata  47040
ttttggggag tacattatta ttctagaaca atactgttgt gctcaagaag cgttccaaag  47100
atgtttcaca acctgtgctc gatgggtttt gagcttaatc ctgggacatt cagtatcatg  47160
atctgtctca ttcttaaaca tggaataaag gatgacagca tgatttcttt gtctctataa  47220
tcttttggct acccacagat aatagctgta aatctatact actttaaaag gagtagtggt  47280
ggtggtgagt ggtgaatctg ccaccacccc accaccaact ctcaaaattc tgacatgtgg  47340
gatcactgtc aatcccttct ccaagacatg tgggatcact gtcaatccct tctccaaacc  47400
aattgtatga tagaacagtg gaaatcacgg acagaccatg gagctctcaa ccataatcat  47460
ccttgcgagt taataacaaa tggagcgtaa acttggcaag caaaaaactc aaattaattc  47520
taaaattaag ctctaggatt caaaatagat ttcctctctg cattgtgctg ttatgatttt  47580
taattccgta acaacgcaaa tgcattttgc tagtcttata aagaagggtt aatgcaaata  47640
ttctgattaa atgattgtat ctatgaagtt tgaatgctag tggaagctcc tttgaccatg  47700
ttttgttgtg cgagcattta agagagtgaa gagaatgctt ctttggtgct gttctggtat  47760
ggaaggatcc acagataaaa ttcaggttct actgcttctc tgcttgtaat tttcatgaag  47820
ctgcagtgaa taccttgttg accacttgat ctgttgcttt gaaggagaat atagtagtgg  47880
ccaaggttgg tgacggtgat ggtggcatgt gatcccccag atcttcagtg acccagagag  47940
gaggggacgg cgcgtggtga gctacaaggc atactcagtg gagggcaaga tcaaggcctc  48000
ccgtccgtag gggactccgc tgcatcaagg ccaactgctc cgaactgatc aatttctggt  48060
acggatcact tctcctttcc tttttttttt caccttaagc actctcttga ttcttcgctg  48120
ctacctccct taatttcttt caatatattg tggcacttga tcatggcgga gacccacctt  48180
ccagtgtgaa tggattttgt caaagaacta aatttattcc attagcttat tttccgatta  48240
catggaagac attcttttct ggaataaata cagaactaaa tcctgtttcc tgaataaaag  48300
ttgttagtgt gtggcatggt gcatttccgc gcttctaaat tttataaaac ctgttcattc  48360
aatttgaacc tgcatccaat ccaatatttt aggtgcagac aggtgcttgc ggtcaggtta  48420
aagaagttgg caaaaatgct tctgaagaaa ggttaattgt tgtttcatct caggaggtaa  48480
tatgcagatg attattccaa ttggcattgc cttgccattt ttatcacgag tctttacaat  48540
tttatatcct cctacatatt ctttccagat tccagatgat ccagtgtctc caacaattga  48600
ggcgcttatt ttgctccata gtaaagtaag tacacttgct gagaaccacc agttgacaac  48660
acggcttgtt gtaccatcaa acaaagttgg ttgtattctt ggggaaggtg gaaaggtaat  48720
tactgaaatg agaagacgga ctggggctga aatccgagtc tactcaaaag cagataaacc  48780
taagtacctg tcttttgatg aggagcttgt gcaggtaatt tatttggcca tacctacacc  48840
agagatccat atattacttt tataactgca gtttttactt gttaacattt cattgtgctt  48900
ttacatttgt tccaagcttt caggttgctg ggcttccagc tattgaaaga ggagccctga  48960
cagagattgc ttcgaggctt tgaactagga cactcagaga tggaagttct tccaataatc  49020
cgacaccttt tgcccctgtt gatggtcctc ctgttgatat cttgcctaac aaggaattca  49080
tgctatatgg acgatctgct aatagtcccc catatggagg gcctgctaat gatccaccat  49140
atggaagacc tgccattgat ccaccatatg gaagaccaat atccacaata tggaagacct  49200
gccaatgatc caccatatag aagacctgtc aatgatacat catattgagg gttgaacaat  49260
gatgggcctc gtgatcaggc ccggtcctga ggggggtcga atggggcgat cgctccgggc  49320
cccccgattc ccagggcccc cacctatctg tgcaacgagt agtagcgatc ttccagcgcg  49380
```

caacgtgagg cgatgtttct ccgtgatttc gccggcctgc aactgcgaga tcgcgagtat 49440
aacgatcagc cgatcgatct catctgccga ctgccatgct gatgccacac gcaagcgcag 49500
catatcagcc ttatcttggt tgatcggcat gctggacgag cacatctgtt gtcgcatcaa 49560
ctgctgactg ctatatatgt gctggtgctg aatcgatcga ttgtcgtcac ggaagtgaag 49620
aacaaccacg gcactgctgc ctgctgggct ctagccgcca tcagtaagta cgctatactg 49680
cctatctaga tctagatcga gattacatag tggaattatc tgtttataac aaaattacaa 49740
ggtatcaatt gataatttaa ggttataacc gtacaaactt cagtgatttg ctggtttcac 49800
attggttaga tttgtttcaa ctaatttggt acttctgtag ccttgtaatt tacgaatcta 49860
gtattaatat tttcttaagt attagcctgt tccttgatat tatgctgttg agaaagtatg 49920
caatagataa caaaaacaag taggtgtgtt gaggatgctc aagagtaata caggcacttc 49980
aataattctg atattatcag gacatcatca ataattctgc gcctacaaat cttcaaagaa 50040
aattttaata taatgcgtat gattttttaa atacgaatat tgattgctat ttaaagatat 50100
ttatattata tggtaattat tatttgaagg tttataataa aggcctccgt ttttagtttc 50160
acgctgggcc ttcagaatct caggaccggc cctgctcatg atccttacac cgtgtatcct 50220
gtagagtact tctctaaaag agagtaccct agtggaagta gcaaagttgc accatctgct 50280
tcatacgaaa gatatgcagc aactactcgc ttgcctaata gagaactgcc ctcatctatt 50340
agtcctggtg ccgattatat gtcctgccgt tcttatcttg accaagtacc tactgatagg 50400
tactctaata gggttacact acaattaggc ctcttgagag ccgggaatag taatgtgcaa 50460
caattaggaa tcaccagagc tggaaattcc aatgcttatg attatactga ggtacatttc 50520
caatgcgtta gcttgcctct tctttgcaaa tggccctcgc ctgatatgtt tccattagaa 50580
acatgaaacc atatatttga ctgttgcatt atgtctattt tcttccatga tggttcagac 50640
gtctgaaaaa aggacaaaaa tattctagaa tatgtcatgg tgatccaaat atatccttct 50700
gtcttgtgcc cactctaata tctatcgttg gtaacactat tcaattgtta ccatgttgtt 50760
gcaaacccta gattcagtta ttcagctgtt ctctgctgct gttgcttacc agtttttcta 50820
gttgggtgtt gatcttttct catttttat ttccttgttt cctggttcac ctgctgcctc 50880
tctgatgcat ctgaatgtat atttttgttc tcttcagtgc ttaatagatt taaatttcat 50940
tcttttcagg ctgcggagct gatccatgga cgtgaggatt accgaagact gtcaggtctc 51000
actgggtatg gcttacgcag actgaatttt tacaggacac aaacatgaat tttgtcctca 51060
taatcattga gtgatgatct ctttgcaggt atccaggtgg ctctgtcgaa ttgtggattc 51120
caaatagtta actggagtct gtcattggtg ttggtggtgt caatctagct gagatccgtc 51180
tggtatagcg taagagaaac atcatgcact atccccagtc ataaccatgc cccaatggcc 51240
accaatagtt ttcctcgtga aaatctcccc ttgatcccag atctctggtg cgagagtgaa 51300
gttgcacgaa gcccatcctg gttcttccga gtccattgtg gagatccagg gcattccgga 51360
tcaagtgaaa gccgcacaga gccttctgca aggcttcatc ggcgcaagca gcaacagcag 51420
gcaggcgccc cagtcctctc gcatggccca ttattttag taagctggag gacattcgca 51480
acaggggggt cagtggtcac tgcaaagctg agtttgttct tcagttcaac tgcagaaaat 51540
tgcagatcgg ttgccgtagt tgctagaacg gtacatagtt gccacctaac tgtagcgagt 51600
ggcataactt attgtgtgtt actgcccaat gttgtctctc cttgtgttca tggattcaga 51660
cttgtgattg tagtatttct ggatcagact ggagtaaaag aaaaaaaaaa aggaagacat 51720
gggtttaaca gtaagctcaa aacgttgaca gtagtaaaat aaaaggggtt tgttcacttt 51780
atttccaata tcaaccttac caacatttgg cgttgaatca tttataccac atcgcttgtg 51840
cagctgaatt tggggctgtt taaaagatgg tctcttggat tgctaattgc ctcgcggcaa 51900
gcgtggtacc ttgtacaata taaatataat tataactatt taatttcata attaaacatg 51960
ttgttacaaa tctctactat tataaaaatt gaagatgttt tttgccggta ttttggtacg 52020
tcatctgtgt atgaatccgt ttttaagttc gtttgctttt ggaaatacat atctgtattt 52080
gattcagttt ataagatcgt tcacttttgg taatacagaa ggaatcatat aagaattctg 52140
tttaaaaaca ctcgtatagt aacttgagac gatcagacgc ctaactacag ctcatgattt 52200
tctaaatata tatatatata tatatatata tactagaaaa aatatatgtg tgttaaaagc 52260
tatcttaatc ttattattgt tatatatttt agttaacaag aaatctattg tgggaacttg 52320
tttggatata tattttttta aaaaaaatca tgagctgcaa ttaggaatcc aatcgtctca 52380
agttagcagg agggcgagtt tttttaaaga gatttcttat acgatttctt ctatatttct 52440
aaaagcaaac gaacttaaaa accgactcaa acatggatct gtatttccaa aaacgaataa 52500
acttaaaaac cgactcatgc acagatgatt aatttttata atagtagaga taaacgaact 52560
cccacagtga attttatttt aactgaacca tataacaata ataagattaa aatagacttc 52620
acccgttgca atgcacgggc attttttcta gttaaagaag aaataaaaaa acacaaaaat 52680
ttataaaatg taaaaaagaa aaatattata attttgttag aattattatt ataatataga 52740
aaaatagttg ccaaaatttc tcaacgaatg tcgaataaac tcagcaatgt catatattta 52800
aatatgatgg taatatttgt tcgcaaaact ttaatcttca atccttcaac aacatagata 52860
tacaacgtcg taatcgccaa caagcccgag tgaccataca ggatagccga gcggtggatc 52920
tgtactgttc ttgggtgaaa taaatctagt acattgtata tcttatctta atatctacta 52980
ttataaaaat tgaagatatt tcttcaaaga tttccatacg ttctctactc cgttacaata 53040
tcggttctac tccgttacaa tatcggtttt gtacaccccg cgcacgcgtt gtgtgttctc 53100
ccgttccaat acatgaagct agagtcttgc ttctccctgg tctggcaggc cctttttcca 53160
ccatccccac cagggccagc gggttacatt gaccgatcac ggcccacatt agtggatgca 53220
gccagccacg ctcttcacaa atcatgtgat gaacattagc tgagttaaaa tttatccttt 53280
gatgattgtt agaaatgttt ttttctccac atcttctctt tcaattttgg aaaaatagat 53340
ttcttgattt ttgtgctcgt acatcactaa taaatcagtt gttacccttc cacacattgt 53400
caatttacca tgtctatttc agctcttacc ttgtatagtc ttgactcttg agtcctcgct 53460
attgactaag ttgctacatg cctcctacaa atcaatagac tgccataaca atattttcta 53520
cgacatgatc catattagtc catgcaatgc aagtacacac acactactgc acgaaaaaac 53580
tatgcaccat aacttcaaaa ctaacatgtt agaatgacgt taatttttca ttacaattat 53640
attcatcgac cgttaattta ctaggcatcc tgtttaaaaa aaatattcac cgaccatacc 53700
cacatgttcc gtagttcatt aggtgatgga tcggtagtta cagcagctgg atttttatat 53760
tttggtcatt ttgaaaaatt tatttcgcaa atagactcct gaaaaaactt atcccagaaa 53820
tagtcccttt tggagcgtca gagtggctgg cgccgtggtc caacgggaca gcgccaacct 53880
ctctggcgcc gccccccgcc tctattcttg tttctctata tagagttgca aactttttat 53940
ttttgtttta tttttttgga tgtttttttca ctcttagaat cacgatacaa ccaactacaa 54000
aaaaaattaa actcgaacgg aatatatcac ttagctagaa gtctgaaaat atagcatacc 54060
acttatctac tttgcacctt caccaaaatt agaccataac ttctttagta aaatcctttg 54120
atcagcatat taaacataat gcactctatc actaggtgaa attacttaat ctaattcaaa 54180

```
atataactac atgtagcctt gaaaaattct acatgccaca tatttcgtcc gtttgagttt  54240
attattttta tggttcgttc atgtgagttc ccaagtgtga aaaaaaaata aaataaaaat  54300
aaaaaagttg cacatcctct cctctgcatt agagaggaga ggagaggaaa aattctacag  54360
gtcacatatt tcgtccattt gagttcattt tttctatggt tggttcttgt gtgttcctaa  54420
gcgtgaaaaa aatatcaaaa aaataataat aaataaaaaa attcgggggg ggggggcgcc  54480
agccactctt aggggtgaaa acgatcggat aatatccgat ccaatctgct ccgaatccat  54540
ccgaaataag gatatggtat gggtttttag aaatctggcg gatatggatg cggatgagga  54600
tatggtatct ccgaaatacg acggattatc cgacattttt gtcggattat ccgataggcc  54660
ctttaccgga taatccgaaa ttatgaacac atgtaaccac tctatctatt gcatataaca  54720
taagttggtc catccaatga cctaattcat caattaccct agatttctta ctatgtggtt  54780
ttcaccattt catgtcacac ttgcgtagct gtatttttat aaaatggaca tcatgtattt  54840
atgttgttta gcacttaagc acataattat tacaatgggt cgtttattga cattgtgtta  54900
tttttacttg cattgctaac tcaatgttgt attgattgca tacacacgta acatctgata  54960
aaatttaatc cgtttctgaa ccgattccgc accatttccg acatctgcat ccgtacacta  55020
tccacaccca ctccgaatcc gcttaaaaat atggtttagg atatggtatg accactatcc  55080
gtccgaatcc gctttatttt caccccctagc cactctggcg cgcttcccct gccacctcag  55140
catcgtccca ccacgtcggc agaaggacgg cggctccagc cactctggcg ccacaaaaaa  55200
ggaccatttc tagcataagt ttttttaggg gtctatttac gaaataagtt tttaaaagga  55260
ccaaaatgtg aaaaatccag gttacagcag actgtgataa gcaatagcta tattgcctat  55320
atatacacgt atatgcattg ctaatccttc aattttgtcc aattctttta aattgtcttc  55380
acctgttgca acgcatgatt ttttttctag tcttaacctt aactaatctt aataactaac  55440
taaaagattc gtatctttcc gatcgtcacc ttgtccatac gctaattttt cgtccgtccc  55500
ccctccccct caaaaaaaaa gggaaaaatc cattttacac cctcgaactc ttatgcttgt  55560
ctaaaataca cccccgaact ataaaaccgg gtataataca ccctcgagct atcaataccg  55620
gacagttcaa gggtgtatta tacctggttt tgtagtttgg gggtgtattt tagataagca  55680
taagagttca agggcgtaaa tggacttttc cccaaaaaaa atcccagtcg ttactttcca  55740
tcctgagaat cggagacagg gaaaactgaa gcatacacgc aaatagaatc aaagataggg  55800
aaaactaagc atatacacac aaatatatcc aaaaattccc atgcagctag atcgggtgcc  55860
accgttgttg ccaaaccacc acattgcaat gtaaatctaa gactaaagcc taaatcctat  55920
gctaagtcat caaattagac tcggttctac caatttggta atatatcaaa ttagacttga  55980
tttttactga tttgaggttc tcgaggtgtc acactatgaa acggaagttt ttcccgttgc  56040
aacgcacggg cactatgcaa tatcttaact aattaaaaga ttcatatttt tcctttcgtc  56100
acaccgatct ttcgtccgtc tgtaacatca cgtgcacctc ctctccaaat cccacatcat  56160
cataatccga cccaaaaaca aaatctcaat ctcaatccaa tcagaatcat cacaaaatca  56220
tccaaaatat caagagatga ttataggaga tggaggggtg agcaggagca acatcatcat  56280
cgcataaaaa ccccaaaatc aatcacaaca acgacatcat tatcacataa gaaaaacaat  56340
acaaacaaca tacacaatca acaacactgg cggatccagc cgaggggaca acggcgtggc  56400
agcgggcaga tcctctcggt cagatccgcc cacgggtgcc actgacgtcg ccgccgccac  56460
cggatccaag ggagaagctt cggacagagg gagagggggg tagaggaccg ctaaatccgc  56520
ccaccggaaa tgccgccgcc accacctccg tcggatttgc ccgagggagc gccgatgccg  56580
```

-continued

```
ccaccgccat cgcgggagaa gcttgggcac ggagggtgag gaggaggggg ggtagagaat  56640
cgccggatcc atccgctgga aaagcctccg ccggatccgc ctgccggaaa caccggtgtc  56700
gccgcctccg ccggattcgg tagcgggagc cgccgatgcc accaccgccg ccggatccgg  56760
tcggtgggag ccactgacac catcgccgcc gcctcctctg ctaccgacaa gggagagacg  56820
agaggggcgg gggcgagggc gggggacgag agggttagag ggagggaccg agtgggagag  56880
agagggacga gtgagaggag ggggacgagt gaataaggat gcgtgacctt atccactcgc  56940
gcggtcgcac cccggctctt tctctcgctc agctgttgcg cttgtggaga ggatgcgaga  57000
tttttttttg agtaaaatgc acgggcggtc cttaaacttg tagcggtctg tcatctaggt  57060
tcccaaactc tcaaaatgca tatccaggtc ctagaatttg tcaaagtgta tcatctagat  57120
cccaaaccga cacatcctct cttggatcct acatggcgct aatgtgactt gtcacatgga  57180
cgtgacacgt cttttttttt cttcttttct ttttcttttc cgttttcttc tcattcttct  57240
ttttttccat cttctgctcg ggtcacatag aaaggaaaag aaaggaaaat acaagagaag  57300
aaaaaaagaa aaaagaaaat ttttaaatgg gtctcattcg tcagtcaaaa ttatgccaca  57360
tcatgtccct gcgacatgcc acatcagcac cacgtagcat cctgaagggg ttgtggcgat  57420
ttgggaccta aatgacacac tatgacaagt tctaggactt ggatatgtat tttgagagtt  57480
taaggattta tatgacacac tactataagt ttaaggaccg cccatgccct ttactttttt  57540
tttttacacg gagagaatgc gaatttgttg gttagttgcg gctgagggtt tctcgcacgg  57600
agaaatttgc ggtgggagaa tttttttttcg aggttctttc tattgggaga agacgggatt  57660
atagggatta ttactggtgt ggtggcccct gttttctttc tttttcgagc ttctttccgt  57720
taaattcact tttctctctt caaggagcgt aggacatgac tgaatgcagc tgctgtaaat  57780
tagaaataaa aaagaaacat attctgtttt tcattttttt caataggtaa atataaagat  57840
ttttaagtaa tatttaaaaa tatatagtgc tgatcaacga cattgttaag tgagattttg  57900
ctgttactat cactttttttt tccattgggc tcacgtacgg cattaaaagt tttagttttg  57960
gttctctcct tttgagtttg ggcatatacc aatattgaga taggtatact aaagttcatt  58020
tggattttat tcgattcaac ttttttgggt tttgttcagt tcttttttac atgtttctca  58080
tctgaaatta ggaaattagg tttggtaaag tcttgaatag ataacgctgt tgacgtttga  58140
acatatattt atctatttat ttatttaaaa atatatgaat aatttttatt ttgttatgac  58200
ttttgtcggt gacatgggac cgggagtatc atgactagag gcttgggcag gagcgatcac  58260
ccacgtggcc tgatgtaaca tcctgaaaat tcccaacaat aaaaatcact aaaattttga  58320
actttttaaa acttttgcat catgctggtt gttatgattg ctattgcttg ccaaaccgta  58380
aatgatcaca aagaaagtaa agtaaggatc taaaatttaa gtaatagata aatttacgag  58440
aatataatat ttaattgcta accctacaaa taattacgca caagaaaaca aagccagaca  58500
aacggaaggt taattactaa tttaaattat ggattaatta ttaaatactt gaaccatgtg  58560
ttgcgtgcca tggcatctaa atacacatga aataatggtc atataattaa attaagcttt  58620
ataaaattat gtgaggtttt aattaagcaa ttagcttaat gttgtaccga gtcttaatat  58680
actatttata gaataaataa attcaaccta tccgtgtaaa atatattgct ataagttcat  58740
tcaatgtact attgtaataa taatggccac attaggatat tttaattaat tttggaaccc  58800
tcaaagcctc caaaattatc taggttaatt ttgaaattat acctcattta agtaatgcaa  58860
tagaaaaata tacataaaaa taaaatatgg gtaatattag aaattgagta aattttcatc  58920
taaattaaaa catatattgg gtaaacctcc tttatgtaaa aattaagatt tatagaatga  58980
```

aatttgtaca agggataaac taaaatcggg ttaaatagaa aatggcactg ttcattgcac 59040
tctaggtgct cgacgtggtc cctggcccta ttttccccct cagccgcgcg cgcctggctg 59100
cctcgcgccc cgcgccacgc cacccgcgtc gcgtcgccgc tgccgcgccg tcgccgtcgg 59160
ccgttccgcg ccgctcgtcc gtcgctccgc cgcctcgcgc cccgcgccgc gtcgtcatcg 59220
cgtcgccgtc gccatcaccg cgcctggccg ccccctgaccc cgcgccgcgc cgcgccgtcc 59280
cgtagccgcg tgcgcgttcc atcgccgctg ccgcgccgcg cgccgtcacc gcgcgccgct 59340
cgtccgccgc gcatagcccc gcgccgccgc gccatcgtgt cgccgcgccg tcgcgtcgct 59400
ctcgagcccc gcatccctct cgagccccgc acgtcgcgtc ttgtcgccgt tgctgccgcg 59460
tcgtcgtcgc cgatgctgtc gcgtcgccgc tgccgcccgt cgcgtcgcct tgcgccccgt 59520
gccgccgctg ccgcgttgtc gctgtcacct tcgcgtcccg cctcgtgccg cgcgccaccg 59580
ctgccgcccc gtcatcgccc gctcgtcgcg cgcgccgccg ccgctgccgc gccgtcaccg 59640
tcgtgtcgcc gtcggcctcg cgccttgagc cgccgcgcgc ccgtcccctc gcgcctgcgc 59700
cccgccgcac ggccgtcccc tcgccgtcgc cctgcgccac tgccgcgccg cccgtcccat 59760
cgcgccgagc cccgtgccgc cgcgcgcgtc gcgtcgcccc gcctgtcacg ccgctcgccg 59820
cctcgagcca cacgcgtcgc gccgtcgcgt cgccattagg gccggccacc cctttccccg 59880
cgccctataa aaccccccgg ccaccccccct ttcaccccac accatcccca cccattcccc 59940
tcttcctctc ctccttcccc tcttcgtccc ctccaccgcg ccgcgccgcc gccttcgtgc 60000
cgccgcgccg tgcgccgtcg tcgcgccgcc ctcgcgccgc cgcaccgccg ccttcgtgcc 60060
gccgcgccgt gcgccgacgt cgtgccgccg tcgccgtcgc cgtcgtcgtg ccgccgtcgc 60120
cgtcgccgtc gtcggtaagc cgccgtccct tccctcgttc cgacgccgtc gccgcccggg 60180
tgggaaggag ccgagagaga gagggaggaa ggagccggga gtaggaagaa agaaaagaaa 60240
agagagagag agaaaagaaa agagaagaaa agagaaaaga gagaaaagaa aagaaaagag 60300
attagagaag ggagggaaga gtgggcccca cctgtcatta gccccatcca attcccctta 60360
gaaaaataat tctgtagaaa agaaaatcaa gatcttgacc ccacctgtca gtcactatag 60420
cgtgtggata aggttgtatt aaaaataaat gaattaggaa cagtactatt tcgcaactat 60480
tagaattaat tcaaatttga atctttacac tagcataact aattcatttt agctccgatt 60540
tgagtggaac ttgaacctaa attcatctaa attcataagc tttccaatgg tatataattt 60600
actattaaat aaaatatatt tataattatt aagtaattaa tatcatatga ttaggttatg 60660
gtcaacttaa aaatatgcta ataaataaaa ttagtattgt ggatgtaata atatttgtct 60720
ctaacatgtc ttgccactgt aacaaccaca caaactaata ttaagtgatg tctgaaatga 60780
atgaatgaat aggaaaatac tagtacttgt ttaatattcg atagccatat aattaaaccc 60840
atggcttata ggttatttaa atcaaatgta gccttgtgat tatgcaacta aaatataaac 60900
acatatagat gaatctttag cttgattagg aggaataata acagagctag tgtgactagt 60960
tatgatatag cttgttgtcg gttgcctata tttagtaaat ggttcaatgt taatacactg 61020
atgcacacac ataccctttt tgataaccta ctagttgcat atattaaact tggtaataaa 61080
tgaagaacca atatattagc taaatactgg tgctagttat aaatcttgac cacacataat 61140
tttagttcaa accacacctg aggattgttc gttataaagt tataaagtta taaagttata 61200
caaaagataa tatgtaacta taatagtatt aaaccacaaa tctaaaatac agggcgcata 61260
attgtcaacc ttttatgcaa acggataata tccatatata tacatcatgt ggataattcg 61320
aataatagct ccattggtaa aataataatg taggcgaatc atggtgatga gatggtttat 61380

```
cctaaacctc cccatcgaca tagccatgct atagggacct gaccatttta ccttcataac  61440
agatctcttc cataagccaa tagctagact aaaccacaga ttagcaaatg tgtacatcat  61500
atattgtgct agttagtacc aatagaacca tcaggacaat ataaatacta aggaatctta  61560
gctcttagct tgattagaat ccaatagcaa acacgagtag tatgagcagc cttaggttcg  61620
acctcaataa ttatattttg cttgtgcata attgcttctt gttgaatatt ggtttttctc  61680
gcatattata gaaattgtat atcggttagt cgtgaggcaa cgtatgcagc tttcaggagg  61740
tgaaggttga tcaagattgt atcaagaata atgactattc taagcaggca agtcatcact  61800
attccttgaa catgttgatc ctaattgcga aattattttg tttacaaata aaattgcatg  61860
caatgatgaa catcctactt gtgattatgc catgccttga ttattgttta cccttaaaat  61920
ccttgtaacc atgattacgt atgagtccct agtcaattat gacaattgct tagagatgct  61980
attctagaat catgcatact catatttatc aaatgctata tgcttgggca attacctttg  62040
ggaaggtaat tgagatgcgg catgtggaga catgaacgcc acattgccat gatattaatg  62100
acatgatttg tgaaaggaga aataaaatta aacaactgtt ttcgactggg gcggacggag  62160
gatttgggtg gtatctggaa aaggctagta ccgtccccgg tcaattaagg accgagccat  62220
gaagttaagc atgaaacgac ccccgtacaa ccgcacttct cgtatgggta tagacctagc  62280
ggagtagata gctgagcgga ggcagtatcc atgcatagtg gtttcttgat gtgtgaggca  62340
ggggctctac ggtggggcag ccattggtag gaccgcaagg cgggtatcta cagtggtgtc  62400
gccatcggta ggactgccat gtgagaatct aaaacataat tataacttaa tgcatgtgtg  62460
agtcttccct tcccgggtgc gccagaactc ctctcactgc tagaaaccgt gtacgcctag  62520
agtgcatgag gatgaaaagt tcatggagcg ggtactgcca atgcgaggtt atcgaaaagc  62580
tctgccgtga cgcatctcat gtgttgggac gaggctcatg tgttgggcag tcgcggagtg  62640
cgggtaaagt gtacatccac tgcagtgtga gtaaaccaaa tctattcgaa tagccgtgct  62700
cgcggttatt gagcaccggg acatgtatta cacttggcta gactctaaat tcttaacttg  62760
tggggaatgg gatattgcat gatgaatttt atgctgatgg agccacatcc cgagaggagg  62820
gaaggtggac atcctcagaa aaccatgacg attcaatggc gggaagctat ccttgggatc  62880
acaatggatg gtggacagaa ccgtcgttgt ttaaagtgaa cactggtact aaaatttgat  62940
cgatctatgc taggttttag gcttgtgaaa agaattgtaa aattagcttt atgcaaaagg  63000
acctgaagcc attccttgaa ataccctcta tcatatgcat tgttattatg gtggcttgct  63060
gagtacggtt ggtactcacc cttgctattt atatatcttt taggagagtg ttgaagagaa  63120
gcccttgtcg gtacgcttgc gtatcccaca agatgatcgg agtgcggtct tgttctaggt  63180
ctcgtttccc cagtcgactg cctgtggcat gttaaccggg cccttatatt attttgtctt  63240
tcgctgttgt tctctgatag ttgttggcct acctggccct aatgtaagta tttaactctt  63300
ttagcctaaa ttcattcgtg atatgttgtg atccaactat gtatgtgtgt accaactact  63360
gatccaggga ttggtacgga taaacacaga agatttccga tttccaaaat cgggggtcta  63420
cacctgaccc cctcaggggg ggggggtcgg gcccgagggt gatgtggccg ccccccctctt  63480
tgtctccccg aggggtcgga ccgctcccgt ttctgccccg agggctgagg cgccccgacc  63540
ccttgtgggt tttgcgccgc gtgtatgggt taggtgagca caacggggct cacctaaccg  63600
tatttattgt ggtttggacg agcgcgtcac gccgcatgta gcgcagtgca gcgcgctcgt  63660
ttatccggtc tgtgaccagt cacagaccgg tcagatcgtg ggttaggtgg caacaggcgg  63720
tctgacacac gcctcgcccc atcccgtcag gataagagcc tccaggcact tgtccctagc  63780
```

```
ccggagccag catgctaact cctggagatg acacgttggt cccggtcaga tatatgccag  63840
gcttcatccc aaccattaca agcaagatat tgtatgaaga agggcgaaca tgcagattgc  63900
tggactgaca cgtggtggac aagaatgacc gatttgtgac cggtctgaca ctggtcatgt  63960
cgtcggcaga caaccatgtt cccacgttgc acctgctttc ggcggagtgg aggtaggtat  64020
gggccatccc atcagaaggt cgttcggaca gcagccattg caagtctccg cccatttatg  64080
aagagatgac agggtgatcc cctggagaga aaaaaaggag gaccttgccc acttaggagg  64140
tgaggacgac tggaagggga gaggatctgg agagtagatc ccacgagagg aaaaaaggga  64200
gaagagggtt tctagagtaa gagctctctg actctccagc tctttgtagc ttcttcgtac  64260
acagatccac cagaaaatag gagtagggta ttacgcttct cagcggcccg aacctgtata  64320
catcgcccgt gtcttgtgct tttttcattc tcgcgaactt tccacagact aggagcttag  64380
aatctcgccc agggccccg gccgaaccgg caaagggggg cctgcgcggt ctcccggtga  64440
ggagccccac gctccgtcaa ctttggctta taattaaaaa tactctaagg atattttttt  64500
atattttatt ttcttatgtc tatatgaaat tttaaataag atagatggtt aaacatatat  64560
tggaaaaaca tatatccaaa agtccactat cacaagcgta gcatagatac gattacaata  64620
cgtttccgcg aagactgttt atacctactc tattccctgt tccttgtgcg gttgtgccat  64680
ttggggctgt tttttcatct cggattaact cgcgtggaaa ccgcgagacg aatgttttga  64740
gcctaattaa tccgtcatta gcatatatgg gttattatag cacttatggc taatcatggc  64800
ctaattagac ttaaaagatt cgtctcatga tttacatgca aactatgcaa ttagtttttc  64860
tttttatcta tatttaatgc ttcatatatg tgtccaaaga tttgatgcga tgttctggga  64920
aaatcttttt ttaactaaac atgcccaagg tgtttctcca attaagttga cccaaaatca  64980
ttcggcgtca cctttgtctt tcactttcct tccactacaa ggtgatgaca ctgacaaaag  65040
gtccaaaagc tacaggatct gatttttgtt catccatctg tgatgtgtcg gcaagccatc  65100
catggagttc atccactcaa ctcctctctc tcagagagag agagagagag agagacagac  65160
agacacatgc atgatagatt gtgctagtac ggtagtaaca ttttattgcc tccttttcta  65220
aaattctagg ttgtttggaa aacaaaaatt ctagattgtt caataaatta ataatattag  65280
gtatttattt taagtcactt taggtgttaa tttttgaatt ttaaactgct taaactctct  65340
ttcgacgcat ctgagagcag gtacaatagc agactataag ccagctataa atatatttta  65400
agtagataaa agaggaaaaa taagagtagc gggctataga tttgtagaca gctgcagcgc  65460
gagctccaag atacatatgt gtatgacatg tgagaccaaa cattaattat gtagtatatg  65520
tttatatgta tctattgtat gaattggcta ttaaattgac tatgggtgtg ttcggaggtg  65580
ggtgttggga accatctccc aagcacggaa aacggagcgg tccattatgg cgtgattaat  65640
taagtattag ctatttttta aaaaaataaa tcaatatgat ttttttaaac aacttttgta  65700
tagaaacttt ttgcaaaaac tcaccgttta gtagtttgaa aagcgtgcgc gcggaatatg  65760
agggagaggg gttgggaacc tcctcatccg aacgcagcct atacatgatt tggagccaat  65820
agttggctat aatattaaac ttgctctgag tggctcttga atcatcgaag tgatagaaat  65880
catatgcaga aatgtttata tttgtgatgt aaaatttgaa tctaaaatta tttatatttt  65940
gaaatggagg aagtactacc taaaacaagt atgagaaaga gacatgaaaa acacaaaatc  66000
tagacttaaa aataattgga attactagca ggaggtcgaa gtcaatcaag acggcgaaga  66060
aaagcacagg ggacagcaga cacgttaaca cgtaagtaaa caaacaagtg gttaattaat  66120
tagggggccc tcaagtctcc cctaaagcca ctaaacatga caggtttgtg taccatggaa  66180
```

aaaagggtga agcaaaactt tattctctct ctcattagat taccagttgg aaagcaatcc 66240
tgggacctct agctaatctc attattgtag aacaacgttt tcttagagag agagagagag 66300
agaaataagt caataaaaat tactactaat ccacttgaac cagttctgtc ggtgtcggat 66360
gatttaccac atttgacgaa acggactatt tattcgacgt ttcgaaaaac acactttttt 66420
agaaaaaaaa aactttcctc tattagccac tcgttttagt tatataccta tccgagtatc 66480
tgttaagttt atttatcaaa atatttaatt tatctctata attaaatata caatccgtaa 66540
aaacaatcac gcagtaattc gtttcaaact gagcctcagc tagaaaatca aaatggaaat 66600
gaataacaat agcaacagta gagttagttt ttcggcttat catccgcaac ccaaatgcga 66660
attttaaact tagccttaga gttaattttt aaggcttgtt taccatactt cattttccca 66720
gcattagttt cttttgtcac taaaaattgt ttttttaagt tgtttcgttc attttctcac 66780
ggtttatcag cagtagagcg aagccattct tggagcctgt ttggcacagc tctagctcca 66840
gctctagctc cactctttct ggagctggag ctcagcccaa cagttttagg tgcaccaaaa 66900
ttaggagtgt agttgggtgg aactctctca caaaaaattg tggagctgga tttagacagc 66960
tccacaactt cactccaaac ccaactcctg aagttaaatt gataagttga agctctatct 67020
atcaagccct ttttcttgat catgcttcta cctactccat ttttgtttct tggccctcac 67080
aggaattgga aaggaaaggc gtatatgcat caatgcatgc atgcgcacat caacctcgtc 67140
catcaaccat cataatcatc atcatctcgc cagctgacga aaatgacctg catccatcca 67200
tcacggacaa tccaagcgaa caccgctacc aacatcacag ccaacctgtt tatcactagc 67260
tcttgatacc actcctacat aaacactacg cgcaggttaa ttaattaagc gtgattactg 67320
aagtaacatc taatcacgtc ctggttagcc tttaataaga caacagttag agcaggtaca 67380
atagcagcag gatataagcc agctataaaa aaagagagaa aagagcaacg ggctacagat 67440
ctatagccag ctgtagcatg gacttcaaga cacaacgtgt gtataacagg tgggaccaga 67500
taataatagt gtagtatagt aagtaactat tatatatatt gactatagat gatttggagc 67560
tattagtgtg ctatagtatt aaacttgctc atagagcagg tacaatagta ggatattagc 67620
cagctataaa catattataa tgagataaac attgatagag aagagcagcg ggctacagat 67680
ctgtagccag ctacaacacg gactccaaga cacaacgagt gtatgacaga tgggaccaga 67740
tattagtagt atagtaagca actattatat aaattaacta ttacattggc tatagatgat 67800
ttggagttag tagtgggcta tactattaaa ctttttctct tagcaaaaat caagcgccta 67860
atcacattag aggagtagct ttgagacaaa ccaattagcg gcgaatcaag cgatctgcgt 67920
ggtcgtacag tgatgggccg ggccgggccc acagcccgac agtgacaggg ggcctgacgc 67980
atgtcagcct cagccctgga cgggagctag ccgttgtgtc cccgggggag gggagggggg 68040
cattcccatc atttcgcccc tcctccgggc ccacatctca gtgggggtaa aggtgtaaat 68100
tactgcgacc gcgagtccag cgagcctaga tttggacctt gtgtccgttt gactgaaccg 68160
gagctactcc ccaatacggg gggattgcgt tgtgtgcatg ccatgtgggc ccgagcgccc 68220
tttgttcgtg gctttgggtt ggaaaggtga ccgtgtgagc tgtgcggtgt tgtactacgt 68280
attagtataa atcatttttg ggtactactc cctccgtcca aagcttattt ataatttgtt 68340
gtactccaac cgtccgtctt atttaaaaaa aatataaaaa aaattaaaaa aataagtcac 68400
acataaaata ttaatcatgt tttatcatct aacaataaaa aatactaatt ataaaaaaat 68460
ttcatataaa acggacagtc aaacattgtc acgaaaatct aatgtttgcc ttttttttta 68520
agaccaaggg agtatctacg aacaaagata atacatgtta taatcatgaa gcccatgatg 68580

```
tgattagccc ggccgtttga ctaacctcac gagctacgtg gctgacaagt ttaacttgtt  68640
aactccatca tttcggatac ttagagcatg tacaatagca gactattagc cagctataaa  68700
catattttaa tgggataaaa gatgagagag aagagcagcg ggctacagat ttatagccag  68760
ctgcagcacg gactccaaga cgcaatatgt gtatgacagg taagaccata tgttaatagt  68820
atagtaagca actattttat aaactggcta ttagatcggc tatagataaa ttggagctag  68880
tagtggacta tactattcaa cttgctctta tatgatataa atattgatat aactatatga  68940
ttttgttaat gacatgtttg tttatggatg gactatgtgg ggtcggtcgc ctccgtagct  69000
gaccaaaata caaacttaaa acccctatct ataaaaatct aacttttgtt tataaatata  69060
gatataaaag ttcataatta gagcctcatc ttttaaacga aaagagtact atgaaaacaa  69120
ctcgtaatac aaagactaat tacgacgaaa agaaaatagt actgacaaga ggaaagcagt  69180
gaacttgcat actccctccg taaaaaaaac caacctagac acggatataa cactatatat  69240
ctagattcgt tcgttgtaat gaagtgtcac ctccgtatct aggttggttt tttcgtacga  69300
aagaagtatg agtaaatcta aagctatgta tacccttcgt caaaaaaaaa aagtaaacct  69360
tgtactggtg cgtgtcacat cctaatataa tattgttttt tatggagggt gtacagttga  69420
aaaaaattga tgtgttttaa ggatgaaaaa tattggtaat gttggctatg taactctaga  69480
aaaaaaaatg cagtaataat aaaatgctaa tttgctggag tactagatta tagacaatcc  69540
agtccaggac acgacaccct ccctactctc tccacttcca ctctcaccgg ccaccgcgcg  69600
ctctctctct ctctctcccc cttctcccgc aagattcttc ccccaaatcc cacccgatcc  69660
accgccgccg cccgctcgcc ggagtcccat cgctgccacc gccgccggag ccgcggcccg  69720
acgcccgccg ggcctgcttg ctgtgtgtgt gaggaggtgg agttgctcgc gctcgttccc  69780
gcggccacct ccgcctgctg ctgcttctgc ttccgctggc attgcgggga ggtcgtgtgc  69840
cgggggacgt gggggctcgt gttggagcgc ggctgccggt gaggtggggg gtgcggcgcg  69900
gcgcggctcg cgctcgtgcg ccggtggcgc gggcgcgggg ggaagcgtac gggggagggg  69960
gagtgtggcg gcggcggcgc gcggggtagg gacgggcgcc gccaccacca ccggctcgtt  70020
cgctggcagg cgctacgcgt ccagatccgt acgccggtat gcttcgtctc gccgcaactc  70080
tctccatttg attagtatcc cctcgccgaa acgaggcctg tgaggcgccc gctttctggc  70140
tggcttccct gtactcgctg cttgctcctg cctgttgggt taacccgttt ccatcgaatt  70200
tgggtaagcg aaacatcgcc tcatatgggc atttggggtt ctggcagcct taggctcgcc  70260
atccgtcgcc gagcttccaa gtgaccggcg cttgttggta tatttgcttg cttgttcctg  70320
tttggtggct gcgctaaatc ttttgtgctg cattgaattt atgccaccca tatacagcaa  70380
attactgagc tgaaataatt cggctaatta ggtccagcaa tatgacatct cgtggattga  70440
atgctaagct gacattgtat cactgatgct ggcttatata taggttgttg agaagtgaag  70500
atgtcgacag gtgaaaccct gcgtgcagag ctatcatcca ggacgccgcc tttcggtttg  70560
aggctatgga ttgtgattgg aatcagtatt tgggtggtga tcttctttat actaggtttc  70620
atgtgcctct ggtccatata ccgaaggaag ccgaagaagt cctttgataa gattccagta  70680
tctcaaatcc cggatgtttc caaggagatt gcagtagatg aagttcgtga gcatgctgtt  70740
gtcgaaaact tccgtgtgca agaaagccac gcgatatcgg tgcaggagaa acattacgag  70800
aaagattcag ggaaaatgct ggcacacttg gttaggagta aatcgagtga tgccgataat  70860
ttgagccaat gcagctcggt gtaccaatgt gatagggctg gtagctcgta ttctggtgat  70920
gaaggcagct cgggcaatgc taggaggcac ttttctcaat atgcaactgt ctcagcatcc  70980
```

cctctggttg gtctcccaga attctctcat ctgggctggg gtcattggtt tactctgaga 71040
gatttggagc atgcaacaaa tcggttttcc aaggagaatg tcattggaga gggtggatat 71100
ggggtagttt accgtggtcg actcataaat ggaactgacg tcgcaataaa gaagcttctt 71160
aataatatgt aagagatcct gaaatctatt ctgcgtttta cagaacttgt gactccttct 71220
gatgccatca tattaatttt cttttgatat ggtgctgcag gggccaggca gaaaaggagt 71280
tcagggttga agttgaggct attggccacg tcaggcataa gaatcttgtc cgccttctag 71340
gatattgtgt tgagggaatc cacaggtaaa gctatttatc aatcaccttt gctgatggat 71400
ggctagcttt tgtttctact ggcacattat ttacttgcat agggatgtag gattgctctt 71460
ggtctatgtc cacctactca ccagattatc tcaagggata ggttattcct gactgcactc 71520
cttatgctat cgattttttc ccttccaaat ctgatggtgg gattcagcat gcccagtgac 71580
agattatgct cagtccacag aaaccttctt tggaccacca ttcttttacc atgaaaatgt 71640
ggccatagct ccgaaagcta ggattcacta gaagcgcaca actgcttatt ggtttgttag 71700
ttggctataa caaggtctta ctgaaatgta cttccatagt tcattacttt gtgaatgcct 71760
gttcttgttc ttcacgtttc ttctcatgca tgttcaattc taaatttgta ttcatgatat 71820
gtccaagcta ctgtattctc caaagaaaat cagaagtcca ttcacctatg tattttccag 71880
ttttccgcca ttttggatac tgctctagaa acaagttaat aatatagata tttatatggt 71940
ttggccagtg ctgcttaagt gaccatcgag atagaaattg cttaagaaat atactaagat 72000
gttgagtgtc aggtgttttc ggataatctt gttaccaaca aataggtcct atgaatataa 72060
tggtgtctgc ttcacgtaat tcaaaatcca cactcagcca aaataatctg caatagggtg 72120
ttgaaaatat gattatgttt ctcccttgtt ttcatcatga ctacagaaat gaacaatgtt 72180
gctacatctt gtaataattt gtggttttca attgaacaaa acatccatca aatgatatct 72240
acagcaatat attttgcact tctgagcaca caataggttt gagtgtattc gagtcatggt 72300
cattgattta agctttttat ttcactacat aaccattgat ttgagtgtat ctaaggagtt 72360
ctgtttccac aagtacttta tgttaatggt gtctccttat gctttggcca tccaaactca 72420
ttactgttgt ttaatatttt tagtggttag tggtgtccaa atctttcttt gtgtacatca 72480
tactatgttt ttgtagtcta ttaaacttcc atcctatcat ctgacttgtt atattccagg 72540
atgcttgtat acgaatatgt gaataacggg aacttagaac agtggcttca tggtgccatg 72600
cgccaacatg gtgttcttac ctgggaagcc cgaatgaaag ttgttcttgg aattgctaaa 72660
gcgtaagaaa caaaccatcg tccccgtcaa aaagaaaaga attgttcttc actttagctc 72720
ttttatatgt atatgtttag ttgcataacc cattttccat aactgaattg gtatacaggc 72780
ttgcttattt acatgaagca atagagccaa aagttgtaca ccgggatatc aaatcaagca 72840
acatactaat cgatgaagaa ttcaatggca aactttctga ttttggcttg gctaagatgc 72900
tgggtgcagg gaagagccat atcacaactc gagttatggg aacttttggg tatgttgata 72960
tttttttgga gttagtatta atctttccta tgcttagctt ttactgttgg aatgtgcagt 73020
acttcgctta ttcatacagt ataaaatttt acatgctgcg aactttgtcc ttcgtatatt 73080
ataacaggta gctttctcat tgctatcatt gattcatttc aggtatgtgg cccctgagta 73140
tgccaacaca ggtctgttaa acgagaagag tgatgtctac agttttggtg tgctattact 73200
ggaagcagtg actggtagag atccagttga ttatggccgg cctgctaatg aggtgagcat 73260
atatcctaca atctcatgcg tattatgtat gttacaaaag tccgtactat tggaaattat 73320
tttacggcaa aataacgtct atactaggag agacgaattt gcttcaggtg tatggctgtc 73380

-continued

```
tggcagttgt ctactgtcta gttacccttg tctcactttt acagtctatt gttttatttt  73440
tcaggagctg actagctgta taccttgtca tatataacaa cactgtaacg tggatgcctt  73500
gcaggtgcat ctagtggagt ggctcaaaat gatggttggc acaagaagag ctgaagaggt  73560
agttgaccct gacatggagg tcaaaccgac cattcgggct cttaagcgtg ctctcctagt  73620
ggcactgagg tgcgtcgacc cagactctga gaaaagacct actatgggtc atgttgttcg  73680
gatgctcgag gcagaagatg tcccatcccg tgaggtggta acgctttctc ctttcctgca  73740
ataacattca tcatattata tcattgcaat aaatctgaag cttttgctgt aatcctactg  73800
aaggaccgga ggagccggag gggcaacact gccaatgcag ataccgagtc caagacaagc  73860
tcaagcgaat tcgagataag tggcgataga agggactcag ggccatcagc aaggtttcaa  73920
ctctaagaag acggtgatca tagtcaagaa caatggcttc aaaactctat gcagtaacat  73980
ggtggttggc agagaaaaag gggtatttct ggagggcatt gcattttgta ttgtaggtct  74040
gcatggcggt agagactgga gagagcacag tgtctgatga tggataccccg gagacctgta  74100
attcccattc agtattctgt ttgttagtca agcagcttgt acagatcgtt gtctgttcca  74160
ttttttcatt cttctggttt ttttgtttag gaggctcttg gattaccagt acgaaccgct  74220
gtctcttttc tagaatcacc aacatggaac ctatcaatat ttactactag tactacgact  74280
tgctttcttc ttgctgagat ctatcatgta ctgtacataa ctgacgtgtt cagctgcact  74340
tggacaagta gatgctcgtt ctgtatgtcg aatttacttg atgaggtcga gcattaagta  74400
ccatggctgc agccggcttc tgtttagttg tgctgacatg cggcggcgac ctcacgctgt  74460
gtggcccatt cttgatcttg ggccgaaact gtagcaacgg gcgtacggcc catctatatc  74520
gggattgttc ggcccgttgt agatgggccg gatcgggatt gcgacttacg tgcgacccat  74580
ttcggttggg ccggtggtcc gctacttcat ctagcagtgg tcggcggcag ggttcacaat  74640
tccaatagaa tccaaacatt attggattga gttaaaaaca caaaccaatc ggctttttgt  74700
caggttcaga aaattttaaa ctgaatttta attttttgac aaaaatctat ttagatttcg  74760
tctgtttttt taggtttgtc aacggattca gcgaaatccg atgatatcgc tcgtgagtgg  74820
atttttgatc cggtatcgag attgtgaacc cttgtcgcgc attgcctgac aaagacaacc  74880
agtgaagcgc cgtgcgcgcc gcgtgcgcgc cgcgtgacgc gaagatgcgc aggaaggaac  74940
aagctggcaa gcggcgcgcc catgacggcg gcggcgacga cgacccgcgc gcgtgcgtgc  75000
gtcaacgcac gcgaccggcc gagatccgtc agtggccgcg gctatatata atacatcgtc  75060
gcctcacacc ccccacacac cgagtcatcg ctcgccggag ttagagttcg tagcggcgaa  75120
ggatatagcc atatattata gatggcgatt ggtgttggtg gctgctgcgc cgtgctgctc  75180
gcggcggcgc tgctcttctc ctctccggcc accacatgta agcacgccca tcttcttctt  75240
cttcttcttt ttttctttct tttttttttt tttttggaaa tgagccgcag ctgacaaaaa  75300
gatcactcac acatggatac actgtcgtga cactaaccaa tgcctaagcc attttgtttt  75360
cttgttttgg atttttcttt ttatgtgtat cacttttgct tgttgctctt gcagatgctt  75420
atgattccct ggatccaaac ggcaacatca cgataaaatg ggatgtgatg caatggactc  75480
ctgatggcta tgctgtaagt agcggtggca gtacaccaac atctctacct ttattttcgt  75540
ctcaacctgt acatttacac tatcttgttc tactacctct aataaaaaaa tatatttgat  75600
gttttaaaat ctattaagtt ctagagatta ggaaagctac acatggtttt atgttttgat  75660
actattaagt agtatatttt ataagttata ttgaaggctg ggtttcaaa agtttgacta  75720
cactagatct tattcaaagc gtctaatgat tactgaacgg aggaagtatg aacttataga  75780
```

```
cttgaagtta aacagcatag ccacatctct tcatgtatac ttcatccgtt tcatattata  75840

agattttcta gcattatcca tattcatata tgtgcgtcta gattcattaa tatctatatg  75900

aattgggcaa tgctataaaa tcttataacc tgagaaacgg agggagtatg tcgcaaacaa  75960

caacaacaat aacaacgagc aaaatctgta tcgaatccgg tttccctctt gtaactgtat  76020

caaagatctg tcctctgaaa cgtcccctgt tcatcaggcc gttgtcacac tgtccaacta  76080

ccagcaattc cggcacatcc agccaccggg gtggcagctg gggtggacat ggcagcagaa  76140

ggaggtgatc tggtccatgt acggcgcgca ggccatcgag cagggcgact gctccatgtc  76200

caaggagggc agcaatgtcc cccacagctg caagaagcat cccaccgtcg tcgacctcct  76260

cccgggcacc ccaatcgacc tgcagatcgc caactgctgc aaggctggat cactgagcgc  76320

attcagccag gacccggcaa attctgccgc gtcgtttcag atc                    76363
```

<210> SEQ ID NO 2
<211> LENGTH: 53905
<212> TYPE: DNA
<213> ORGANISM: Orza sativa Asominori

<400> SEQUENCE: 2

```
gatcagtgag tgagagtgat gtgctattga ttttcgtcta ggattttgct gtgctcttct     60

tcttcttctc ctctctacca agaaagatcg atggaggaga atttgtagga cgcgtttctc    120

acgaattact tagctgttaa tgatcagctt gatgtgtacg atatgatggt gcagagtgaa    180

agttgtgttg ttcactggtg gatcatggga tgggaatatg ggattgttgt aagatgtaac    240

tcaagtgttt tctttttgg gattactttt ggtaataaga gcttgggtga tcgaaaacta    300

cagatggttt ttcttttaag ttgtatgatc tctgtagagt ttttgagtaa tttgtagttt    360

tgtaccctat caaagatcat ctctagctgc ctctgagctc tccaactcta tatgtccatc    420

tctagtatat atgtcccata tttctgactg aaaattttca agtcggttgg ttccctccgc    480

ctggatattc tttcagctaa ttagattttt tttaaatgat aaatttgcta aaagcttgtt    540

caaattcagc taagatctat tcaaacttca atttctctat cgaaattccc ggaaatttca    600

attcaatcat tccccaatac atgccgattt ccgtaatatt gaaccatgac atgtaaacaa    660

cgaaggaatc aagggcatat ttagtttcat ctcacatcga atatacggac acacatttga    720

agtattaaat gcactctaat aacaaaacaa attacagatt ccgccagaaa actacgagac    780

gaatctatta agcctaatta atacatcatt agcaaatgtt tactatagca ccacattgtc    840

aactcatgac gcaattaggc ttaaaagatt cgtctcgcag tttcctgacg aaccgtgtaa    900

ttattatttt ttctacgttt aatactttat gtatgtgccc aaatattcaa tgtgacaacg    960

tgaaaatttt tatttggaac taaataggcc ctaatattct ttcaagatat tagaatagtt   1020

atccctctcc acctccctgc acaaacagtg aacttctttc tccttgggca caggagtagt   1080

agcagctccc ggaaacagaa agcaatcaag caaagtcctg aacctgaagc atcctgaaac   1140

cagcagacgg cagaaaccag tgggcgcagg cgatagcagt ttttcgtggt ccggcgtaca   1200

gccaaaatac tggccatcgg gtgcctacat agaatgagtc cactggacgc agctaccacc   1260

gtgtgtgcta cactgaccgc cgctgctcgt cgaccagttg tacggggctg acttattctg   1320

aatttctaat ggtttatttg ggggtttaga acactgaggg gtgctttaga tccaaagatg   1380

tgaagtttgg gcgtgtcaca tcgggtatta tatatagtgt cgcacagggt gtttgggcac   1440

taataaaaat actaattatt gatcctatac gataagctat ataatactcg atgtgacacg   1500

ccaaaacttt acatccctga atctaaacac ccttttaaat agagtatttg gtgtgaaata   1560
```

-continued taattttgat ttgggaagaa ggtgagtgag atttggaaaa aaaaagcatt tcaattaaaa 1620
aatttgccag cagtaaataa agaaactact cggttttgta attaaagtga ggttttggca 1680
cttctttgcc ctaaactggc ctccatttta taaagtgaga accgtgcagc aaaagcctga 1740
aaaggcaaaa agaaagaaat tgtagaggtt tttcaggagg atacaactag gtgggtctct 1800
aactctctat gcagctgtgg tctgtggagc aaaacgatga aatggaagac gggacgttga 1860
cgagggtgaa gaaaacgagc gtttgaccag cgtcaaccat ggcgtgaaca gtagcaccac 1920
taacctgacc gagaggttga agaagatgca atcaacgggg tactatagtt cccacgaatt 1980
tcccagcaac aacgggttgg ttctcactac tcacgaattc cctgtggctc aacaactact 2040
agtacatcct tttgtccatt atgataaaag ttctatctta atttttattt acacgttttt 2100
caaactgttt tttaattttc tatataaaaa atacttaaaa tatcaaataa aatctatttt 2160
tggagtttta aaaaactcaa ttaatcatat atattattga cttattttat tttacgtgga 2220
ctaaaatatc ttcatcttca tttaggttat gttcttttct catcaagata catgatacat 2280
tagcatgttt ttcaaactgt tttttaattt tgtatataaa cttactctaa aatatcaaat 2340
aaaatttact tttagggttt ataaaagtaa aactcaatta atcattacta acttgtttca 2400
ttttacgtgg actaaaatat cttcatcttc atctaaggtg gtgtttggat ccaaggacta 2460
aattttaatc cctatcacat cggatatttg acactaatta gaagtattaa acatagatta 2520
atgatgaaac ccattccata accctggact aattcgcgag acgaatatat tgagcataat 2580
taatccatga ttagcctatg tgatgctgta gtaaacatgt actaattacg gattaattaa 2640
gcttaaaaaa tttatcttac gaattagctc tcatttatac aattaatttt attgttagtt 2700
tacgtttaat acttttaatt agtatacatc cgacgtaaca ctgatcgata caaacaccaa 2760
ctaaatcgaa aatcaccgaa tggctcgtca tcctcccaca tgagatgcca agatggaaca 2820
ccaacaatcc aacggctagg aagcgcccca tcccacccac cgcctaaccg ccttcctatg 2880
caagtgggtc ccaccccttc cttccttttt tttttctttt tacaaatccc cttccctttc 2940
ttggctagct agctagcttg gcccaacgcc acgagccgag ccgagcacat ccggagccaa 3000
gccgagctca gcgcctcagc tccccctcct cctcgtccca ttcccggttt cctcctccga 3060
tttcccccaa atccgcacgc ctctcccctc cgcctccatt tttcccgatt cccaattccc 3120
aaatccggat cagccgcagc cgcagcagca aaaaatttcg aaatccaaat ccaaacccat 3180
cccccccacg acgacgtcac ccacatcccc acccccgcga gacgagacga gacgactccc 3240
aaatctctct ctcctctctc ctatgcgcgc cgccgccgcc gccgcagcag cagcagctag 3300
gaggcggagc agcagcagca gcagcagctg agatgatcgt gcgcacctac ggccgcagat 3360
cccgctcctt ctccgacggg ggaggagggg agcgcggcgg cggcggtggg ttctcgtcgt 3420
cgcaagacgc gttcgaattc gacggggagg aggaggacga cctcgtcctg ctggggtcgt 3480
cgtcgcagtc gtcgcacccg cccgcgccgt cgcaggagtc gtcgtcgatg tgggacttcg 3540
acgaggaccc gccgccgccg ccccggcggc ggcgggggag gggtgggggt ggggactacg 3600
cggagcccgc cacggcggcg gcggcggcgg cggcggccac ctcgctcatg gaggcggagg 3660
agtacggcga gatgatggag agcgtggacg aggcgaactt cgcgctcgac gggctgcgcg 3720
ccaccgcgcc gaggcgggtg cgccgggcca gcttcctcgc gctgctcggg atctgcgcct 3780
ccgcgccgcg ccgccgcgtc ctccgggccc aggggtcggt acaccaaaga accctccttt 3840
tttttttctt acttgtctgc gctgtaagta aagaataaca attcgcgttc ttgctcttgc 3900
ttcgcgggca atcttggtga ggaatcttgt tagggttatg aaattgggca gccagttctt 3960

-continued

```
gtttcttctg cgtaatcttg gcggaaacag tgggattttg tacgattatg gctccgtaat   4020
cggcatttct gtgggaaatg aaccaccttt agggcatttg accttcgaac agcatgcttg   4080
gtgttgcaat ccgtagctat tgccttcatc ttaggcacaa gaacttgttc tgaattatga   4140
tttaccaact tgtgtttgtt ttcttgttct gagttttctt gcttggttag ggttagggtt   4200
atcaccgtgg tggtgcagaa ttagatgttc gctacttgtc ttaacctctg ccttgcccaa   4260
tttggtaccg agtgttacag ctgggtttag gaagtgtgat ctttgagcat ttctagcatg   4320
ttggtctctt tattttgcta atctcacatg gttgtagagg aaggaagcat agtgactgat   4380
gatgaatgcc tagatactag aaatacatct ttattaactg aattaggatt gcttgggtat   4440
ctatgtagat atgactgtag aatgttactg ctggaaatgc tatccaatat ccattgatct   4500
ctagcctaat atatctctcg aggccaagag atcagtcaat tttgaacttt caggagagtt   4560
tctatttggt acttaatctc ttttatttgt tacttttggt gcctggctct cttttcatga   4620
ttgctaagta gacaggtaaa gttctaccta aaattattct taaaagttca aaatcgcttt   4680
agattaagga gtgccagcca gagccttagg cagagtctta taaaccaaaa gcacaatgct   4740
acaatgttca caaaactttt gtggaatttc cacttgagct gtataaacat cgcaatctac   4800
tgtgaataaa agaagcactt gatggaagtt catgttagca aatgacatgt tttctgtgag   4860
gaggttgatt gcttgaactg ttatggactc ttgcaacttt ttattttact tcgtacccat   4920
ttatgctaat gtgcacaaat aaaattgctg agagtaaaaa tgtacaactt gttacgcacc   4980
agcacacttc ctatttgtat ccattttcct gttgaatttc aaatgtattc aattgctgaa   5040
attgttccat tcaacaaaca catattccgt taatgaaatt attatacatt gcgttttgtt   5100
ttcttactca caagtgtcct cttttcttat atcctataga ttggtgcaac aaattattga   5160
tgcaattttg gttttgaaca ttgatgatcc tccctgcact attggtgcag ctgctcttct   5220
attcgttttg gcaagtgatg tgagtacctc tcaatcccat ccttgtgctt ctgtgcatgc   5280
ttcattctat tttttacgca tatcgattgt tttcttttat ataacagccc ataaaaataa   5340
tcacatcatg gcaaagttat ttatttctcc agtacagtta tataagtatt caccactttt   5400
ccatgaatat cttggcatgt gattacaaag aagattattt aagaaagtcc atgcttttat   5460
ttcatcattt tgtttgaagt tgaactttaa tttatggtgt aaatttcagt taatattgct   5520
agcagctcgt attctttaat ggcataactt cacttgtgct tattctccaa tatctccctt   5580
cttgttgttc aggttcaaga aaatcatttg ttggattcag aatcttgtgt ccattttctt   5640
cttaaattat taaatcctcc agtgaatctt gttgattcca aagcaccatc gataggttcc   5700
aaacttcttg gaatcagtaa agttcaaatg cttaatggat caaataagga ttctgactgc   5760
atttcagagg aaatcctttc aaaagttgaa gagattctct taagctgtca agagatcaag   5820
tcgctcgaca aagatgacaa gaaaacaaca aggccagaac tgtgtccaaa gtggcttgct   5880
ttgttgacaa tggaaaaggc atgcttgtct gctgtttcag tggagggtaa gttttaatca   5940
aatttcttgg tcatgatttc cctttatgac cattataatt atttttatga gccaaataag   6000
cagttgccat aagttacata gcacctgttt acaatattca tgggtggttt gcttagccct   6060
ttgcttcacc tgcctttgat tgatgacttc catccgtgtt gcacaactga attggagtaa   6120
ttgactgcac tagaagcacc tatggccatt gtcatactag gaaggttttc ccttatcaaa   6180
tatttgattg ttacagagac ttctgacact gtgtccagag tcggaggaaa ttttaaagag   6240
acattaaggg agttgggcgg tcttgatagt atttttgacg ttatgatgga ttgccattca   6300
acattggagg tgagatctcg ctaacatcgc atattttaca cttcctttgt tcaactctaa   6360
```

-continued

```
aggatggtgc aagttttgtt cctttttgcc attttagctt taatgtgctt gaagccacat   6420
gaaagcaatg cttgtccaga tacatagcca aaggttgtta tattttggga catggaaaat   6480
gcttgaggta gtaactattt tcatcaggac atggaaaatt ggctgcatca caaattatgt   6540
tgtttcatgt tgcaaaatag tttttaata cttttttatt ctgcatgtgg tgttagtgtc   6600
ttacagtgat tcctctgatg attatatccc ccacgataat aatacttgac atatctacac   6660
caagtggaca ttattcattt ggatgttact tttccagcta tacttgctgt tcttgcataa   6720
actttggagt aaattgcgta tccctttaag agataaactg cttggtgctc ctatctgtgt   6780
actttttatg cccccaacta ataatgcaat catattacgc tgataaactg aataaataaa   6840
ttaacaatat acttctggtg gaaaccttgt gtatcagaat ctcataaagg atacctcaac   6900
ttcagctttg gacctaaatg aaggaacatc tttgcaaagt gccgctctcc tcttgaaatg   6960
tttgaaaata ttggaaaatg ccacatttct aagcgatgat aacaaggtaa tgttccttat   7020
atattctgtt tcagtttagt acccatttc ttcttctgta ccatcttctc ccctcatttg   7080
ttctgtgcaa aatgtgcaaa cagtgtgact ttgtatttct gcttaacatt tttcttttt   7140
tcctgaaaag cagtataaac tcttacactc attttgcttc ttgcagaccc atttgcttaa   7200
tatgagtaga aaattgtacc cgaaacgctc ctcgctttct tttgttggtg tcattatcag   7260
tattattgag ttattatcag gtatttttct taataataca atatgtccgc taacacaata   7320
aaatgtttta aacatccagt atgttaaagt tgcagtctga cgcctatttt gttttgctgc   7380
agctctttca atactgcaga attcttctgt tgtttccagc tctacatatc cgaaatcgtc   7440
taaagtctct caacagagtt gctctggtaa taacaaacac caaatttgtt tgatcaactc   7500
gttggctttt ctgtgcactg tttcaatata gtttggtcgc cattcaagtc tcactacaga   7560
tgttgaactt gacctgacac ggtggcacca atatttataa aacgctacct gatattttta   7620
atatttcatg tttcctgacc cagattatct tgttggttcc tcatataagt ttaattagtg   7680
tcgttcttga aactttgtta tgcagcagat gtcatggggg gaacttcatt taatgatgga   7740
aagcgcaaga actcgaagaa aaaaaacctt ttgtcgaacc agacacgcca tagttgctta   7800
tcttcaaaat cagaagtttc tcatattact atatcttctg gtagtgatgc tggtctgtca   7860
cagaaggcat tcaattgttc tccatctata tcaagcaatg gggcatcaag tggttcatta   7920
ggcgagagac atagcaatgg tggtgctttg aagttgaata taaaaaagga tcgtggcaat   7980
gcaaatccaa ttagaggctc aagtgggtgg atttcaataa gagcgcacag ttctgatggg   8040
aactccagag aaatggcaaa aagacgccgt ctatctgaaa atgtaatcac cgacagtggt   8100
ggcggtgatg accctttgc ttttgatgat gttgatcagg agccttcaaa ttgggaactg   8160
cttggtccaa aaaagaaatc gcctcagaaa catcaagaca aatcaggaaa tggagtgcta   8220
gttgcaagtc atgaaccaga ccaacctgaa gatcttaatc agtcgggtac aacatctctt   8280
tttagtgcta aagatgaatc cagtcttttg gaagactgcc tcttggcatc agttaaggta   8340
attaaatatg tttccttctg atctttcttg tttcttcttc aagagaatat acattcttgg   8400
gtcacagttt ctcggtttgt ctttgtgact ttgttgagtg acatattttg aattcacaaa   8460
atttcctttt caatatggct cctcaatcta tagcatctgt cgtgtatgta ttctgtacaa   8520
aatagtattg taacatctcc tagaagaaat tggcaccatc catatcatac agtagcaatt   8580
tatgagacgt gatcctgatt ggaggtttag gacagagcct cgagctaaat tgctattgta   8640
ttgtatctac tatcttttag tacatgatat gtgctgggca ctctgtgtct gagtgtagtg   8700
agtgcttaag tttacatagt tcagctaaca tgcatatgta agacagttta tgattaaatt   8760
```

```
taagtgtaga aagaaggtac tttcaaaaga tttttaagga caatataatt gtttcaccgg   8820
gactcatgct tgttctgact gtgagcctaa tgttaccttt acatgccctt acattgtcta   8880
tttttatcg ttttatgaga tcttccaaac aacttgatct gtcttaatgt tttttgcta    8940
gctcctttct tggatatctg gtaaatggtt aggccgaagt atgaactttg ccttattgtt   9000
tcaaagaaaa tgtaacaact cctggaaaag tctaattttg gttgcccttt attttgctga   9060
ccgtattggc acacatctaa ttctgctgtt cctttctggc aggttcttat gaacttagca   9120
aatgacaacc catctggttg tgaattgatt gcgtcatgtg gtggacttaa caccatggcc   9180
tccttgatca tgaagcattt cccctcattt tgttttgtcg tggacaacaa ctataacacg   9240
agagatgtca atcttgatca tgagttatca tcttctcaaa acagcaaggc acaccaggtc   9300
aaaattaagc aattgcgaga tcatgaactt gattttctgg ttgccatatt gggcttgctt   9360
gttaaccttg tagagaagga tagccttaat aggtaagtcc ctcacatgct tccttccatt   9420
tgctcaattc atatcagtgt tactgttctg gcagttcctt ggggtcagga ctcagaaaca   9480
tccaattaat gttcatgttc tcttaacgac tcagaaatac tttataacct ctccacaggg   9540
tacggctttc atctgcccgt gttcctgttg atctatctca gaatccacag agtgaagaga   9600
cacagagaga tgtcatagca ctcctctgtt ctgtattctt agcaagtcaa ggtgctagtg   9660
aagcttctgg aactatatca ccggtaattc aaaattcttc aagttccttt tgtatgtaga   9720
ttatatcttt gtaaaactcg gcatttatta cctgctcttt gtttcaaaaa gcagtatttt   9780
atttgctcc ttagcatagg tcagcagaac agttgatctt attcagaaaa caatattttg    9840
catgtaacat actgttatct atgagatgaa aattaatgca tgtgtaataa tgtcaatgat   9900
aaatatttgc tatctgaatc cagtctacca actctagtta gaccgaaatt actgaggttc   9960
tatttcaaag aataatttag tgcaccattt gttcaactac tatgaagtaa aatggtattc  10020
ccttctattg acatcgggtt agaagtgaaa ggccatctta atgcaatgtt ctcaatgcca  10080
caaacccaca aatttcatta acacatacag attattatta acatagctat aaattggatt  10140
tccagaagct tgagttgaat ttattttgtt acaattgaaa gcactgggaa cattagcatt  10200
ttttttagt tcttggttat tgcaatttat aatgttatac agaactgtgt acctcacaat   10260
gcattcatta tgacattcta tgaaccattt gattgactgt tgcttgtaaa caacaggatg  10320
atgaggagtc tttgatgcaa ggagcacggg aagctgaaat gatgatcgta gaggcctatg  10380
cagcccttct tcttgcgttt ctttcaactg aaaggtttgc aatctgtagt tgatggattg  10440
ttttattaat gtctaactac ttgcataatg tcagcactat ggcatttaac ttatactgtc  10500
tgttaactgc aacagcatga aggttcgtgg agccatttcc agctgccttc caaataacag  10560
cttaaaaatc cttgtgcctg cgctagagaa atttgtggta tgtctccata attcttgaac  10620
tactgtttgt ataaaaaagt atggatgatc tttgaattta ctccattttg gaaatcatta  10680
atttttcatg tctgaggtgt gaggtgtcac cataattgta cttcccatcc aggaagcctg  10740
tttgcaaaat ttcacataaa taaggaaaat ttgaacttgt ttcaagtttg aatagtaaca  10800
ggatgtttta tttctcaact ggagaaaaca ttccggctgg gacttttaac ccttaaaatg  10860
ctagtgtgct cccactgtaa gattgtctgc tgtcacattt gaaactttgt gtaatacctt  10920
tatcactacc cttgagatga gagacacaat ctggtaccga gttaagttat tgataactcc  10980
cagttgaagt acagcaccaa atcaagccaa catgttggct acgtaattaa atgttctctt  11040
acaacagata gaggtaaaaa gggagtttct aagtatctaa cctcttaccc tcttggctta  11100
gcactccagg cacaactctt tcttaacttg cgatttagga cttgactctg agaatattgt  11160
```

gtgcccacac tggttgagtg catgcctatc taagctgcta gtttttgttc attttgatta 11220
actctgaagc tgcctgagct tattctgctt ccatcattta ttaatccatc atgtttctct 11280
ttcagtcgtt ccatctgcag ctcaatatga tcacagagga aacgcactca gctgtcacag 11340
aagttatcga gaaatgcaaa ctttcataga aagagtgaag aggggcctgt acagatcaac 11400
taacaacctc tttgcagcaa aaaagcatac acacaagtgt ttgtcttggc ctggggctct 11460
gcagatggac tgatactctg acctgcagtg ggcttgggag ctaacaatgg tttcattctt 11520
ttttttttta tgttttcccc tgttgttttt gctcatgttt tgtgtaattt tttcttctca 11580
tctagcgatg ttatttttct tagcatgatg ggagtagccc tcctttttttt tttctctaat 11640
taagtgtaaa gtagcaacag catagggatg aatgttcagt gtagtgtgtg gtgtttcagt 11700
tattcagaga cgtccataca gtttgtacct tgtgaccaca cgtcttaatc tgatgaagct 11760
tagaataaat cacatgttag caatgcaata tcatctgcgt cttctctcac tttggtggcc 11820
atcaaattct gtgtagaagt gtatggttgg tgtgctgttg caaatgccgt attccgctct 11880
gttttgtgga agttaagaag tccctagttg aaataccgat ttttcatgat ctcggagatt 11940
gatgcaactc tgattgcagc atttcttttt attagaatgt acactccatg ctatcatgat 12000
gtttattgtt tagtactaca agatttggtt aaccattatt ttaatatcat aataatttta 12060
taaaatcttg gagtaacaag ttcataatac atgatagcat aactttttga ggctagtcta 12120
tgtatattgt ctcctttgtt tttaaactaa gcactcaata aattattgat ggctgtaatt 12180
ttctgaaggt ttcaccggtt tcggcccgtg ctttataaat agcttcggca caaaagacaa 12240
aacggtccct ccaacacata aatggttgag tttacgtttt cattatcttt ggtaaaatca 12300
agtccaccac gtagacactc ataacaaaag tttgaatatc ctcagaaatt ttgacttgag 12360
tctatcttac ctttgatatc ggacatccaa ccctccctcc ctccctgaac tttatattat 12420
tcatattaca cctgaacttt atattattca tattacaccc tgaagtggtt ttcatttaat 12480
tgcatacatg ctgaaatagt ttgacaacgt gagatgcaca aaatctacac gttcgtctta 12540
agttgcaatt cattttatcc cttttctttt tctctcttac ataggaatat caatagtact 12600
aattcacatt acaatatagt ataaattggt gatcgattat tggcaatata ctatattaaa 12660
tattcaaaac tagtcattta agctgccaaa taagtaaacc actatcgaaa accacaatat 12720
aaatggcatt acaaaactta gggggttgaa tatccaattt taaagttcat gatgctagag 12780
gaatttctat caaaagttta tgggtacata tggacttttt ccttttttaaa agaagctatt 12840
cttatcgtaa acgttaaata ttttttgtac tttatttttt atgattgaaa aaaaaactta 12900
gttttcaaaa tgattggtct gtatacaagc atcaattaga cttaataaat tcatctaaca 12960
gtttcctggc agaaactgta atttgttttt gttattagac tacgtttatt atttcaaatg 13020
tgtgtacgta tatccgatgt gacaaccaaa cccaaaaatt ttccctaact ccatgaggcc 13080
ttacagatat atttgatggg tgtaaagttt tttaagttct ttgggtgcaa agtttttaaa 13140
gtatacggac acacatttga agtattaaat atagacaaat aacaaaacat attacatatt 13200
ctgcctgtaa acaacgagac aaatttatta agcctaatta atctgtcatt agcaaacgtt 13260
tactgcagca tcacattgtc aaatcatagc gtaattaggc tcaaaaatat tcgtctcgta 13320
atttacatgc aaactgtgta attggttttt tttttcgtca acatttaata ctccatgcat 13380
gtccaaatat ttgatgcgat ctttttggcc aaattttgtt ggaatctaaa caaggatcaa 13440
atttgctgaa tttttccaga cgtcacggct tgttcatcca tcgttcgcat cgcgattcgc 13500
caccgacgcc ttggtttcca acgaatttta tcatccgctt aaatacatcc aaagctctcc 13560
atcgccatcg gcggccaacg gcgaccgctc cgctctaccc aatccaccca tccactcgcc 13620
gccgccccct gatccaaagc ctccgccgcg ccgccgtcga gaggaggagg aggaggagga 13680
ggaggaggag gaggcgtgag cccctatggg gaccctcctc cggccgcgtc cgctcgccca 13740
cgccgccggc gccggcgacg ccacgccgtc gaccgcgcac ggtagccacg cgcctctcga 13800
gaggcccccc ccccgccgct cgctgatctc tcttctcatc ctgtttgggt ttgggtttgt 13860
gatttgggtg ttttttttt tccgcagcgg tggtggtgag cggtggccgc ggccgtggcg 13920
tggagtgcca gccgcatcgg gtgcgccgcc gcccgggtcc gcaggttgcg gtggcgacgg 13980
cgagctggag gaggcggagg gagaccgtgg tgagatcgga tttcgccgct ggtggtgccg 14040
ctaccatggg ggattcgccg caggcgctct caggtttgca gcctcctcca ctctcttctc 14100
gcaaaatgtg ttgctatgtt cctctcgctg ggctggcctc atagccatta atgtagtttg 14160
ctggaacatt acattcggaa cgttgttggc aattgcttga caaaatgtgg aattgtggag 14220
gggagaaaaa tcgtttgaac ctgcagtgac aaaattgcca tctataattt taaaactgaa 14280
ggtgtggaaa tcaaacataa tcattgccag cacatcattc ttgttaacca ccttgacata 14340
ttgttggctt ataacagtta gctccacacc aacttggaag gtgtcaatgg aatgtaagta 14400
taaattgagg ataactggca gttgttaaga ctttctacag aacttgtagc agctaaaact 14460
agctattgtg catttatgtt tcatggaatt tgagcggcaa tggatatttc ttactaagac 14520
gtataatgca aaacaaaaaa aaaaaaaact atgtctatgc agtttacatg taatgtgcgg 14580
atgcaaataa aatcatgttc atggacaaac taatgggatt cataccaaat tccagaattg 14640
catttcttat gtggttactt ttgtttgttg atttggttac cagacatcga tgtggtttca 14700
agggtcagag gggtttgctt ctacgcggtg actgcagttg cagcaatctt tttgtttgtc 14760
gccatggttg tggttcatcc acttgtgctc ctatttgacc gataccggag gagagctcag 14820
cactacattg caaagatttg ggcaactctg acaatttcca tgttctacaa gcttgacgtc 14880
gagggaatgg agaacctgcc accgaatagt agccctgctg tctatgttgc gaaccatcag 14940
agtttcttgg atatctatac ccttctaact ctaggaaggt gtttcaagtt tataagcaag 15000
acaagtatat ttatgttccc aattattgga tgggcaatgt atctcttagg agtaattcct 15060
ttgcggcgta tggacagcag gagccagctg gtatggctgt agtctcatcc ctgctttctt 15120
aagtagacat atatacattt acagtatttg gtaaataaac aagattttat gaatcatata 15180
tgattttggg gaaaacacaa aactctcttt gttggctgcc ttgaacatag ttctgttcac 15240
acagttatag caccttcttt aaaatgaaga actttgttgc atacacataa ggccaaacca 15300
cataatgaat tttgtttatt tctatctttg aatgttagca tcgtttttgt ttaatgcatg 15360
atcgccttcc tatatatttg tagtatgtca acattgtatt ccatgctgag cataacaaat 15420
ggtttgttaa aattcaggac tgtcttaaac ggtgtgtgga tttggtgaaa aaaggagcat 15480
ctgtattttt ctttccagag gggactagaa gcaaagatgg aaagctaggt gcatttaagg 15540
ttcagtaacc aaacttaggt tacattacat ctaatgagat ttttatattc agtatataat 15600
gttaaccttc tcatggtgta ctgacgtggt tataaatgtc cccagagagg tgcattcagt 15660
gtggctacaa agaccggtgc tcctgtgata cctattactc ttctcgggac agggaaactg 15720
atgccttctg gaatggaagg catccttaat tcaggttcag taaagctcat tattcaccat 15780
ccaattgaag ggaatgatgc tgagaaatta tgttctgaag caaggaaggt gatagctgac 15840
actcttattc taaacggtta tggagtgcac taaagaaaga tggtgttttt ttttattata 15900
tggaacctat tcaaaggcac agacaggctt tcaaggctaa gcttgttaca ggtactgata 15960

```
ctagttacta attactttcg taatcagtat aaataagctt gtgtagtgta atggcattgt  16020
acatttctgc acttggtaaa tttacagaag aggcaagtaa tattttagag gattgagttt  16080
attcacccag tcatatagtt gaagaggcaa gtaacctgta agagaggact gaacattaac  16140
acctcttgtt cgattaaaaa tgaccaaaga gcatcaaaca tgtattcgag gctgttactt  16200
tagatatggc ccattaattt gtttagttgt ctatgtacat cctagttggt gtaaatgcca  16260
gttaccattt ctatgatcta aaacaatcaa ctcttttagt atattttcaa aaacgaaaat  16320
tcagtacaca tgtatgaatc ttaatattct tctctagctc gttacaaaag caacaaaggc  16380
accgtgtcag ctggttcaca ttagctagtt tgtacttagc attatccact agcaccttat  16440
tttcatgcat atcatgctaa tttgcttgcc cacgttgagt gggaattttt ttcatgtttt  16500
ataatttata tatgttttag acttctagtc cacaatttat gtacttcatg ttcctgagcc  16560
tctagtatgg ctgatagcag actaggtgct gagtgctgtc ctttttgca gactgaagag  16620
agaagaaata caagactgtc cattgttagt cagatttgta aaaatagact ctgatgtagt  16680
ttacttttgc ccctatttta tttttaacaa tacaaatata taacagatcc taagaactta  16740
tcttaattta ggagaagttg ctcgtttcat taaattaaat tgtgaagtaa aaatgtgtgc  16800
tcgagtctgt caatgcaatc ctgtgttctt gtttgaagat atggtgtagg gcaggccagg  16860
attgaacact gaatggtaag actgcttctg ccttcagacg ttattgctaa atttttagct  16920
acttgcagtt agtgctgcca cgccgattaa gcagtagaac aaagtagttt tgtcgtgcac  16980
aaatgagtta tatttcattg gaaatcgaag cgaaaacgaa tcaaaagtta gaagaaaagg  17040
ggaaacttgg taattactcc ataaagagag tgcattttat tggtaagatg gtatccggaa  17100
gctgtgagct ccgggctgta tgtattctgg caaatttgat atgagatgct cgattattgg  17160
cttaagttag cgatatcaaa tttggggaag caccaaagga attattgtga aggagttatg  17220
ggtgcgtgac gttatctgct aggttcaaat ccttgtggct atgaatattt atctgctagg  17280
ttcaaatcct agtgactatg aatattaatg ggtaaggtaa gggatttatt gttaatttta  17340
gtttctttaa gattgtgcca tcggacgcca ttcggtaact gtaataatgc tttgtattgg  17400
attcacttgt gttacatgca cgcactaaac atgtgcttta ccttttcatc tgtttttgcg  17460
ttctgggcta gaaactcaaa cgttgaattt tccatggtct gctcaacttg acaattactg  17520
cgtgtcaagc gatcttatac gcatactatg cgcacaagtg attgtatacg gatatgatga  17580
cagtataacg tgtgatattg atttttttaa taaaaaaatg atgttccttt ccttgatgaa  17640
ggaacaaaga ctttttttaa aagaagggta ttactaaaaa caaaaatgac aaaaacaaaa  17700
tatcagtgca catggcaagt gtgctcggca atttttctc tgtactttaa acaaaaatac  17760
ttctatatgt tctttttat aagggtggca caaatctttt aaatgagcca aatatctaca  17820
ttggatttat taaaaactgt ataaattata atttatactc tgaaaggttg tgtgcatctc  17880
tcttggagaa aatgtataag ttgcaaacaa acattaatcc acgttatgta actttttttc  17940
gccggaaagg ccgaaggagg cctgacggag cgtggggctc ctcaccggga gaccgcgcag  18000
gccccccttt gccggttcgg ccggggactc agggtgaaat tctaagctct ctgtatgtgg  18060
aaggttcgcg accgtcgaaa gagcataaga cacgggcgat gtatacaggt tcgggccgct  18120
gagaagcgta ataccctact cctgtgtttt ggggggatct gtgtatgaag gagctacaaa  18180
gtatgagcca gcctctccct tgttctgggt tccgaatctg gaaaagtcca gtccagtccc  18240
cccctctaag tgggcaaggt cctcctttta tatcttaagg ggataccaca tgcaccatct  18300
ccctcctttc tgtggggact taccctacct tttcataaat ggacggagat ttgtatagtt  18360
```

-continued

```
gccgtccgaa tgaccttctg ataggacggc ccatacctac ctccacttcc gccgaaagca  18420
ggtgcgacgt gggattatgg ctgtctgctg acgacatgac cagtgtcaga ctggtcacaa  18480
attgctcatt cctgtccacc acgcgtcagt ttagcaatct acatgttggc ccttcttcac  18540
acaacatctt gcctgtaatg gttaggatga agcctggcat atatctaacc aggactaacg  18600
tgccatctct aggaggtaac acgctagctc cagctgggga cgagcgccta gaagccctcg  18660
tcctgacggg atggggcgag gcgtgcgtca gatcgcctgt cgccacctaa cccgcgatct  18720
gaccggtctg tgactggtca cagaccggat aaacgagtgc actgcacttc gttacatgcc  18780
gcgtgacacg ctcagccaaa ccgcaataaa tgtggttagg tgagccccgc tgtgctcacc  18840
taacccatac acgcggagca aaaacccacg aggggtcggg gcgcctcggc cctcggggcc  18900
gaggcgggtg cggtccgacc ccctcggggg gactaagagg agggcgaaca catcaccctc  18960
gggcccgacg tcccccgagg gtgccaggcc acgtgggcga ttgtgtctgc ctcaaacctc  19020
tagtcatgat actcctgatc ccatgtcacc gacagtagcc cccggcgtta tgccagggcg  19080
atcgccctct ttaagggaag cggtcgggcg tgacgccact cctaaggcct ggtgacaggt  19140
gggaccggtc tccacaattg ggcagaaacc caacggtcac aaatcacgca catcggcaat  19200
ggtaactcta ctatcaataa tgagcggtct cttcaagact gccacattac tcgagtagca  19260
cacgaatctg gacatggcga ttcgtttcgt ctggagatat ggtaacgtcg ctttggtcgg  19320
cgagcgtaat taacgcgcgc acgatatgat ctatctcgac tgccacaacc gcatatccac  19380
ctcatgcgcc gcaagcgggc gaatgggatt agtggaagcg tgggcgcgag aaacgagggg  19440
gcgaaatagt gggcgcgaga agcgaggagc cgggcacagc gttggcaaga gtataaaggc  19500
actgaggaaa ggatctgttt ccttcctttc gccatcattt cccttgtctt cgccgcttgc  19560
gccctaactc cttctttcct gtgctctact ttcgccacac gcgctcgctc tcaatcttct  19620
cttcctccgg cgccatggca cggggctccg ctctgctcga tggtagcgtg ctgccgcctt  19680
cccgcatcgt gagcgagagg caggctgggc tgccgcgccg cttcatgccg gaatctgcca  19740
ccggccggga gatagtcacg ctgggtgagg gacgcccggc gccagactac ccggggcggt  19800
ccgtcttctt tctccccttt gcaatggcag ggctggttcc gccattttct tctttcttca  19860
tggatgttct gaagttctac gatctccaga tggcgcacct cacccccaac gcggtgatga  19920
cattggccat cttcgcgcat ctgtgcgaga tgttcattgg ggtgcgccca tctcttcggc  19980
tgttccggtg gttcttcacc gtgcagtcgg tgtcgccgcc atcggtagtt ggtggctgct  20040
acttccagcc atgggggccg gtgctgaatc gctacatccc ctgcgccctc cgcaagaagt  20100
gggacgactg gaagagcgac tggttctaca ccccccctcgc cgacgaagcg cgcctctgac  20160
ttccgagcca gcccccggcg caggcctcca gctggcgggc gccggtagat ctgggggatg  20220
gctatgacgc cgtcctcgac cgcctggcgg gcctacgatc ccaggggctc acaggggcca  20280
tggtgtacgg cgactacctc cgtcgtcgga ttgcgccgct ccagcggcgc gctcggggcg  20340
cctgggagta caccgggtcc gaagactaca tgaggaccca ccagggagtc agatgggact  20400
gggctcctga ggatttcaag atagtggtcc aacgggtgct gaatctcaac tccatggagg  20460
cgtccctcat tccccaagga atcctccctc tctgcagcga tccagaccgc gcctccatcc  20520
tgaccattat gacggcggtc ggggcctcag aggagtgagc tccaaagggc cacgacggcg  20580
caggcgggag ccgtaggggg gatcaatcta ccccgggagg gggtcgtgct tctgggtctc  20640
gcgacggagg cccgaggagc agccgccctg ccgacgcccg ggggaagagg aagcagggag  20700
gaacacctcc cccatctcct ccccgagggg gcggggcggt gcgtgccaac agcaggcgcc  20760
```

-continued cggagggggc cgcgccgaca tcgcagcccg agggggagcg caagaagaag cggctccgca 20820
agatggggga gacagaacca tctcggggaa accttatttc ccctccaaag tggtcgttta 20880
accgaccccc tcgcaggttc gtctctcacc catcgtggct gtattcattc tctcaacgcg 20940
agttttcact cacccatctt gttcgtcttc tggtcttttc ttctgtttca gcgagatccc 21000
gtcgcgtccc tcccgccatt ccaagtccgg ccagtctgag gccgaggatc cggcggccgc 21060
agaggcccgg aggcgggaat ctgaccggcg agaggccgcg gatcgcctac gggaagccga 21120
ggaggccgcc caggaggccg cccgggctcg ccagggcgag gaaaccgctc gggaggaggc 21180
cgcccgggcc cgccaggccg aggaagccgc tcgggaggag gccgcccgag cccaccaggc 21240
cgaggaagcc gctcgggaga aagccggatt tcgccaggac gaggcaatgg cgacttccga 21300
ggcagctcgc gatgaggtcg cgggcgcgtc gcttgagccc gcttcctcgg gcgacgctca 21360
ggcgacaact tccggggcag ctggcgacga ggctgcgggc gcgtcgcttg ggcccactcc 21420
ctcaggcgac gcccaggacc aaccaggtct gagggacatc cccgagtccg gcacttccat 21480
cggcggcccg agccgcgtgg catcctctcc aaggcggctc ttccccacgc cttctatcgc 21540
cccgctgagc gcagagcccc ttctgcaggc cttggccgcc gcaaacatcg cggtgttgga 21600
cgggcttagt gcccaggtgg aggccctgca agcagagtgg gcggagctcg acgccgcgtg 21660
ggcgcgtgtc gaggaggggc ggcgctcagt ggaggccatg gtggaggtgg gccgcaaggc 21720
acaccgccgg catgtctcgg agcttgaagc ccgtaagaag gtgttggcgg aaatcgccaa 21780
ggaagtggag gaggagcggg gggctgccct cattgccacc agcgtgatga acgaggcgca 21840
ggacaccctc cgccttcaat acgggagctg ggaggcggag ctagggaaaa agctcgacgc 21900
cgcccagggg gtgcttgacg ttgccgctgc ccgagaacag cgggcggggg agaccgaagc 21960
ggcgtcccga cggcgcgaag agacccttga ggcgcgcgcc atggcgctgg aagagcgcgc 22020
ctgcgtcgtg gagagggatc tggcggaccg cgaggccgcc gtcactatcc gggaggcaac 22080
actggcggcg cacgagtccg cctgtgccga agaggagtcc gcactccgcc tccacgagga 22140
cgcgctcacc gagcgggagc gagctctcga ggaggccgag gccgcggcgc aacggctggc 22200
ggacagcctg tccctccgcg aggcagcgca ggaggagcag gcgcgccgca ctctggaatg 22260
tgtccgcgcc gagaggaccg cactaaacca gcgggccgct gacctcgagg cgcgggagaa 22320
ggagctggac gcgagggcgc gcagcggcgg ggcggctgcg ggcgaaaacg acttagccgc 22380
ccgcctcgct gctgccgaac ataccatcgc cgatctgcag ggcacgctaa actcgtccgc 22440
cggggaggtc gaggccctcc gcttggcagg cgaggtaggg cccggcatgc tttgggacgc 22500
cgtctcccgc ctagatcgcg ccggtcggca ggtgggcctc tggagagggc ggaccgtaaa 22560
gtacgccgcc aaccatggag gcctcgccca gcgcctctcg aagatggccg gggctctcca 22620
acggctcccc gaggagctcg agaagacaat taagtcatcc tcgagggacc tcgcccaagg 22680
agcggtggag ctcgtactgg cgagttacca ggccagggac cccaatttct ctccatggat 22740
ggcgctggat gagttccctc ctgggaccga ggacagcgcg cgcgcaggtc cgggatgccg 22800
ccgaccatat cgtccacagc ttcgagggct cagcccctcg gctcgcgttc gcccccaact 22860
ccgacgagga ggacaatgcc ggtggtgcag acgacagtga cgatgaggcc ggcgacccgg 22920
gcgtatcgga ttgatccccc aagcccccgc cattcttcag ttttttcttc ttttccttct 22980
tctaaggcct tcgggcctct tttttgtata gatcaactta atctgtaatc aaaaatgaag 23040
aaatttttgt gtcaatttca tcttgctgtg tgtatgagat gaggatgatc tgtgacgtgg 23100
tccttttgcg tcttagcttg attaagggct cgtgcccagg tcccagtcct caaaaggcgt 23160
gggtcggggc tagtgcctgg ggagatccac atgtcgagac tggccaggcc gggaacgtgg 23220
tgaccgaggg ttatgggtga cccgattgtg ggtttttgcc gattcccccc cggagttcac 23280
cacgccccgg ggcacggctc ggttctgggc cccgtttggc gattttagcc gacccgagcc 23340
cccgagggca ggattgagca cgagtgacct atttcaagtc aagattcttc aaaaggaaaa 23400
aaaaacacag atacagcctt taggaaattg aaactgcttt tattgaaata ctgaaataag 23460
agaaataaga atgtgcatgt gtggcagccc ccggccaacc ctgcacgccc gagggggtgc 23520
ggggttggcc cgagcccgaa acctgacacc cgacccccc cctcaggggt agaagcgacg 23580
aaggtgttcg atgttccacg ggttaggcag ctcaatgccg tcgcccgtgg ccagccgtat 23640
ggagcccggc cgggggacgc cgaccactcg atacggaccc tcccacattg gtgagagctt 23700
gctcaatcca gcacgcgttt ggacgcggcg taggacgagg tcgtcgacgc agagtgatcg 23760
ggcccggacg tgacgctgat ggtagcgccg caggctctgc tggtagcgcg cggctctgag 23820
ggccgcgcgt cgccttcgct cttccaagta gtcgaggtca tctctgcgaa gctgatcttg 23880
atcagcctcg cagtacatgg tggcccgagg agacctcagg gtgagctcgg atgggagaac 23940
cgcttccgcg ccgtagacga ggaagaaagg cgtttccccg gttgctcggc ttggtgtagt 24000
tcggtttgcc cagagcaccg ctggcaactc ctcgatccat gaatcgccgt gcttcttgag 24060
tatgttgaag gtcttggttt taaggccttt gaggatttct gaattggcgc gctccacttg 24120
gccattgctt ctggggtggg caggtgaggc gaagcagagc ttgatgccca tgtcttcgca 24180
gtagtcgccg aagagttcac tagtgaattg ggtgccatta tccgtaataa tacggttagg 24240
cactccaaac cgggccgtga tgcccttaat gaatttaagt gcggagtgct tatcgatctt 24300
gacgaccgga taagcctcgg gccacttagt gaacttgtcg atcgcgacat acagatactc 24360
aaacccgccc ggggcccgcc taaacggtcc caggatatcg agcccccaga cagcaaatgg 24420
ccacgaaagt ggtatggtct gcagggcctg ggccggctga tggatttgct tggcgtggaa 24480
ttgacacgct ctacatcgcc ggaccaggtc gaccgcatca ttgagagctg tcggccaata 24540
gaaaccctgg cgaaaagctt taccaaccaa ggtgcgcgag gcggagtggg ctccgcattc 24600
gccttcatgg atatcggcaa gaagcacaac gccttgttcc cgaggaatgc acttcaggag 24660
gattccatta gccgcgcgcc gatagagggt cccttctacc agcacgtagc gtttggagat 24720
gcgatggacg cgttcactcc cttcgcggtc ctcgggtaaa gtcttatctg tgaggtatgc 24780
ttggatctcg gcaatccaag caatcaatct aagggagctg ggagcgctcc cctcgggtcc 24840
cgaggcctgg acttcaacgg gcctcggggg ccggtcaggc gcgtccgtct cccctaaggg 24900
gtcgggtcgc gccgacggct gggcaagcct ttcttcaaag gcgcccggtg gggtctgggc 24960
tcgcgtggac gcgagccgtg agagttcgtc ggcaatcatg ttatcccgtc tgggcacatg 25020
ccgaagctca atcccgtcaa aatggcgctc catacgccgt acttggcgca cgtaggcgtc 25080
catctgcggg tcagagcacc ggtactcctt acagacttgg ttaacgacca gctgggagtc 25140
gcctaacacc aggaggcggc ggatccccag tccagctgcc actctgagtc cggcaaggag 25200
tccctcgtac tctgccatat tgttggtcgc tcgaaagtcg aggcggacca agtatctgag 25260
gacgtctccg ctcggagagg tcaacgtgac ccccgcaccg gcgccctgaa gagacaggga 25320
gccgtcgaac tgcattaccc agtgggcggt gtgaggcagc tgcgaggggt ccgtgctggc 25380
ctcggggatt gagacgggct cgggagccgg ggtccactct gccacaaaat cggcgagagc 25440
ctggctcttg atagcgtggc gtggttcaaa gtgcaaatcg aactcagaaa gttcgattgc 25500
ccatttcacc acccgtcctg taccgtctcg attatgcaag atttgaccga gggggtaaga 25560
cgtaaccaca gtgacccgat gcgcctggaa ataatggcgc agtttcctcg aggccatcag 25620
aatagcgtaa agcatcttct gggcctgagg gtatcgggtt ttggcgtccc ggagggcctc 25680
actaacaaag tagacgggcc gctgcacctt tcggtggggc cgatcctctt cgctaggggc 25740
cgcatccctg gggcactctt cgtccaagca gcctcgcggg gcgcacttgt cttctgtgct 25800
gatgacctcg gggtcggagg ataacagggg cggccttccc acagtggctt tggggccgtc 25860
ctgggggtca ggggctcctg gcgtcgtcgg acaagcgggc aaagggccaa ctccggtcgt 25920
caggggcctt aggcctccgt tcggctcggg ggcctcttct ccctgctctt tcccgggtcg 25980
agtcagcaca gggttagcct cggggtcaaa gggcgatagg tgcggccttc ccacagtggc 26040
ctcagggcct tcctgggggt cgggggctcc tagcaccgtc tgacaagcgg gcagagggcc 26100
aactccggtc gtcgggggcc tcgggccacc gttcggctcg gggcctctc ctccctgctc 26160
tctcccgggc caagtcggca cagggtgggg aagcgcgaaa tgagaattgt cctcatcgcg 26220
ctccacaacc aatgccgcac taactacttg cggggtcgcc gctaagtaga gtagcaaggg 26280
ctcgtctggc tccggggcga ccagaactgg gggagagctt agatacgcct tcaactgggt 26340
gagggcattt tcagcttcct tcgtccaggt aaacggtccg gagcgtttga gaagcttaaa 26400
taagggtaac gccttctctc ccagcctcga tatgaaccga cttagggcgg ccatgcaacc 26460
ggtgacgtat tgcacatccc taagtttgct gggggggcgc atccgctcta tagcccgtat 26520
cttctcgggg ttggcctcaa tgccccgggc agagaccaag aacccgagaa gcttgcccgc 26580
aggtacaccg aacacacact tatcggggtt taattttatg cgggcggagc ggagactctc 26640
aaaagtttcc gctagatcta tgagtaacgt ttcctggttg cgcgtcttta caaccaagtc 26700
atcgacataa gcttcaatat tacgtcctaa ttggctaccc aaagaaattc gagtagtacg 26760
ttgaaaagta ggacctgcat tctttaaccc gaagggcatt gtcgtataac aataggttcc 26820
tatgggggta atgaacgcag ttttttcctc atcctcccta gccatgcgaa tctgatggta 26880
accagagtat gcatctagaa aacacaaaag gtcgcacccc gcagtggagt cgacaatctg 26940
atctatgcga ggcagggggt aaggatcctt aggacatgcc ttgttaaggt cggtgtagtc 27000
gatgcacatc cgaagcttgc cgttcgcctt gggaacgacc accgggttcg ctagccactc 27060
ggcggggttg acgctgccat catatttttc ggcgatggtg ggccggaacc ttgggggcca 27120
acggacattc cgaagactcg ccacaaaggc tctacagccg acaccaccaa ccgggggcac 27180
ggagggctga ttcccgcgtc cgtgttgagg tgacactctg gacgaggaag cgccctccgt 27240
tgcgtgggca gcacttcggt cattacgccg gcgctcgatg ctggtgcggg cgtccggccc 27300
cccacgcaga tctttctggg tcgaaggagt cgacgaagga gtggcggccg aatggcgaac 27360
agcggctgcc gctcgtcgtg ccctccgtct tgacgacgcg gagccggtgg tagcagcacc 27420
agaggccttg gtggcggagg accgcccacc agcatctagg cgctgccgta ccgtcatgac 27480
taatttggcc acgtcgtcca gccatcgttg ggctggagac tccgggtcag ggacgacagg 27540
cgggtgacgt aagagcgcgc ccgcagcttg gagcgcgccc tggggcgtgc tgccgtcgcc 27600
gtagacgagg aggcgacgct ccccatctcg ccgttcttct ccatcgcccg cgatcggtga 27660
agtcgcggat ctttcgaccc tctcgagcgc ctccccccgc ttaggacttt ggcgtggagg 27720
gagcggtgga gtacgagctc gacggcgtgg gttcggctcc ccgtcgtcgc cactcacact 27780
cggagagagg tcgtgcgcct ttgcttgctc ggccatcagg ctgaacagga aaagcttggc 27840
gcacacggaa gagtacgaga gctcagaaaa acacacactg agtcccctac ctggcgcgcc 27900
agatgacgga gcgtggggct cctcaccggg agaccgcgca ggcccccctt tgccggttcg 27960
gccggggact cagggtgaaa ttctaagctc tctgtatgtg gaaggttcgc gaccgtcgaa 28020
agagcataag acacgggcga tgtatacagg ttcgggccgc tgagaagcgt aataccctac 28080
tcctgtgttt tggggggatc tgtgtatgaa ggagctacaa agtatgagcc agcctctccc 28140
ttgttctggg ttccgaatct ggaaaagtcc agtccagtcc ccccctctaa gtgggcaagg 28200
tcctcctttt atatcttaag gggataccac atgcaccatc tccctccttt ctgtggggac 28260
ttaccctacc ttttcataaa tggacggaga tttgtatagt tgccgtccga atgaccttct 28320
gataggacgg cccataccta cctccacttc cgccgaaagc aggtgcgacg tgggattatg 28380
gctgtctgct gacgacatga ccagtgtcag actggtcaca aattgctcat tcctgtccac 28440
cacgcgtcag tttagcaatc tacatgttgg cccttcttca cacaacatct tgcctgtaat 28500
ggttaggatg aagcctggca tatatctaac caggactaac gtgccatctc taggaggtaa 28560
cacgctagct ccagctgggg acgagcgcct agaagccctc gtcctgacgg gatggggcga 28620
ggcgtgcgtc agatcgcctg tcgccaccta acccgcgatc tgaccggtct gtgactggtc 28680
acagaccgga taaacgagtg cactgcactt cgttacatgc ggcgtgacac gctcagccaa 28740
accgcaataa atgtggttag gtgagccccg ctgtgctcac ctaacccata cacgcggagc 28800
aaaaacccac gaggggtcgg ggcgcctcgg ccctcggggc cgaggcgggt gcggtccgac 28860
cccctcgggg ggactaagag gagggcgaac acatcaccct cgggcccgac gtcccccgag 28920
ggtgccaggc cacgtgggcg attgtgtctg cctcaaacct ctagtcatga tactcctgat 28980
cccatgtcat cgacaaggcc atccgaatgt attaaggagt aaaagttaca agaaaaaaca 29040
ccacaatgca ccaaggtgca tgaccacaca ccatacacta cccccaagca caaaccactg 29100
agggtgaagc ctagcaccaa acgaccgcca ctaagtgtga ccaaacgccg ctaggcctac 29160
ggcagcaaca catagatgag acttcgaaaa cgatgccacc aaggtggtca cgacatgtag 29220
gatgctgcca tcgtccatct aaaaagatgt ggttttcacc cagagaaact catcaagaag 29280
gggagagggt aacccttgac agcgccccaa ggaggttacg acgcccgaag gcgtagccgc 29340
tgccggtccg gtgaaccacc ggactaggct tccgcctagg accctatagc cttgatcgca 29400
gatcaccgtc caccactcag aaccaccaca cagacaaaag gtagcacgta gcttccaccg 29460
caccgcaccg acgccccttc gtcggccgac tccatcgaac caccatccct gagagctggc 29520
ccaggacccc tccgttccac cacccgccgg ccgccttgcc agttttggcc aaaggagaac 29580
ccgggactgg gtgacattgc ttcggcagcc tgagcttccc ccgctggcga gctgctgtct 29640
caatccaacc tagaaactcc ccgcaaaaga aggggatgag ctctaggaag ggcgagggtg 29700
ccgaccggca acgaggaaga caacccatcg actccagctc cctttgcact accatctggg 29760
cctgcgccaa tgccggatac gctgtcgctc cggctccggc gccacccacc tgcacccccct 29820
ttgcctggtc tccgcgcccc tcctggctgc gtcgcgccgc ccagctggcc gctaagggca 29880
ccacgacggc cgcccggcta ccgaggcctg gccgcgccat gggacagctc gcgctggcac 29940
cagcgagcca cggccgtcgc gctgttgccg gcgccagcga gcacaaccgc cagctccaag 30000
ggccgagcat gccactgagc cgccgccgct gccgcccggg ccggctgcac gtcaccggcg 30060
cacacgaccg cacgccgcca cgctccgcct ccgcgcccga ggcagcccca tgccattgcc 30120
gcgcacctcg cccgcccgct gccgagccgc caccgcgcac cttgctgagc cgccaccgcc 30180
gtccctagcc gcctcgtgcc gccgccacgc cagatccagg cgcgggatgg ccggatccgg 30240
ccttgggggc gccggatccg ccgcctcccc acaccgccac ggcgtcacca cctccgaccg 30300
cagtgagggc ttcgtcgttt gccccatcct catcgcgtcg aggaggaaga cgccaagaaa 30360
aaagggcctc gccgctgcct tccttgctcg ctgccggctt cgccgccggc gagctccggc 30420
ggcggcgagg tgggggagaa gaagtgggga gtgggcagct agggtttttt cgccccccaa 30480
gccgcccgtg cgagagcgac ggtggggggg gggggacttt ccaacctctt ccagtgttct 30540
agttctccac gttatgtaac tcaatttgtt taaccataga aagtaagaaa cctaccagcg 30600
tgttaagctc tctttcattc cctttcttct tcctggtttt gcttccatca catgtcaagt 30660
gaagggttct taactaccat tactcctaca catctaattt ttttctcaga tctttcgcag 30720
gtatatattg atgctacatt ttatgatctt aagataatct ccttcacatt accctctgct 30780
gaaactttag cttgaaccgt catcttcacc acaatttgag cccaatttgc acagagcaca 30840
acgagcaata gcttgccctt acgttcatta tttagcatga actactacta actacccaag 30900
aatcaataca ccggtttaat aacgccattt tatcacgtta atatatgttt cattcaacac 30960
accggttttg gcacagttgc aaacttgcaa taaattcttt cctacttctc catcccataa 31020
tataacaaat tggtatgtct cgtctggtac taagttgcta tattatgaga tggagggagc 31080
acttcttttc ttccaaaata taagaatata gtattggatt agatattatc tagattcacg 31140
aattcgatta ggttgtctag atttatagtt gtatgtaatg tataattcgg taataggtta 31200
ttacctctcg ggatggaggg agtagttttg actttttttt ttcttataaa tcgctttgat 31260
ttttatatta gtcaaatttt atcgagttta actaagttta tagaaaaaaa ttagcaacat 31320
ttaagcacca cactagtttc attaaattta gcatggaata tattttgata atatatttgt 31380
tctgtgttaa aaatgctgct atatttttct ataaacgtag tcaaatttaa ataagttaga 31440
ctaaaaaaaa tcaaaacgac ttataaatatg aaatggagga agtagtagac tataacaaat 31500
ttaaaccgtg ctttgatttt agagcatcac taatatgtta gcaataatct atccctaaaa 31560
tttatttttt ttcctaaact gaaaatagga agtggaaata ctcctccatc taagagagag 31620
cctaaattca ataaaaaact aaaaaactaa aggtggatcc ctctattaaa ctaccgcaaa 31680
aaatttatgt ttttttctc ttccacgcgc gcagaacaga tatctcgatc aagttagcat 31740
gtaaaatttt taaagagata ccttatacga ctccttccgt atttccaaaa gcaaacggat 31800
ttaaaatctg actcaaataa agatctatat atccaattta catgacacat gtttcgccga 31860
atttttatat taataataat taatattttt aaaattaaat tattagcaat ttgtttggag 31920
gatttatcaa aacaggatgg acgttgttta taacagcgtc tagacctaga cgcgcttgca 31980
aactgcggcc accctttat cacacaaatt tttgacaatt tgacactttc caaaaattaa 32040
ttttataaat taaccgtgac caaaacttat ttaaaaataa tctttttgtt gagcgcaaaa 32100
tcgtatactt cagcgccaaa tagcacggcg ccgacctccc ccttcccctc ccctctatcc 32160
tccactgctg ccgcccacct ctccgtatca gctgcgtcgc gttggtttcc gccggcgctg 32220
ctgctgctgc accagtccgc tagggcgggc gggcatggcg cgccgcgccg cttcccgcgt 32280
ccgcgccggc gctgttggcg cccttcgctc ggagggctcg acccaagggc gagggggccg 32340
cacggggggc agtggcgccg aggacgcacg ccacgtgttc gacgaattgc tccggcgtgg 32400
caggggcgcc tcgatctacg gcttgaactg cgccctcgcc gacgtcgcgc gtcacagccc 32460
cgcggccgcc gtgtcccgct acaaccgcat ggcccgagcc ggcgccgacg aggtaactcc 32520
caacttgtgc acctacggca ttctcatcgg ttcctgctgc tgcgcgggcc gcttggacct 32580
cggtttcgcg gccttgggca atgtcattaa gaagggattt agagtggacg ccatcgcctt 32640
cactcctctg ctcaagggcc tctgtgctga caagaggacg agcgacgcaa tggacatagt 32700
gctccgcaga atgacccagc ttggctgcat accaaatgtc ttctcctaca atattcttct 32760
caaggggctg tgtgatgaga acagaagcca agaagctctc gagctgctcc aaatgatgcc 32820
tgatgatgga ggtgactgcc cacctgatgt ggtgtcgtat accactgtca tcaatggctt 32880
cttcaaggag ggggatctgg acaaagctta cggtacatac catgaaatgc tggaccgggg 32940
gattttacca aatgttgtta cctacagctc tattattgct gcgttatgca aggctcaagc 33000
tatggacaaa gccatggagg tacttaccag catggttaag aatggtgtca tgcctaattg 33060
caggacgtat aatagtatcg tgcatgggta ttgctcttca gggcagccga aagaggctat 33120
tggatttctc aaaaagatgc acagtgatgg tgtcgaacca gatgttgtta cttataactc 33180
gctcatggat tatctttgca agaacggaag atgcacggaa gctagaaaga tgttcgattc 33240
tatgaccaag aggggcctaa agcctgaaat tactacctat ggtaccctgc ttcaggggta 33300
tgctaccaaa ggagcccttg ttgagatgca tggtctcttg gatttgatgg tacgaaacgg 33360
tatccaccct aatcattatg ttttcagcat tctaatatgt gcatacgcta aacaagggaa 33420
agtagatcag gcaatgcttg tgttcagcaa aatgaggcag caaggattga atccggatac 33480
agtgacctat ggaacagtta taggcatact ttgcaagtca ggcagagtag aagatgctat 33540
gcgttatttt gagcagatga tcgatgaaag actaagccct ggcaacattg tttataactc 33600
cctaattcat agtctctgta tctttgacaa atgggacaag gctaaagagt taattcttga 33660
aatgttggat cgaggcatct gtctggacac tattttcttt aattcaataa ttgacagtca 33720
ttgcaaagaa gggagggtta tagaatctga aaaactcttt gacctgatgg tacgtattgg 33780
tgtgaagccc gatatcatta cgtacagtac tctcatcgat ggatattgct tggcaggtaa 33840
gatggatgaa gcaacgaagt tacttgccag catggtctca gttggaatga aacctgattg 33900
tgttacatat aatactttga ttaatggcta ctgtaaaatt agcaggatgg aagatgcgtt 33960
agttcttttt agggagatgg agagcagtgg tgttagtcct gatattatta cgtataaatat 34020
aattctgcaa ggtttatttc aaaccagaag aactgctgct gcaaaagaac tctatgtcgg 34080
gattaccgaa agtggaacgc agcttgaact tagcacatac aacataatcc ttcatgggct 34140
ttgcaaaaac aatctcactg acgaggcact tcgaatgttt cagaacctat gtttgacgga 34200
tttacagctg gagactagga cttttaacat tatgattggt gcattgctta aagttggcag 34260
aaatgatgaa gccaaggatt tgtttgcagc tctctcggct aacggtttag tgccagatgt 34320
taggacctac agtttaatgg cagaaaatct tatagagcag gggttgctag aagaattgga 34380
tgatctattt ctttcaatgg aggagaatgg ctgtactgcc aactcccgca tgctaaattc 34440
cattgttagg aaactgttac agaggggtga tataaccagg gctggcactt acctgttcat 34500
gattgatgag aagcacttct ccctcgaagc atccactgct tccttgtttt tagatctttt 34560
gtctggggga aaatatcaag aatatcatag gtttctccct gaaaaatata agtcctttat 34620
agaatctttg agctgctgaa gccttttgca gctttgaaat tctgtgttgg agttcttttc 34680
tcctacagtt gtattagagg agggatcttc tctttatgtg taaatagcga ggtatgtatg 34740
tcacctctcc gaattatttt tactctggtt cctagacggt aaacaagcaa ttatgttctg 34800
cctttgatgc cagaaaaaac acaaaagttt gtcgttatct ctactaacgg atcataaagg 34860
aatttgtaac tggagtttca aacttaattt gtctaggcag tagttttggc attagatcca 34920
acattgtgta ggattcattt gtgtgtatca atctataggg tttcattaaa tttcgttaat 34980
gtgtactgtt taggtgttga atagtttgac ttgtttttta actgaacaaa agatactgaa 35040
atcgttccat tcaacaaaca catgttccgt taatgaaatt attgtacgtt accttttgtt 35100
ttcttactca caagtgtcct cttttcttat atcctataga ttggtacaac aaattattga 35160
ttcaattttg gttttgaaca ttgatgatcc tccctgcact attggtgcag ctgctcttct 35220
attcattttg tgaagtgatg tgagtacctc tcaatcccat ccttatgctt ctgtgcatgc 35280
ttcattccaa tttttacgc atatcgattg ttttctttta tataacagtc cataaagata 35340
atcacatcat gacaaagtta tttatttcta cagtatagtt atataagtat tcaccagttt 35400
tccatgaata ttttggcatg tgattacaaa gaagattatt tgagaaaatc catgctttta 35460
tttcatcttt ttgtttgaag ttgaacttta atttatggtg taaatttcag ttattattgc 35520
tagcagctcg tactctttaa tggtataact tcacttgtgc ttattctcca atatctccct 35580
tcttgttgtt caggttcaag aaaatcattt gttggattca gaatctggtg tccattttct 35640
tcttaaatta ttaaatcctc cagtgaatct tgttgattcc aaagcaccat cgataggttc 35700
caaacttctt ggaatcagta aagttcaaat gcttaatgga tcaaataagg attctgactg 35760
catttcagag gaaatccttt caaaagttga agagattctc ttaagctgtc aagtgatcaa 35820
gtcgctcgac aaagatgaca agaaaacaac aaggccagaa ctgtgtccaa agtggcttgc 35880
tttgttgaca atggaaaatg catgcttgtc tgctgtttca gtagagggta agttttaatc 35940
aaatttcttg gtcatgattt ccctttatga ccattatatt tatttatatg agccaaataa 36000
gcagttgtca acttgtcata agttacatag cacctatttg caatattcat gggtggtttg 36060
cttagccctt ttcttcacct gcttttgatt gatgacttcc atctgtgttg cagaattgaa 36120
ttggagtagt ggactgcact agaagcacct atggccattg tcatactagg aaggttttcc 36180
cttatcaaat atttgattgt tacagagact tctgacacag tgtccagagt tggaggaaat 36240
tttaaagaga cattaaggga gatgggaggt cttgatagta tttttgacgt tatggtggat 36300
tttcattcaa cattggaggt gagatctcgc taacatcgca tattttacat ttcctttgtt 36360
caactctaat ggattgtgca ggcttgttcc ttttcgccat tttagcttta atgtgcttga 36420
agccacatga aagtaatgct tgtccagata catagccaaa ggttgttata ttttggggca 36480
tggaaaatgc ttgaggtagt aactattttc atcaggacat ggaaaattgg ctgcaacaca 36540
aattatgttg ttttatgttg caaaaatagt tttttaatac ttttttattc tgcatgtggt 36600
gttagtatct tacagttcct ctgatgatta tatcccccac gataataaca cttgaaacga 36660
taataacact tgacatatct acaccaagtg aacattattc atttggatgt tacttttcca 36720
gctatacttg ctgttcttgc atgtgtaagc aagtttggag taaattgcgc attaatttaa 36780
atgcttggtg ttcctatctg tgtacttttt attccccaac taataatgca atcatattac 36840
gctgataaac tgaataaata aattaacaat atacttctgg tggcaaacct tgtgtatcag 36900
aatctcataa aggatacatc cacttcagct ttggaccgaa atgaaggaac atctttgcaa 36960
agtgctgctc tcctcttgaa atgtttgaaa atattggaaa atgccatatt tctaagcgat 37020
gataacaagg taatgctcct tatatgttct gtttcagttt agtacccatt tccttcttct 37080
gtactatctt ctctcctgat ttgttctgtg caaaatgtgc aaacagtgcg actttgtatg 37140
tctgcttaac aattttcttt tcttcctgaa aaagcaatat gaactcttac attcattttg 37200
cttcttgcag acccatttgc ttaatatgag tagaaaattg aacccgaaac gctccttgct 37260
ttcttttgtt ggtgtcatta tcaatactat tgagttatta tcaggtattt ttcttaataa 37320
tacaatgtgt tcgctaacac aataaaatgt tttaaacatc cagtatgtta aagttgcagt 37380
ctgacgccta ttttgttttg ctgcagctct ttcaatactt cagaattctt ctgttgtttc 37440
cagctctaca tatccgaaat cgtctaaagt ctctcaacag agttactctg gtaataacaa 37500
acaccaattt tgtttgatca gttgatctcg ttggcttttc tatgcactgt ctcaatatag 37560
tttggtcgcc attcaagtct cactacagat gttgaacttg gcctgacacc aaatatttat 37620
aaaatgctac ctgatatttt taatatttca tgtttcctga cccagattat cttgttggtt 37680
cctcgtataa gtttaattag tgacattctt gaagctttgt tatgcagcag atgtcatggg 37740
gggaacttca tttaatgatg gaaagagcaa gaactcgaaa aaaaaaaact tttgtcgaac 37800
cagacacgtc attgttgctt atcttcaaaa tcagaagttt ctcatattac tatatcttct 37860
ggtagtgatg ctggtctgtc acagaaggca ttcaattgtt ctccatttat atcaagcaat 37920
ggggcatcaa gtggttcatt aggcgagagg cacagcaatg gtagtggttt gaagttgaat 37980
ataaaaaagg atcgtggcaa tgcaaatcca attagaggct caactggatg gatttcaata 38040
agagcgcaca gttctgatgg gaactccaga gaaatggcaa aaagactccg tctatcttaa 38100
aatgtaatca ccgacagtgg tggtggtgat gacccttttg catttgaccg ccgcgtcggc 38160
gtcgccacca cgtaatcgcc cacgtcgctg cccccgctgc cacgtcgtcg accgcgcacg 38220
gtaatcacac gcatctcgag gccgccgcta gctgatatct tctcatccgg ttgatttgtg 38280
attttggcgt ttttgcagtg gtgatggcgg ggggcgaccg tggccgaggc gtggagtgcc 38340
atccgcatca gggtgtatcg gccgcgctgc tccgccctgg tccgcaggct ttggcggcga 38400
gctggcggcg gagggagact gtggtgagat cggatttcgc cgctggtggt gtcgctacca 38460
tgggggattc gccgcaggcg ctctcaggtt tgcagcctcc tccactctct tccctttttt 38520
attttttttt ctcgcaaaat gtgttgtgat gttcgtctcg ctgggcaggc ctcatagcca 38580
ttaatgtagt ttgctggaac atttacattt ggaacgttgt tggcaattgc ttgacaaaat 38640
gtggaattgt ggaggggaga aaaatcattt gaacctgcag tgacaaaatt gccatctcta 38700
attttaaaac tgaaggtgtg gaaatcaaac ataatcattg ccagcgcatc attcttgtta 38760
accaccatga tatattgttg gttataacag ttagctccac accaaccttg aaggtgtcaa 38820
tagaatgttt agtataaatt gaggagaaca ggcagttgtt aagactttct aaagaacttg 38880
tagcagctaa tactagctat tgtgcatttg tgtttcatgg aatttgagca gcaatggata 38940
tttcttacta agatgtatga tgcaaaacaa aaaactatgt ctatacagtt tacatgtaat 39000
gtgcggatgc aaataaaatc atgtacatgg acaaactcat gggattcata ccgaattcca 39060
gaattgcatt tcttatgtgg ttacttttgt tgttgatttg gttaccagac atcgatgtga 39120
tttcaagggt cagaggggtt tgcttctacg cggtggctgc agttgcagca atctttttgt 39180
ttgtcgccat ggttgtggtt catccacttg tgctcctatt tgaccgatac cggaggagag 39240
ttcaggaaaa aaatttgaaa atacccattt tttgaaaaag atttacgttt atatacacta 39300
gtatgaagaa tttgcgaaaa tataactaat ccgcagatcg gttatgcggg agcgcaacaa 39360
aagtatggcg tggcggcgcg gagtggacgg ccgaggcgtt cgcgcggaat ggggctgcgg 39420
gaccgagcca gtctcgcttg ccggtaacgc ggaaccggta cgctcccgca gcgccagtgt 39480
gcggaaccgc ggcgccaaca tttttttact gcatggcact gtgtttaata ctgtttgaca 39540
ctgtttctgg tactgtttta cacagttccc gggtcagttc cgcacaatgg aggcgcggca 39600
ccgaccatga acaatgtgtg aacagtgctg cacagggtta aaacagtgta taaactgcgc 39660
tgcacagtgc tggagtcgct ggccactgcg gttccgcgtt ttggaaccgc gggaccgtcg 39720
cgattccgcg ttttggagct gccggaccat gacggttccg cgcaggatcg tcggtcccgt 39780
attttgaatc tgcggaaccg tcgctgtccc gcgtttccgt ttcgcgggat gcgtatattt 39840
ttataaaacc tctccatgca tgtatataaa cataaattat tgaaaaaata agtatatttg 39900
caaatttttt tcgagagctc agcactacat tgcaaagatt tgggcaactc tgacaatttc 39960

```
catgttctac aagcttgacg tcgagggaat ggagaacctg ccaccgaata gtagccctgc  40020
tatctatgtt gcgaaccatc agagtttttt ggatatctat acccttctaa ctctaggaag  40080
gtgtttcaag tttataagca agacaagtat atttatgttc cgaattattt gatgggcaat  40140
gtatctctta ggagtaattc ctttgcggcg tatggacagc aggagccagc tggtatggct  40200
gtagtctcat ccctgctttc ttaagtagac atatatgcaa ttacagaatt tggtaaacaa  40260
acaagatttt atgaatcata tatgattttg gggaaaacac caaactctct ttggtggctg  40320
ccttgaacat agttctattc acacagttat agcaccttct ttaaaatgaa gaactttgtt  40380
gcatacacat atggccaaac cacataatga attttgttta tttctatctt tgaatgttag  40440
caccttattt tcatgcatat catgctaatt tgcttgccca cgttgagtgg gaattttttt  40500
ccatgtttta taatttatat atgttctaga cttctagtcc acaatttatc tacttcatgt  40560
tcctgagcct ctagtatggc tggtagcaga ctaggtgctg agtgctgtcc atttttgcag  40620
actgaagaga ggagaaatac aggactgtcc gttgttagtc agatttgtaa aaatagactc  40680
tgatgtagtt tattttagcc cctattttat atttaacaat acaaatatat aacgtatcct  40740
aagaacttat cgtaatttag gagaagttgc tcgtttcatt aaattaaact gtgaagtaaa  40800
aatgtgtgct cgagtctgtc aatgcaatcc tgtgttcttg tttgaagata tggtgtaggg  40860
caggctagga tcgaacactg aatggtaaga ctgcttctgc cttcatttgt gcacttggtg  40920
ctgccacgcc gattaagcag tagaacaaag taattttgtc gtgcacaaat gagttatatt  40980
tcattgaaaa tcgaagtgaa aatgaaccaa aagatagaag aaaaggggaa acttggtaat  41040
tatatactcc acaaatttat tggtaagatt tgatattaga cgctcgatta cttggcttaa  41100
gttaaggata tcaaatttgg ggaagcacca aaggaattat tgtgaaggag ttgtgggtgc  41160
ataacgttat ctactaggtt caaatcctag tgactatgaa tattaatgag taaggtaagg  41220
gatttattgt taattttagt ttctttaaga ttgtgtccgg gtacaccatt cggtaagtgt  41280
aataatgttt tgtattggat tcacttgtgt tacgtgcatg tgatttacct tttcatttgt  41340
ttctgcgttc tgggtatgaa tttgacgaga ttccatggtc agctcaacat atcagttact  41400
gcgtgtcaag cgatcttata tggtatgcgc acaagcgatt gtatacggat atgacagtat  41460
aacgtgtgat attgatacga tgttcctttc ctttataaag gaacaaagac tttttttaaaa  41520
aaaagaaggg gtattactaa aaaccaaaat gtcaaaaaca aaatatcagt gcacatggca  41580
agtgtgcacg agcaatagct tgcccttacg ttcattattt agcatgtact actactaact  41640
acgcaaaaat caattcaccg attattaaac tgttaacatc attttagcac gttaacatat  41700
gtttcattca acacaccggt tttggcacat ttacaaactt gcaaagttgc aatactccct  41760
tcgttacata gcataagaga ttttaggtga atgtgacaca tctatccaaa ttcattatac  41820
tagaatgtat caccgcctcc acgccgggag ggagagcgcc gccggtggag aaagggggag  41880
ggagtggtcg aggggaacca gtagggtgcc ctccccgtcg ccgcctcccc gtggccgcgc  41940
cggcgagaca ggaggaagag ggggatatgg agcggcgccg ccggtgaggg cgcgcgcgcg  42000
ggggggagcg gcgacgccgg tgaggaaggg aaggggagtg gtggctttga gagagatagg  42060
ggggaggaaa aatgatttta gagttagggt ttgggctgct gagtttttat atagatcggg  42120
atcaatcagg accgtccatc agatcggaca actacggctt ctcccgcgtt gggccgggtg  42180
ccactcctag gttgcccaca ctattgggcc acatgtacgc tccgcgtgaa ataagttcac  42240
tttaggtcct ttaagttgcc tctgaattgt tcccaggccg gccgcactat tgggccaccc  42300
cataggccat gtgtacgctc cgcacagaat aatttcgctt tagctccctt aatttgtccc  42360
```

ctcaaactcc taaaaccagt gcaaatcttt aatttttagt tcacccattg caactcacgg 42420
gcatatttgc tagtgacata taatatgaaa cgaaggatgt agcagactat agaatttaaa 42480
ctgtgctttc attttagagc atcactaact gttatttaga tttttattta aataaatgct 42540
gaaatgatgt ttttattatg aaaattagca ataaagctcc caaaatttca aaaaaaaatt 42600
aaaagagatt tattaatcat ggttaattta attaaaaatt aaatctaacc atatcatatt 42660
atttcacggt ccgtgatgag gaaatggcag ctgctatcac ttacggtggg agagaagggg 42720
cattgtttat ttttataact atctcttata actcccatga aactataaaa taaatataat 42780
cattatcata acattagttt tttttccatt gcaacgcaag ggtaattttt cagtacaata 42840
aaaaaaataa aagtgggcca ttctgaacgg aaatttctgg tttttttttcc caagagcgcc 42900
gcacacaact gcgcaagaga tcgatcgcga tcaccctgct cgtcgccgat ctcctacacc 42960
atccctgcca tctccttccc ctccactggc tgctgctgca cctgtcagct agggcgggca 43020
tggcgcgccg cgccgcttcc cgcgctgctg gcgcccttcg ctcggagggc tcgatccaag 43080
ggcgaggggg ccgcgcgggg ggcagtggcg gtggcgcgga ggacgcacgc cacgtgttcg 43140
acgaattgct ccgtcgtggc ataccagatg tcttctccta caatattctt ctcaacgggc 43200
tgtgtgatga gaacagaagc caagaagctc tcgagttact gcacataatg gctgatgatg 43260
gaggtgactg cccacctgat gtggtgtcgt acagcaccgt catcaatggc ttcttcaagg 43320
agggggatct ggacaaaatg cttgaccaga ggatttcgcc aaatgttgtg acctacaact 43380
ctattattgc tgcgctatgc aaggctcaaa ctgtggacaa ggccatggag gtacttacca 43440
ccatggttaa gagtggtgtc atgcctgatt gcatgacata taatagtatt gtgcatgggt 43500
tttgctcttc agggcagccg aaagaggcta ttgtatttct caaaaagatg cgcagtgatg 43560
gtgtcgaacc agatgttgtt acttataact cgctcatgga ttatctttgc aagaacggaa 43620
gatgcacgga agcaagaaag atttttgatt ctatgaccaa gaggggccta aagcctgata 43680
ttactaccta tggtaccctg cttcaggggt atgctaccaa aggagccctt gttgagatgc 43740
atggtctctt ggatttgatg gtacgaaacg gtatccaccc taatcattat gttttcagca 43800
ttctagtatg tgcatacgct aaacaagaga aagtagaaga ggcaatgctt gtattcagca 43860
aaatgaggca gcaaggattg aatccgaatg cagtgaccta tggaacagtt atagatgtac 43920
tttgcaagtc aggtagagta gaagatgcta tgctttattt tgagcagatg atcgatgaag 43980
gactaagacc tgacagcatt gtttataact ccctaattca tagtctctgt atctttgaca 44040
aatgggagaa ggctgaagag ttatttcttg aaatgttgga tcgaggcatc tgtcttagca 44100
ctattttctt taattcaata attgacagtc attgcaaaga agggagggtt atagaatctg 44160
gaaaactctt tgacttgatg gtacgaattg gtgtgaagcc cgatatcatt acccttggca 44220
ggtaagatgg atgaagcaat gaagttactt tctggcatgg tctcagttgg gttgaaacct 44280
aatactgtta cttatagcac tttgattaat ggctactgca aaattagtag gatggaagac 44340
gcgttagttc tttttaagga gatggagagc agtggtgtta gtcctgatat tattacgtat 44400
aacataattc tgcaaggttt atttcaaacc agaagaactg ctgctgcaaa agaactctat 44460
gtcaggatta ccgaaagtgg aatgcagatt gaactttgtt agatttaatt ggataattaa 44520
tccatttaaa tcaattaaat caaataaatt ccaaggctca ttatgctagg aattcatgtg 44580
aattcattct tctatgggat atcaatggga tgaagagttt tgagaattaa tccatttgat 44640
taaggaattg gtaacttata tcaattaatc ctaattgatg gatggttgat ggttgtgtag 44700
tggaggatgg ttcatggcta gttgatgaca attagttgct ctattcctct tcctattcca 44760
ttggtaactt acatcaatta ctcttaattg attgttggtt gatggttgtg tagtggagga 44820
tggttcatgg ctagttgatg acaattagtt gctccattcc tcttcctatt ccatgactct 44880
tactcttcat cttccattcc tcttataaaa tgagaatgga tttgatctcc cgcgagaaga 44940
agaagacaca ctttcatcca ttttcaaaag ctgttgctgc tacggtaatc ccatcccgac 45000
gagtgtgtgc acacgcgttg ggagagtagg cctccgaaac cacgcgttgc tgcgacgttt 45060
gcacagacgg gcgggcgatc aggtttttgg ggagcgcaag gcgcgactac tcactgttcg 45120
tcaacatcta cttcatcttc accaacatgt cgaacactgg agacaaggag aaggagactc 45180
ccgtcaacac caacggaggc aatactgcct caaactccag cggaggacca ttcttggggt 45240
ataaccttat tacattattt caattagaag ttttactgtt aatgttcatc gcaatgtcaa 45300
cattgtgtca ttatgtgatt gttgatgctt attcaacgtt aagcatgctc atgttgatta 45360
cattcaccac tatcactgga tcaaatccta ttgtaaatat catgtttatt atcttgttat 45420
tttggattaa aatatgccga attatgacca aatttccaac aaacttagca catacaacat 45480
aatccttcat ggactttgca aaaacaaact cactgatgat gcacttcgaa tgtttcagaa 45540
cctatgtttg atggatttga agcttgaggc taggactttc aacattatga ttgatgcatt 45600
gcttaaagtt ggcagaaatg atgaagccaa ggatttgttt gttgctttct cgtctaacgg 45660
tttagtgccg aattattgga cgtacagatt gatggctgaa aatattatag gacaggggtt 45720
gctagaagaa ttggatcaac tctttctttc aatggaggac aatggctgta ctgttgactc 45780
tggcatgcta aatttcattg ttagggaact gttgcagaga ggtgagataa ccagggctgg 45840
cacttacctt tccatgattg atgagaagca cttttccctc gaagcatcca ctgcttcctt 45900
gtttatagat cttttgtctg gggaaaaata tcaagaatat catatatttc tccctgaaaa 45960
atacaagtcc tttatagaat ctttgagctg ctgaagcatt ttgcagcttt gaaattctgt 46020
gttggaattc ttttctccta cagtccgatt agaggaggga tcttctctgt atgtgtaaat 46080
agcgaggtat gtatgtcacc tctccgaatt attttgactg tggttcctgg actgtaaaca 46140
agctattatc ttctggtgtt gatgccagaa aaaacacaaa agtttgtcgt tatctctact 46200
aacggatcat aaaggggttt gtaactggag tttcaaactt aaggtatcta ggcagtaggt 46260
atatattgat cctacatctt atgatcttaa gatgatatcc ttctcattat cctctgctga 46320
aactttagct tgaaccgtca tctacaccac aatttgagcc ccttagcaca gagcacaacg 46380
agcaatagct tgcccttacg ttcattattt agcatgcact actactaact acccaataat 46440
caatacatcg gttattaaac tgtttgtaca gtttaataat gtcattttat cacgttaaca 46500
tatgtttcat tcaacaccac accggttttg gcacagttgc aaacttgcaa taacattttt 46560
actacttctc cgccccataa tataacaatc tcgttccata ctatattgct atattacggg 46620
acggatgaag tacttctttc cttccaaaat ataagaatct agtcctagat tagatattat 46680
ttggattcac gaatttgatt aggctatcta gatttgtagt cgtatgtaat gtctaattcg 46740
gtaataggtt attacctctt tggatggagg gagtagtttt tatttcgtac tccctctgtt 46800
tcatattata agttgttttg actttttttct tagtcaaatt ttattgagtt tgactaaatt 46860
tatagaaaaa aaattagcaa catttaagca ccacattagt ttcattaaat gtagcatgga 46920
atatattttt ataatatgtt tgttttttta ttaaaatgct actatatttt tctataaatg 46980
tagccaaatt taaagaagtt tgattacgaa aaaaaatcaa aatgacatat aatatgaaac 47040
tgaggatgta gcagactata gcaaatttaa actatgcttt tattttagag catcaccaaa 47100
agagatagcc taaatcttat cttaactaat taaaatattc ataattttcc tttcgtcaca 47160
ttaaattttc gtccgtaaat ccgattgaaa tccaactaga caatccaaaa aatagagaaa 47220
aagaacagaa aaaataataa aaagcacaca aatcttatct caatcccgcg ggaagctgcc 47280
gatgccgccg aatccgctcg agcgccgccg ccgccgctca cggggaacga tgtcgctgct 47340
atcgcacgtg gtatgggagg gcgccgccgc cgctgcttgg gagataggat atggagagag 47400
aaggaaatgt gagggagggt taggtttttc cccattcgta tcttcagcga cacggaggcg 47460
atccaagctg tccatcagat cagacggctc agaacgcctc catcttcagg ccgcgcatgc 47520
ttgatgggcc gagggaaggc cggagggtcg aacaaacgta gtcagaggag gagttggagg 47580
aggtaaagta gaatttattt gcgggctgag atagtaaatg gactgaaaat ggcccataga 47640
gaaattggga attttattta aataaatgtt gaaaaggtgt ttatattatc aaaattagaa 47700
attaagctcc gaaaatttta aaaaatattc aaagagcatt attaatcatg attaatttaa 47760
taaaaattaa atccaaccat atcatattat ttcacggcgc gcagtaggaa aatgcgcagc 47820
tgttgtcgct tacggtggga gagaagggac attgtttatt ttcagaacta tcttttataa 47880
ctcccatgga actttaaaat aaatataatc attattatag cattagtttt tttctgtctt 47940
ttttttcccc aagagcgccg cgcagaagag atcgatcgcg atctccctgc cccgacgtcg 48000
ccggccgatc tctcattctc tccacgccct gctcgtcgcc gatctcctac accatccctg 48060
ccatctcctc cttcccctcc cctctatcct ccactggtgc cgcccacctc tccgtataag 48120
acaaactgcg ttgcggcgtt ggtttccgcc ggcgctgctg ctgcacctgt cagctagggc 48180
gggcatggcg cgccgcgccg cttcccgcgc tgttggcgcc cttcgctcgg acggctcgat 48240
ccaagggcga ggaggccgcg cggggggcag tggcgccgag gacgcacgcc acgtgttcga 48300
cgaattgctc cggcgtggca ggggcgcctc gatctacggc ttgaaccgcg ccctcgccga 48360
cgtcgcgcgt cacagccccg cggccgccgt gtcccgctac aaccgcatgg cccgagctgg 48420
cgccgacgag gtaactcccg acttgtgcac ctacggcatt ctcatcggtt gctgctgccg 48480
cgcgggccgc ttggacctcg gtttcgcggc cttgggcaat gtcattaaga agggatttag 48540
agtggaagcc atcaccttca ctcctctgct caagggcctc tgtgccgaca agaggacgag 48600
cgacgcaatg gacatagtgc tccgcagaat gaccgagctc ggttgcatac caaatgtctt 48660
ctcctacaat aatcttctca acgggctgtg tgatgagaac agaagccaag aagctctcga 48720
gttgctgcac atgatggctg atgatcgagg aggaggtagc ccacctgatg tggtgtcgta 48780
taccactgtc atcaatggct tcttcaaaga gggggattca gacaaagctt acagtacata 48840
ccatgaaatg ctggaccggg ggattttacc tgatgttgtg acctacagct ctattattgc 48900
tgcgttatgc aagggtcaag ctatggacaa gccatggagg tacttaccac gatggttaag 48960
aatggtgtca tgcctgattg catgacatat aatagttatt tcttgaaatg ttggatcgag 49020
gcatttgtct ggacactatt ttctttaatt caataattga cagtcattgc aaagaaggga 49080
gggttataga atctgaaaaa ctctttgacc tgatggtacg tattggtgtg aagcctgata 49140
tcattacata cagtacactc atcgatggat attgcttggc aggtaagatg gatgaagcaa 49200
tgaagttact ttctggcatg gtctcagttg ggttgaaacc taatactgtt acttatagca 49260
ctttgattaa tggctactgc aaaattagta ggatggaaga cgcgttagtt ctttttaagg 49320
agatggagag cagtggtgtt agtcctgata ttattacgta taacataatt ctgcaaggtt 49380
tatttcaaac cagaagaact gctgctgcaa aagaactcta tgtcaggatt accgaaagtg 49440
gaacgcagat tgaacttagc acatacaaca taatccttca tggactttgc aaaaacaaac 49500
tcactgatga tgcacttcag atgtttcaga acctatgttt gatggatttg aagcttgagg 49560

-continued

```
ctaggacttt caacattatg attgatgcat tgcttaaagt tggcagaaat gatgaagcca  49620
aggatttgtt tgttgctttc tcgtctaacg gtttagtgcc gaattattgg acgtacaggt  49680
tgatggctga aaatattata ggacaggggt tgctagaaga attggatcaa ctctttcttt  49740
caatggagga caatggctgt actgttgact ctggcatgct aaatttcatt gttagggaac  49800
tgttgcagag aggtgagata accagggctg gcacttacct ttccatgatt gatgagaagc  49860
acttttccct cgaagcatcc actgcttcct tgtttataga tcttttgtct gggggaaaat  49920
atcaagaata ttataggttt ctccctgaaa aatacaagtc ctttatagaa tctttgagct  49980
gctgaagcat tttgcagctt tgaaattctg tgttggaatt cttttctcct acagtcctat  50040
tagaggaggg atcttctctg tatgtgtaaa tagcgaggta tgtatgccac ctctccgaat  50100
tatttttact gtggttccta gactgtaaac aagcaattat gttatgctgt tgatgccaga  50160
aaaaacataa aagtttgtcg ttatctctac taacggatca taaagggatt tgtgactgga  50220
gtttcaaact taatgtgtct aggcagtaat tttgacatta gatccaaaac aatttatagg  50280
gtttcattaa atttcatcta tgtgtactgt ttaggtgttg aatagtttga cttgtttttt  50340
aactgaacaa aagatatgtc tgaagctttg ttctttacca aatgcagtac tgatcatcac  50400
aatatatttt ttatggaaca agattggatt gtatagaatg gtttccgatc tgattatctt  50460
atctcaacgt attattatgc acatgtacta atcatgaaat atctgatgga atgatgtttc  50520
tatttacctg tgtgaggcag caaggagtga gatggataac accacatact ccctctatcc  50580
cagaatataa gaagttttag agttggacac gattattaag aaagtaggta gaagtgagta  50640
gtggagggtt gtgattgcat gagtagtgga ggtaggtggg aaaagtgaat ggtggagggt  50700
tgtgattggt tgggaagaga atgttggtag agaagttgtt atattttggg gagtacatta  50760
ttattctaga acaatactgt tgtgctcaag aagcgttcca aagatgtttc acaacctgtg  50820
ctcgatgggt tttgagctta atcctgggac attcagtatc atgatctgtc tcattcttaa  50880
acatggaata aaggatgaca gcatgatttc tttgtctcta taatcttttg gctacccaca  50940
gataatagct gtaaatctat actactttaa aaggagtagt ggtggtggtg agtggtgaat  51000
ctgccaccac cccaccacca actctcaaaa ttctgacatg tgggatcact gtcaatccct  51060
tctccaagac atgtgggatc actgtcaatc ccttctccaa accaattgta tgatagaaca  51120
gtggaaatca cggacagacc atggagctct caaccataat catccttgcg agttaataac  51180
aaatggagcg taaacttggc aagcaaaaaa ctcaaattaa ttctaaaatt aagctctagg  51240
attcaaaata gatttcctct ctgcattgtg ctgttatgat ttttaattcc gtaacaacgc  51300
aaatgcattt tgctagtctt ataaagaagg gttaatgcaa atattctgat taaatgattg  51360
tatctatgaa gtttgaatgc tagtggaagc tcctttgacc atgttttgtt gtgcgagcat  51420
ttaagagagt gaagagaatg cttctttggt gctgttctgg tatggaagga tccacagata  51480
aaattcaggt tctactgctt ctctgcttgt aattttcatg aagctgcagt gaataccttg  51540
ttgaccactt gatctgttgc tttgaaggag aatatagtag tggccaaggt tggtgacggt  51600
gatggtggca tgtgatcccc cagatcttca gtgacccaga gaggagggga cggcgcgtgg  51660
tgagctacaa ggcatactca gtggagggca agatcaaggc ctcccgtccg taggggactc  51720
cgctgcatca aggccaactg ctccgaactg atcaatttct ggtacggatc acttctcctt  51780
tccttttttt tttcacctta agcactctct tgattcttcg ctgctacctc ccttaatttc  51840
tttcaatata ttgtggcact tgatcatggc ggagacccac cttccagtgt gaatggattt  51900
tgtcaaagaa ctaaatttat tccattagct tattttctga ttacatggaa gacattcttt  51960
```

tctggaataa atacagaact aaatcctgtt tcctgaataa aagttgttag tgtgtggcat 52020
ggtgcatttc cgcgcttcta aattttataa aacctgttca ttcaatttga acctgcatcc 52080
aatccaatat tttaggtgca gacaggtgct tgcggtcagg ttaaagaagt tggcaaaaat 52140
gcttctgaag aaaggttaat tgttgtttca tctcaggagg taatatgcag atgattattc 52200
caattggcat tgccttgcca tttttatcac gagtctttac aattttatat cctcctacat 52260
attctttcca gattccagat gatccagtgt ctccaacaat tgaggcgctt attttgctcc 52320
atagtaaagc aagtacactt gctgagaacc accagttgac aacacggctt gttgtaccat 52380
caaacaaagt tggttgtatt cttggggaag gtggaaaggt aattactgaa atgagaagac 52440
ggactggggc tgaaatccga gtctactcaa aagcagataa acctaagtac ctgtcttttg 52500
atgaggagct tgtgcaggta atttatttgg ccatacctac accagagatc catatattac 52560
ttttataact gcagttttta cttgttaaca tttcattgtg cttttacatt tgttccaagc 52620
tttcaggttg ctgggcttcc agctattgaa agaggagccc tgacagagat tgcttcgagg 52680
ctttgaacta ggacactcag agatggaagt tcttccaata atccgacacc ttttgcccct 52740
gttgatggtc ctcctgttga tatcttgcct aacaaggaat tcatgctata tggacgatct 52800
gctaatagtc ccccatatgg agggcctgct aatgatccac catatggaag acctgccatt 52860
gatccaccat atggaagacc aatatccaca atatggaaga cctgccaatg atccaccata 52920
tagaagacct gtcaatgata catcatattg agggttggac aatgatgggc ctcgtgatca 52980
ggcccggtcc tgaggggggt cgaatggggc gatcgctccg ggcccccgat tcccagggcc 53040
cccacctatc tgtgcaacga gtagtagcga tcttccagcg cgcaacgtga ggcgatgttt 53100
ctccgtgatt tcgccggcct gcaactgcga gatcgcgagt ataacgatca gccgatcgat 53160
ctcatctgcc gactgccatg ctgatgccac acgcaagcgc agcatatcag ccttatcttg 53220
gttgatcggc atgctggacg agcacatctg ttgtcgcatc aactgctgac tgctatatat 53280
gtgctggtgc tgaatcgatc gattgtcgtc gcggaagtga agaacaacca cggcactgct 53340
gcctgctggg ctctagccgc catcagtaag tacgctatac tgcctatcta gatctagatc 53400
gagattacat agtggaatta tctgtttata acaaaattac aaggtatcaa ttgataattt 53460
aaggttataa ccgtacaaac ttcagtgatt tgctggtttc acattggtta gatttgtttc 53520
aactaatttg gtacttctgt agccttgtaa tttacgaatc tagtattaat attttcttaa 53580
gtattagcct gttccttgat attatgctgt tgagaaagta tgcaatagat aacaaaaaca 53640
agtaggtgtg ttgaggatgc tcaagagtaa tacagccact tcaataattc tgatattatc 53700
aggacatcat caataattct gcgcctacaa atcttcaaag aaaattttaa tataatgcgt 53760
atgatttttt aaatacgaat attgattgct atttaaagat atttatatta tatggtaatt 53820
attatttgaa ggtttataat aaaggcctcc gtttttagtt tcacgctggg ccttcagaat 53880
ctcaggaccg gccctgctca tgatc 53905

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 3
atcaggagcc ttcaaattgg gaac 24

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 4
ctcgcaaatt gcttaatttt gacc 24

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 5
tgaaggagtt atgggtgcgt gacg 24

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 6
ttgccgagca cacttgccat gtgc 24

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 7
gcgacgcaat ggacatagtg ctcc 24

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 8
ttacctgcca agcaatatcc atcg 24

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 9
aaggcatact cagtggaggg caag 24

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 10

-continued ttaacctgac cgcaagcacc tgtc 24

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 11
tggatggact atgtggggtc agtc 24

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 12
agtggaagtg gagagagtag ggag 24

<210> SEQ ID NO 13
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 13
ccctccaaca cataaatggt tgag 24

<210> SEQ ID NO 14
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 14
tttctgccag gaaactgtta gatg 24

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 15
gcgatcttat acgcatacta tgcg 24

<210> SEQ ID NO 16
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 16
aaagtctttg ttccttcacc aagg 24

<210> SEQ ID NO 17
<211> LENGTH: 26
<212> TYPE: DNA
<213> ORGANISM: Artificial Sequence
<220> FEATURE:
<223> OTHER INFORMATION: Oligonucleotide primer for amplification

<400> SEQUENCE: 17
gaggatttat caaaacagga tggacg 26

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 18
tgggcggcag cagtggagga taga 24

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 19
aagaagggag ggttatagaa tctg 24

<210> SEQ ID NO 20
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 20
atatcaggac taacaccact gctc 24

<210> SEQ ID NO 21
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 21
acgagtagta gcgatcttcc agcg 24

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 22
cagcgtgaaa ctaaaaacgg aggc 24

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 23
atcccacatc atcataatcc gacc 24

-continued

<210> SEQ ID NO 24
<211> LENGTH: 25
<212> TYPE: DNA
<213> ORGANISM: Artificial Sequence
<220> FEATURE:
<223> OTHER INFORMATION: Oligonucleotide primer for amplification

<400> SEQUENCE: 24
agcttctccc ttggatacgg tggcg 25

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 25
atttgttggt tagttgcggc tgag 24

<210> SEQ ID NO 26
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 26
gcccaaactc aaaaggagag aacc 24

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 27
cctcaagtct cccctaaagc cact 24

<210> SEQ ID NO 28
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 28
gctctactgc tgataaaccg tgag 24

<210> SEQ ID NO 29
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 29
tggatggact atgtggggtc agtc 24

<210> SEQ ID NO 30
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 30

-continued

```
agtggaagtg gagagagtag ggag                                           24


<210> SEQ ID NO 31
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 31

tacgacgcca tttcactcca ttgc                                           24


<210> SEQ ID NO 32
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 32

catttctcta tgggcgttgc tctg                                           24


<210> SEQ ID NO 33
<211> LENGTH: 26
<212> TYPE: DNA
<213> ORGANISM: Artificial Sequence
<220> FEATURE:
<223> OTHER INFORMATION: Oligonucleotide primer for amplification

<400> SEQUENCE: 33

acctgtaggt atggcacctt caacac                                         26


<210> SEQ ID NO 34
<211> LENGTH: 26
<212> TYPE: DNA
<213> ORGANISM: Artificial Sequence
<220> FEATURE:
<223> OTHER INFORMATION: Oligonucleotide primer for amplification

<400> SEQUENCE: 34

ccaaggaacg aagttcaaat gtatgg                                         26


<210> SEQ ID NO 35
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 35

tgatgtgttt gggcatccct ttcg                                           24


<210> SEQ ID NO 36
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 36

gagatagggg acgacagaca cgac                                           24


<210> SEQ ID NO 37
<211> LENGTH: 26
<212> TYPE: DNA
<213> ORGANISM: Artificial Sequence
```

<220> FEATURE:
<223> OTHER INFORMATION: Oligonucleotide primer for amplification

<400> SEQUENCE: 37
tcctatggct gtttagaaac tgcaca 26

<210> SEQ ID NO 38
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 38
caagttcaaa cataactggc gttg 24

<210> SEQ ID NO 39
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 39
cactgtcctg taagtgtgct gtgc 24

<210> SEQ ID NO 40
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 40
caagcgtgtg ataaaatgtg acgc 24

<210> SEQ ID NO 41
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 41
tgcctactgc cattactatg tgac 24

<210> SEQ ID NO 42
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 42
acatactacc gtaaatggtc tctg 24

<210> SEQ ID NO 43
<211> LENGTH: 4820
<212> TYPE: DNA
<213> ORGANISM: rice

<400> SEQUENCE: 43
atcgatcgcg atctccctgc cccgacgtcg ccggccgatc tctcattctc tccacgccct 60
gctcgtcgcc gatctcctac accatccctg ccatctcctc cttcccctcc cctctatcct 120
ccactggtgc cgcccacctc tccgtataag acaaactgcg ttgcggcgtt ggtttccgcc 180

```
ggcgctgctg ctgcacctgt cagctagggc gggcatggcg cgccgcgccg cttcccgcgc    240
tgttggcgcc cttcgctcgg acggctcgat ccaagggcga ggaggccgcg cgggggggcag    300
tggcgccgag gacgcacgcc acgtgttcga cgaattgctc cgccgtggca ggggcgcctc    360
gatctacggc ttgaaccgcg ccctcgccga cgtcgcgcgt gacagccccg cggccgccgt    420
gtcccgctac aaccgcatgg cccgagccgg cgccgacgag gtaactcccg acttgtgcac    480
ctacggcatt ctcatcggtt gctgctgccg cgcgggccgc ttggacctcg gtttcgcggc    540
cttgggcaat gtcattaaga agggatttag agtggacgcc atcgccttca ctcctctgct    600
caagggcctc tgtgccgaca agaggacgag cgacgcaatg gacatagtgc tccgcagaat    660
gaccgagctc ggctgcatac caaatgtctt ctcctacaat attcttctca aggggctgtg    720
tgatgagaac agaagccaag aagctctcga gctgctgcac atgatggctg atgatcgagg    780
aggaggtagc ccacctgatg tggtgtcgta taccactgtc atcaatggct tcttcaaaga    840
gggggattca gacaaagctt acagtacata ccatgaaatg ctggaccggg ggattttacc    900
tgatgttgtg acctacaact ctattattgc tgcgttatgc aaggctcaag ctatggacaa    960
agccatggag gtacttaaca ccatggttaa gaatggtgtc atgcctgatt gcatgacata   1020
taatagtatt ctgcatggat attgctcttc agggcagccg aaagaggcta ttggatttct   1080
caaaaagatg cgcagtgatg gtgtcgaacc agatgttgtt acttatagct tgctcatgga   1140
ttatctttgc aagaacggaa gatgcatgga agctagaaag attttcgatt ctatgaccaa   1200
gaggggccta aagcctgaaa ttactaccta tggtaccctg cttcaggggt atgctaccaa   1260
aggagccctt gttgagatgc atggtctctt ggatttgatg gtacgaaacg gtatccaccc   1320
tgatcattat gttttcagca ttctaatatg tgcatacgct aaacaaggga aagtagatca   1380
ggcaatgctt gtgttcagca aaatgaggca gcaaggattg aatccgaatg cagtgacgta   1440
tggagcagtt ataggcatac tttgcaagtc aggcagagta gaagatgcta tgctttattt   1500
tgagcagatg atcgatgaag gactaagccc tggcaacatt gtttataact ccctaattca   1560
tggtttgtgc acctgtaaca aatgggagag ggctgaagag ttaattcttg aaatgttgga   1620
tcgaggcatc tgtctgaaca ctattttctt taattcaata attgacagtc attgcaaaga   1680
agggagggtt atagaatctg aaaaactctt tgagctgatg gtacgtattg gtgtgaagcc   1740
caatgtcatt acctacaata ctcttatcaa tggatattgc ttggcaggta agatggatga   1800
agcaatgaag ttactttctg gcatggtctc agttgggttg aaacctaata ctgttactta   1860
tagcactttg attaatggct actgcaaaat tagtaggatg gaagacgcgt tagttctttt   1920
taaggagatg gagagcagtg gtgttagtcc tgatattatt acgtataaca taattctgca   1980
aggtttattt caaaccagaa gaactgctgc tgcaaaagaa ctctatgtta ggattaccga   2040
aagtggaacg cagattgaac ttagcacata caacataatc cttcatggac tttgcaaaaa   2100
caaactcact gatgatgcac ttcagatgtt tcagaaccta tgtttgatgg atttgaagct   2160
tgaggctagg actttcaaca ttatgattga tgcattgctt aaagttggca gaaatgatga   2220
agccaaggat ttgtttgttg ctttctcgtc taacggttta gtgccgaatt attggacgta   2280
caggttgatg gctgaaaata ttataggaca ggggttgcta gaagaattgg atcaactctt   2340
tctttcaatg gaggacaatg gctgtactgt tgactctggc atgctaaatt tcattgttag   2400
ggaactgttg cagagaggtg agataaccag ggctggcact tacctttcca tgattgatga   2460
gaagcacttt tccctcgaag catccactgc ttccttgttt atagatcttt tgtctggggg   2520
aaaatatcaa gaatattata ggtttctccc tgaaaaatac aagtccttta tagaatcttt   2580
```

-continued

```
gagctgctga agcattttgc agctttgaaa ttctgtgttg gaattctttt ctcctacagt   2640
cctattagag gagggatctt ctctgtatgt gtaaatagcg agtttgaatg ctagtggaag   2700
ctcctttgac catgttttgt tgtgcgagca tttaagagag tgaagagaat gcttctttgg   2760
tgctgttctg gtatggaagg atccacagat aaaattcagt agtggccaag gttggtgacg   2820
gtgatggtgg catgtgatcc cccagatctt cagtgaccca gagaggaggg gacggcgcgt   2880
ggtgagctac aaggcatact cagtggaggg caagatcaag gcctcccgtc cgtaggggac   2940
tccgctgcat caaggccaac tgctccgaac tgatcaattt ctggtgcaga caggtgcttg   3000
cggtcaggtt aaagaagttg gcaaaaatgc ttctgaagaa aggttaattg ttgtttcatc   3060
tcaggagatt ccagatgatc cagtgtctcc aacaattgag gcgcttattt tgctccatag   3120
taaagtaagt acacttgctg agaaccacca gttgacaaca cggcttgttg taccatcaaa   3180
caaagttggt tgtattcttg ggaaggtggg aaaggtaatt actgaaatga gaagacggac   3240
tggggctgaa atccgagtct actcaaaagc agataaacct aagtacctgt cttttgatga   3300
ggagcttgtg caggttgctg ggcttccagc tattgaaaga ggagccctga cagagattgc   3360
ttcgaggctt tgaactagga cactcagaga tggaagttct tccaataatc cgacaccttt   3420
tgcccctgtt gatggtcctc ctgttgatat cttgcctaac aaggaattca tgctatatgg   3480
acgatctgct aatagtcccc catatggagg gcctgctaat gatccaccat atggaagacc   3540
tgccattgat ccaccatatg gaagaccaat atccacaata tggaagacct gccaatgatc   3600
caccatatag aagacctgtc aatgatacat catattgagg gttgaacaat gatgggcctc   3660
gtgatcaggc ccggtcctga ggggggtcga atggggcgat cgctccgggc cccccgattc   3720
ccagggcccc cacctatctg tgcaacgagt agtagcgatc ttccagcgcg caacgtgagg   3780
cgatgtttct ccgtgatttc gccggcctgc aactgcgaga tcgcgagtat aacgatcagc   3840
cgatcgatct catctgccga ctgccatgct gatgccacac gcaagcgcag catatcagcc   3900
ttatcttggt tgatcggcat gctggacgag cacatctgtt gtcgcatcaa ctgctgactg   3960
ctatatatgt gctggtgctg aatcgatcga ttgtcgtcac ggaagtgaag aacaaccacg   4020
gcactgctgc ctgctgggct ctagccgcca tcagctgcgg agctgatcca tggacgtgag   4080
gattaccgaa gactgtcagg tctcactggg tatccaggtg gctctgtcga attgtggatt   4140
ccaaatagtt aactggagtc tgtcattggt gttggtggtg tcaatctagc tgagatccgt   4200
ctggtatagc gtaagagaaa catcatgcac tatccccagt cataaccatg ccccaatggc   4260
caccaatagt tttcctcgtg aaaatctccc cttgatccca gatctctggt gcgagagtga   4320
agttgcacga agcccatcct ggttcttccg agtccattgt ggagatccag ggcattccgg   4380
atcaagtgaa agccgcacag agccttctgc aaggcttcat cggcgcaagc agcaacagca   4440
ggcaggcgcc ccagtcctct cgcatggccc attattttta gtaagctgga ggacattcgc   4500
aacagggggg tcagtggtca ctgcaaagct gagtttgttc ttcagttcaa ctgcagaaaa   4560
ttgcagatcg gttgccgtag ttgctagaac ggtacatagt tgccacctaa ctgtagcgag   4620
tggcataact tattgtgtgt tactgcccaa tgttgtctct ccttgtgttc atggattcag   4680
acttgtgatt gtagtatttc tggatcagac tggagtaaaa gaaaaaaaaa aaggaagaca   4740
tgggtttaac agtaagctca aaacgttgac agtagtaaaa taaaaggggt ttgttcactt   4800
taaaaaaaaa aaaaaaaaaa                                               4820
```

<210> SEQ ID NO 44
<211> LENGTH: 4821

<212> TYPE: DNA
<213> ORGANISM: rice

<400> SEQUENCE: 44

```
cgatcgcgat ctccctgccc cgacgtcgcc ggccgatctc tcattctctc cacgccctgc     60
tcgtcgccga tctcctacac catccctgcc atctcctcct tcccctcccc tctatcctcc    120
actggtgccg cccacctctc cgtataagac aaactgcgtt gcggcgttgg tttccgccgg    180
cgctgctgct gcacctgtca gctagggcgg gcatggcgcg ccgcgccgct tcccgcgctg    240
ttggcgccct tcgctcggac ggctcgatcc aagggcgagg aggccgcgcg gggggcagtg    300
gcgccgagga cgcacgccac gtgttcgacg aattgctccg ccgtggcagg ggcgcctcga    360
tctacggctt gaaccgcgcc ctcgccgacg tcgcgcgtga cagccccgcg gccgccgtgt    420
cccgctacaa ccgcatggcc cgagccggcg ccgacgaggt aactcccgac ttgtgcacct    480
acggcattct catcggttgc tgctgccgcg cgggccgctt ggacctcggt ttcgcggcct    540
tgggcaatgt cattaagaag ggatttagag tggacgccat cgccttcact cctctgctca    600
agggcctctg tgccgacaag aggacgagcg acgcaatgga catagtgctc cgcagaatga    660
ccgagctcgg ctgcatacca aatgtcttct cctacaatat tcttctcaag ggctgtgtg     720
atgagaacag aagccaagaa gctctcgagc tgctgcacat gatggctgat gatcgaggag    780
gaggtagccc acctgatgtg gtgtcgtata ccactgtcat caatggcttc ttcaaagagg    840
gggattcaga caaagcttac agtacatacc atgaaatgct ggaccggggg attttacctg    900
atgttgtgac ctacaactct attattgctg cgttatgcaa ggctcaagct atggacaaag    960
ccatggaggt acttaacacc atggttaaga atggtgtcat gcctgattgc atgacatata   1020
atagtattct gcatggatat tgctcttcag ggcagccgaa agaggctatt ggatttctca   1080
aaaagatgcg cagtgatggt gtcgaaccag atgttgttac ttatagcttg ctcatggatt   1140
atctttgcaa gaacggaaga tgcatggaag ctagaaagat tttcgattct atgaccaaga   1200
ggggcctaaa gcctgaaatt actacctatg gtaccctgct tcaggggtat gctaccaaag   1260
gagcccttgt tgagatgcat ggtctcttgg atttgatggt acgaaacggt atccaccctg   1320
atcattatgt tttcagcatt ctaatatgtg catacgctaa acaagggaaa gtagatcagg   1380
caatgcttgt gttcagcaaa atgaggcagc aaggattgaa tccgaatgca gtgacgtatg   1440
gagcagttat aggcatactt tgcaagtcag gcagagtaga agatgctatg ctttattttg   1500
agcagatgat cgatgaagga ctaagccctg gcaacattgt ttataactcc ctaattcatg   1560
gtttgtgcac ctgtaacaaa tgggagaggg ctgaagagtt aattcttgaa atgttggatc   1620
gaggcatctg tctgaacact attttcttta attcaataat tgacagtcat tgcaaagaag   1680
ggagggttat agaatctgaa aaactctttg agctgatggt acgtattggt gtgaagccca   1740
atgtcattac ctacaatact cttatcaatg gatattgctt ggcaggtaag atggatgaag   1800
caatgaagtt actttctggc atggtctcag ttgggttgaa acctaatact gttacttata   1860
gcactttgat taatggctac tgcaaaatta gtaggatgga agacgcgtta gttcttttta   1920
aggagatgga gagcagtggt gttagtcctg atattattac gtataacata attctgcaag   1980
gtttatttca aaccagaaga actgctgctg caaaagaact ctatgttagg attaccgaaa   2040
gtggaacgca gattgaactt agcacataca acataatcct tcatggactt tgcaaaaaca   2100
aactcactga tgatgcactt cagatgtttc agaacctatg tttgatggat ttgaagcttg   2160
aggctaggac tttcaacatt atgattgatg cattgcttaa agttggcaga aatgatgaag   2220
ccaaggattt gtttgttgct ttctcgtcta acggtttagt gccgaattat tggacgtaca   2280
```

-continued

```
ggttgatggc tgaaaatatt ataggacagg ggttgctaga agaattggat caactctttc   2340
tttcaatgga ggacaatggc tgtactgttg actctggcat gctaaatttc attgttaggg   2400
aactgttgca gagaggtgag ataaccaggg ctggcactta cctttccatg attgatgaga   2460
agcacttttc cctcgaagca tccactgctt ccttgtttat agatcttttg tctgggggaa   2520
aatatcaaga atattatagg tttctccctg aaaaatacaa gtcctttata gaatctttga   2580
gctgctgaag cattttgcag ctttgaaatt ctgtgttgga attcttttct cctacagtcc   2640
tattagagga gggatcttct ctgtatgtgt aaatagcgag tttgaatgct agtggaagct   2700
cctttgacca tgttttgttg tgcgagcatt taagagagtg aagagaatgc ttctttggtg   2760
ctgttctggt atggaaggat ccacagataa aattcagtag tggccaaggt tggtgacggt   2820
gatggtggca tgtgatcccc cagatcttca gtgacccaga gaggagggga cggcgcgtgg   2880
tgagctacaa ggcatactca gtggagggca agatcaaggc ctcccgtccg taggggactc   2940
cgctgcatca aggccaactg ctccgaactg atcaatttct ggtgcagaca ggtgcttgcg   3000
gtcaggttaa agaagttggc aaaaatgctt ctgaagaaag gttaattgtt gtttcatctc   3060
aggagattcc agatgatcca gtgtctccaa caattgaggc gcttattttg ctccatagta   3120
aagtaagtac acttgctgag aaccaccagt tgacaacacg gcttgttgta ccatcaaaca   3180
aagttggttg tattcttggg gaaggtggaa aggtaattac tgaaatgaga agacggactg   3240
gggctgaaat ccgagtctac tcaaaagcag ataaacctaa gtacctgtct tttgatgagg   3300
agcttgtgca ggttgctggg cttccagcta ttgaaagagg agccctgaca gagattgctt   3360
cgaggctttg aactaggaca ctcagagatg gaagttcttc caataatccg acaccttttg   3420
cccctgttga tggtcctcct gttgatatct tgcctaacaa ggaattcatg ctatatggac   3480
gatctgctaa tagtccccca tatggagggc ctgctaatga tccaccatat ggaagacctg   3540
ccattgatcc accatatgga agaccaatat ccacaatatg gaagacctgc caatgatcca   3600
ccatatagaa gacctgtcaa tgatacatca tattgagggt tgaacaatga tgggcctcgt   3660
gatcaggccc ggtcctgagg ggggtcgaat ggggcgatcg ctccgggccc cccgattccc   3720
agggccccca cctatctgtg caacgagtag tagcgatctt ccagcgcgca acgtgaggcg   3780
atgtttctcc gtgatttcgc cggcctgcaa ctgcgagatc gcgagtataa cgatcagccg   3840
atcgatctca tctgccgact gccatgctga tgccacacgc aagcgcagca tatcagcctt   3900
atcttggttg atcggcatgc tggacgagca catctgttgt cgcatcaact gctgactgct   3960
atatatgtgc tggtgctgaa tcgatcgatt gtcgtcacgg aagtgaagaa caaccacggc   4020
actgctgcct gctgggctct agccgccatc agctgcggag ctgatccatg gacgtgagga   4080
ttaccgaaga ctgtcaggtc tcactgggta tccaggtggc tctgtcgaat tgtggattcc   4140
aaatagttaa ctggagtctg tcattggtgt tggtggtgtc aatctagctg agatccgtct   4200
ggtatagcgt aagagaaaca tcatgcacta tccccagtca taaccatgcc ccaatggcca   4260
ccaatagttt tcctcgtgaa aatctcccct tgatcccaga tctctggtgc gagagtgaag   4320
ttgcacgaag cccatcctgg ttcttccgag tccattgtgg agatccaggg cattccggat   4380
caagtgaaag ccgcacagag ccttctgcaa ggcttcatcg gcgcaagcag caacagcagg   4440
caggcgcccc agtcctctcg catggcccat tatttttagt aagctggagg acattcgcaa   4500
caggggggtc agtggtcact gcaaagctga gtttgttctt cagttcaact gcagaaaatt   4560
gcagatcggt tgccgtagtt gctagaacgg tacatagttg ccacctaact gtagcgagtg   4620
gcataactta ttgtgtgtta ctgcccaatg ttgtctctcc ttgtgttcat ggattcagac   4680
```

ttgtgattgt agtatttctg gatcagactg gagtaaaaga aaaaaaaaaa ggaagacatg 4740
ggtttaacag taagctcaaa acgttgacag tagtaaaata aaaggggttt gttcacttta 4800
aaaaaaaaaa aaaaaaaaaa a 4821

<210> SEQ ID NO 45
<211> LENGTH: 5005
<212> TYPE: DNA
<213> ORGANISM: rice

<400> SEQUENCE: 45
gagatcgatc gcgatctccc tgccccgacg tcgccggccg atctctcatt ctctccacgc 60
cctgctcgtc gccgatctcc tacaccatcc ctgccatctc ctccttcccc tcccctctat 120
cctccactgg tgccgcccac ctctccgtat aagacaaact gcgttgcggc gttggtttcc 180
gccggcgctg ctgctgcacc tgtcagctag ggcgggcatg gcgcgccgcg ccgcttcccg 240
cgctgttggc gcccttcgct cggacggctc gatccaaggg cgaggaggcc gcgcgggggg 300
cagtggcgcc gaggacgcac gccacgtgtt cgacgaattg ctccgccgtg gcaggggcgc 360
ctcgatctac ggcttgaacc gcgccctcgc cgacgtcgcg cgtgacagcc ccgcggccgc 420
cgtgtcccgc tacaaccgca tggcccgagc cggcgccgac gaggtaactc ccgacttgtg 480
cacctacggc attctcatcg gttgctgctg ccgcgcgggc cgcttggacc tcggtttcgc 540
ggccttgggc aatgtcatta agaagggatt tagagtggac gccatcgcct tcactcctct 600
gctcaagggc ctctgtgccg acaagaggac gagcgacgca atggacatag tgctccgcag 660
aatgaccgag ctcggctgca taccaaatgt cttctcctac aatattcttc tcaaggggct 720
gtgtgatgag aacagaagcc aagaagctct cgagctgctg cacatgatgg ctgatgatcg 780
aggaggaggt agcccacctg atgtggtgtc gtataccact gtcatcaatg gcttcttcaa 840
agagggggat tcagacaaag cttacagtac ataccatgaa atgctggacc gggggatttt 900
acctgatgtt gtgacctaca actctattat tgctgcgtta tgcaaggctc aagctatgga 960
caaagccatg gaggtactta acaccatggt taagaatggt gtcatgcctg attgcatgac 1020
atataatagt attctgcatg gatattgctc ttcagggcag ccgaaagagg ctattggatt 1080
tctcaaaaag atgcgcagtg atggtgtcga accagatgtt gttacttata gcttgctcat 1140
ggattatctt tgcaagaacg gaagatgcat ggaagctaga aagattttcg attctatgac 1200
caagaggggc ctaaagcctg aaattactac ctatggtacc ctgcttcagg ggtatgctac 1260
caaaggagcc cttgttgaga tgcatggtct cttggatttg atggtacgaa acggtatcca 1320
ccctgatcat tatgttttca gcattctaat atgtgcatac gctaaacaag ggaaagtaga 1380
tcaggcaatg cttgtgttca gcaaaatgag gcagcaagga ttgaatccga atgcagtgac 1440
gtatggagca gttataggca tactttgcaa gtcaggcaga gtagaagatg ctatgcttta 1500
ttttgagcag atgatcgatg aaggactaag ccctggcaac attgtttata actccctaat 1560
tcatggtttg tgcacctgta acaaatggga gagggctgaa gagttaattc ttgaaatgtt 1620
ggatcgaggc atctgtctga acactatttt ctttaattca ataattgaca gtcattgcaa 1680
agaagggagg gttatagaat ctgaaaaact ctttgagctg atggtacgta ttggtgtgaa 1740
gcccaatgtc attacctaca atactcttat caatggatat tgcttggcag gtaagatgga 1800
tgaagcaatg aagttacttt ctggcatggt ctcagttggg ttgaaaccta atactgttac 1860
ttatagcact ttgattaatg gctactgcaa aattagtagg atggaagacg cgttagttct 1920
ttttaaggag atggagagca gtggtgttag tcctgatatt attacgtata acataattct 1980

```
gcaaggttta tttcaaacca gaagaactgc tgctgcaaaa gaactctatg ttaggattac   2040
cgaaagtgga acgcagattg aacttagcac atacaacata atccttcatg gactttgcaa   2100
aaacaaactc actgatgatg cacttcagat gtttcagaac ctatgtttga tggatttgaa   2160
gcttgaggct aggactttca acattatgat tgatgcattg cttaaagttg gcagaaatga   2220
tgaagccaag gatttgtttg ttgctttctc gtctaacggt ttagtgccga attattggac   2280
gtacaggttg atggctgaaa atattatagg acaggggttg ctagaagaat tggatcaact   2340
ctttctttca atggaggaca atggctgtac tgttgactct ggcatgctaa atttcattgt   2400
tagggaactg ttgcagagag gtgagataac cagggctggc acttaccttt ccatgattga   2460
tgagaagcac ttttccctcg aagcatccac tgcttccttg tttatagatc ttttgtctgg   2520
gggaaaatat caagaatatt ataggtttct ccctgaaaaa tacaagtcct ttatagaatc   2580
tttgagctgc tgaagcattt tgcagctttg aaattctgtg ttggaattct tttctcctac   2640
agtcctatta gaggagggat cttctctgta tgtgtaaata gcgagtttga atgctagtgg   2700
aagctccttt gaccatgttt tgttgtgcga gcatttaaga gagtgaagag aatgcttctt   2760
tggtgctgtt ctggtatgga aggatccaca gataaaattc aggagaatat agtagtggcc   2820
aaggttggtg acggtgatgg tggcatgtga tcccccagat cttcagtgac ccagagagga   2880
ggggacggcg cgtggtgagc tacaaggcat actcagtgga gggcaagatc aaggcctccc   2940
gtccgtaggg gactccgctg catcaaggcc aactgctccg aactgatcaa tttctggtgc   3000
agacaggtgc ttgcggtcag gttaaagaag ttggcaaaaa tgcttctgaa gaaaggttaa   3060
ttgttgtttc atctcaggag attccagatg atccagtgtc tccaacaatt gaggcgctta   3120
ttttgctcca tagtaaagta agtacacttg ctgagaacca ccagttgaca acacggcttg   3180
ttgtaccatc aaacaaagtt ggttgtattc ttggggaagg tggaaaggta attactgaaa   3240
tgagaagacg gactggggct gaaatccgag tctactcaaa agcagataaa cctaagtacc   3300
tgtcttttga tgaggagctt gtgcaggttg ctgggcttcc agctattgaa agaggagccc   3360
tgacagagat tgcttcgagg ctttgaacta ggacactcag agatggaagt tcttccaata   3420
atccgacacc ttttgcccct gttgatggtc ctcctgttga tatcttgcct aacaaggaat   3480
tcatgctata tggacgatct gctaatagtc cccatatgg agggcctgct aatgatccac   3540
catatggaag acctgccatt gatccaccat atggaagacc aatatccaca atatggaaga   3600
cctgccaatg atccaccata tagaagacct gtcaatgata catcatattg agggttgaac   3660
aatgatgggc ctcgtgatca ggcccggtcc tgaggggggt cgaatggggc gatcgctccg   3720
ggccccccga ttcccagggc ccccacctat ctgtgcaacg agtagtagcg atcttccagc   3780
gcgcaacgtg aggcgatgtt tctccgtgat ttcgccggcc tgcaactgcg agatcgcgag   3840
tataacgatc agccgatcga tctcatctgc cgactgccat gctgatgcca cacgcaagcg   3900
cagcatatca gccttatctt ggttgatcgg catgctggac gagcacatct gttgtcgcat   3960
caactgctga ctgctatata tgtgctggtg ctgaatcgat cgattgtcgt cacggaagtg   4020
aagaacaacc acggcactgc tgcctgctgg gctctagccg ccatcagctg cggagctgat   4080
ccatggacgt gaggattacc gaagactgtc aggtctcact gggtatccag gtggctctgt   4140
cgaattgtgg attccaaata gttaactgga gtctgtcatt ggtgttggtg gtgtcaatct   4200
agctgagatc cgtctggtat agcgtaagag aaacatcatg cactatcccc agtcataacc   4260
atgccccaat ggccaccaat agttttcctc gtgaaaatct cccettgatc ccagatctct   4320
ggtgcgagag tgaagttgca cgaagcccat cctggttctt ccgagtccat tgtggagatc   4380
```

```
cagggcattc cggatcaagt gaaagccgca cagagccttc tgcaaggctt catcggcgca   4440
agcagcaaca gcaggcaggc gccccagtcc tctcgcatgg cccattattt ttagtaagct   4500
ggaggacatt cgcaacaggg gggtcagtgg tcactgcaaa gctgagtttg ttcttcagtt   4560
caactgcaga aaattgcaga tcggttgccg tagttgctag aacggtacat agttgccacc   4620
taactgtagc gagtggcata acttattgtg tgttactgcc caatgttgtc tctccttgtg   4680
ttcatggatt cagacttgtg attgtagtat ttctggatca gactggagta aaagaaaaaa   4740
aaaaaggaag acatgggttt aacagtaagc tcaaaacgtt gacagtagta aaataaaagg   4800
ggtttgttca ctttatttcc aatatcaacc ttaccaacat ttggcgttga atcatttata   4860
ccacatcgct tgtgcagctg aatttggggc tgtttaaaag atggtctctt ggattgctaa   4920
ttgcctcgcg gcaagcgtgg taccttgtac aatataaata taattataac tatttaattt   4980
cataaaaaaa aaaaaaaaaa aaaaa                                         5005
```

<210> SEQ ID NO 46
<211> LENGTH: 4978
<212> TYPE: DNA
<213> ORGANISM: rice

<400> SEQUENCE: 46

```
gcgatctccc tgccccgacg tcgccggccg atctctcatt ctctccacgc cctgctcgtc     60
gccgatctcc tacaccatcc ctgccatctc ctccttcccc tcccctctat cctccactgg    120
tgccgcccac ctctccgtat aagacaaact gcgttgcggc gttggtttcc gccggcgctg    180
ctgctgcacc tgtcagctag ggcgggcatg gcgcgccgcg ccgcttcccg cgctgttggc    240
gcccttcgct cggacggctc gatccaaggg cgaggaggcc gcgcgggggg cagtggcgcc    300
gaggacgcac gccacgtgtt cgacgaattg ctccgccgtg gcaggggcgc ctcgatctac    360
ggcttgaacc gcgccctcgc cgacgtcgcg cgtgacagcc ccgcggccgc cgtgtcccgc    420
tacaaccgca tggcccgagc cggcgccgac gaggtaactc ccgacttgtg cacctacggc    480
attctcatcg gttgctgctg ccgcgcgggc cgcttggacc tcggtttcgc ggccttgggc    540
aatgtcatta agaagggatt tagagtggac gccatcgcct tcactcctct gctcaagggc    600
ctctgtgccg acaagaggac gagcgacgca atggacatag tgctccgcag aatgaccgag    660
ctcggctgca taccaaatgt cttctcctac aatattcttc tcaaggggct gtgtgatgag    720
aacagaagcc aagaagctct cgagctgctg cacatgatgg ctgatgatcg aggaggaggt    780
agcccacctg atgtggtgtc gtataccact gtcatcaatg gcttcttcaa agagggggat    840
tcagacaaag cttacagtac ataccatgaa atgctggacc gggggatttt acctgatgtt    900
gtgacctaca actctattat tgctgcgtta tgcaaggctc aagctatgga caaagccatg    960
gaggtactta acaccatggt taagaatggt gtcatgcctg attgcatgac atataatagt   1020
attctgcatg gatattgctc ttcagggcag ccgaaagagg ctattggatt tctcaaaaag   1080
atgcgcagtg atggtgtcga accagatgtt gttacttata gcttgctcat ggattatctt   1140
tgcaagaacg gaagatgcat ggaagctaga aagatttttcg attctatgac caagaggggc  1200
ctaaagcctg aaattactac ctatggtacc ctgcttcagg ggtatgctac caaaggagcc   1260
cttgttgaga tgcatggtct cttggatttg atggtacgaa acggtatcca ccctgatcat   1320
tatgttttca gcattctaat atgtgcatac gctaaacaag ggaaagtaga tcaggcaatg   1380
cttgtgttca gcaaaatgag gcagcaagga ttgaatccga atgcagtgac gtatggagca   1440
gttataggca tactttgcaa gtcaggcaga gtagaagatg ctatgcttta ttttgagcag   1500
```

-continued

```
atgatcgatg aaggactaag ccctggcaac attgtttata actccctaat tcatggtttg   1560
tgcacctgta acaaatggga gagggctgaa gagttaattc ttgaaatgtt ggatcgaggc   1620
atctgtctga acactatttt ctttaattca ataattgaca gtcattgcaa agaagggagg   1680
gttatagaat ctgaaaaact ctttgagctg atggtacgta ttggtgtgaa gcccaatgtc   1740
attacctaca atactcttat caatggatat tgcttggcag gtaagatgga tgaagcaatg   1800
aagttacttt ctggcatggt ctcagttggg ttgaaaccta atactgttac ttatagcact   1860
ttgattaatg gctactgcaa aattagtagg atggaagacg cgttagttct ttttaaggag   1920
atggagagca gtggtgttag tcctgatatt attacgtata acataattct gcaaggttta   1980
tttcaaacca gaagaactgc tgctgcaaaa gaactctatg ttaggattac cgaaagtgga   2040
acgcagattg aacttagcac atacaacata atccttcatg gactttgcaa aaacaaactc   2100
actgatgatg cacttcagat gtttcagaac ctatgtttga tggatttgaa gcttgaggct   2160
aggactttca acattatgat tgatgcattg cttaaagttg gcagaaatga tgaagccaag   2220
gatttgtttg ttgctttctc gtctaacggt ttagtgccga attattggac gtacaggttg   2280
atggctgaaa atattatagg acaggggttg ctagaagaat tggatcaact ctttctttca   2340
atggaggaca atggctgtac tgttgactct ggcatgctaa atttcattgt tagggaactg   2400
ttgcagagag gtgagataac cagggctggc acttaccttt ccatgattga tgagaagcac   2460
ttttccctcg aagcatccac tgcttccttg tttatagatc ttttgtctgg gggaaaatat   2520
caagaatatt ataggtttct ccctgaaaaa tacaagtcct ttatagaatc tttgagctgc   2580
tgaagcattt tgcagctttg aaattctgtg ttggaattct tttctcctac agtcctatta   2640
gaggagggat cttctctgta tgtgtaaata gcgagtttga atgctagtgg aagctccttt   2700
gaccatgttt tgttgtgcga gcatttaaga gagtgaagag aatgcttctt tggtgctgtt   2760
ctggtatgga aggatccaca gataaaattc aggttctact gcttctctgc ttgtaatttt   2820
catgaagctg cagtgaatac cttgttgacc acttgatctg ttgctttgaa ggagaatata   2880
gtagtggcca aggttggtga cggtgatggt ggcatgtgat cccccagatc ttcagtgacc   2940
cagagaggag gggacggcgc gtggtgagct acaaggcata ctcagtggag ggcaagatca   3000
aggcctcccg tccgtagggg actccgctgc atcaaggcca actgctccga actgatcaat   3060
ttctggtgca gacaggtgct tgcggtcagg ttaaagaagt tggcaaaaat gcttctgaag   3120
aaaggttaat tgttgtttca tctcaggaga ttccagatga tccagtgtct ccaacaattg   3180
aggcgcttat tttgctccat agtaaagtaa gtacacttgc tgagaaccac cagttgacaa   3240
cacggcttgt tgtaccatca aacaaagttg gttgtattct tggggaaggt ggaaaggtaa   3300
ttactgaaat gagaagacgg actggggctg aaatccgagt ctactcaaaa gcagataaac   3360
ctaagtacct gtcttttgat gaggagcttg tgcaggttgc tgggcttcca gctattgaaa   3420
gaggagccct gacagagatt gcttcgaggc tttgaactag gacactcaga gatggaagtt   3480
cttccaataa tccgacacct tttgcccctg ttgatggtcc tcctgttgat atcttgccta   3540
acaaggaatt catgctatat ggacgatctg ctaatagtcc cccatatgga gggcctgcta   3600
atgatccacc atatggaaga cctgccattg atccaccata tggaagacca atatccacaa   3660
tatggaagac ctgccaatga tccaccatat agaagacctg tcaatgatac atcatattga   3720
gggttgaaca atgatgggcc tcgtgatcag gcccggtcct gaggggggtc gaatggggcg   3780
atcgctccgg gccccccgat tcccagggcc cccacctatc tgtgcaacga gtagtagcga   3840
tcttccagcg cgcaacgtga ggcgatgttt ctccgtgatt tcgccggcct gcaactgcga   3900
```

```
gatcgcgagt ataacgatca gccgatcgat ctcatctgcc gactgccatg ctgatgccac   3960
acgcaagcgc agcatatcag ccttatcttg gttgatcggc atgctggacg agcacatctg   4020
ttgtcgcatc aactgctgac tgctatatat gtgctggtgc tgaatcgatc gattgtcgtc   4080
acggaagtga agaacaacca cggcactgct gcctgctggg ctctagccgc catcagtaag   4140
ctgcggagct gatccatgga cgtgaggatt accgaagact gtcaggtctc actgggtatc   4200
caggtggctc tgtcgaattg tggattccaa atagttaact ggagtctgtc attggtgttg   4260
gtggtgtcaa tctagctgag atccgtctgg tatagcgtaa gagaaacatc atgcactatc   4320
cccagtcata accatgcccc aatggccacc aatagttttc ctcgtgaaaa tctccccttg   4380
atcccagatc tctggtgcga gagtgaagtt gcacgaagcc catcctggtt cttccgagtc   4440
cattgtggag atccagggca ttccggatca agtgaaagcc gcacagagcc ttctgcaagg   4500
cttcatcggc gcaagcagca acagcaggca ggcgccccag tcctctcgca tggcccatta   4560
tttttagtaa gctggaggac attcgcaaca ggggggtcag tggtcactgc aaagctgagt   4620
ttgttcttca gttcaactgc agaaaattgc agatcggttg ccgtagttgc tagaacggta   4680
catagttgcc acctaactgt agcgagtggc ataacttatt gtgtgttact gcccaatgtt   4740
gtctctcctt gtgttcatgg attcagactt gtgattgtag tatttctgga tcagactgga   4800
gtaaaagaaa aaaaaaaagg aagacatggg tttaacagta agctcaaaac gttgacagta   4860
gtaaaataaa aggggtttgt tcactttaaa aaaaaaaaaa aaaaaaaaaa aaaaaaaaaa   4920
aaaaaaaaaa aaaaaaaaaa aaaaaaaaaa aaaaaaaaaa aaaaaaaaaa aaaaaaaa     4978
```

<210> SEQ ID NO 47
<211> LENGTH: 4722
<212> TYPE: DNA
<213> ORGANISM: rice

<400> SEQUENCE: 47

```
cgccgatctc ctacaccatc cctgccatct cctccttccc ctcccctcta tcctccactg     60
gtgccgccca cctctccgta taagacaaac tgcgttgcgg cgttggtttc cgccggcgct    120
gctgctgcac ctgtcagcta gggcgggcat ggcgcgccgc gccgcttccc gcgctgttgg    180
cgcccttcgc tcggacggct cgatccaagg gcgaggaggc cgcgcggggg gcagtggcgc    240
cgaggacgca cgccacgtgt tcgacgaatt gctccgccgt ggcaggggcg cctcgatcta    300
cggcttgaac cgcgccctcg ccgacgtcgc gcgtgacagc cccgcggccg ccgtgtcccg    360
ctacaaccgc atggcccgag ccggcgccga cgaggtaact cccgacttgt gcacctacgg    420
cattctcatc ggttgctgct gccgcgcggg ccgcttggac ctcggtttcg cggccttggg    480
caatgtcatt aagaagggat ttagagtgga cgccatcgcc ttcactcctc tgctcaaggg    540
cctctgtgcc gacaagagga cgagcgacgc aatggacata gtgctccgca gaatgaccga    600
gctcggctgc ataccaaatg tcttctccta caatattctt ctcaaggggc tgtgtgatga    660
gaacagaagc caagaagctc tcgagctgct gcacatgatg gctgatgatc gaggaggagg    720
tagcccacct gatgtggtgt cgtataccac tgtcatcaat ggcttcttca aagaggggga    780
ttcagacaaa gcttacagta cataccatga aatgctggac cgggggattt tacctgatgt    840
tgtgacctac aactctatta ttgctgcgtt atgcaaggct caagctatgg acaaagccat    900
ggaggtactt aacaccatgg ttaagaatgg tgtcatgcct gattgcatga catataatag    960
tattctgcat ggatattgct cttcagggca gccgaaagag gctattggat ttctcaaaaa   1020
gatgcgcagt gatggtgtcg aaccagatgt tgttacttat agcttgctca tggattatct   1080
```

-continued ttgcaagaac ggaagatgca tggaagctag aaagattttc gattctatga ccaagagggg 1140
cctaaagcct gaaattacta cctatggtac cctgcttcag ggtatgcta ccaaaggagc 1200
ccttgttgag atgcatggtc tcttggattt gatggtacga aacggtatcc accctgatca 1260
ttatgttttc agcattctaa tatgtgcata cgctaaacaa gggaaagtag atcaggcaat 1320
gcttgtgttc agcaaaatga ggcagcaagg attgaatccg aatgcagtga cgtatggagc 1380
agttataggc atactttgca agtcaggcag agtagaagat gctatgcttt attttgagca 1440
gatgatcgat gaaggactaa gccctggcaa cattgtttat aactccctaa ttcatggttt 1500
gtgcacctgt aacaaatggg agagggctga agagttaatt cttgaaatgt tggatcgagg 1560
catctgtctg aacactattt tctttaattc aataattgac agtcattgca aagaagggag 1620
ggttatagaa tctgaaaaac tctttgagct gatggtacgt attggtgtga agcccaatgt 1680
cattacctac aatactctta tcaatggata ttgcttggca ggtaagatgg atgaagcaat 1740
gaagttactt tctggcatgg tctcagttgg gttgaaacct aatactgtta cttatagcac 1800
tttgattaat ggctactgca aaattagtag gatggaagac gcgttagttc tttttaagga 1860
gatggagagc agtggtgtta gtcctgatat tattacgtat aacataattc tgcaaggttt 1920
atttcaaacc agaagaactg ctgctgcaaa agaactctat gttaggatta ccgaaagtgg 1980
aacgcagatt gaacttagca catacaacat aatccttcat ggactttgca aaaacaaact 2040
cactgatgat gcacttcaga tgtttcagaa cctatgtttg atggatttga agcttgaggc 2100
taggactttc aacattatga ttgatgcatt gcttaaagtt ggcagaaatg atgaagccaa 2160
ggatttgttt gttgctttct cgtctaacgg tttagtgccg aattattgga cgtacaggtt 2220
gatggctgaa aatattatag gacaggggtt gctagaagaa ttggatcaac tctttctttc 2280
aatggaggac aatggctgta ctgttgactc tggcatgcta aatttcattg ttagggaact 2340
gttgcagaga ggtgagataa ccagggctgg cacttacctt tccatgattg atgagaagca 2400
cttttccctc gaagcatcca ctgcttcctt gtttatagat cttttgtctg gggaaaata 2460
tcaagaatat tataggtttc tccctgaaaa atacaagtcc tttatagaat ctttgagctg 2520
ctgaagcatt ttgcagcttt gaaattctgt gttggaattc ttttctccta cagtcctatt 2580
agaggaggga tcttctctgt atgtgtaaat agcgagtttg aatgctagtg gaagctcctt 2640
tgaccatgtt ttgttgtgcg agcatttaag agagtgaaga gaatgcttct ttggtgctgt 2700
tctggtatgg aaggatccac agataaaatt caggttctac tgcttctctg cttgtaattt 2760
tcatgaagct gcagtgaata ccttgttgac cacttgatct gttgctttga aggagaatat 2820
agtagtggcc aaggttggtg acggtgatgg tggcatgtga tcccccagat cttcagtgac 2880
ccagagagga ggggacggcg cgtggtgagc tacaaggcat actcagtgga gggcaagatc 2940
aaggcctccc gtccgtaggg gactccgctg catcaaggcc aactgctccg aactgatcaa 3000
tttctggtgc agacaggtgc ttgcggtcag gttaaagaag ttggcaaaaa tgcttctgaa 3060
gaaaggttaa ttgttgtttc atctcaggag attccagatg atccagtgtc tccaacaatt 3120
gaggcgctta ttttgctcca tagtaaagtg gaaaggtaat tactgaaatg agaagacgga 3180
ctggggctga aatccgagtc tactcaaaag cagataaacc taagtacctg tcttttgatg 3240
aggagcttgt gcaggttgct gggcttccag ctattgaaag aggagccctg acagagattg 3300
cttcgaggct ttgaactagg acactcagag atggaagttc ttccaataat ccgacacctt 3360
ttgcccctgt tgatggtcct cctgttgata tcttgcctaa caaggaattc atgctatatg 3420
gacgatctgc taatagtccc ccatatggag ggcctgctaa tgatccacca tatggaagac 3480
ctgccattga tccaccatat ggaagaccaa tatccacaat atggaagacc tgccaatgat 3540
ccaccatata gaagacctgt caatgataca tcatattgag ggttgaacaa tgatgggcct 3600
cgtgatcagg cccggtcctg aggggggtcg aatggggcga tcgctccggg ccccccgatt 3660
cccagggccc ccacctatct gtgcaacgag tagtagcgat cttccagcgc gcaacgtgag 3720
gcgatgtttc tccgtgattt cgccggcctg caactgcgag atcgcgagta taacgatcag 3780
ccgatcgatc tcatctgccg actgccatgc tgatgccaca cgcaagcgca gcatatcagc 3840
cttatcttgg ttgatcggca tgctggacga gcacatctgt tgtcgcatca actgctgact 3900
gctatatatg tgctggtgct gaatcgatcg attgtcgtca cggaagtgaa gaacaaccac 3960
ggcactgctg cctgctgggc tctagccgcc atcagctgcg gagctgatcc atggacgtga 4020
ggattaccga agactgtcag gtctcactgg gtatccaggt ggctctgtcg aattgtggat 4080
tccaaatagt taactggagt ctgtcattgg tgttggtggt gtcaatctag ctgagatccg 4140
tctggtatag cgtaagagaa acatcatgca ctatccccag tcataaccat gccccaatgg 4200
ccaccaatag ttttcctcgt gaaaatctcc ccttgatccc agatctctgg tgcgagagtg 4260
aagttgcacg aagcccatcc tggttcttcc gagtccattg tggagatcca gggcattccg 4320
gatcaagtga aagccgcaca gagccttctg caaggcttca tcggcgcaag cagcaacagc 4380
aggcaggcgc cccagtcctc tcgcatggcc cattattttt agtaagctgg aggacattcg 4440
caacaggggg gtcagtggtc actgcaaagc tgagtttgtt cttcagttca actgcagaaa 4500
attgcagatc ggttgccgta gttgctagaa cggtacatag ttgccaccta actgtagcga 4560
gtggcataac ttattgtgtg ttactgccca atgttgtctc tccttgtgtt catggattca 4620
gacttgtgat tgtagtattt ctggatcaga ctggagtaaa agaaaaaaaa aaaggaagac 4680
atgggtttaa cagtaaaaaa aaaaaaaaaa aaaaaaaaaa aa 4722

<210> SEQ ID NO 48
<211> LENGTH: 6164
<212> TYPE: DNA
<213> ORGANISM: rice

<400> SEQUENCE: 48
cgcagaagag atcgatcgcg atctccctgc cccgacgtcg ccggccgatc tctcattctc 60
tccacgccct gctcgtcgcc gatctcctac accatccctg ccatctcctc cttcccctcc 120
cctctatcct ccactggtgc cgcccacctc tccgtataag acaaactgcg ttgcggcgtt 180
ggtttccgcc ggcgctgctg ctgcacctgt cagctagggc gggcatggcg cgccgcgccg 240
cttcccgcgc tgttggcgcc cttcgctcgg acggctcgat ccaagggcga ggaggccgcg 300
cggggggcag tggcgccgag gacgcacgcc acgtgttcga cgaattgctc cgccgtggca 360
ggggcgcctc gatctacggc ttgaaccgcg ccctcgccga cgtcgcgcgt gacagccccg 420
cggccgccgt gtcccgctac aaccgcatgg cccgagccgg cgccgacgag gtaactcccg 480
acttgtgcac ctacggcatt ctcatcggtt gctgctgccg cgcgggccgc ttggacctcg 540
gtttcgcggc cttgggcaat gtcattaaga agggatttag agtggacgcc atcgccttca 600
ctcctctgct caagggcctc tgtgccgaca agaggacgag cgacgcaatg gacatagtgc 660
tccgcagaat gaccgagctc ggctgcatac caaatgtctt ctcctacaat attcttctca 720
aggggctgtg tgatgagaac agaagccaag aagctctcga gctgctgcac atgatggctg 780
atgatcgagg aggaggtagc ccacctgatg tggtgtcgta taccactgtc atcaatggct 840
tcttcaaaga gggggattca gacaaagctt acagtacata ccatgaaatg ctggaccggg 900

```
ggattttacc tgatgttgtg acctacaact ctattattgc tgcgttatgc aaggctcaag    960
ctatggacaa agccatggag gtacttaaca ccatggttaa gaatggtgtc atgcctgatt   1020
gcatgacata taatagtatt ctgcatggat attgctcttc agggcagccg aaagaggcta   1080
ttggatttct caaaaagatg cgcagtgatg gtgtcgaacc agatgttgtt acttatagct   1140
tgctcatgga ttatctttgc aagaacggaa gatgcatgga agctagaaag attttcgatt   1200
ctatgaccaa gaggggccta aagcctgaaa ttactaccta tggtaccctg cttcaggggt   1260
atgctaccaa aggagccctt gttgagatgc atggtctctt ggatttgatg gtacgaaacg   1320
gtatccaccc tgatcattat gttttcagca ttctaatatg tgcatacgct aaacaaggga   1380
aagtagatca ggcaatgctt gtgttcagca aaatgaggca gcaaggattg aatccgaatg   1440
cagtgacgta tggagcagtt ataggcatac tttgcaagtc aggcagagta gaagatgcta   1500
tgctttattt tgagcagatg atcgatgaag gactaagccc tggcaacatt gtttataact   1560
ccctaattca tggtttgtgc acctgtaaca aatgggagag ggctgaagag ttaattcttg   1620
aaatgttgga tcgaggcatc tgtctgaaca ctattttctt taattcaata attgacagtc   1680
attgcaaaga agggagggtt atagaatctg aaaaactctt tgagctgatg gtacgtattg   1740
gtgtgaagcc caatgtcatt acctacaata ctcttatcaa tggatattgc ttggcaggta   1800
agatggatga agcaatgaag ttactttctg gcatggtctc agttgggttg aaacctaata   1860
ctgttactta tagcactttg attaatggct actgcaaaat tagtaggatg gaagacgcgt   1920
tagttctttt taaggagatg gagagcagtg gtgttagtcc tgatattatt acgtataaca   1980
taattctgca aggtttattt caaaccagaa gaactgctgc tgcaaaagaa ctctatgtta   2040
ggattaccga aagtggaacg cagattgaac ttagcacata caacataatc cttcatggac   2100
tttgcaaaaa caaactcact gatgatgcac ttcagatgtt tcagaaccta tgtttgatgg   2160
atttgaagct tgaggctagg actttcaaca ttatgattga tgcattgctt aaagttggca   2220
gaaatgatga agccaaggat ttgtttgttg ctttctcgtc taacggttta gtgccgaatt   2280
attggacgta caggttgatg gctgaaaata ttataggaca ggggttgcta gaagaattgg   2340
atcaactctt tctttcaatg gaggacaatg gctgtactgt tgactctggc atgctaaatt   2400
tcattgttag ggaactgttg cagagaggtg agataaccag ggctggcact tacctttcca   2460
tgattgatga gaagcacttt tccctcgaag catccactgc ttccttgttt atagatcttt   2520
tgtctggggg aaaatatcaa gaatattata ggtttctccc tgaaaaatac aagtccttta   2580
tagaatcttt gagctgctga agcattttgc agctttgaaa ttctgtgttg gaattctttt   2640
ctcctacagt cctattagag gagggatctt ctctgtatgt gtaaatagcg aggtatgtat   2700
gccacctctc cgaattattt ttactgtggt tcctagactg taaacaagca attatgttat   2760
gctgttgatg ccagaaaaaa cataaaagtt tgtcgttatc tctactaacg gatcataaag   2820
ggatttgtga ctggagtttc aaacttaatg tgtctaggca gtaattttga cattagatcc   2880
aaaacaattt atagggtttc attaaatttc atctatgtgt actgtttagg tgttgaatag   2940
tttgacttgt tttttaactg aacaaaagat atgtctgaag ctttgttctt taccaaatgc   3000
agtactgatc atcacaatat attttttatg gaacaagatt ggattgtata gaatggtttc   3060
tgatctgatt atcttatctc aacgtattat tatgcacatg tactaatcat gaaatatctg   3120
atggaatgat gtttctattt acctgtgtga ggcagcaagg agtgagatgg ataacaccac   3180
atactccctc tgtcccagaa tataagaagt tttagagttg gacacgatta ttaagaaagt   3240
aggtagaagt gagtagtgga gggttgtgat tgcatgagta gtggaggtag gtgggaaaag   3300
```

```
tgaatggtgg agggttgtga ttggttggga agagaatgtt ggtagagaag ttgttatatt   3360
ttggggagta cattattatt ctagaacaat actgttgtgc tcaagaagcg ttccaaagat   3420
gtttcacaac ctgtgctcga tgggttttga gcttaatcct gggacattca gtatcatgat   3480
ctgtctcatt cttaaacatg gaataaagga tgacagcatg atttctttgt ctctataatc   3540
ttttggctac ccacagataa tagctgtaaa tctatactac tttaaaagga gtagtggtgg   3600
tggtgagtgg tgaatctgcc accaccccac caccaactct caaaattctg acatgtggga   3660
tcactgtcaa tcccttctcc aagacatgtg ggatcactgt caatcccttc tccaaaccaa   3720
ttgtatgata gaacagtgga aatcacggac agaccatgga gctctcaacc ataatcatcc   3780
ttgcgagtta ataacaaatg gagcgtaaac ttggcaagca aaaaactcaa attaattcta   3840
aaattaagct ctaggattca aaatagattt cctctctgca ttgtgctgtt atgattttta   3900
attccgtaac aacgcaaatg cattttgcta gtcttataaa gaagggttaa tgcaaatatt   3960
ctgattaaat gattgtatct atgaagtttg aatgctagtg gaagctcctt tgaccatgtt   4020
ttgttgtgcg agcatttaag agagtgaaga gaatgcttct ttggtgctgt tctggtatgg   4080
aaggatccac agataaaatt caggttctac tgcttctctg cttgtaattt tcatgaagct   4140
gcagtgaata ccttgttgac cacttgatct gttgctttga aggagaatat agtagtggcc   4200
aaggttggtg acggtgatgg tggcatgtga tcccccagat cttcagtgac ccagagagga   4260
ggggacggcg cgtggtgagc tacaaggcat actcagtgga gggcaagatc aaggcctccc   4320
gtccgtaggg gactccgctg catcaaggcc aactgctccg aactgatcaa tttctggtgc   4380
agacaggtgc ttgcggtcag gttaaagaag ttggcaaaaa tgcttctgaa gaaaggttaa   4440
ttgttgtttc atctcaggag attccagatg atccagtgtc tccaacaatt gaggcgctta   4500
ttttgctcca tagtaaagta agtacacttg ctgagaacca ccagttgaca acacggcttg   4560
ttgtaccatc aaacaaagtt ggttgtattc ttggggaagg tggaaaggta attactgaaa   4620
tgagaagacg gactggggct gaaatccgag tctactcaaa agcagataaa cctaagtacc   4680
tgtcttttga tgaggagctt gtgcaggttg ctgggcttcc agctattgaa agaggagccc   4740
tgacagagat tgcttcgagg ctttgaacta ggacactcag agatggaagt tcttccaata   4800
atccgacacc ttttgcccct gttgatggtc ctcctgttga tatcttgcct aacaaggaat   4860
tcatgctata tggacgatct gctaatagtc ccccatatgg agggcctgct aatgatccac   4920
catatggaag acctgccatt gatccaccat atggaagacc aatatccaca atatggaaga   4980
cctgccaatg atccaccata tagaagacct gtcaatgata catcatattg agggttgaac   5040
aatgatgggc ctcgtgatca ggcccggtcc tgaggggggt cgaatggggc gatcgctccg   5100
ggccccccga ttcccagggc ccccacctat ctgtgcaacg agtagtagcg atcttccagc   5160
gcgcaacgtg aggcgatgtt tctccgtgat ttcgccggcc tgcaactgcg agatcgcgag   5220
tataacgatc agccgatcga tctcatctgc cgactgccat gctgatgcca cacgcaagcg   5280
cagcatatca gccttatctt ggttgatcgg catgctggac gagcacatct gttgtcgcat   5340
caactgctga ctgctatata tgtgctggtg ctgaatcgat cgattgtcgt cacggaagtg   5400
aagaacaacc acggcactgc tgcctgctgg gctctagccg ccatcagctg cggagctgat   5460
ccatggacgt gaggattacc gaagactgtc aggtctcact gggtatccag gtggctctgt   5520
cgaattgtgg attccaaata gttaactgga gtctgtcatt ggtgttggtg gtgtcaatct   5580
agctgagatc cgtctggtat agcgtaagag aaacatcatg cactatcccc agtcataacc   5640
atgccccaat ggccaccaat agttttcctc gtgaaaatct ccccttgatc ccagatctct   5700
```

```
ggtgcgagag tgaagttgca cgaagcccat cctggttctt ccgagtccat tgtggagatc   5760

cagggcattc cggatcaagt gaaagccgca cagagccttc tgcaaggctt catcggcgca   5820

agcagcaaca gcaggcaggc gccccagtcc tctcgcatgg cccattattt ttagtaagct   5880

ggaggacatt cgcaacaggg gggtcagtgg tcactgcaaa gctgagtttg ttcttcagtt   5940

caactgcaga aaattgcaga tcggttgccg tagttgctag aacggtacat agttgccacc   6000

taactgtagc gagtggcata acttattgtg tgttactgcc caatgttgtc tctccttgtg   6060

ttcatggatt cagacttgtg attgtagtat ttctggatca gactggagta aaagaaaaaa   6120

aaaaaggaag acatgggttt aacagtaaaa aaaaaaaaaa aaaa                    6164


<210> SEQ ID NO 49
<211> LENGTH: 791
<212> TYPE: PRT
<213> ORGANISM: rice

<400> SEQUENCE: 49

Met Ala Arg Arg Ala Ala Ser Arg Ala Val Gly Ala Leu Arg Ser
  1               5                  10                  15

Asp Gly Ser Ile Gln Gly Arg Gly Gly Arg Ala Gly Gly Ser Gly
                 20                  25                  30

Ala Glu Asp Ala Arg His Val Phe Asp Glu Leu Leu Arg Arg Gly
                 35                  40                  45

Arg Gly Ala Ser Ile Tyr Gly Leu Asn Arg Ala Leu Ala Asp Val
                 50                  55                  60

Ala Arg Asp Ser Pro Ala Ala Ala Val Ser Arg Tyr Asn Arg Met
                 65                  70                  75

Ala Arg Ala Gly Ala Asp Glu Val Thr Pro Asp Leu Cys Thr Tyr
                 80                  85                  90

Gly Ile Leu Ile Gly Cys Cys Cys Arg Ala Gly Arg Leu Asp Leu
                 95                 100                 105

Gly Phe Ala Ala Leu Gly Asn Val Ile Lys Lys Gly Phe Arg Val
                110                 115                 120

Asp Ala Ile Ala Phe Thr Pro Leu Leu Lys Gly Leu Cys Ala Asp
                125                 130                 135

Lys Arg Thr Ser Asp Ala Met Asp Ile Val Leu Arg Arg Met Thr
                140                 145                 150

Glu Leu Gly Cys Ile Pro Asn Val Phe Ser Tyr Asn Ile Leu Leu
                155                 160                 165

Lys Gly Leu Cys Asp Glu Asn Arg Ser Gln Glu Ala Leu Glu Leu
                170                 175                 180

Leu His Met Met Ala Asp Asp Arg Gly Gly Gly Ser Pro Pro Asp
                185                 190                 195

Val Val Ser Tyr Thr Thr Val Ile Asn Gly Phe Phe Lys Glu Gly
                200                 205                 210

Asp Ser Asp Lys Ala Tyr Ser Thr Tyr His Glu Met Leu Asp Arg
                215                 220                 225

Gly Ile Leu Pro Asp Val Val Thr Tyr Asn Ser Ile Ile Ala Ala
                230                 235                 240

Leu Cys Lys Ala Gln Ala Met Asp Lys Ala Met Glu Val Leu Asn
                245                 250                 255

Thr Met Val Lys Asn Gly Val Met Pro Asp Cys Met Thr Tyr Asn
                260                 265                 270

Ser Ile Leu His Gly Tyr Cys Ser Ser Gly Gln Pro Lys Glu Ala
```

-continued

```
                275                 280                 285
Ile Gly Phe Leu Lys Lys Met Arg Ser Asp Gly Val Glu Pro Asp
                290                 295                 300
Val Val Thr Tyr Ser Leu Leu Met Asp Tyr Leu Cys Lys Asn Gly
                305                 310                 315
Arg Cys Met Glu Ala Arg Lys Ile Phe Asp Ser Met Thr Lys Arg
                320                 325                 330
Gly Leu Lys Pro Glu Ile Thr Thr Tyr Gly Thr Leu Leu Gln Gly
                335                 340                 345
Tyr Ala Thr Lys Gly Ala Leu Val Glu Met His Gly Leu Leu Asp
                350                 355                 360
Leu Met Val Arg Asn Gly Ile His Pro Asp His Tyr Val Phe Ser
                365                 370                 375
Ile Leu Ile Cys Ala Tyr Ala Lys Gln Gly Lys Val Asp Gln Ala
                380                 385                 390
Met Leu Val Phe Ser Lys Met Arg Gln Gln Gly Leu Asn Pro Asn
                395                 400                 405
Ala Val Thr Tyr Gly Ala Val Ile Gly Ile Leu Cys Lys Ser Gly
                410                 415                 420
Arg Val Glu Asp Ala Met Leu Tyr Phe Glu Gln Met Ile Asp Glu
                425                 430                 435
Gly Leu Ser Pro Gly Asn Ile Val Tyr Asn Ser Leu Ile His Gly
                440                 445                 450
Leu Cys Thr Cys Asn Lys Trp Glu Arg Ala Glu Glu Leu Ile Leu
                455                 460                 465
Glu Met Leu Asp Arg Gly Ile Cys Leu Asn Thr Ile Phe Phe Asn
                470                 475                 480
Ser Ile Ile Asp Ser His Cys Lys Glu Gly Arg Val Ile Glu Ser
                485                 490                 495
Glu Lys Leu Phe Glu Leu Met Val Arg Ile Gly Val Lys Pro Asn
                500                 505                 510
Val Ile Thr Tyr Asn Thr Leu Ile Asn Gly Tyr Cys Leu Ala Gly
                515                 520                 525
Lys Met Asp Glu Ala Met Lys Leu Leu Ser Gly Met Val Ser Val
                530                 535                 540
Gly Leu Lys Pro Asn Thr Val Thr Tyr Ser Thr Leu Ile Asn Gly
                545                 550                 555
Tyr Cys Lys Ile Ser Arg Met Glu Asp Ala Leu Val Leu Phe Lys
                560                 565                 570
Glu Met Glu Ser Ser Gly Val Ser Pro Asp Ile Ile Thr Tyr Asn
                575                 580                 585
Ile Ile Leu Gln Gly Leu Phe Gln Thr Arg Arg Thr Ala Ala Ala
                590                 595                 600
Lys Glu Leu Tyr Val Arg Ile Thr Glu Ser Gly Thr Gln Ile Glu
                605                 610                 615
Leu Ser Thr Tyr Asn Ile Ile Leu His Gly Leu Cys Lys Asn Lys
                620                 625                 630
Leu Thr Asp Asp Ala Leu Gln Met Phe Gln Asn Leu Cys Leu Met
                635                 640                 645
Asp Leu Lys Leu Glu Ala Arg Thr Phe Asn Ile Met Ile Asp Ala
                650                 655                 660
Leu Leu Lys Val Gly Arg Asn Asp Glu Ala Lys Asp Leu Phe Val
                665                 670                 675
```

Ala Phe Ser Ser Asn Gly Leu Val Pro Asn Tyr Trp Thr Tyr Arg
680 685 690

Leu Met Ala Glu Asn Ile Ile Gly Gln Gly Leu Leu Glu Glu Leu
695 700 705

Asp Gln Leu Phe Leu Ser Met Glu Asp Asn Gly Cys Thr Val Asp
710 715 720

Ser Gly Met Leu Asn Phe Ile Val Arg Glu Leu Leu Gln Arg Gly
725 730 735

Glu Ile Thr Arg Ala Gly Thr Tyr Leu Ser Met Ile Asp Glu Lys
740 745 750

His Phe Ser Leu Glu Ala Ser Thr Ala Ser Leu Phe Ile Asp Leu
755 760 765

Leu Ser Gly Gly Lys Tyr Gln Glu Tyr Tyr Arg Phe Leu Pro Glu
770 775 780

Lys Tyr Lys Ser Phe Ile Glu Ser Leu Ser Cys
785 790 791

<210> SEQ ID NO 50
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 50
tctcattctc tccacgccct gctc 24

<210> SEQ ID NO 51
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 51
acggcggagc aattcgtcga acac 24

<210> SEQ ID NO 52
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 52
agtgtgtggc atggtgcatt tccg 24

<210> SEQ ID NO 53
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 53
ctctacagga tacacggtgt aagg 24

<210> SEQ ID NO 54
<211> LENGTH: 4746
<212> TYPE: DNA
<213> ORGANISM: rice

<400> SEQUENCE: 54

-continued

```
gccgcgcaga agagatcgat cgcgatctcc ctgccccgac gtcgccggcc gatctctcat     60
tctctccacg ccctgctcgt cgccgatctc ctacaccatc cctgccatct cctccttccc    120
ctcccctcta tcctccactg gtgccgccca cctctccgta taagacaaac tgcgttgcgg    180
cgttggtttc cgccggcgct gctgctgcac ctgtcagcta gggcgggcat ggcgcgccgc    240
gccgcttccc gcgctgttgg cgcccttcgc tcggacggct cgatccaagg gcgaggaggc    300
cgcgcggggg gcagtggcgc cgaggacgca cgccacgtgt tcgacgaatt gctccgccgt    360
ggcaggggcg cctcgatcta cggcttgaac cgcgccctcg ccgacgtcgc gcgtgacagc    420
cccgcggccg ccgtgtcccg ctacaaccgc atggcccgag ccggcgccga cgaggtaact    480
cccgacttgt gcacctacgg cattctcatc ggttgctgct gccgcgcggg ccgcttggac    540
ctcggtttcg cggccttggg caatgtcatt aagaagggat ttagagtgga cgccatcgcc    600
ttcactcctc tgctcaaggg cctctgtgcc gacaagagga cgagcgacgc aatggacata    660
gtgctccgca gaatgaccga gctcggctgc ataccaaatg tcttctccta caatattctt    720
ctcaaggggc tgtgtgatga gaacagaagc caagaagctc tcgagctgct gcacatgatg    780
gctgatgatc gaggaggagg tagcccacct gatgtggtgt cgtataccac tgtcatcaat    840
ggcttcttca aagaggggga ttcagacaaa gcttacagta cataccatga aatgctggac    900
cgggggattt tacctgatgt tgtgacctac aactctatta ttgctgcgtt atgcaaggct    960
caagctatgg acaaagccat ggaggtactt aacaccatgg ttaagaatgg tgtcatgcct   1020
gattgcatga catataatag tattctgcat ggatattgct cttcagggca gccgaaagag   1080
gctattggat ttctcaaaaa gatgcgcagt gatggtgtcg aaccagatgt tgttacttat   1140
agcttgctca tggattatct ttgcaagaac ggaagatgca tggaagctag aaagattttc   1200
gattctatga ccaagagggg cctaaagcct gaaattacta cctatggtac cctgcttcag   1260
gggtatgcta ccaaaggagc ccttgttgag atgcatggtc tcttggattt gatggtacga   1320
aacggtatcc accctgatca ttatgttttc agcattctaa tatgtgcata cgctaaacaa   1380
gggaaagtag atcaggcaat gcttgtgttc agcaaaatga ggcagcaagg attgaatccg   1440
aatgcagtga cgtatggagc agttataggc atactttgca agtcaggcag agtagaagat   1500
gctatgcttt attttgagca gatgatcgat gaaggactaa gccctggcaa cattgtttat   1560
aactccctaa ttcatggttt gtgcacctgt aacaaatggg agagggctga agagttaatt   1620
cttgaaatgt tggatcgagg catctgtctg aacactattt tctttaattc aataattgac   1680
agtcattgca aagaagggag ggttatagaa tctgaaaaac tctttgagct gatggtacgt   1740
attggtgtga agcccaatgt cattacctac aatactctta tcaatggata ttgcttggca   1800
ggtaagatgg atgaagcaat gaagttactt tctggcatgg tctcagttgg gttgaaacct   1860
aatactgtta cttatagcac tttgattaat ggctactgca aaattagtag gatggaagac   1920
gcgttagttc tttttaagga gatggagagc agtggtgtta gtcctgatat tattacgtat   1980
aacataattc tgcaaggttt atttcaaacc agaagaactg ctgctgcaaa agaactctat   2040
gttaggatta ccgaaagtgg aacgcagatt gaacttagca catacaacat aatccttcat   2100
ggactttgca aaaacaaact cactgatgat gcacttcaga tgtttcagaa cctatgtttg   2160
atggatttga agcttgaggc taggactttc aacattatga ttgatgcatt gcttaaagtt   2220
ggcagaaatg atgaagccaa ggatttgttt gttgctttct cgtctaacgg tttagtgccg   2280
aattattgga cgtacaggtt gatggctgaa aatattatag gacaggggtt gctagaagaa   2340
ttggatcaac tctttctttc aatggaggac aatggctgta ctgttgactc tggcatgcta   2400
```

-continued

```
aatttcattg ttagggaact gttgcagaga ggtgagataa ccagggctgg cacttacctt   2460
tccatgattg atgagaagca cttttccctc gaagcatcca ctgcttcctt gtttatagat   2520
cttttgtctg gggaaaaata tcaagaatat tataggtttc tccctgaaaa atacaagtcc   2580
tttatagaat ctttgagctg ctgaagcatt ttgcagcttt gaaattctgt gttggaattc   2640
ttttctccta cagtcctatt agaggaggga tcttctctgt atgtgtaaat agcgagtttg   2700
aatgctagtg gaagctcctt tgaccatgtt ttgttgtgcg agcatttaag agagtgaaga   2760
gaatgcttct ttggtgctgt tctggtatgg aaggatccac agataaaatt cagtagtggc   2820
caaggttggt gacggtgatg gtggcatgtg atcccccaga tcttcagtga cccagagagg   2880
aggggacggc gcgtggtgag ctacaaggca tactcagtgg agggcaagat caaggcctcc   2940
cgtccgtagg ggactccgct gcatcaaggc caactgctcc gaactgatca atttctggtg   3000
cagacaggtg cttgcggtca ggttaaagaa gttggcaaaa atgcttctga agaaaggtta   3060
attgttgttt catctcagga gattccagat gatccagtgt ctccaacaat tgaggcgctt   3120
attttgctcc atagtaaagt aagtacactt gctgagaacc accagttgac aacacggctt   3180
gttgtaccat caaacaaagt tggttgtatt cttggggaag gtggaaaggt aattactgaa   3240
atgagaagac ggactggggc tgaaatccga gtctactcaa aagcagataa acctaagtac   3300
ctgtcttttg atgaggagct tgtgcaggtt gctgggcttc cagctattga aagaggagcc   3360
ctgacagaga ttgcttcgag gctttgaact aggacactca gagatggaag ttcttccaat   3420
aatccgacac cttttgcccc tgttgatggt cctcctgttg atatcttgcc taacaaggaa   3480
ttcatgctat atggacgatc tgctaatagt cccccatatg gagggcctgc taatgatcca   3540
ccatatggaa gacctgccat tgatccacca tatggaagac caatatccac aatatggaag   3600
acctgccaat gatccaccat atagaagacc tgtcaatgat acatcatatt gagggttgaa   3660
caatgatggg cctcgtgatc aggcccggtc ctgagggggg tcgaatgggg cgatcgctcc   3720
gggccccccg attcccaggg cccccaccta tctgtgcaac gagtagtagc gatcttccag   3780
cgcgcaacgt gaggcgatgt ttctccgtga tttcgccggc ctgcaactgc gagatcgcga   3840
gtataacgat cagccgatcg atctcatctg ccgactgcca tgctgatgcc acacgcaagc   3900
gcagcatatc agccttatct tggttgatcg gcatgctgga cgagcacatc tgttgtcgca   3960
tcaactgctg actgctatat atgtgctggt gctgaatcga tcgattgtcg tcacggaagt   4020
gaagaacaac cacggcactg ctgcctgctg ggctctagcc gccatcagct gcggagctga   4080
tccatggacg tgaggattac cgaagactgt caggtctcac tgggtatcca ggtggctctg   4140
tcgaattgtg gattccaaat agttaactgg agtctgtcat tggtgttggt ggtgtcaatc   4200
tagctgagat ccgtctggta tagcgtaaga gaaacatcat gcactatccc cagtcataac   4260
catgccccaa tggccaccaa tagttttcct cgtgaaaatc tccccttgat cccagatctc   4320
tggtgcgaga gtgaagttgc acgaagccca tcctggttct tccgagtcca ttgtggagat   4380
ccagggcatt ccggatcaag tgaaagccgc acagagcctt ctgcaaggct tcatcggcgc   4440
aagcagcaac agcaggcagg cgccccagtc ctctcgcatg gcccattatt tttagtaagc   4500
tggaggacat tcgcaacagg ggggtcagtg gtcactgcaa agctgagttt gttcttcagt   4560
tcaactgcag aaaattgcag atcggttgcc gtagttgcta gaacggtaca tagttgccac   4620
ctaactgtag cgagtggcat aacttattgt gtgttactgc ccaatgttgt ctctccttgt   4680
gttcatggat tcagacttgt gattgtagta tttctggatc agactggagt aaaagaaaaa   4740
aaaaaa                                                              4746
```

<210> SEQ ID NO 55
<211> LENGTH: 4779
<212> TYPE: DNA
<213> ORGANISM: rice

<400> SEQUENCE: 55
tctcattctc tccacgccct gctcgtcgcc gatctcctac accatccctg ccatctcctc 60
cttcccctcc cctctatcct ccactggtgc cgcccacctc tccgtataag acaaactgcg 120
ttgcggcgtt ggtttccgcc ggcgctgctg ctgcacctgt cagctagggc gggcatggcg 180
cgccgcgccg cttcccgcgc tgttggcgcc cttcgctcgg acggctcgat ccaagggcga 240
ggaggccgcg cggggggcag tggcgccgag gacgcacgcc acgtgttcga cgaattgctc 300
cgccgtggca ggggcgcctc gatctacggc ttgaaccgcg ccctcgccga cgtcgcgcgt 360
gacagccccg cggccgccgt gtcccgctac aaccgcatgg cccgagccgg cgccgacgag 420
gtaactcccg acttgtgcac ctacggcatt ctcatcggtt gctgctgccg cgcgggccgc 480
ttggacctcg gtttcgcggc cttgggcaat gtcattaaga agggatttag agtggacgcc 540
atcgccttca ctcctctgct caagggcctc tgtgccgaca agaggacgag cgacgcaatg 600
gacatagtgc tccgcagaat gaccgagctc ggctgcatac caaatgtctt ctcctacaat 660
attcttctca aggggctgtg tgatgagaac agaagccaag aagctctcga gctgctgcac 720
atgatggctg atgatcgagg aggaggtagc ccacctgatg tggtgtcgta taccactgtc 780
atcaatggct tcttcaaaga gggggattca gacaaagctt acagtacata ccatgaaatg 840
ctggaccggg ggattttacc tgatgttgtg acctacaact ctattattgc tgcgttatgc 900
aaggctcaag ctatggacaa agccatggag gtacttaaca ccatggttaa gaatggtgtc 960
atgcctgatt gcatgacata taatagtatt ctgcatggat attgctcttc agggcagccg 1020
aaagaggcta ttggatttct caaaaagatg cgcagtgatg gtgtcgaacc agatgttgtt 1080
acttatagct tgctcatgga ttatctttgc aagaacggaa gatgcatgga agctagaaag 1140
attttcgatt ctatgaccaa gaggggccta aagcctgaaa ttactaccta tggtaccctg 1200
cttcaggggt atgctaccaa aggagccctt gttgagatgc atggtctctt ggatttgatg 1260
gtacgaaacg gtatccaccc tgatcattat gttttcagca ttctaatatg tgcatacgct 1320
aaacaaggga aagtagatca ggcaatgctt gtgttcagca aaatgaggca gcaaggattg 1380
aatccgaatg cagtgacgta tggagcagtt ataggcatac tttgcaagtc aggcagagta 1440
gaagatgcta tgctttattt tgagcagatg atcgatgaag gactaagccc tggcaacatt 1500
gtttataact ccctaattca tggtttgtgc acctgtaaca aatgggagag ggctgaagag 1560
ttaattcttg aaatgttgga tcgaggcatc tgtctgaaca ctatttttct taattcaata 1620
attgacagtc attgcaaaga agggagggtt atagaatctg aaaaactctt tgagctgatg 1680
gtacgtattg gtgtgaagcc caatgtcatt acctacaata ctcttatcaa tggatattgc 1740
ttggcaggta agatggatga agcaatgaag ttactttctg gcatggtctc agttgggttg 1800
aaacctaata ctgttactta tagcactttg attaatggct actgcaaaat tagtaggatg 1860
gaagacgcgt tagttctttt taaggagatg gagagcagtg gtgttagtcc tgatattatt 1920
acgtataaca taattctgca aggtttattt caaaccagaa gaactgctgc tgcaaaagaa 1980
ctctatgtta ggattaccga aagtggaacg cagattgaac ttagcacata caacataatc 2040
cttcatggac tttgcaaaaa caaactcact gatgatgcac ttcagatgtt tcagaaccta 2100
tgtttgatgg atttgaagct tgaggctagg actttcaaca ttatgattga tgcattgctt 2160

-continued

```
aaagttggca gaaatgatga agccaaggat ttgtttgttg ctttctcgtc taacggttta   2220
gtgccgaatt attggacgta caggttgatg gctgaaaata ttataggaca ggggttgcta   2280
gaagaattgg atcaactctt tctttcaatg gaggacaatg gctgtactgt tgactctggc   2340
atgctaaatt tcattgttag ggaactgttg cagagaggtg agataaccag ggctggcact   2400
tacctttcca tgattgatga gaagcacttt tccctcgaag catccactgc ttccttgttt   2460
atagatcttt tgtctggggg aaaatatcaa gaatattata ggtttctccc tgaaaaatac   2520
aagtccttta tagaatcttt gagctgctga agcattttgc agctttgaaa ttctgtgttg   2580
gaattctttt ctcctacagt cctattagag gagggatctt ctctgtatgt gtaaatagcg   2640
agtttgaatg ctagtggaag ctcctttgac catgttttgt tgtgcgagca tttaagagag   2700
tgaagagaat gcttctttgg tgctgttctg gtatggaagg atccacagat aaaattcagg   2760
agaatatagt agtggccaag gttggtgacg gtgatggtgg catgtgatcc cccagatctt   2820
cagtgaccca gagaggaggg gacggcgcgt ggtgagctac aaggcatact cagtggaggg   2880
caagatcaag gcctcccgtc cgtaggggac tccgctgcat caaggccaac tgctccgaac   2940
tgatcaattt ctggtgcaga caggtgcttg cggtcaggtt aaagaagttg gcaaaaatgc   3000
ttctgaagaa aggttaattg ttgtttcatc tcaggagatt ccagatgatc cagtgtctcc   3060
aacaattgag gcgcttattt tgctccatag taaagtaagt acacttgctg agaaccacca   3120
gttgacaaca cggcttgttg taccatcaaa caaagttggt tgtattcttg gggaaggtgg   3180
aaaggtaatt actgaaatga gaagacggac tggggctgaa atccgagtct actcaaaagc   3240
agataaacct aagtacctgt cttttgatga ggagcttgtg caggttgctg ggcttccagc   3300
tattgaaaga ggagccctga cagagattgc ttcgaggctt tgaactagga cactcagaga   3360
tggaagttct tccaataatc cgacaccttt tgcccctgtt gatggtcctc ctgttgatat   3420
cttgcctaac aaggaattca tgctatatgg acgatctgct aatagtcccc catatggagg   3480
gcctgctaat gatccaccat atggaagacc tgccattgat ccaccatatg gaagaccaat   3540
atccacaata tggaagacct gccaatgatc caccatatag aagacctgtc aatgatacat   3600
catattgagg gttgaacaat gatgggcctc gtgatcaggc ccggtcctga ggggggtcga   3660
atggggcgat cgctccgggc cccccgattc ccagggcccc cacctatctg tgcaacgagt   3720
agtagcgatc ttccagcgcg caacgtgagg cgatgtttct ccgtgatttc gccggcctgc   3780
aactgcgaga tcgcgagtat aacgatcagc cgatcgatct catctgccga ctgccatgct   3840
gatgccacac gcaagcgcag catatcagcc ttatcttggt tgatcggcat gctggacgag   3900
cacatctgtt gtcgcatcaa ctgctgactg ctatatatgt gctggtgctg aatcgatcga   3960
ttgtcgtcac ggaagtgaag aacaaccacg gcactgctgc ctgctgggct ctagccgcca   4020
tcagctgcgg agctgatcca tggacgtgag gattaccgaa gactgtcagg tctcactggg   4080
tatccaggtg gctctgtcga attgtggatt ccaaatagtt aactggagtc tgtcattggt   4140
gttggtggtg tcaatctagc tgagatccgt ctggtatagc gtaagagaaa catcatgcac   4200
tatccccagt cataaccatg ccccaatggc caccaatagt tttcctcgtg aaaatctccc   4260
cttgatccca gatctctggt gcgagagtga agttgcacga agcccatcct ggttcttccg   4320
agtccattgt ggagatccag ggcattccgg atcaagtgaa agccgcacag agccttctgc   4380
aaggcttcat cggcgcaagc agcaacagca ggcaggcgcc ccagtcctct cgcatggccc   4440
attattttta gtaagctgga ggacattcgc aacagggggg tcagtggtca ctgcaaagct   4500
gagtttgttc ttcagttcaa ctgcagaaaa ttgcagatcg gttgccgtag ttgctagaac   4560
```

```
ggtacatagt tgccacctaa ctgtagcgag tggcataact tattgtgtgt tactgcccaa   4620

tgttgtctct ccttgtgttc atggattcag acttgtgatt gtagtatttc tggatcagac   4680

tggagtaaaa gaaaaaaaaa aaggaagaca tgggtttaac agtaaaaaaa aaaaaaaaaa   4740

aaaaaaaaaa aaaaaaaaaa aaaaaaaaaa aaaaaaaaa                          4779
```

<210> SEQ ID NO 56
<211> LENGTH: 6158
<212> TYPE: DNA
<213> ORGANISM: rice

<400> SEQUENCE: 56

```
cgcgcagaag agatcgatcg cgatctccct gccccgacgt cgccggccga tctctcattc     60

tctccacgcc ctgctcgtcg ccgatctcct acaccatccc tgccatctcc tccttcccct    120

cccctctatc ctccactggt gccgcccacc tctccgtata agacaaactg cgttgcggcg    180

ttggtttccg ccggcgctgc tgctgcacct gtcagctagg gcgggcatgg cgcgccgcgc    240

cgcttcccgc gctgttggcg cccttcgctc ggacggctcg atccaagggc gaggaggccg    300

cgcggggggc agtggcgccg aggacgcacg ccacgtgttc gacgaattgc tccgccgtgg    360

caggggcgcc tcgatctacg gcttgaaccg cgccctcgcc gacgtcgcgc gtgacagccc    420

cgcggccgcc gtgtcccgct acaaccgcat ggcccgagcc ggcgccgacg aggtaactcc    480

cgacttgtgc acctacggca ttctcatcgg ttgctgctgc cgcgcgggcc gcttggacct    540

cggtttcgcg gccttgggca atgtcattaa gaagggattt agagtggacg ccatcgcctt    600

cactcctctg ctcaagggcc tctgtgccga caagaggacg agcgacgcaa tggacatagt    660

gctccgcaga atgaccgagc tcggctgcat accaaatgtc ttctcctaca atattcttct    720

caaggggctg tgtgatgaga acagaagcca agaagctctc gagctgctgc acatgatggc    780

tgatgatcga ggaggaggta gcccacctga tgtggtgtcg tataccactg tcatcaatgg    840

cttcttcaaa gagggggatt cagacaaagc ttacagtaca taccatgaaa tgctggaccg    900

ggggatttta cctgatgttg tgacctacaa ctctattatt gctgcgttat gcaaggctca    960

agctatggac aaagccatgg aggtacttaa caccatggtt aagaatggtg tcatgcctga   1020

ttgcatgaca tataatagta ttctgcatgg atattgctct tcagggcagc cgaaagaggc   1080

tattggattt ctcaaaaaga tgcgcagtga tggtgtcgaa ccagatgttg ttacttatag   1140

cttgctcatg gattatcttt gcaagaacgg aagatgcatg gaagctagaa agattttcga   1200

ttctatgacc aagaggggcc taaagcctga aattactacc tatggtaccc tgcttcaggg   1260

gtatgctacc aaaggagccc ttgttgagat gcatggtctc ttggatttga tggtacgaaa   1320

cggtatccac cctgatcatt atgttttcag cattctaata tgtgcatacg ctaaacaagg   1380

gaaagtagat caggcaatgc ttgtgttcag caaaatgagg cagcaaggat tgaatccgaa   1440

tgcagtgacg tatggagcag ttataggcat actttgcaag tcaggcagag tagaagatgc   1500

tatgctttat tttgagcaga tgatcgatga aggactaagc cctggcaaca ttgtttataa   1560

ctccctaatt catggtttgt gcacctgtaa caaatgggag agggctgaag agttaattct   1620

tgaaatgttg gatcgaggca tctgtctgaa cactattttc tttaattcaa taattgacag   1680

tcattgcaaa gaagggaggg ttatagaatc tgaaaaactc tttgagctga tggtacgtat   1740

tggtgtgaag cccaatgtca ttacctacaa tactcttatc aatggatatt gcttggcagg   1800

taagatggat gaagcaatga agttactttc tggcatggtc tcagttgggt tgaaacctaa   1860

tactgttact tatagcactt tgattaatgg ctactgcaaa attagtagga tggaagacgc   1920
```

-continued

```
gttagttctt tttaaggaga tggagagcag tggtgttagt cctgatatta ttacgtataa   1980
cataattctg caaggtttat ttcaaaccag aagaactgct gctgcaaaag aactctatgt   2040
taggattacc gaaagtggaa cgcagattga acttagcaca tacaacataa tccttcatgg   2100
actttgcaaa aacaaactca ctgatgatgc acttcagatg tttcagaacc tatgtttgat   2160
ggatttgaag cttgaggcta ggactttcaa cattatgatt gatgcattgc ttaaagttgg   2220
cagaaatgat gaagccaagg atttgtttgt tgctttctcg tctaacggtt tagtgccgaa   2280
ttattggacg tacaggttga tggctgaaaa tattatagga caggggttgc tagaagaatt   2340
ggatcaactc tttctttcaa tggaggacaa tggctgtact gttgactctg gcatgctaaa   2400
tttcattgtt agggaactgt tgcagagagg tgagataacc agggctggca cttacctttc   2460
catgattgat gagaagcact ttccctcga agcatccact gcttccttgt ttatagatct   2520
tttgtctggg ggaaaatatc aagaatatta taggtttctc cctgaaaaat acaagtcctt   2580
tatagaatct ttgagctgct gaagcatttt gcagctttga aattctgtgt tggaattctt   2640
ttctcctaca gtcctattag aggagggatc ttctctgtat gtgtaaatag cgaggtatgt   2700
atgccacctc tccgaattat ttttactgtg gttcctagac tgtaaacaag caattatgtt   2760
atgctgttga tgccagaaaa aacataaaag tttgtcgtta tctctactaa cggatcataa   2820
agggatttgt gactggagtt tcaaacttaa tgtgtctagg cagtaatttt gacattagat   2880
ccaaaacaat ttatagggtt tcattaaatt tcatctatgt gtactgttta ggtgttgaat   2940
agtttgactt gtttttaac tgaacaaaag atatgtctga agctttgttc tttaccaaat   3000
gcagtactga tcatcacaat atattttta tggaacaaga ttggattgta tagaatggtt   3060
tctgatctga ttatcttatc tcaacgtatt attatgcaca tgtactaatc atgaaatatc   3120
tgatggaatg atgtttctat ttacctgtgt gaggcagcaa ggagtgagat ggataacacc   3180
acatactccc tctgtcccag aatataagaa gttttagagt tggacacgat tattaagaaa   3240
gtaggtagaa gtgagtagtg gagggttgtg attgcatgag tagtggaggt aggtgggaaa   3300
agtgaatggt ggagggttgt gattggttgg gaagagaatg ttggtagaga agttgttata   3360
ttttggggag tacattatta ttctagaaca atactgttgt gctcaagaag cgttccaaag   3420
atgtttcaca acctgtgctc gatgggtttt gagcttaatc ctgggacatt cagtatcatg   3480
atctgtctca ttcttaaaca tggaataaag gatgacagca tgatttcttt gtctctataa   3540
tcttttggct acccacagat aatagctgta aatctatact actttaaaag gagtagtggt   3600
ggtggtgagt ggtgaatctg ccaccacccc accaccaact ctcaaaattc tgacatgtgg   3660
gatcactgtc aatcccttct ccaagacatg tgggatcact gtcaatccct tctccaaacc   3720
aattgtatga tagaacagtg gaaatcacgg acagaccatg gagctctcaa ccataatcat   3780
ccttgcgagt taataacaaa tggagcgtaa acttggcaag caaaaaactc aaattaattc   3840
taaaattaag ctctaggatt caaaatagat ttcctctctg cattgtgctg ttatgatttt   3900
taattccgta acaacgcaaa tgcattttgc tagtcttata aagaagggtt aatgcaaata   3960
ttctgattaa atgattgtat ctatgaagtt tgaatgctag tggaagctcc tttgaccatg   4020
ttttgttgtg cgagcattta agagagtgaa gagaatgctt ctttggtgct gttctggtat   4080
ggaaggatcc acagataaaa ttcaggagaa tatagtagtg gccaaggttg gtgacggtga   4140
tggtggcatg tgatccccca gatcttcagt gacccagaga ggaggggacg gcgcgtggtg   4200
agctacaagg catactcagt ggagggcaag atcaaggcct cccgtccgta ggggactccg   4260
ctgcatcaag gccaactgct ccgaactgat caatttctgg tgcagacagg tgcttgcggt   4320
```

-continued

```
caggttaaag aagttggcaa aaatgcttct gaagaaaggt taattgttgt ttcatctcag   4380

gagattccag atgatccagt gtctccaaca attgaggcgc ttattttgct ccatagtaaa   4440

gtaagtacac ttgctgagaa ccaccagttg acaacacggc ttgttgtacc atcaaacaaa   4500

gttggttgta ttcttgggga aggtggaaag gtaattactg aaatgagaag acggactggg   4560

gctgaaatcc gagtctactc aaaagcagat aaacctaagt acctgtcttt tgatgaggag   4620

cttgtgcagg ttgctgggct tccagctatt gaaagaggag ccctgacaga gattgcttcg   4680

aggctttgaa ctaggacact cagagatgga agttcttcca ataatccgac accttttgcc   4740

cctgttgatg gtcctcctgt tgatatcttg cctaacaagg aattcatgct atatggacga   4800

tctgctaata gtcccccata tggagggcct gctaatgatc caccatatgg aagacctgcc   4860

attgatccac catatggaag accaatatcc acaatatgga agacctgcca atgatccacc   4920

atatagaaga cctgtcaatg atacatcata ttgagggttg aacaatgatg ggcctcgtga   4980

tcaggcccgg tcctgagggg ggtcgaatgg ggcgatcgct ccgggccccc cgattcccag   5040

ggcccccacc tatctgtgca acgagtagta gcgatcttcc agcgcgcaac gtgaggcgat   5100

gtttctccgt gatttcgccg gcctgcaact gcgagatcgc gagtataacg atcagccgat   5160

cgatctcatc tgccgactgc catgctgatg ccacacgcaa gcgcagcata tcagccttat   5220

cttggttgat cggcatgctg gacgagcaca tctgttgtcg catcaactgc tgactgctat   5280

atatgtgctg gtgctgaatc gatcgattgt cgtcacggaa gtgaagaaca accacggcac   5340

tgctgcctgc tgggctctag ccgccatcag ctgcggagct gatccatgga cgtgaggatt   5400

accgaagact gtcaggtctc actgggtatc caggtggctc tgtcgaattg tggattccaa   5460

atagttaacc ggagtctgtc attggtgttg gtggtgtcaa tctagctgag atccgtctgg   5520

tatagcgtaa gagaaacatc atgcactatc cccagtcata accatgcccc aatggccacc   5580

aatagttttc ctcgtgaaaa tctccccttg atcccagatc tctggtgcga gagtgaagtt   5640

gcacgaagcc catcctggtt cttccgagtc cattgtggag atccagggca ttccggatca   5700

agtgaaagcc gcacagagcc ttctgcaagg cttcatcggc gcaagcagca acagcaggca   5760

ggcgccccag tcctctcgca tggcccatta tttttagtaa gctggaggac attcgcaaca   5820

ggggggtcag tggtcactgc aaagctgagt ttgttcttca gttcaactgc agaaaattgc   5880

agatcggttg ccgtagttgc tagaacggta catagttgcc acctaactgt agcgagtggc   5940

ataacttatt gtgtgttact gcccaatgtt gtctctcctt gtgttcatgg attcagactt   6000

gtgattgtag tatttctgga tcagactgga gtaaaagaaa aaaaaaaagg aagacatggg   6060

tttaacagta aaaaaaaaaa aaaaaaaaaa aaaaaaaaaa aaaaaaaaaa aaaaaaaaaa   6120

aaaaaaaaaa aaaaaaaaaa aaaaaaaaaa aaaaaaaa                           6158
```

<210> SEQ ID NO 57
<211> LENGTH: 2864
<212> TYPE: DNA
<213> ORGANISM: rice

<400> SEQUENCE: 57

```
aagagatcga tcgcgatctc cctgccccga cgtcgccggc cgatctctca ttctctccac     60

gccctgctcg tcgccgatct cctacaccat ccctgccatc tcctccttcc cctcccctct    120

atcctccact ggtgccgccc acctctccgt ataagacaaa ctgcgttgcg gcgttggttt    180

ccgccggcgc tgctgctgca cctgtcagct agggcgggca tggcgcgccg cgccgcttcc    240

cgcgctgttg gcgcccttcg ctcggacggc tcgatccaag ggcgaggagg ccgcgcgggg    300
```

-continued

```
ggcagtggcg ccgaggacgc acgccacgtg ttcgacgaat tgctccgccg tggcaggggc    360
gcctcgatct acggcttgaa ccgcgccctc gccgacgtcg cgcgtgacag ccccgcggcc    420
gccgtgtccc gctacaaccg catggcccga gccggcgccg acgaggtaac tcccgacttg    480
tgcacctacg gcattctcat cggttgctgc tgccgcgcgg gccgcttgga cctcggtttc    540
gcggccttgg gcaatgtcat taagaaggga tttagagtgg acgccatcgc cttcactcct    600
ctgctcaagg gcctctgtgc cgacaagagg acgagcgacg caatggacat agtgctccgc    660
agaatgaccg agctcggctg cataccaaat gtcttctcct acaatattct tctcaagggg    720
ctgtgtgatg agaacagaag ccaagaagct ctcgagctgc tgcacatgat ggctgatgat    780
cgaggaggag gtagcccacc tgatgtggtg tcgtatacca ctgtcatcaa tggcttcttc    840
aaagaggggg attcagacaa agcttacagt acataccatg aaatgctgga ccgggggatt    900
ttacctgatg ttgtgaccta caactctatt attgctgcgt tatgcaaggc tcaagctatg    960
gacaaagcca tggaggtact taacaccatg gttaagaatg gtgtcatgcc tgattgcatg   1020
acatataata gtattctgca tggatattgc tcttcagggc agccgaaaga ggctattgga   1080
tttctcaaaa agatgcgcag tgatggtgtc gaaccagatg ttgttactta tagcttgctc   1140
atggattatc tttgcaagaa cggaagatgc atggaagcta gaaagatttt cgattctatg   1200
accaagaggg gcctaaagcc tgaaattact acctatggta ccctgcttca ggggtatgct   1260
accaaaggag cccttgttga gatgcatggt ctcttggatt tgatggtacg aaacggtatc   1320
caccctgatc attatgtttt cagcattcta atatgtgcat acgctaaaca agggaaagta   1380
gatcaggcaa tgcttgtgtt cagcaaaatg aggcagcaag gattgaatcc gaatgcagtg   1440
acgtatggag cagttatagg catactttgc aagtcaggca gagtagaaga tgctatgctt   1500
tattttgagc agatgatcga tgaaggacta agccctggca acattgttta taactcccta   1560
attcatggtt tgtgcacctg taacaaatgg gagagggctg aagagttaat tcttgaaatg   1620
ttggatcgag gcatctgtct gaacactatt ttctttaatt caataattga cagtcattgc   1680
aaagaaggga gggttataga atctgaaaaa ctctttgagc tgatggtacg tattggtgtg   1740
aagcccaatg tcattaccta caatactctt atcaatggat attgcttggc aggtaagatg   1800
gatgaagcaa tgaagttact ttctggcatg gtctcagttg ggttgaaacc taatactgtt   1860
acttatagca ctttgattaa tggctactgc aaaattagta ggatggaaga cgcgttagtt   1920
ctttttaagg agatggagag cagtggtgtt agtcctgata ttattacgta taacataatt   1980
ctgcaaggtt tatttcaaac cagaagaact gctgctgcaa aagaactcta tgttaggatt   2040
accgaaagtg gaacgcagat tgaacttagc acatacaaca taatccttca tggactttgc   2100
aaaaacaaac tcactgatga tgcacttcag atgtttcaga acctatgttt gatggatttg   2160
aagcttgagg ctaggacttt caacattatg attgatgcat tgcttaaagt tggcagaaat   2220
gatgaagcca aggatttgtt tgttgctttc tcgtctaacg gtttagtgcc gaattattgg   2280
acgtacaggt tgatggctga aaatattata ggacaggggt tgctagaaga attggatcaa   2340
ctctttcttt caatggagga caatggctgt actgttgact ctggcatgct aaatttcatt   2400
gttagggaac tgttgcagag aggtgagata accagggctg gcacttacct ttccatgatt   2460
gatgagaagc acttttccct cgaagcatcc actgcttcct tgtttataga tcttttgtct   2520
gggggaaaat atcaagaata ttataggttt ctccctgaaa aatacaagtc ctttatagaa   2580
tctttgagct gctgaagcat tttgcagctt tgaaattctg tgttggaatt cttttctcct   2640
acagtcctat tagaggaggg atcttctctg tatgtgtaaa tagcgaggta tgtatgccac   2700
```

ctctccgaat tatttttact gtggttccta gactgtaaac aagcaattat gttatgctgt 2760
tgatgccaga aaaaacataa aagtttgtcg ttatctctac taacggatca taaagggatt 2820
tgtgactgga gtttcaaaaa aaaaaaaaaa aaaaaaaaaa aaaa 2864

<210> SEQ ID NO 58
<211> LENGTH: 2819
<212> TYPE: DNA
<213> ORGANISM: rice

<400> SEQUENCE: 58
ctcattctct ccacgccctg ctcgtcgccg atctcctaca ccatccctgc catctcctcc 60
ttcccctccc ctctatcctc cactggtgcc gcccacctct ccgtataaga caaactgcgt 120
tgcggcgttg gtttccgccg gcgctgctgc tgcacctgtc agctagggcg ggcatggcgc 180
gccgcgccgc ttcccgcgct gttggcgccc ttcgctcgga cggctcgatc caagggcgag 240
gaggccgcgc ggggggcagt ggcgccgagg acgcacgcca cgtgttcgac gaattgctcc 300
gccgtggcag gggcgcctcg atctacggct tgaaccgcgc cctcgccgac gtcgcgcgtg 360
acagccccgc ggccgccgtg tcccgctaca accgcatggc ccgagccggc gccgacgagg 420
taactcccga cttgtgcacc tacggcattc tcatcggttg ctgctgccgc gcgggccgct 480
tggacctcgg tttcgcggcc ttgggcaatg tcattaagaa gggatttaga gtggacgcca 540
tcgccttcac tcctctgctc aagggcctct gtgccgacaa gaggacgagc gacgcaatgg 600
acatagtgct ccgcagaatg accgagctcg gctgcatacc aaatgtcttc tcctacaata 660
ttcttctcaa ggggctgtgt gatgagaaca gaagccaaga agctctcgag ctgctgcaca 720
tgatggctga tgatcgagga ggaggtagcc cacctgatgt ggtgtcgtat accactgtca 780
tcaatggctt cttcaaagag gggggattcag acaaagctta cagtacatac catgaaatgc 840
tggaccgggg gattttacct gatgttgtga cctacaactc tattattgct gcgttatgca 900
aggctcaagc tatggacaaa gccatggagg tacttaacac catggttaag aatggtgtca 960
tgcctgattg catgacatat aatagtattc tgcatggata ttgctcttca gggcagccga 1020
aagaggctat tggatttctc aaaaagatgc gcagtgatgg tgtcgaacca gatgttgtta 1080
cttatagctt gctcatggat tatctttgca agaacggaag atgcatggaa gctagaaaga 1140
ttttcgattc tatgaccaag aggggcctaa agcctgaaat tactacctat ggtaccctgc 1200
ttcaggggta tgctaccaaa ggagcccttg ttgagatgca tggtctcttg gatttgatgg 1260
tacgaaacgg tatccacccct gatcattatg ttttcagcat tctaatatgt gcatacgcta 1320
aacaagggaa agtagatcag gcaatgcttg tgttcagcaa aatgaggcag caaggattga 1380
atccgaatgc agtgacgtat ggagcagtta taggcatact ttgcaagtca ggcagagtag 1440
aagatgctat gctttatttt gagcagatga tcgatgaagg actaagccct ggcaacattg 1500
tttataactc cctaattcat ggtttgtgca cctgtaacaa atgggagagg gctgaagagt 1560
taattcttga aatgttggat cgaggcatct gtctgaacac tattttcttt aattcaataa 1620
ttgacagtca ttgcaaagaa gggagggtta tagaatctga aaaactcttt gagctgatgg 1680
tacgtattgg tgtgaagccc aatgtcatta cctacaatac tcttatcaat ggatattgct 1740
tggcaggtaa gatggatgaa gcaatgaagt tactttctgg catggtctca gttgggttga 1800
aacctaatac tgttacttat agcactttga ttaatggcta ctgcaaaatt agtaggatgg 1860
aagacgcgtt agttcttttt aaggagatgg agagcagtgg tgttagtcct gatattatta 1920
cgtataacat aattctgcaa ggtttatttc aaaccagaag aactgctgct gcaaaagaac 1980

-continued

```
tctatgttag gattaccgaa agtggaacgc agattgaact tagcacatac aacataatcc   2040

ttcatggact ttgcaaaaac aaactcactg atgatgcact tcagatgttt cagaacctat   2100

gtttgatgga tttgaagctt gaggctagga ctttcaacat tatgattgat gcattgctta   2160

aagttggcag aaatgatgaa gccaaggatt tgtttgttgc tttctcgtct aacggtttag   2220

tgccgaatta ttggacgtac aggttgatgg ctgaaaatat tataggacag gggttgctag   2280

aagaattgga tcaactcttt ctttcaatgg aggacaatgg ctgtactgtt gactctggca   2340

tgctaaattt cattgttagg gaactgttgc agagaggtga gataaccagg gctggcactt   2400

acccttccat gattgatgag aagcactttt ccctcgaagc atccactgct tccttgttta   2460

tagatctttt gtctgggga aaatatcaag aatattatag gtttctccct gaaaaataca   2520

agtcctttat agaatctttg agctgctgaa gcattttgca gctttgaaat tctgtgttgg   2580

aattcttttc tcctacagtc ctattagagg agggatcttc tctgtatgtg taaatagcga   2640

ggtatgtatg ccacctctcc gaattatttt tactgtggtt cctagactgt aaacaagcaa   2700

ttatgttatg ctgttgatgc cagaaaaaac ataaaagttt gtcgttatct ctactaacgg   2760

atcataaagg gatttgtgac tggagtttca aaaaaaaaaa aaaaaaaaaa aaaaaaaaa    2819
```

<210> SEQ ID NO 59
<211> LENGTH: 2649
<212> TYPE: DNA
<213> ORGANISM: rice

<400> SEQUENCE: 59

```
ggtgccgccc acctctccgt ataagacaaa ctgcgttgcg gcgttggttt ccgccggcgc     60

tgctgctgca cctgtcagct agggcgggca tggcgcgccg cgccgcttcc cgcgctgttg    120

gcgcccttcg ctcggacggc tcgatccaag ggcgaggagg ccgcgcgggg ggcagtggcg    180

ccgaggacgc acgccacgtg ttcgacgaat tgctccgccg tggcaggggc gcctcgatct    240

acggcttgaa ccgcgccctc gccgacgtcg cgcgtgacag ccccgcggcc gccgtgtccc    300

gctacaaccg catggcccga gccggcgccg acgaggtaac tcccgacttg tgcacctacg    360

gcattctcat cggttgctgc tgccgcgcgg gccgcttgga cctcggtttc gcggccttgg    420

gcaatgtcat taagaaggga tttagagtgg acgccatcgc cttcactcct ctgctcaagg    480

gcctctgtgc cgacaagagg acgagcgacg caatggacat agtgctccgc agaatgaccg    540

agctcggctg cataccaaat gtcttctcct acaatattct tctcaagggg ctgtgtgatg    600

agaacagaag ccaagaagct ctcgagctgc tgcacatgat ggctgatgat cgaggaggag    660

gtagcccacc tgatgtggtg tcgtatacca ctgtcatcaa tggcttcttc aaagaggggg    720

attcagacaa agcttacagt acataccatg aaatgctgga ccgggggatt ttacctgatg    780

ttgtgaccta caactctatt attgctgcgt tatgcaaggc tcaagctatg gacaaagcca    840

tggaggtact taacaccatg gttaagaatg gtgtcatgcc tgattgcatg acatataata    900

gtattctgca tggatattgc tcttcagggc agccgaaaga ggctattgga tttctcaaaa    960

agatgcgcag tgatggtgtc gaaccagatg ttgttactta tagcttgctc atggattatc   1020

tttgcaagaa cggaagatgc atggaagcta gaaagatttt cgattctatg accaagaggg   1080

gcctaaagcc tgaaattact acctatggta ccctgcttca ggggtatgct accaaaggag   1140

cccttgttga gatgcatggt ctcttggatt tgatggtacg aaacggtatc caccctgatc   1200

attatgtttt cagcattcta atatgtgcat acgctaaaca agggaaagta gatcaggcaa   1260

tgcttgtgtt cagcaaaatg aggcagcaag gattgaatcc gaatgcagtg acgtatggag   1320
```

cagttatagg catactttgc aagtcaggca gagtagaaga tgctatgctt tattttgagc 1380
agatgatcga tgaaggacta agccctggca acattgttta taactcccta attcatggtt 1440
tgtgcacctg taacaaatgg gagagggctg aagagttaat tcttgaaatg ttggatcgag 1500
gcatctgtct gaacactatt ttctttaatt caataattga cagtcattgc aaagaaggga 1560
gggttataga atctgaaaaa ctctttgagc tgatggtacg tattggtgtg aagcccaatg 1620
tcattaccta caatactctt atcaatggat attgcttggc aggtaagatg gatgaagcaa 1680
tgaagttact ttctggcatg gtctcagttg ggttgaaacc taatactgtt acttatagca 1740
ctttgattaa tggctactgc aaaattagta ggatggaaga cgcgttagtt ctttttaagg 1800
agatggagag cagtggtgtt agtcctgata ttattacgta taacataatt ctgcaaggtt 1860
tatttcaaac cagaagaact gctgctgcaa aagaactcta tgttaggatt accgaaagtg 1920
gaacgcagat tgaacttagc acatacaaca taatccttca tggactttgc aaaaacaaac 1980
tcactgatga tgcacttcag atgtttcaga acctatgttt gatggatttg aagcttgagg 2040
ctaggacttt caacattatg attgatgcat tgcttaaagt tggcagaaat gatgaagcca 2100
aggatttgtt tgttgctttc tcgtctaacg gtttagtgcc gaattattgg acgtacaggt 2160
tgatggctga aaatattata ggacaggggt tgctagaaga attggatcaa ctctttcttt 2220
caatggagga caatggctgt actgttgact ctggcatgct aaatttcatt gttagggaac 2280
tgttgcagag aggtgagata accagggctg gcacttacct ttccatgatt gatgagaagc 2340
acttttccct cgaagcatcc actgcttcct tgtttataga tcttttgtct gggggaaaat 2400
atcaagaata ttataggttt ctccctgaaa aatacaagtc ctttatagaa tctttgagct 2460
gctgaagcat tttgcagctt tgaaattctg tgttggaatt cttttctcct acagtcctat 2520
tagaggaggg atcttctctg tatgtgtaaa tagcgaggta tgtatgccac ctctccgaat 2580
tatttttact gtggttccta gactgtaaac aagcaattat gttatgctgt tgatgccaga 2640
aaaaaaaaa 2649

<210> SEQ ID NO 60
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 60
cagttgggtt gaaacctaat actg 24

<210> SEQ ID NO 61
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 61
cactaaaccg ttagacgaga aagc 24

<210> SEQ ID NO 62
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 62
attgagggtt gaacaatgat gggc 24

<210> SEQ ID NO 63
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 63
ctctacagga tacacggtgt aagg 24

<210> SEQ ID NO 64
<211> LENGTH: 30
<212> TYPE: DNA
<213> ORGANISM: Artificial Sequence
<220> FEATURE:
<223> OTHER INFORMATION: Oligonucleotide primer for amplification

<400> SEQUENCE: 64
agattgaatc ctgttgccgg tcttgcgatg 30

<210> SEQ ID NO 65
<211> LENGTH: 30
<212> TYPE: DNA
<213> ORGANISM: Artificial Sequence
<220> FEATURE:
<223> OTHER INFORMATION: Oligonucleotide primer for amplification

<400> SEQUENCE: 65
tcatctatgt tactagatcc gatgataagc 30

<210> SEQ ID NO 66
<211> LENGTH: 26
<212> TYPE: DNA
<213> ORGANISM: Artificial Sequence
<220> FEATURE:
<223> OTHER INFORMATION: Oligonucleotide primer for amplification

<400> SEQUENCE: 66
acttcaacta gcaccctctc tcacct 26

<210> SEQ ID NO 67
<211> LENGTH: 26
<212> TYPE: DNA
<213> ORGANISM: Artificial Sequence
<220> FEATURE:
<223> OTHER INFORMATION: Oligonucleotide primer for amplification

<400> SEQUENCE: 67
tctgctggtt gaacatggtg tgatag 26

<210> SEQ ID NO 68
<211> LENGTH: 17
<212> TYPE: DNA
<213> ORGANISM: Artificial Sequence
<220> FEATURE:
<223> OTHER INFORMATION: Oligonucleotide primer for amplification

<400> SEQUENCE: 68 cccccccct ctcctct 17

<210> SEQ ID NO 69
<211> LENGTH: 26
<212> TYPE: DNA
<213> ORGANISM: Artificial Sequence
<220> FEATURE:

-continued

```
<223> OTHER INFORMATION: Oligonucleotide primer for amplification

<400> SEQUENCE: 69

tcccaccaaa gggcattcct ctcatc                                    26


<210> SEQ ID NO 70
<211> LENGTH: 24
<212> TYPE: DNA
<213> ORGANISM: Artificial Sequence
<220> FEATURE:
<223> OTHER INFORMATION: Oligonucleotide primer for amplification

<400> SEQUENCE: 70

ggctagggtt tggggaaatg ggcg                                      24


<210> SEQ ID NO 71
<211> LENGTH: 26
<212> TYPE: DNA
<213> ORGANISM: Artificial Sequence
<220> FEATURE:
<223> OTHER INFORMATION: Oligonucleotide primer for amplification

<400> SEQUENCE: 71

cgtcatcatc ttctcccaaa acagcc                                    26


<210> SEQ ID NO 72
<211> LENGTH: 26
<212> TYPE: DNA
<213> ORGANISM: Artificial Sequence
<220> FEATURE:
<223> OTHER INFORMATION: Oligonucleotide primer for amplification

<400> SEQUENCE: 72

cctttatacc tccccacttc ttatcc                                    26
```

METHOD FOR IMPROVING FERTILITY OF HYBRID PLANTS COMPRISING PLACING FERTILITY RESTORER GENES INTO MULTIPLE GENE LOCI

TECHNICAL FIELD

This application is a National Stage Application under 35 U.S.C. §371(c) of PCT Application No. PCT/JP2004/008025, filed Jun. 9, 2004, which claims the priority of Japanese Patent Application No. 2003-173927 filed Jun. 18, 2003, and Japanese Patent Application No. 2003-359158 filed Oct. 20, 2003. The entire disclosure and contents of the above applications are hereby incorporated by reference herein.

TECHNICAL FIELD OF THE INVENTION

The present invention relates to hybrid plants in which a plurality of fertility restorer genes have been introduced at multiple gene loci, and to the use thereof.

BACKGROUND ART

When two varieties of a self-fertilizing plant such as rice are to be crossed, it is necessary to first avoid self-fertilization by removing all stamens in a glumous flower just before it flowers. The flower is then fertilized using pollen from the pollen parent variety with which it is being crossed. However, a crossing technique that involves such manual operations is poorly suited for the production of a large quantity of hybrid seed on a commercial scale.

Accordingly, hybrid cultivars are produced by a three-line method which makes use of cytoplasmic male sterility. As used herein, "a three-line method" refers to a procedure that employs a sterile line containing male-sterile cytoplasm, a restorer line having a gametophytic fertility restorer gene, and a maintainer line having the same nuclear genes as the sterile line but lacking sterile cytoplasm. Using these three lines, (i) hybrid seeds can be obtained by fertilizing the sterile line with pollen from the restorer line, and (ii) the sterile line can be maintained by fertilizing it with pollen from the maintainer line.

The male-sterile cytoplasm and fertility restorer genes encoded in the nucleus are employed to commercially produce hybrid seed. Fertility restorer genes are classified as gametic or sporophytic type according to their mechanism of action. In the case of gametic fertility restorer genes, the genotype of the pollen determines whether or not the pollen fertility is restored; known examples include the fertility restorer gene Rf-1 for rice BT-type male-sterile cytoplasm and the restorer gene for maize S-type male-sterile cytoplasm. In the case of sporophytic fertility restorer genes, the genotype of the plant that produces the pollen determines whether or not the pollen fertility is restored; known examples include the fertility restorer gene for rice WA-type male-sterile cytoplasm and the fertility restorer gene for maize T-type male-sterile cytoplasm.

When a hybrid is bred by using a gametic fertility restorer gene, the anther of the hybrid variety shows a 1:1 segregation of pollen carrying the fertility restorer gene and pollen lacking the gene, and so the theoretical pollen fertility is 50%. This is half of the theoretical pollen fertility of 100% for a common variety, and has been of concern as a factor that lowers the stability of seed production in hybrids. In fact, hybrids obtained using rice BT-type male-sterile cytoplasm and the fertility restorer gene Rf-1 are generally known to have a poor cold hardiness, which is thought to be attributable to the low (50%) theoretical pollen fertility.

The following problems are associated with sporophytic fertility restorer genes. Although fertility restoration in rice WA cytoplasm is thought to be imparted by a plurality of fertility restorer genes, the number of such genes and their chromosomal positions have not been identified in detail. Hence, to be used in cross breeding, a restorer line for WA cytoplasm, in addition to having excellent properties such as yield and plant type, must also have the ability, as demonstrated in a seed fertility study on $F_1$ plants obtained after being crossed with a sterile line, to completely restore fertility to WA cytoplasm. Regardless of the excellence of properties other than the fertility restoring ability, if the seed fertility in $F_1$ plants obtained after the restorer line has been crossed with a WA cytoplasmic male-sterile line is incomplete, use as a restorer line will be impossible. Moreover, as noted above, because the number and positions of fertility restorer genes in restorer lines have not yet been precisely identified, it is difficult to improve only the fertility restoring ability while retaining the other properties.

A desire thus exists for a method of preparing hybrid cultivars having a high fertility.

Patent Publication No. 1: Japanese Patent Public Disclosure No. 2002-345485

Patent Publication No. 2: WO 02/014506 A1

Patent Publication No. 3: WO 03/027290 A1

Patent Publication No. 4: WO 02/019803 A1

Non-Patent Publication No. 1:
Ahmed, M. I., and Siddiq, E. A. (1998). Rice. In Hybrid cultivar development, S. S. Banga and S. K. Banga, eds (Berlin: Springer Verlag), pp. 221-256.
Non-Patent Publication No. 2:
Dhillon, B. S. (1998). Maize. In Hybrid cultivar development, S. S. Banga and S. K. Banga, eds (Berlin: Springer Verlag, pp. 282-315.
Non-Patent Publication No. 3:
Wen, L. & Chase, C. D. (1999). Curr. Genet. 35, p. 521-526
Non-Patent Publication No. 4:
Fukuta et al. 1992, Jpn J. Breed. 42 (supl. 1) p. 164-165
Non-Patent Publication No. 5:
Hiei et al., Plant Journal (1994), 6(2), p. 272-282
Non-Patent Publication No. 6:
Komari et al., Plant Journal (1996) 10, p. 165-174
Non-Patent Publication No. 7:
Ditta et al., Proc. Natl. Acad. Sci. USA (1980), 77:p. 7347-7351
Non-Patent Publication No. 8:
Lemas et al., Plasmid 1992, 27, p. 161-163
Non-Patent Publication No. 9:
Cui, X., Wise, R. P. and Schanble, P. S. (1996) The rf2 nuclear restorer gene of male-sterile T-cytoplasm maize. Science, 272, 1334-1336
Non-Patent Publication No. 10:
Liu, F., Cui, X., Horner, H. T., Weiner, H. and Schnable, P. S. (2001) Mitochondrial aldehyde dehydrogenase activity is required for male fertility in maize. The Plant Cell, 13, 1063-1078
Non-Patent Publication No. 11:
Michaels and Amasino 1998, The Plant Journal 14(3) p. 381-385
Non-Patent Publication No. 12:
Neff et al. 1998, The plant Journal 14(3) p. 387-392
Non-Patent Publication No. 13:
Komari, T., Saito, Y., Nakakido, F., and Kumashiro, T. (1989). Efficient selection of somatic hybrids in *Nicotiana*

*tabacum L.* using a combination of drug-resistance markers introduced by transformation. Theor. Appl. Genet. 77, 547-552.

Non-Patent Publication No. 14:

Altschul, S. F., Gish, W., Miller, W., Myers, E. W., and Lipman, D. J. (1990). Basic local alignment search tool. J. Mol. Biol. 215, 403-410.

Non-Patent Publication No. 15:

Komori, T., Yamamoto, T., Takemori, N., Kashihara, M., Matsushima, H., and Nitta, N. (2002). Fine mapping of a restorer gene, Rf-1, that restores the BT-type cytoplasmic male sterility. Breed. Res. 4 (Suppl. 2), 243.

Non-Patent Publication No. 16:

Harushima, Y., et al. (1998). A high-density rice genetic linkage map with 2275 markers using a single F2 population. Genetics 148, 479-494.

Non-Patent Publication No. 17:

Kariya, K. (1989). Sterility caused by cooling treatment at the flowering stage in rice plants III. Establishment of a method of in vitro pollen germination. Jap. J. Crop Sci. 58, 96-102.

DISCLOSURE OF THE INVENTION

Problems to be Solved by the Invention

An object of the present invention is to provide a hybrid plant having a high fertility. The hybrid plants of the invention are characterized by having two or more copies of a fertility restorer gene at two or more gene loci which do not have a complete linkage relationship.

In the present invention, the phrase "gene loci which do not have a complete linkage relationship" preferably refers to gene loci on distinct chromosomes.

In this invention, the fertility restorer gene is preferably a gametic fertility restorer gene, and more preferably the rice restorer gene for BT-type male sterility.

Another object of the invention is to provide a method for producing hybrid plants, which method comprises introducing a fertility restorer gene by genetic engineering and placing two or more copies of a fertility restorer gene at two or more gene loci which do not have a complete linkage relationship.

Means for Solving the Problems

As a result of extensive investigations, the present inventors have succeeded in obtaining a hybrid plant of a high fertility and have ultimately arrived at the present invention.

Hybrid Plant

Accordingly, the present invention provides a hybrid plant of a high fertility. The hybrid plant of the invention is characterized by having two or more copies of a fertility restorer gene at two or more gene loci which do not have a complete linkage relationship.

In the plant, during the formation of pollen as the gametophytes, meiosis occurs and the respective pairs of homologous chromosomes segregate. Hence, when a hybrid cultivar is bred using a gametic fertility restorer gene and male-sterile cytoplasm, the hybrid anther exhibits a 1:1 segregation of pollen carrying the fertility restorer gene and pollen lacking the gene, resulting in a theoretical pollen fertility of 50%. The hybrid plant of the invention is characterized in that a) two or more copies of the fertility restorer gene are present, and b) these copies of the gene are located at two or more gene loci which do not have complete linkage relationship. It thus has the advantage that when pollen is formed by meiosis, there is a higher possibility that a gametic restorer gene will be present on one of the chromosomes.

To illustrate, in rice, which has 12 pairs of homologous chromosomes, with gene transfer and repeated crossing, a gametic restorer gene may be located on, for example, chromosomes 6, 7 and 10. When pollen is formed, the homologous chromosomes which contain the gametic restorer gene and the homologous chromosomes which do not contain this gene segregate independently of the segregation with the other pair of homologous chromosomes. As a result, pollen which carries the gametic fertility restorer gene in three places (chromosomes 6, 7 and 10), pollen which carries it in two places (chromosomes 6 and 7, chromosomes 6 and 10, or chromosomes 7 and 10), pollen which has it in one place (chromosome 6, 7 or 10), and pollen which has it in 0 places forms in a ratio of 1:3:3:1. The present inventors have shown that gametic fertility restorer genes introduced by genetic engineering function in the same way as intrinsic genes, that fertility can be obtained even if the pollen has a single gametic fertility restorer gene, and that pollen having a multiple gametic fertility restorer genes develops normally. Therefore, theoretically all of the pollen aside from the ⅛ fraction which has no gametic fertility restorer gene whatsoever, that is, 87.5% of the pollen, has fertility. In Example 4 described later in the specification, three-loci Rf-1 heterozygotes are shown to have a pollen fertility of about 87.5%, demonstrating that the above theory is correct.

To explain the technical features of the invention, examples were given above in which two or more copies of a fertility restorer gene are located on distinct chromosomes. However, even if the genes are present at a multiple, for example, two loci on the same chromosome, so long as there is some degree of genetic distance there between, they are inherited independently as if they were located on distinct chromosomes. Alternatively, even if they are not inherited completely independently, so long as they do not behave in complete unison, it is possible to achieve the object of this invention, which is to enhance pollen fertility by placing two or more copies of a fertility restorer gene at multiple gene loci. Hence, in this specification, "not have complete linkage relationship" includes not only cases where the genes are located on distinct chromosomes and so-called "independent cases" where the genes are likewise inherited completely independently, but also "cases where the gene loci exist in a close or moderate linkage relationship" which, although not independent, is not completely linked. Without being limitative, when two gene loci are separated by a distance of at least about 1 cM, and preferably at least about 5 cM, both are inherited without behaving in complete unison; that is, they can be said to be "not have a complete linkage relationship"

With regard to sporophytic fertility restorer genes, it is entirely conceivable that the fertility restorer gene Rf-1 for BT cytoplasm exhibits some fertility restoring ability in WA cytoplasm. Moreover, there is a possibility that the degree of restoration will be enhanced by the placement of a plurality of copies of the Rf-1 gene. Experiments to ascertain these points are currently being carried out.

As noted above, the hybrid plant of the invention, which is a hybrid plant having two or more copies of a fertility restorer gene at two or more gene loci which do not have complete linkage relationship, has a high pollen fertility compared with fertility restorer gene single-locus heterozygotes containing only one copy of the fertility restorer gene (prior-art hybrid plants). Moreover, the cold hardiness, that is, the seed fertility under a low temperature condition, is also improved (Example 7). Here, "under a low temperature condition" refers to cultivation at 20 to 28° C. under lighted conditions and at 15 to 23° C. under dark conditions following transplantation and up to the ripening stage. For example, in the subsequently described Example 7, when cultivated for 12 hours under lighted conditions (24° C.) and 12 hours under dark conditions (19° C.) following transplantation and up to the ripening stage, hybrid plants according to this invention ($F_1$ plants of FR Koshihikari crossed with 16T1-35) maintained a higher seed fertility compared to that of fertility restorer gene single-locus heterozygotes ($F_1$ plants of MS Koshihikari crossed with FR Koshihikari), which are prior art hybrid plants having only a single copy of the fertility restorer gene.

The hybrid plants of the invention include all states: pollen, seed and adult plants.

The genus and species of the hybrid plants obtained in the invention, while not subject to any specific limitation, include rice and maize. Rice is especially preferred.

The "fertility restorer gene" of the invention includes both gametic genes and sporophytic genes. In gametic genes, the genotype of the pollen determines whether or not the pollen fertility is restored; known examples include the fertility restorer gene Rf-1 for rice BT-type male-sterile cytoplasm and the restorer gene for maize S-type male-sterile cytoplasm. In the case of sporophytic fertility restorer genes, the genotype of the plant that produces the pollen determines whether or not the pollen fertility is restored; known examples include the fertility restorer gene for rice WA-type male-sterile cytoplasm (Ahmed and Siddiq, 1998) and the fertility restorer gene for maize T-type male-sterile cytoplasm (Dhillon, 1998).

Known genes may be used as a "gametic fertility restorer gene" depending on the type of hybrid plant. For example, in the case of hybrid rice, the rice restorer gene for BT-type male sterility, Rf-1 may be used. The present inventors have isolated, identified, and filed a patent application for the Rf-1 gene. In the case of hybrid maize, restorer genes for S-type male-sterile cytoplasm are known; examples include those mentioned by L. Wen and C. D. Chase in Curr. Genet. 35, 521-526 (1999).

The hybrid plant of the invention includes two or more copies of a fertility restorer gene. This invention makes use of the nature of genes that are not completely linked to be inherited completely or partly independently. Therefore, even when there are a plurality of fertility restorer genes on the same chromosome, it is desirable for them to be present at a distance therebetween of at least about 1 cM, and preferably at least about 5 cM. Most preferably, it is desirable for each copy of the gene to be present on different chromosomes. Therefore, the fertility restorer gene, while not subject to any particular limitation, is present in a number that is preferably at most the number of chromosome pairs.

The hybrid plant of the invention has two or more copies of the fertility restorer gene at two or more gene loci which do not have complete linkage relationship. It is preferable for the respective copies of the genes to all exist at gene loci which do not have complete linkage relationship. However, in cases where the hybrid plant has three or more copies of the gene, if some of these genes are present at linked loci but the other genes are present at gene loci which do not have complete linkage relationship, a higher fertility can be achieved than in a single-copy (heterozygous) plant; such cases are included among the hybrid plants of the invention. For example, this includes hybrid plants containing four copies of the gene in which two copies are present at gene loci in a linked relationship on the same chromosome and the other two copies are each present on other, separate chromosomes. The larger the number of genes that are not completely linked, the higher the probability that the pollen will be fertile. Theoretically, when there is only one copy of the fertility restorer gene, this probability is 50%, but when the number of copies rises to two, three, four and five, the probability increases respectively to 75%, 87.5%, 93.75% and 96.875%. In Example 4 of the invention, hybrid rice having the fertility restorer gene Rf-1 at a maximum of four loci was created, and a value very close to the theoretical pollen fertility of 93.75% was observed. This showed that pollen having multiple (e.g., four) fertility restorer genes also develops normally. Therefore, although not subject to particular limitation, the number of copies of the fertility restorer gene in the hybrid plant is preferably from two to the number of chromosome pairs in the host plant, and more preferably from two to four.

One of the two or more copies of the fertility restorer gene in the hybrid plant of the invention may come from a fertility restorer line plant having an intrinsic fertility restorer gene. For example, rice is known have an Rf-1 locus on chromosome 10 (Fukuta et al., Jpn. J. Breed. 42 (suppl. 1), 164-165 (1992)). Such an intrinsic fertility restorer gene can be used to create the hybrid plant of the invention.

Method of Producing Hybrid Plant

The present invention also provides a method for producing the inventive hybrid plant of increased fertility. The method of the invention comprises introducing a fertility restorer gene by genetic engineering and placing two or more copies of a fertility restorer gene at two or more gene loci which do not have a complete linkage relationship.

Without imposing any limitation, the invention is preferably a method for producing comprises 1) introducing a fertility restorer gene by genetic engineering to produce a plant of fertility restoring line containing the fertility restorer genes homozygously at two or more loci; and 2) crossing the plant of fertility restoring line produced by the step of 1) with a plant of sterility line.

In step 1), the method of introducing the fertility recovery gene to the plant is not subject to any particular limitation; a known method that is suitable for the type of plant may be used. Any suitable expression system for transduction by a genetic engineering technique can be employed. Recombinant expression vectors are composed of a nucleic acid containing a fertility restorer gene that can be introduced into the plant (e.g., rice Rf-1) and is operably linked to suitable transcriptional or translational regulatory base sequences, such as ones derived from a mammalian, microbial, viral or insect gene.

Illustrative examples of regulatory sequences include transcriptional promoters, operators and enhancers, mRNA ribosome binding sites, and appropriate sequences which control transcription and translation initiation and termination. The base sequences are linked so as to be capable of functioning when the regulatory sequences are functionally associated with the DNA sequence. Thus, a promoter base sequence is operably linked to a DNA sequence if the promoter base sequence controls the transcription of the DNA sequence. The expression vectors generally incorporate an origin of replication that confers the ability to replicate in a plant, and a selection gene for identifying the transformant. Any commonly used selectable marker may be employed by a standard method. Illustrative examples include genes resistant to antibiotics such as tetracycline, ampicillin, kanamycin, neomycin, hygromycin or spectinomycin.

If necessary, a sequence encoding an appropriate signal peptide (native or heterologous) can be incorporated into the expression vectors. A DNA sequence for a signal peptide (secretory leader) may be fused in frame to a nucleic acid sequence so that first the DNA is transcribed, then the mRNA is translated into a fusion protein containing the signal peptide.

Methods for integrating a DNA fragment of a gene into a vector such as a plasmid are described in, e.g., Sambrook, J., and Russell, D. W.: Molecular Cloning, A Laboratory Manual ($3^{rd}$ edition), (New York: Cold Spring Harbor Laboratory Press, 2001). Commercially available ligation kits (such as those available from Takara Co., Ltd.) can be conveniently used. The recombinant vectors (e.g. recombinant plasmids) thus obtained are transferred into the host plant cells.

Vectors can be conveniently prepared by linking a desired gene to a recombinant vector available in the art (e.g. plasmid DNA) by an ordinary method. Plant transforming vectors are especially useful for conferring a plant with fertility using a nucleic acid fragment of the present invention. Vectors for plants are not specifically limited so far as they can express the gene of interest in plant cells to produce the desired protein. Examples include pBI221, pBI121 (Clontech), and vectors derived therefrom. Examples of vectors for transforming monocotyledons in particular include pIG121Hm and pTOK233 (both from Hiei et al., Plant J. 6, 271-282 (1994)), and pSB424 (Komari et al., Plant J., 10, 165-174 (1996)).

Transgenic plants can be prepared by replacing the β-glucuronidase (GUS) gene in the above vectors with a nucleic acid fragment of the present invention so to construct a plant transforming vector, and introducing the vector into a plant. The plant transforming vector preferably comprises at least a promoter, a translation start codon, a desired gene (the nucleic acid sequence of the fertility restorer gene, or a portion thereof), a translation stop codon and a terminator. It may also contain DNA encoding a signal peptide, an enhancer sequence, non-translated regions at the 5' and 3' ends of the desired gene, and a selectable marker region, as appropriate. Promoters and terminators are not specifically limited so long as they are functional in plant cells. Examples of constitutive expression promoters include the 35S promoter initially contained in the above vectors, as well as promoters for actin and ubiquitin genes.

Examples of suitable methods for introducing a plasmid into a host cell include those mentioned by Sambrook, J. et al. (2001), such as the calcium phosphate method, calcium chloride/rubidium chloride method, electroporation, electroinjection, chemical treatment such as with PEG, and methods involving the use of a gene gun or the like. Plant cells can be transformed by, for example, the leaf disc method (Science 227, 129 (1985)) or electroporation (Nature 319, 791 (1986)).

Examples of methods for transferring a gene into a plant include methods involving the use of *Agrobacterium* (Horsch et al., Science 227, 129 (1985); Hiei et al., Plant J. 6, 271-282 (1994)), electroporation (Fromm et al., Nature 319, 791 (1986)), a PEG method (Paszkowski et al., EMBO J. 3, 2717 (1984)), microinjection (Crossway et al., Mol. Gen. Genet. 202, 179 (1986)), and particle bombardment (McCabe et al., Bio/Technology 6, 923 (1988)). No particular limitation is imposed on the method used, insofar as it is suitable for introducing nucleic acid into the desired plant.

Illustrative, non-limiting examples of *Agrobacterium*-mediated methods for establishing plant (e.g., rice) restorer lines include those described in Hiei et al., Plant J. 6, 271-282 (1994); Komari et al., Plant J. 10, 165-174 (1996); and Ditta et al., Proc. Natl. Acad. Sci. USA 77, 7347-7351 (1980).

First, a plasmid vector containing the nucleic acid fragment to be introduced is prepared. Suitable plasmid vectors include pSB11 and pSB22, plasmid maps for which are described in the above-referenced Komari et al., Plant J. 10, 165-174 (1996). Alternatively, those skilled in the art may themselves construct a suitable vector based on the foregoing plasmid vectors such as pSB11 or pSB22. In the reference examples described later in the specification, an intermediate vector pSB200 having a hygromycin-resistant gene cassette was prepared based on pSB11 and used. Specifically, a nopaline synthase terminator (Tnos) was first fused to a ubiquitin promoter and a ubiquitin intron (Pubi-ubiI). A hygromycin-resistant gene (HYG(R)) was inserted between ubiI and Tnos on the resulting Pubi-ubiI-Tnos complex to give a Pubi-ubiI-HYG(R)-Tnos assembly. This assembly was fused to a HindIII/EcoRI fragment of pSB11 (Komari et al., supra) to give pKY205. Linker sequences for adding restriction enzyme sites NotI, NspV, EcoRV, KpnI, SacI and EcoRI were inserted at HindIII sites upstream of Pubi on this pKY205 to give a vector pSB200 having a hygromycin-resistant gene cassette.

Next, *Escherichia coli* cells (e.g. DH5α, JM109, MV1184, all commercially available from suppliers such as Takara) are transformed with the recombinant vector containing the introduced nucleic acid.

The resulting transformed *E. coli* cells are used to carry out triparental mating with an *Agrobacterium strain*, preferably in combination with a helper *E. coli* strain, according to the method of Ditta et al. (1980), for example. Suitable *Agrobacterium* strains include the *A. tumefaciens* strains LBA4404/pSB1, LBA4404/pNB1 and LBA4404/pSB3. Plasmid maps for all of these are described in the above-referenced Komari et al., Plant J. 10, 165-174 (1996) and may be used by those skilled in the art to construct a vector. Suitable helper *E. coli* strains include, but not are limited to, HB101/pRK2013 (available from Clontech). Although less common, it has been reported that pRK2073-carrying *E. coli* cells can be used as helper *E. coli* (Lemas et al., Plasmid 27, 161-163 (1992)).

Next, the *Agrobacterium* cells mated as intended are used to carry out the transformation of a male sterile plant such as rice according to, inter alia, the method of Hiei et al. (1994). The immature rice seeds required for transformation can be prepared by, for example, pollinating male-sterile rice with a japonica cultivar.

The restoration of fertility in transformed plants can be examined by, for example, seed fertility evaluation in standing plants about one month after heading. "Evaluation in standing plants" refers herein to the examination of plants as grown in, typically, a field. Alternatively, a laboratory study may be conducted on the grain ripening percentage in the panicles of grain.

Although not subject to any particular limitation, the preparation of a fertility restorer line plant that is homozygous for the fertility restorer gene at two or more loci by using a genetic engineering technique to introduce the fertility restorer gene may be carried out as follows.

First, DNA is extracted by a standard method from a transformant in which fertility has been restored as described above, and genomic Southern analysis is carried out. The probe used at this time is prepared from a portion of the introduced gene fragment. A plurality of individuals having a single copy insertion are selected based on the results of analysis. Next, individuals homozygous for the introduced gene are selected from $T_1$ plants obtained by self-fertilization in each case (these are referred to below as "A plants" and "B plants"). Selection can be carried out by the above-mentioned genomic Southern analysis, or by means of a PCR marker designed from base sequence information in the vicinity of the locus of gene introduction. Individuals homozygously containing the fertility restorer gene at two gene loci are selected from $F_2$ plants obtained by crossing the native restorer line with an A plant. The genotype of the fertility restorer gene derived from the native restorer line can be inferred by, for example, the method described in International Disclosure No. WO 03/027290 A1. As noted above, the genotype of the fertility restorer gene derived from A plants can be inferred by genomic Southern analysis, or by using PCR markers.

A similar method was used to select, from among $F_1$ plants obtained by crossing of (a native restorer line/A individuals)/(a native restorer line/B individuals), individuals homozygously containing the fertility restorer gene originating from the native restorer line, and heterozygously containing the fertility restorer genes originating from A plants and B plants. By selecting, from among $F_2$ plants obtained by the self-fertilization of selected individuals, those plants which homozygously contain fertility restorer genes originating from A individuals and B individuals, plants which homozygously have the fertility restorer gene at three gene loci can be prepared.

Before and after each step, it is possible to verify the chromosomal locations at which extrinsic genes have been inserted. An illustrative, non-limiting example of a method for verifying these chromosomal locations is described below.

A sequence not native to the host plant is inserted along with the fertility restorer gene. For example, in the subsequently described examples, a nopaline synthetase terminator (Tnos) (Nos in FIG. 9) is incorporated together with the rice Rf-1 gene. The Tnos sequence is included in the cloning vector pBI121 (Accession No. AF485783) deposited with a public database (Genbank). In Example 3, Nos was used to identify the sites of gene insertion on the chromosomes. Specifically, a primer (e.g., NosF2 in FIG. 9) was prepared based on a known Nos base sequence, and a polymerase chain reaction (PCR) was carried out. The end base sequence of the resulting PCR-amplified product was analyzed and a homology search was carried out on the Genbank database, from which the sequence was found to match the complementary strand sequence on a genomic clone of a specific chromosome on rice (e.g., AP004007 in FIG. 9). To further confirm the presence of the inserted genes on specific chromosomes, two primers may be designed (e.g., No6F and No6R in FIG. 9) and the PCR carried out on the specific chromosomes. When a hybrid plant genome containing the inserted genes is used as the template, an amplification product cannot be obtained by the PCR, whereas fragments of the desired length are amplified when a plant genome without the inserted genes is used. Conversely, if a single primer based on the base sequence for Nos (e.g., NosF2 in FIG. 9) and one primer of a primer pair based on the chromosomal sequence (e.g., Nos6R in FIG. 9), both of which are used to identify the chromosomal sites of the inserted genes, are employed as a primer pair, a fragment of the desired length is amplified when a hybrid plant genome containing the inserted genes is used as the template, whereas amplification product is not observed when a plant genome without the inserted genes is used.

The above verification technique can be employed in plants for which all or part of the base sequence of the genome has been confirmed. For example, the base sequences of the genomes for rice and maize are disclosed in databanks such as Genbank, EMBL and DDBJ.

In step 2) of the inventive method, the plant of fertility restorer line produced in step 1) is crossed with a plant of sterile line, thereby enabling the inventive plant to be obtained.

After the cross has been performed, plants having two or more copies of the fertility restorer gene at two or more gene loci which do not have a complete linkage relationship can be selected. The presence of two or more copies of the fertility restorer gene on the hybrid plant can be confirmed from the number and/or intensity of bands in a Southern analysis.

The present invention also comprises a plant of fertility restoring line homozygously containing the fertility restorer genes at two or more loci produced in step 1). By crossing such a fertility restorer line plant with a desired male-sterile line, the hybrid plant of the invention can be obtained.

Fertility Restorer Gene Rf-1 for Rice BT-Type Male-Sterile Cytoplasm

The present inventors have isolated and identified the fertility restorer gene Rf-1 for rice BT-type male-sterile cytoplasm (reference examples). In the subsequently described examples of the invention, hybrid rice is prepared using the Rf-1 gene as a gametic fertility restorer gene. The present inventors are separately applying for patents on the Rf-1 gene. The details are as follows.

Related Patent Applications Already Filed by the Inventors:

Japanese Patent Application No. 2002-345485; International Disclosure No. WO 02/14506 A1

Japanese Patent Applications No. 2001-285247, 2001-309135 and 2002-185709; International Disclosure No. WO 03/027290 A1

Japanese Patent Application No. 2002-197560; International Patent Application No. PCT/JP03/03154

Firstly, the present inventors have restricted the Rf-1 locus to a very small region on chromosome 10. Based of the results, we developed PCR markers situated close to the Rf-1 locus and found a method for detecting the Rf-1 gene by utilizing the linkage of these PCR markers to the Rf-1 locus. Specifically, making use of the fact that the locus for the Rf-1 gene lies between the loci for the PCR markers S12564 Tsp509I and C1361 MwoI on chromosome 10 in rice, a study is performed to determine whether the Rf-1 gene is present and individuals homozygous for the Rf-1 gene are selected by genotyping the novel PCR marker loci situated nearby. The present inventors previously filed a patent application for a method of detecting the Rf-1 gene as Japanese Patent Application No. 2000-247204, later published as Japanese Patent Public Disclosure No. 2002-345485. Based on this Japanese patent application, an international patent application (PCT/JP01/07052) was also filed, and published as International Disclosure No. WO 02/14506 A1. The entire contents of these patent applications are incorporated herein by reference.

In addition, as improvements to the method disclosed in Japanese Patent Application No. 2000-247204, the present inventors have filed Japanese Patent Applications No. 2001-285247 (Sep. 19, 2001), 2001-309135 (Oct. 4, 2001) and 2002-185709 (Jun. 26, 2002) in which the region of the Rf-1 locus containing the Rf-1 gene is further restricted. Based on the three foregoing Japanese patent applications, the present inventors have also filed an international patent application (PCT/JP02/09429). Moreover, the present inventors have conducted further research and identified the Rf-1 gene, for which Japanese Patent Application No. 2002-197560 on Jul. 5, 2002 was filed. Based on the latter application, an international patent application (PCT/JP03/03154) was filed, and published as International Disclosure No. WO 03/027290 A1. The entire contents of these patent applications are incorporated herein by reference.

In Japanese Patent Public Disclosure No. 2002-345485, the present inventors disclosed that the locus of the Rf-1 gene lies between the loci for the DNA markers S12564 Tsp509I and C1361 MwoI, and describe a RFLP-PCR marker that uses the same. In addition, based on the close linkage between the Rf-1 locus and the DNA marker locus S12564 Tsp509I, the present inventors used chromosome walking and genetic analysis to search in the region between DNA marker loci S12564 Tsp509I and C1361 MwoI for regions linked to the Rf-1 gene. As a result, the present inventors restricted the Rf-1 gene-containing Rf-1 locus region to about 76 kb and successfully determined its entire base sequence.

Specifically, in Japanese Patent Public Disclosure No. 2002-345485, linkage analyses on a population of 1042 individuals prepared by pollinating MS Koshihikari with MS-FR Koshihikari (heterozygous at the Rf-1 locus) revealed one recombinant between the Rf-1 and S12564 Tsp509I loci and two recombinants between the Rf-1 and C1361 MwoI loci. The present inventors added another 4103 individuals to the population, and carried out an analysis on a total of 5145 individuals. As a result, one recombinant between the Rf-1 and S12564 Tsp509I loci and six recombinants between the Rf-1 and C1361 MwoI loci were newly discovered, bringing the total numbers of the respective recombinants to two and eight. These ten individuals were submitted to high-precision segregation analysis as recombinants very near the Rf-1 locus (Reference example 1).

The higher frequency with which recombinants appeared between the Rf-1 and C1361 MwoI loci (8 recombinants) as opposed to between the Rf-1 and S12564 Tsp509I loci (2 recombinants) means that, of the S12564 Tsp509I locus and the C1361 MwoI locus, the former is genetically closer to the Rf-1 locus. The genetic distance (expressed as the recombination rate in cM units) and physical distance (expressed as the number of base pairs, or bp) are not always proportional to each other, but if the genetic distance is short, it can generally be expected that the physical distance will also be short.

Accordingly, the present inventors decided to isolate the Rf-1 locus by carrying out chromosome walking starting at the S12564 Tsp509I locus (Reference example 2). Chromosome walking was performed on a genomic library constructed with the λ DASH II vector using genomic DNA from the indica cultivar IR24 and the japonica cultivar Asominori. IR24 is a cultivar which carries Rf-1, and Asominori is a cultivar which does not carry Rf-1. As a result of chromosome walking, the present inventors were able to prepare contigs (ordered sets of overlapping clones on a chromosome) covering a chromosomal region of about 76 kb from genomic clones of IR24, and went on to determine the entire base sequence (76363 bp) of this region.

Next, using in part the base sequence information thus acquired, the present inventors developed 12 new markers and performed a high-precision segregation analysis on the above-described ten recombinants very near the Rf-1 locus (Reference example 3). The results showed that a 65 kb sequence included in the above-described approximately 76 kb chromosomal region contains a sequence which determines whether the Rf-1 gene has functionality. This region is covered by a contig consisting of 8 genomic clones. Each clone has a length of about 12 to 22 kb and has overlapping domains of at least 4.7 kb. Rice genes are known to vary in length from short genes to long genes, but most are thought to have a length of no more than several kilobases. Hence, it is expected that at least one of these eight genomic clones should contain the full-length Rf-1 gene.

The present inventors further restricted the Rf-1 gene region in the above chromosomal region of about 76 kb and performed complementation tests to directly demonstrate the presence of a fertility restoring ability.

Specifically, ten partial fragments (each 10 to 21 kb) in the above 76 kb region were separately introduced into immature seeds of the male-sterile line MS Koshihikari by genetic engineering techniques (FIG. 5). Of the ten partial fragments used, eight were derived from the eight genomic clones previously obtained by chromosome walking (XSE1, XSE7, XSF4, XSF20, XSG22, XSG16, XSG8 and XSH18 shown in FIG. 1 and described in Reference example 3). Complementation tests were also performed on fragments derived from the two clones XSF18 and XSX1. XSF18 is identical to XSF20 at the 5' and 3' ends (respectively bases 20328 and 41921 of SEQ ID NO:1), but lacks the intermediate bases 33947 to 38591. This is because the clone XSF18 was initially isolated but found to have incurred the above deletion during amplification after isolation; hence, the amplification step was carried out once again and the complete clone was isolated and named XSF20. XSX1 is a clone that was newly prepared from clones XSG8 and XSH18 by restriction enzyme treatment and ligation so as to contain a sufficiently overlapping domain because the overlapping domain of these two original clones was relatively small (about 7 kb).

Because Rf-1 is a dominant gene, if the inserted fragment contains the entire Rf-1 gene, fertility will be restored in primary transformants. In complementation tests, plants transformed with each fragment were evaluated for seed fertility. Seed fertility was found to be restored in those plants transformed with a 15.6 kb fragment (including bases 38538 to 54123 of SEQ ID NO:1) derived from the λ phage clone XSG16 (Reference example 4). Plants transformed with the other fragments were all sterile. These results showed that the above 15.6 kb fragment completely contains the Rf-1 gene. Moreover, a method for introducing the Rf-1 gene by genetic engineering techniques was provided and demonstrated to be effective.

To further specify the portion of the λ phage clone XSG16 that contains the Rf-1 gene, the present inventors conducted seed fertility studies by complementary tests on fragments shorter than the above 15.6 kb fragment (which includes bases 38538 to 54123 of SEQ ID NO:1). As a result, the present inventors found that seed fertility was restored in plants transformed with an 11.4 kb fragment derived from XSG16 (containing bases 42357 to 53743 of SEQ ID NO:1) (Reference example 4(2)). Seed fertility was also restored in plants transformed with an even shorter 6.8 kb fragment (containing bases 42132 to 48883 of SEQ ID NO:1) (Reference example 4(3)). These results showed that the above 6.8 kb fragment contains the Rf-1 gene.

Continuing our research further, the present inventors have identified the nucleic acid that has a fertility restoring ability and also determined the amino acid sequence encoded thereby. Specifically, as described subsequently in Reference examples 5 and 6, first, DNA fragments corresponding to bases 43733 to 44038 and bases 48306 to 50226 of SEQ ID NO:1 were prepared using the PCR. Using these two fragments as probes (probes P and Q), the present inventors screened a cDNA library constructed from a line obtained by introducing Rf-1 into Koshihikari. As a result, the end base sequences of six of the clones matched the sequence of XSG16. These clones were isolated as Rf-1 gene-containing clones, and their base sequences were analyzed (SEQ ID NOS: 43 to 48).

All of these sequences (SEQ ID NOS. 43 to 48) encode a protein having amino acid sequence 1 to 791 (SEQ ID NO:49). Specifically, bases 215 to 2587 of SEQ ID NO:43, bases 213 to 2585 of SEQ ID NO:44, bases 218 to 2590 of SEQ ID NO:45, bases 208 to 2580 of SEQ ID NO:46, bases 149 to 2521 of SEQ ID NO:47 and bases 225 to 2597 of SEQ ID NO:48 all encode the amino acid sequence 1 to 791 of SEQ ID NO:49. Moreover, the above base sequence corresponds to bases 43907 to 46279 of SEQ ID NO:1.

The amino acid sequence of SEQ. ID NO:49 was compared with the putative amino acid sequence for the maize fertility restorer gene (Rf2) (Cui et al., 1996), whereupon the seven amino acid residues at the N terminus (Met-Ala-Arg-Arg-Ala-Ala-Ser) were found to agree. These seven amino acid residues are thought to be part of a mitochondrial targeting signal (Liu et al., 2001). Based on these results, it appears that the cDNA isolated in this study is completely contained within the coding region of the Rf-1 gene. Aside from the foregoing region, no homology at the amino acid level was observed between the rice Rf-1 gene and the maize Rf-2 gene.

In addition, the cDNA sequences isolated in the present study were compared with the genome sequence of IR24 (SEQ ID NO:1), revealing the structures of the exons and introns for the Rf-1 gene (FIG. 7). This demonstrated that various transcription products of different splicing modes and poly (A) addition sites are present together within an individual plant. No introns are present within the encoding region of the Rf-1 gene.

The present inventors also performed a complementation assay on the 6.8 kg fragment that restored seed fertility in the complementation test in Reference example 4(3). Specifically, in Reference example 7, seed fertility was restored when a complementation test was conducted using a 4.2 kb fragment (bases 42132 to 46318 on SEQ ID NO:1) containing the promoter region and the anticipated translation region of the RF-1 gene in the above-mentioned 6.8 kb fragment.

In addition, six new clones containing nucleic acid having a fertility restoring ability were obtained in Reference example 8. First, a PCR was performed using two different primers corresponding to bases 45522 to 45545 and bases 45955 to 45932 of SEQ ID NO:1 and using the genomic clone XSG16 of IR24 as the template, thereby giving a DNA fragment. Using this DNA fragment as probe R, plaque hybridization was then carried out together with above probe P. Six new clones (#7 to #12) were then obtained from the plaques that were positive for either of probe P and probe R. The results are shown in SEQ ID NOS: 54 to 59.

All of these sequences (SEQ ID NOS: 54 to 59) presumably encode the protein of amino acid sequence 1 to 791 (SE ID NO:49). Specifically, bases 229 to 2601 of SEQ ID NO:54, bases 175 to 2547 of SEQ ID NO:55, bases 227 to 2599 of SEQ ID NO:56, bases 220 to 2592 of SEQ ID NO:57, bases 174 to 2546 of SEQ ID NO:58 and bases 90 to 2462 of SEQ ID NO:59 all encode the amino acid sequence 1 to 791 of SEQ ID NO:49. Moreover the above base sequence corresponds to bases 43907 to 46279 of SEQ ID NO:1.

The cDNA sequences isolated this time were compared with the genome sequence of IR24 (SEQ ID NO:1 in Japanese Patent Application No. 2001-285247), revealing the exon and intron structures (FIG. 8). Three of these isolated cDNA sequences contained no exons unrelated to the anticipated translation region and had only a single exon (#10 to #12; SEQ ID NOS: 57 to 59).

The nucleic acid containing a fertility restorer gene (Rf-1) locus is nuclei acid having the base sequence of SEQ ID NO:1 or a base sequence that is at least 70% identical to the base sequence of SEQ ID No:1, and includes nucleic acid having a fertility restoring ability. Moreover, as mentioned in Reference example 4, of the base sequences in SEQ ID NO:1, it was confirmed in particular that the Rf-1 gene is completely included in bases 38538 to 54123. The Rf-1 gene-containing region was further specified as preferably bases 38538 to 54123, more preferably bases 42357 to 53743, even more preferably bases 42132 to 48883, and still more preferably bases 42132 to 46318, of SEQ ID NO:1.

The following regions were identified as nucleic acid containing the Rf-1 gene:

a) bases 215 to 2587 of SEQ ID NO:43,
b) bases 213 to 2585 of SEQ ID NO:44,
c) bases 218 to 2590 of SEQ ID NO:45,
d) bases 208 to 2580 of SEQ ID NO:46,
e) bases 149 to 2521 of SEQ ID NO:47,
f) bases 225 to 2597 of SEQ ID NO:48,
h) bases 229 to 2601 of SEQ ID NO:54,
i) bases 175 to 2547 of SEQ ID NO:55,
j) bases 227 to 2599 of SEQ ID NO:56,
k) bases 220 to 2592 of SEQ ID NO:57,
l) bases 174 to 2546 of SEQ ID NO:58, and
m) bases 90 to 2462 of SEQ ID NO:59, The above base sequences correspond to g) bases 43907 to 46279 of SEQ ID NO:1, and all encode the amino acid sequence 1 to 791 of SEQ ID NO:49.

In this specification, depending on the context, the phrase “base sequence of SEQ ID NO:1” refers to all of SEQ ID NO:1, or to a portion thereof which takes part in fertility restoring ability, particularly bases 38538 to 54123. It refers more preferably to bases 42357 to 53743, even more preferably to bases 42132 to 48883, and still more preferably to bases 42132 to 46318. It refers most preferably to g) bases 43907 to 46279 of SEQ ID NO:1, or to any one of a) bases 215 to 2587 of SEQ ID NO:43, b) bases 213 to 2585 of SEQ ID NO:44, c) bases 218 to 2590 of SEQ ID NO:45, d) bases 208 to 2580 of SEQ ID NO:46, e) bases 149 to 2521 of SEQ ID NO:47, f) bases 225 to 2597 of SEQ ID NO:48, h) bases 229 to 2601 of SEQ ID NO:54, i) bases 175 to 2547 of SEQ ID NO:55, j) bases 227 to 2599 of SEQ ID NO:56, k) bases 220 to 2592 of SEQ ID NO:57, l) bases 174 to 2546 of SEQ ID NO:58, and m) bases 90 to 2462 of SEQ ID NO:59 which corresponds thereto.

In the reference examples below, as the nucleic acid containing a fertility restorer gene (Rf-1), nucleic acid was isolated from a genomic library of indica rice IR24 containing the Rf-1 gene and was determined to have the base sequence of SEQ ID NO:1. However, the nucleic acid containing a fertility restorer gene (Rf-1) of the present invention can be derived, without particular limitation, from any indica variety carrying the Rf-1 gene. Illustrative examples of indica varieties carrying the Rf-1 gene include IR24, IR8, IR36, IR64, Chinsurah and BoroII. Japonica varieties which do not carry the Rf-1 gene include, but are not limited to, Asominori, Koshihikari, Kirara 397, Akihikari, Akitakomachi, Sasanishiki, Kinuhikari, Nipponbare, Hatsuboshi, Koganebare, Hinohikari, Mineasahi, Aichinokaori, Hatsushimo, Akebono, Fujihikari, Minenoyukimochi, Kokonoemochi, Fukuhibiki, Dontokoi, Gohyakumangoku, Hanaechizen, Todorokiwase, Haenuki, Domannaka and Yamahikari. “Indica varieties” and “japonica varieties” are terms familiar to those skilled in the art, and so it will be readily apparent to those conversant in the art which rice cultivars are encompassed by the present invention.

Nucleic acids that may be used in the present invention include genomic DNA (including corresponding cDNA), chemically synthesized DNA, DNA amplified by the PCR, and combinations thereof.

Nucleic acids containing the Rf-1 gene of the present invention preferably have the base sequence of SEQ ID NO:1. At least one codon may encode the same amino acid; this is called degeneracy of the genetic code. Hence, a DNA sequence not completely identical to SEQ ID NO:1 may encode a protein having an amino acid sequence completely identical to that encoded by SEQ ID NO:1. Such a variant DNA sequence may result from silent mutation (e.g., occurring during PCR amplification), or can be a product of the deliberate mutagenesis of a native sequence.

The Rf-1 gene preferably encodes the amino acid sequence in SEQ ID NO:49, but is not limited to this sequence, and may instead code for a similar amino acid sequence having one or more amino acid deletion, addition or substitution.

All homologous proteins are included, provided they have a fertility restoring ability. There may be one or more "amino acid variations," the number of such variations being preferably from 1 to 20, more preferably from 1 to 10, and most preferably from 1 to 5. The amino acid sequence which encodes the Rf-1 gene is at least about 70%, preferably at least about 80%, more preferably at least about 90%, even more preferably at least about 95%, and most preferably at least about 98% identical with the amino acid sequence of SEQ ID NO:49.

The percent identity of the amino acid sequence may be determined by visual inspection and mathematical calculation. Alternatively, the percent identity between two protein sequences may be determined based on the algorithm of S. B. Needleman and C. D. Wunsch (J. Mol. Biol. 48, 443-453 (1970), and by comparing sequence information using the GAP computer program available from the University of Wisconsin Genetics Computer Group (UWGCG). The preferred default parameters for the GAP program include: (1) a scoring matrix such as blosum62 mentioned by S. Henikoff and J. G. Henikoff (Proc. Natl. Acad. Sci. USA 89, 10915-10919 (1992)); (2) gap penalty of 12; (3) gap length penalty of 4; (4) no penalty for end gaps.

Use can also be made of other sequence comparison programs employed by those skilled in the art. The percent identity can be determined by comparing sequence information using the BLAST program described by Altschul et al. (Nucl. Acids. Res. 25, 3389-3402 (1997). This program can be used from the National Center for Biotechnology Information (NCBI) or DNA Data Bank of Japan (DDBJ) web site on the Internet. Various parameters for homology searches using the BLAST program are described in detail at the same web sites. Some of the settings can be changed as appropriate, although the searches are generally conducted using default values.

It is a well-known fact among those skilled in the art that, even among proteins having the same function, there may exist differences in the amino acid sequences depending on the cultivars from which they are derived. The Rf-1 gene, so long as it has a fertility restoring ability, also includes such homologs and variants of the base sequence of SEQ ID NO:1. Here, "has a fertility restoring ability" means to confer fertility to rice plants or seeds when a DNA fragment has been inserted. The restoration of fertility may rely on protein expression by the Rf-1 gene, or the nucleic acid (DNA or RNA) of the Rf-1 gene may itself play some function in the conferring of fertility.

In a non-limiting example of a method which may be used to determine whether a homolog or variant of the Rf-1 gene functions to restore fertility, the nucleic acid fragment of interest is introduced into immature seeds obtained by pollinating MS Koshihikari (sterile line) with Koshihikari according to the method of Hiei et al. (Plant Journal 6, No. 2, 272-282 (1994)). When the resulting transformants are grown under normal conditions, the seeds mature only if the inserted nucleic acid fragment has a fertility restoring ability.

The nucleic acid derived from a corresponding region of japonica Asominori not carrying the Rf-1 gene has the base sequence shown in SEQ ID NO:2. Corresponding parts of SEQ ID NO:2 and SEQ ID NO:1 have an overall identity of about 98%. Thus, nucleic acids containing the locus of the fertility restorer gene (Rf-1) are at least about 70%, preferably at least about 80%, more preferably at least about 90%, still more preferably at least about 95%, and most preferably at least about 98% identical to SEQ ID NO:1. "SEQ ID NO:1" is most preferably g) bases 43907 to 46279 of SEQ ID NO:1 or any one of a) bases 215 to 2587 of SEQ ID NO:43, b) bases 213 to 2585 of SEQ ID NO:44, c) bases 218 to 2590 of SEQ ID NO:45, d) bases 208 to 2580 of SEQ ID NO:46, e) bases 149 to 2521 of SEQ ID NO:47, f) bases 225 to 2597 of SEQ ID NO:48, h) bases 229 to 2601 of SEQ ID NO:54, i) bases 175 to 2547 of SEQ ID NO:55, j) bases 227 to 2599 of SEQ ID NO:56, k) bases 220 to 2592 of SEQ ID NO:57, 1) bases 174 to 2546 of SEQ ID NO:58, and m) bases 90 to 2462 of SEQ ID NO:59 which corresponds thereto.

The percent identity of the nucleic acid may be determined by visual inspection and mathematical calculation. Alternatively, the percent identity between two nucleic acid sequences can be determined by comparing sequence information using the GAP computer program, version 6.0, described by Devereux et al. in Nucl. Acids Res. 12, 387 (1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14, 6745 (1986), as described by Schwartz and Dayhoff, eds., Atlas of Protein Sequence and Structure (National Biomedical Research Foundation, 1979), pp. 353-358; (2) a penalty of 3.0 for each gap and an additional 0.10 penalty for each symbol in each gap; and (3) no penalty for end gaps. Other sequence comparison programs used by those skilled in the art may also be employed.

Preferred nucleic acids of the present invention also include nucleic acids which are capable of hybridizing to the base sequence of SEQ ID NO:1 under moderately stringent conditions and have a fertility restoring ability, and nucleic acids which are capable of hybridizing to the base sequence of SEQ ID NO:1 under highly stringent conditions and have a fertility restoring ability.

As used herein, conditions of moderate stringency can be readily determined by those of ordinary skill in the art based on, for example, the length of the DNA. The basic conditions are set forth by Sambrook et al. in Molecular Cloning: A Laboratory Manual, $2^{nd}$ Ed., Vol. 1 (Cold Spring Harbor Laboratory Press, 1989), pp. 1.101-104, and include the use of a prewashing solution for nitrocellulose filters of 5×SSC, 0.5% SDS, 1.0 mM EDTA (pH 8.0); hybridization conditions of about 1×SSC to 6×SSC at about 40° C. to 60° C. (or some other similar hybridization solution such as Stark's solution within approximately 50% formamide at about 42° C.); and washing conditions of about 60° C., 0.5×SSC and 0.1% SDS. The hybridization temperature is about 15 to 20° C. lower when the hybridization solution contains about 50% formamide. Conditions of high stringency can also be readily determined by one skilled in the art based on, for example, the length of the DNA. Highly stringent conditions generally include hybridization and/or washing conditions at higher temperature and/or lower salt concentration than the moderately stringent conditions described above. For example, such conditions include hybridization conditions of 0.1×SSC to 0.2×SSC at about 60 to 65° C. and/or washing conditions of 0.2×SSC and 0.1% SDS at about 65 to 68° C. It will be recognized by those skilled in the art that the temperature and the salt concentrations of the washing solution may be adjusted if necessary according to such factors as the length of the probe.

"SEQ ID NO:1" is most preferably g) bases 43907 to 46279 of SEQ ID NO:1 or any one of a) bases 215 to 2587 of SEQ ID NO:43, b) bases 213 to 2585 of SEQ ID NO:44, c) bases 218 to 2590 of SEQ ID NO:45, d) bases 208 to 2580 of SEQ ID NO:46, e) bases 149 to 2521 of SEQ ID NO:47, f) bases 225 to 2597 of SEQ ID NO:48, h) bases 229 to 2601 of SEQ ID NO:54, i) bases 175 to 2547 of SEQ ID NO:55, j) bases 227 to 2599 of SEQ ID NO:56, k) bases 220 to 2592 of SEQ ID NO:57, 1) bases 174 to 2546 of SEQ ID NO:58, and m) bases 90 to 2462 of SEQ ID NO:59 which corresponds thereto.

The DNA of the invention also includes nucleic acids that differ from the base sequence of SEQ ID NO:1 on account of the deletion, insertion or substitution of one or more base, yet retain a fertility restoring ability. Insofar as a fertility restoring ability is retained, the number of bases that are deleted, inserted or substituted is not subject to any particular limitation, although the number of such bases is preferably from 1 to several thousand, more preferably from 1 to 1,000, even more preferably from 1 to 500, more preferably yet from 1 to 200, and most preferably from 1 to 100.

Once the Rf-1 gene is further specified based on the descriptions provided herein, one skilled in the art will be able to use the nucleic acid exclusive of regions other than the Rf-1 gene and exclusive of intron regions within the Rf-1 gene. Given amino acids (particularly amino acid sequences in SEQ ID NO:49) may be substituted with, for example, residues having similar physiochemical characteristics. Examples of such conservative substitutions include changes from one aliphatic residue to another, such as substitutions among Ile, Val, Leu and Ala; changes from one polar residue to another, such as substitutions between Lys and Arg, Glu and Asp, or Gln and Asn; and changes from one aromatic residue to another, such as substitutions among Phe, Trp and Tyr. Other well-known conservative substitutions include changes between entire regions having similar hydrophobic characteristics. Those skilled in the art will be capable of introducing desired deletions, insertions or substitutions using familiar gene engineering techniques, such as site-specific mutagenesis as described in Sambrook et al. (2001, supra).

The present inventors compared an indica variety IR24 (SEQ ID NO:27) that carries the Rf-1 gene with the japonica variety Asominori (SEQ ID NO:28) and a Nipponbare BAC clone deposited with GenBank (Accession No. AC068923), both of which do not carry it. As a result, the present inventors found that the Rf-1 region of the indica variety which includes the Rf-1 gene has at least the following single-base polymorphisms (SNP):

1) a base corresponding to base 1239 of SEQ ID NO:1 is A;

2) a base corresponding to base 6227 of SEQ ID NO:1 is A;

3) a base corresponding to base 20680 of SEQ ID NO:1 is G;

4) a base corresponding to base 45461 of SEQ ID NO:1 is A;

5) a base corresponding to base 49609 of SEQ ID NO:1 is A;

6) a base corresponding to base 56368 of SEQ ID NO:1 is T;

7) a base corresponding to base 57629 of SEQ ID NO:1 is C; and 8) a base corresponding to base 66267 of SEQ ID NO:1 is G.

Thus, nucleic acids containing the Rf-1 region of the present invention preferably meet anywhere from one to all of above conditions 1) to 8).

In Reference example 3 below, the chromosomal organization of the Rf-1 region was examined for recombinants very near the Rf-1 gene (RS1 and RS2, RC1 to RC8). The results showed that a sequence determinative for the presence or absence of Rf-1 gene function is included in the sequence of bases 1239 to 66267 in SEQ ID NO:1, i.e. in a region estimated to extend at most from the P4497 MboI locus to the B56691 XbaI locus (about 65 kb) (FIG. 3). However, there is a possibility that part of the genotype of the Rf-1 gene is important for the expression of genetic function by the Rf-1 gene in indica varieties, while the remainder of the genotype gives rise to little difference in genetic function both in japonica varieties and indica varieties. In extreme cases, it may even be possible for the encoding region to be completely identical in japonica and indica, with only the promoter regions differing, and for only part of the promoter regions and encoding regions to be included in the above region from the P4497 MboI locus to the B56691 XbaI locus (approx. 65 kb). Therefore, it cannot be categorically stated that the above-described common indica region (bases 1239 to 66267 of SEQ ID NO:1) include the entire Rf-1 gene. Nonetheless, it does appear for the following reasons that at least SEQ ID NO:1 includes the Rf-1 gene in its entirety:

1) a gene is generally several kilobases in size, and rarely exceeds 10 kb;

2) the genomic base sequence of IR24 (SEQ ID NO:1) completely contains the common indica region above;

3) the 5' end of SEQ ID NO:1 is located 1238 bp upstream of the 5' end of the above common indica region and forms a part of another gene (S12564); and 4) the 3' end of SEQ ID NO:1 is located 10096 bp downstream of the 3' end of the above common indica region.

Moreover, the present inventors have confirmed from complementation tests that the Rf-1 gene is completely contained within, of the base sequence of SEQ ID NO:1, particularly bases 38538 to 54123. Therefore, in one embodiment of the invention, a base sequence which is at least 70% identical to the base sequence of SEQ ID NO:1 or with the base sequence of bases 38538 to 54123 in SEQ ID NO:1 satisfies at least one of the following conditions 1) and 2):

1) a base corresponding to base 45461 of SEQ ID NO:1 is A; and 2) a base corresponding to base 49609 of SEQ ID NO:1 is A.

In addition, the present inventors have identified the following regions as the nucleic acid containing RF-1 gene:

a) bases 215 to 2587 of SEQ ID NO:43,
b) bases 213 to 2585 of SEQ ID NO:44,
c) bases 218 to 2590 of SEQ ID NO:45,
d) bases 208 to 2580 of SEQ ID NO:46,
e) bases 149 to 2521 of SEQ ID NO:47,
f) bases 225 to 2597 of SEQ ID NO:48,
h) bases 229 to 2601 of SEQ ID NO:54,
i) bases 175 to 2547 of SEQ ID NO:55,
j) bases 227 to 2599 of SEQ ID NO:56,
k) bases 220 to 2592 of SEQ ID NO:57,
l) bases 174 to 2546 of SEQ ID NO:58, and
m) bases 90 to 2462 of SEQ ID NO:59, The above base sequence corresponds to g) bases 43907 to 46279 of SEQ ID NO:1. Preferred nucleic acids of the invention are:

n) nucleic acids which are at least 70% identical to the nucleic acid of any one of regions a) to m) above, and which have a fertility restoring ability;

o) nucleic acids which hybridize to the nucleic acid of any one of regions a) to m) above under conditions that are moderately or highly stringent, and which have a fertility restoring ability; and p) nucleic acids which are obtained by the deletion, insertion or substitution of one or more base in any one of regions a) to m) above, and which have a fertility restoring ability.

Base 45461 of above SEQ ID NO:1 corresponds to 1) base 1769 of SEQ ID NO:43, 2) base 1767 of SEQ ID NO:44, 3) base 1772 of SEQ ID NO:45, 4) base 1762 of SEQ ID NO:46, 5) base 1703 of SEQ ID NO:47, 6) base 1779 of SEQ ID NO:48, 7) base 1783 of SEQ ID NO:54, 8) base 1729 of SEQ ID NO:55, 9) base 1781 of SEQ ID NO:56, 10) base 1774 of SEQ ID NO:57, 11) base 1728 of SEQ ID NO:58 and 12) base 1644 of SEQ ID NO:59. Therefore, it is especially preferable for the nucleic acid used in the method of the invention to satisfy at least one of the following conditions 1) to 12):

1) a base corresponding to base 1769 of SEQ ID NO:43 is A;

2) a base corresponding to base 1767 of SEQ ID NO:44 is A;

3) a base corresponding to base 1772 of SEQ ID NO:45 is A;

4) a base corresponding to base 1762 of SEQ ID NO:46 is A;

5) a base corresponding to base 1703 of SEQ ID NO:47 is A;

6) a base corresponding to base 1779 of SEQ ID NO:48 is A;

7) a base corresponding to base 1783 of SEQ ID NO:54 is A;

8) a base corresponding to base 1729 of SEQ ID NO:55 is A;

9) a base corresponding to base 1781 of SEQ ID NO:56 is A;

10) a base corresponding to base 1774 of SEQ ID NO:57 is A;

11) a base corresponding to base 1728 of SEQ ID NO:58 is A; or 12) a base corresponding to base 1644 of SEQ ID NO:59 is A.

In the complementation tests described in Reference examples 4 and 7 of the specification, MS Koshihikari (containing BT cytoplasm and having substantially the same nuclear genes as Koshihikari) was transformed by a method which uses the fragments derived from the ten clones shown in FIG. 5 and uses *Agrobacterium*. As a result, it was demonstrated that the fertility restorer line is bred using nucleic acid containing the base sequence of bases 38538 to 54123, preferably bases 42357 to 53743, more preferably bases 42132 to 48883, and even more preferably bases 42132 to 46318, of SEQ ID NO:1.

It was confirmed in the examples of the invention that pollen fertility can be obtained using a 15.6 kb fragment derived from XSG16 as the Rf-1 gene. It will be readily apparent to one conversant in the art that longer fragments containing the foregoing fragment and, as described above, shorter fragments which have been identified as containing the Rf-1 gene can likewise be used. The use of shorter fragments is preferred.

EXAMPLES

Figure 1:
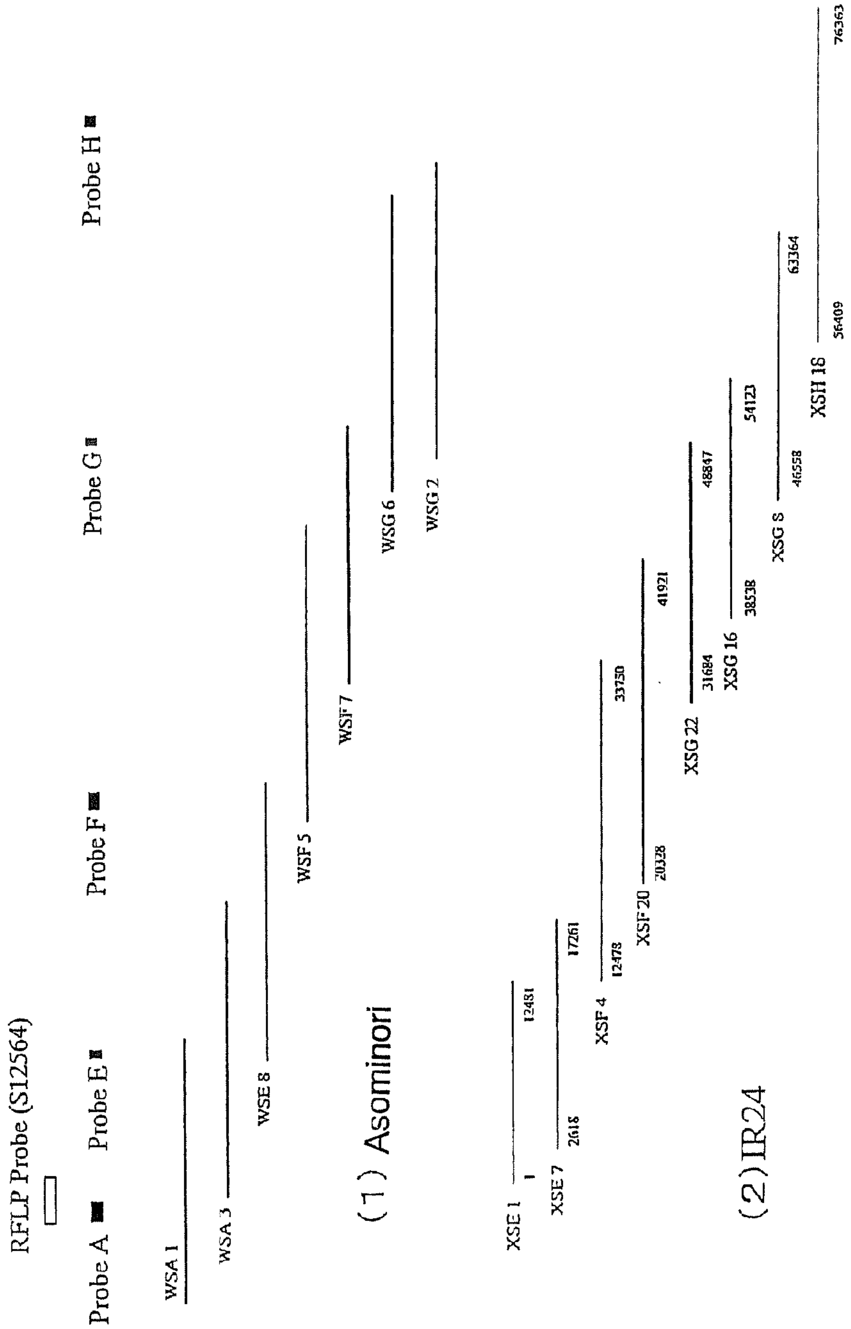
FIG. 1 shows the results of chromosomal walking started from the RFLP marker locus S12564.

The following examples further illustrate the present invention but are not intended to limit the technical scope thereof. Those skilled in the art will readily be capable of making various modifications and changes to the present invention based on the description provided herein. Such modifications and changes are encompassed within the technical scope of the invention.

REFERENCE EXAMPLES

The following reference examples describe isolation and identification of the rice restorer gene for BT-type male sterility, as well as confirmation of the activity to restore fertility.

Reference Example 1

Acquisition of Recombinant Individuals Proximal to the Rf-1 Locus (Materials and Methods)

DNA was extracted from each of 4103 individuals of BC10F1 population produced by pollinating MS Koshihikari (generation: BC10F1) with MS-FR Koshihikari (generation: BC9F1, heterozygous at the Rf-1 locus), and genotyped at the S12564 Tsp509I and C1361 MwoI loci in the same manner as described in Reference example 2 above. Individuals having a genotype homozygous for Koshihikari at the S12564

Tsp509I locus were regarded as those generated by recombination between the Rf-1 and S12564 Tsp509I loci, while individuals having a genotype homozygous for Koshihikari at the C1361 MwoI locus were regarded as those generated by recombination between the Rf-1 and C1361 MwoI loci.

(Results and Discussion)

A survey of 4103 individuals revealed one recombinant individual between the Rf-1 and S12564 Tsp509I loci and 6 recombinant individuals between the Rf-1 and C1361 MwoI loci. The previous survey of 1042 individuals obtained by crossing in Reference example 2 above had already revealed one recombinant individual between the Rf-1 and S12564 Tsp509I loci and 2 recombinant individuals between the Rf-1 and C1361 MwoI loci as shown in Table 3.

Thus, a total of 2 recombinant individuals between the Rf-1 and S12564 Tsp509I loci and 8 recombinant individuals between the Rf-1 and C1361 MwoI loci were able to be obtained from 5145 individuals. These 10 individuals were tested by high-precision segregation analysis in the reference examples below.

Reference Example 2

Chromosomal Walking (1) First Chromosomal Walking (Materials and Methods)

A genomic library was constructed from the genomic DNA of Asominori japonica (not carrying Rf-1) using Lambda DASH II vector as described in Reference example 1 and tested by chromosomal walking.

PCR was routinely performed using total DNA of Asominori as a template in combination with the following primer pair:

```
5'-atcaggagccttcaaattgggaac-3'    (SEQ ID NO: 3)
and

5'-ctcgcaaattgcttaattttgacc-3'    (SEQ ID NO: 4)
```

designed for a partial base sequence (Accession No. D47284) of RFLP probe S12564. The resulting amplification products of about 1200 bp were electrophoresed on an agarose gel and then purified by QIAEXII (QIAGEN). The purified DNA was labeled with a rediprime DNA labelling system (Amersham Pharmacia) to give a library screening probe (probe A, FIG. 1).

The library was routinely screened after plaques were blotted onto Hybond-$N^+$ (Amersham Pharmacia). Single plaques were separated, after which phage DNA was purified by the plate lysate method using Lambda Midi kit (QIAGEN).

(Results and Discussion)

The results of terminal base sequence analysis and restriction enzyme fragment length analysis showed that two (WSA1 and WSA3) of 4 clones obtained by screening were in a relative position as shown in FIG. 1. The Asominori genomic base sequences corresponding to WSA1 and WSA3 were determined by primer walking (DNA Sequencer 377, ABI).

(2) Second Chromosomal Walking (Materials and Methods)

In addition to the Asominori genomic library described above, an IR24 genomic library was similarly constructed from the genomic DNA of an indica variety IR24 (carrying Rf-1) and tested by chromosomal walking.

PCR was routinely performed using DNA of WSA3 as a template in combination with the following primer pair:

```
5'-tgaaggagttatgggtgcgtgacg-3'    (SEQ ID NO: 5)
and

5'-ttgccgagcacacttgccatgtgc-3'    (SEQ ID NO: 6)
```

designed for the Asominori genomic base sequence determined in (1). The resulting amplification products of 524 bp were purified and labeled by the method described above to give a library screening probe (probe E, FIG. 1).

Library screening and phage DNA purification were performed by the method described above.

(Results and Discussion)

The results of terminal base sequence analysis and restriction enzyme fragment length analysis showed that one (WSE8) of 15 clones obtained by screening of the Asominori genomic library was in a relative position as shown in FIG. 1. The Asominori genomic base sequence corresponding to WSE8 was determined by primer walking.

The results of terminal base sequence analysis and restriction enzyme fragment length analysis showed that two (XSE1 and XSE7) of 7 clones obtained by screening of the IR24 genomic library were in a relative position as shown in FIG. 1. The IR24 genomic base sequences corresponding to XSE1 and XSE7 were determined by primer walking.

(3) Third Chromosomal Walking (Materials and Methods)

The Asominori genomic library and IR24 genomic library described above were tested by chromosomal walking.

PCR was routinely performed using DNA of WSE8 as a template in combination with the following primer pair:

```
5'-gcgacgcaatggacatagtgctcc-3'    (SEQ ID NO: 7)
and

5'-ttacctgccaagcaatatccatcg-3'    (SEQ ID NO: 8)
```

designed for the Asominori genomic base sequence determined in (2). The resulting amplification products of 1159 bp were purified and labeled by the method described above to give a library screening probe (probe E, FIG. 1).

Library screening and phage DNA purification were performed by the method described above.

(Results and Discussion)

The results of terminal base sequence analysis and restriction enzyme fragment length analysis showed that two (WSF5 and WSF7) of 8 clones obtained by screening of the Asominori genomic library were in a relative position as shown in FIG. 1. The Asominori genomic base sequences corresponding to WSF5 and WSF7 were determined by primer walking.

The results of terminal base sequence analysis and restriction enzyme fragment length analysis showed that two (XSF4 and XSF20) of 13 clones obtained by screening of the IR24 genomic library were in a relative position as shown in FIG. 1. The IR24 genomic base sequences corresponding to XSF4 and XSF20 were determined by primer walking.

(4) Fourth Chromosomal Walking (Materials and Methods)

The Asominori genomic library and IR24 genomic library described above were tested by chromosomal walking.

PCR was routinely performed using DNA of WSF7 as a template in combination with the following primer pair:

```
5'-aaggcatactcagtggagggcaag-3'    (SEQ ID NO: 9)
and

5'-ttaacctgaccgcaagcacctgtc-3'    (SEQ ID NO: 10)
```

designed for the Asominori genomic base sequence determined in (3). The resulting amplification products of 456 bp were purified and labeled by the method described above to give a library screening probe (probe G, FIG. 1).

Library screening and phage DNA purification were performed by the method described above.

(Results and Discussion)

The results of terminal base sequence analysis and restriction enzyme fragment length analysis showed that two (WSG2 and WSG6) of 6 clones obtained by screening of the Asominori genomic library were in a relative position as shown in FIG. 1. The Asominori genomic base sequences corresponding to WSG2 and WSG6 were determined by primer walking.

The results of terminal base sequence analysis and restriction enzyme fragment length analysis showed that three (XSG8, XSG16 and XSG22) of 14 clones obtained by screening of the IR24 genomic library were in a relative position as shown in FIG. 1. The IR24 genomic base sequences corresponding to XSG8, XSG16 and XSG22 were determined by primer walking.

(5) Fifth Chromosomal Walking (Materials and Methods)

The IR24 genomic library described above was tested by chromosomal walking.

Figure 2:
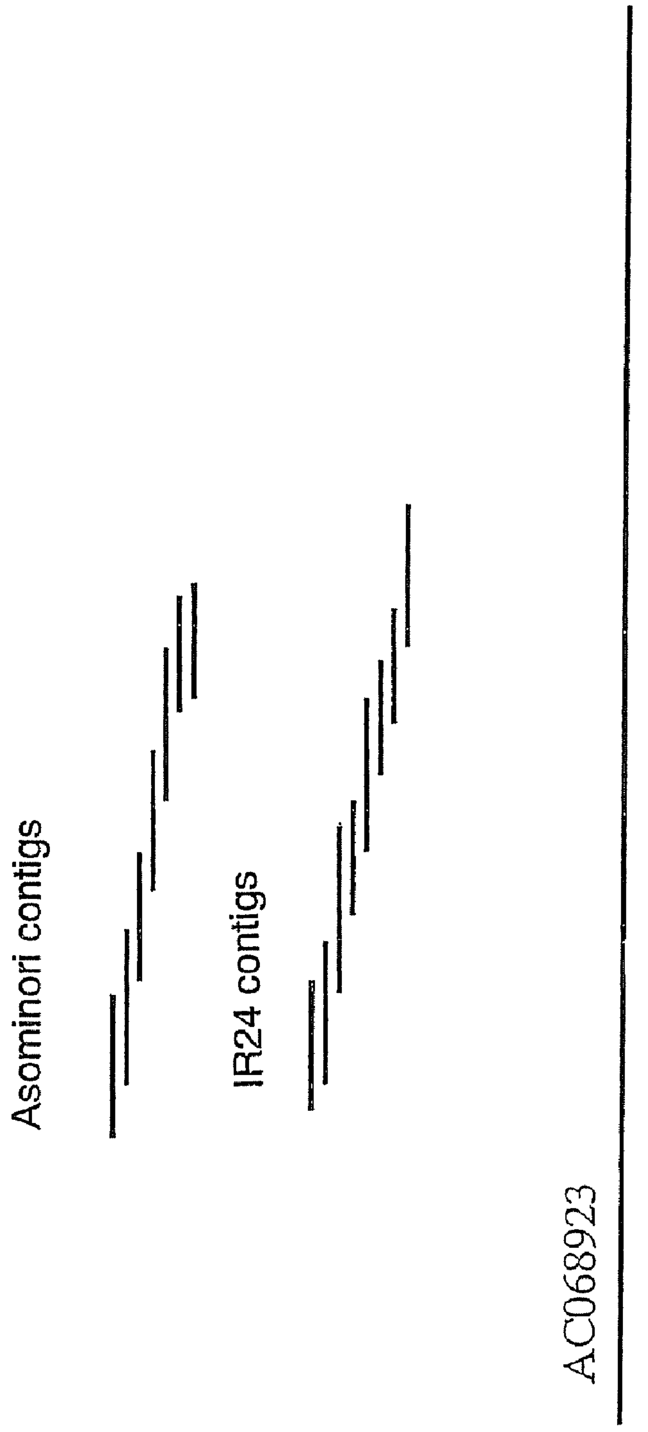
FIG. 2 shows an alignment of lambda clone contigs in relation to the BAC clone AC068923.

The present inventors perused the public website of TIGR (The Institute for Genomic Research) and found that a BAC (Bacterial Artificial Chromosome) clone (Accession No. AC068923) containing RFLP marker S12564 had been deposited with a public database (GenBank). This BAC clone contains the genomic DNA of Nipponbare japonica and it was shown from base sequence comparison to completely include the contig regions of Asominori and IR24 prepared in (1)-(4) (FIG. 2).

Thus, PCR was routinely performed using total DNA of IR24 as a template in combination with the following primer pair:

```
5'-tggatggactatgtggggtcagtc-3'    (SEQ ID NO: 11)
and

5'-agtggaagtggagagagtagggag-3'    (SEQ ID NO: 12)
```

designed to amplify a part of this BAC clone. The resulting amplification products of about 600 bp were purified and labeled by the method described above to give a library screening probe (probe H, FIG. 1).

Library screening and phage DNA purification were performed by the method described above.

(Results and Discussion)

The results of terminal base sequence analysis and restriction enzyme fragment length analysis showed that one (XSH18) of 15 clones obtained by screening of the IR24 genomic library was in a relative position as shown in FIG. 1. The IR24 genomic base sequence corresponding to XSH18 was determined by primer walking.

Reference Example 3

High precision Segregation Analysis (1) Development of PCR Marker P4497 MboI Comparison between the genomic base sequence corresponding to the IR24 contig (SEQ ID NO:1) and the genomic base sequence corresponding to the Asominori contig (SEQ ID NO:2) determined in Reference example 2 revealed that the 1239th base of SEQ ID NO:1 is A while the 12631st base of SEQ ID NO:2 corresponding to said position is G.

For detecting this change, fragments of about 730 bp are first amplified by PCR from a region surrounding said position using the following primer pair:

```
P4497 MboI F:
5'-ccctccaacacataaatggttgag-3'    (SEQ ID NO: 13)
```

(corresponding to bases 853-876 of SEQ ID NO:1)

(corresponding to bases 12247-12270 of SEQ ID NO:2) and

```
P4497 MboI R:
5'-tttctgccaggaaactgttagatg-3'    (SEQ ID NO: 14)
```

(corresponding to bases 1583-1560 of SEQ ID NO:1)

(corresponding to bases 12975-12952 of SEQ ID NO:2). The amplification products can be visualized by electrophoresis on an agarose gel after treatment with MboI. Thus, the change can be detected as a difference in mobility in the agarose gel due to the difference in the length of DNA after MboI treatment because the amplification products from Asominori DNA having an MboI recognition sequence (GATC) are cleaved with MboI while the amplification products from IR24 DNA are not cleaved with MboI for the lack of the MboI recognition sequence.

(2) Development of PCR Marker P9493 BslI

Comparison between the genomic base sequence corresponding to the IR24 contig (SEQ ID NO:1) and the genomic base sequence corresponding to the Asominori contig (SEQ ID NO:2) determined in Reference example 2 revealed that the 6227th base of SEQ ID NO:1 is A while the 17627th base of SEQ ID NO:2 corresponding to said position is C.

For detecting this change, fragments of 126 bp are first amplified by PCR from a region surrounding said position using the following primer pair:

```
P9493 BslI F:
5'-gcgatcttatacgcatactatgcg-3'    (SEQ ID NO: 15)
```

(corresponding to bases 6129-6152 of SEQ ID NO:1)

(corresponding to bases 17529-17552 of SEQ ID NO:2) and

```
P9493 BslI R:
5'-aaagtctttgttccttcaccaagg-3'    (SEQ ID NO: 16)
```

(corresponding to bases 6254-6231 of SEQ ID NO:1)

(corresponding to bases 17654-17631 of SEQ ID NO:2). The amplification products can be visualized by electrophoresis on an agarose gel after treatment with BslI. Thus, the change can be detected as a difference in mobility in the agarose gel due to the difference in the length of DNA after BslI treatment because the amplification products from Asominori DNA having a BslI recognition sequence (CCNNNNNNNGG) are cleaved with BslI while the amplification products from IR24 DNA are not cleaved with BslI for the lack of the BslI recognition sequence.

This marker was developed by applying the dCAPS method (Michaels and Amasino 1998, Neff et al., 1998). Specifically, g is substituted for a at the base 6236 of SEQ ID NO:1 and the base 17636 of SEQ ID NO:2 by the use of P9493 BslI R primer described above. Thus, the fragments from Asominori DNA come to have a sequence of CCtttcct-tGG at 17626-17636 of SEQ ID NO:28 so that they are cleaved with BslI.

(3) Development of PCR Marker P23945 MboI

Comparison between the genomic base sequence corresponding to the IR24 contig (SEQ ID NO:1) and the genomic base sequence corresponding to the Asominori contig (SEQ ID NO:2) determined in Reference example 2 revealed that the 20680th base of SEQ ID NO:1 is G while the 32079th base of SEQ ID NO:2 corresponding to said position is A.

For detecting this change, fragments of 260 bp are first Amplified by PCR from a region surrounding said position using the following primer pair:

```
P23945 MboI F:
5'-gaggatttatcaaaacaggatggacg-3'   (SEQ ID NO: 17)
```

(corresponding to bases 20519-20544 of SEQ ID NO:1)

(corresponding to bases 31918-31.943 of SEQ ID NO:2) and

```
P23945 MboI R:
                              (SEQ ID NO: 18)
5'-tgggcggcagcagtggaggataga-3'
```

(corresponding to bases 20778-20755 of SEQ ID NO:1)

(corresponding to bases 32177-32154 of SEQ ID NO:2). The amplification products can be visualized by electrophoresis on an agarose gel after treatment with MboI. Thus, the change can be detected as a difference in mobility in the agarose gel due to the difference in the length of DNA after MboI treatment because the amplification products from IR24 DNA having an MboI recognition sequence (GATC) are cleaved with MboI while the amplification products from Asominori DNA are not cleaved with MboI for the lack of the MboI recognition sequence.

(4) Development of PCR Marker P41030 TaqI

Comparison between the genomic base sequence corresponding to the IR24 contig (SEQ ID NO:1) and the genomic base sequence corresponding to the Asominori contig (SEQ ID NO:2) determined in Reference example 2 revealed that the 45461st base of SEQ ID NO:1 is A while the 49164th base of SEQ ID NO:2 corresponding to said position is G.

For detecting this change, fragments of 280 bp are first amplified by PCR from a region surrounding said position using the following primer pair:

```
P41030 TaqI F:
                              (SEQ ID NO: 19)
5'-aagaagggagggttatagaatctg-3'
```

(corresponding to bases 45369-45392 of SEQ ID NO:1)

(corresponding to bases 49072-49095 of SEQ ID NO:2) and

```
P41030 TaqI R:
                              (SEQ ID NO: 20)
5'-atatcaggactaacaccactgctc-3'
```

(corresponding to bases 45648-45625 of SEQ ID NO:1)

(corresponding to bases 49351-49328 of SEQ ID NO:2). The amplification products can be visualized by electrophoresis on an agarose gel after treatment with TaqI. Thus, the change can be detected as a difference in mobility in the agarose gel due to the difference in the length of DNA after TaqI treatment because the amplification products from Asominori DNA having a TaqI recognition sequence (TCGA) are cleaved with TaqI while the amplification products from IR24 DNA are not cleaved with TaqI for the lack of the TaqI recognition sequence.

(5) Development of PCR Marker P451.77 BstUI

Comparison between the genomic base sequence corresponding to the IR24 contig (SEQ ID NO:1) and the genomic base sequence corresponding to the Asominori contig (SEQ ID NO:2) determined in Reference example 2 revealed that the 49609th base of SEQ ID NO:1 is A while the 53311st base of SEQ ID NO:2 corresponding to said position is G.

For detecting this change, fragments of 812 bp are first amplified by PCR from a region surrounding said position using the following primer pair:

```
P45177 BstUI F:
                              (SEQ ID NO: 21)
5'-acgagtagtagcgatcttccagcg-3'
```

(corresponding to bases 49355-49378 of SEQ ID NO:1)

(corresponding to bases 53057-53080 of SEQ ID NO:2) and

```
P45177 BstUI R:
                              (SEQ ID NO: 22)
5'-cagcgtgaaactaaaaacggaggc-3'
```

(corresponding to bases 50166-50143 of SEQ ID NO:1)

(corresponding to bases 53868-53845 of SEQ ID NO:2). The amplification products can be visualized by electrophoresis on an agarose gel after treatment with BstUI. Thus, the change can be detected as a difference in mobility in the agarose gel due to the difference in the length of DNA after BstUI treatment because the amplification products from IR24 DNA having a BstUI recognition sequence (CGCG) at two positions are cleaved into 3 fragments with BstUI while the amplification products from Asominori DNA having the BstUI recognition sequence at three positions are cleaved with BstUI into four fragments.

(6) Development of PCR Marker B60304 MspI

Comparison between the genomic base sequence corresponding to the IR24 contig (SEQ ID NO:1) determined in Reference example 2 and the base sequence of the BAC clone described above (Accession No. AC068923) revealed that the 56368th base of SEQ ID NO:1 is T while the base of AC068923 corresponding to said position is C.

For detecting this change, fragments of about 330 bp are first amplified by PCR from a region surrounding said position using the following primer pair:

```
B60304 MspI F:
                              (SEQ ID NO: 23)
5'-atcccacatcatcataatccgacc-3'
```

(corresponding to bases 56149-56172 of SEQ ID NO:1) and

```
B60304 MspI R:
                              (SEQ ID NO: 24)
5'-agcttctcccttggatacggtggcg-3'
```

(corresponding to bases 56479-56455 of SEQ ID NO:1).

The amplification products can be visualized by electrophoresis on an agarose gel after treatment with MspI. Thus, the change can be detected as a difference in mobility in the agarose gel due to the difference in the length of DNA after MspI treatment because the amplification products from Nipponbare DNA having an MspI recognition sequence (CCGG) are cleaved with MspI while the amplification products from IR24 DNA are not cleaved with MspI for the lack of the MspI recognition sequence.

This marker was developed by applying the dCAPS method. Specifically, t is substituted for g at base 56463 of SEQ ID NO:1 by the use of B60304 MspI R primer. As a result, the MspI recognition sequence of bases 56460-56463 of SEQ ID NO:1 changes from CCGG into ccgt so that the fragments from SEQ ID NO:1 become unable to be cleaved with MspI. Thus, the fragments from IR24 have no MspI recognition sequence, while DNA from Nipponbare has the MspI recognition sequence at one position in a region corresponding to bases 56367-56370 of SEQ ID NO:1.

(7) Development of PCR Marker B59066 BsaJI

Comparison between the genomic base sequence corresponding to the IR24 contig (SEQ ID NO:1) determined in Reference example 2 and the base sequence of the BAC clone described above (Accession No. AC068923) revealed that the 57629th base of SEQ ID NO:1 is C while the base of AC068923 corresponding to said position is CC.

For detecting this change, fragments of about 420 bp are first amplified by PCR from a region surrounding said position using the following primer pair:

```
B59066 BsaJI F:
                                    (SEQ ID NO: 25)
5'-atttgttggttagttgcggctgag-3'
```

(corresponding to bases 57563-57586 of SEQ ID NO:1) and

```
B59066 BsaJI R:
                                    (SEQ ID NO: 26)
5'-gcccaaactcaaaaggagagaacc-3'
```

(corresponding to bases 57983-57960 of SEQ ID NO:1). The amplification products can be visualized by electrophoresis on an agarose gel after treatment with BsaJI. Thus, the change can be detected as a difference in mobility in the agarose gel due to the difference in the length of DNA after BsaJI treatment because the amplification products from Nipponbare DNA having a BsaJI recognition sequence (CCNNGG) are cleaved with BsaJI while the amplification products from IR24 DNA are not cleaved with BsaJI for the lack of the BsaJI recognition sequence.

(8) Development of PCR Marker B56691 XbaI

Comparison between the genomic base sequence corresponding to the IR24 contig (SEQ ID NO:1) determined in Reference example 2 and the base sequence of the BAC clone described above (Accession No. AC068923) revealed that the 66267th base of SEQ ID NO:1 is G while the base of AC068923 corresponding to said position is C.

For detecting this change, fragments of about 670 bp are first amplified by PCR from a region surrounding said position using the following primer pair:

```
B56691 XbaI F:
                                    (SEQ ID NO: 27)
5'-cctcaagtctcccctaaagccact-3'
```

(corresponding to bases 66129-66152 of SEQ ID NO:1) and

```
B56691 XbaI R:
                                    (SEQ ID NO: 28)
5'-gctctactgctgataaaccgtgag-3'
```

(corresponding to bases 66799-66776 of SEQ ID No:1). The amplification products can be visualized by electrophoresis on an agarose gel after treatment with XbaI. Thus, the change can be detected as a difference in mobility in the agarose gel due to the difference in the length of DNA after XbaI treatment because the amplification products from Nipponbare DNA having an XbaI recognition sequence (TCTAGA) are cleaved with XbaI while the amplification products from IR24 DNA are not cleaved with XbaI for the lack of the XbaI recognition sequence.

(9) Development of PCR Marker B53627 BstZ17I

Comparison between the genomic base sequence corresponding to the IR24 contig (SEQ ID NO:1) determined in Reference example 2 and the base sequence of the BAC clone described above (Accession No. AC068923) revealed that the 69331st base of SEQ ID NO:1 is T while the base of AC068923 corresponding to said position is C.

For detecting this change, fragments of about 620 bp are first amplified by PCR from a region surrounding said position using the following primer pair:

```
B53627 BstZ17I F:
                                    (SEQ ID NO: 29)
5'-tggatggactatgtggggtcagtc-3'
```

(corresponding to bases 68965-68988 of SEQ ID NO:1) and

```
B53627 BstZ17I R:
                                    (SEQ ID NO: 30)
5'-agtggaagtggagagagtagggag-3'
```

(corresponding to bases 69582-69559 of SEQ ID NO:1). The amplification products can be visualized by electrophoresis on an agarose gel after treatment with BstZ17I. Thus, the change can be detected as a difference in mobility in the agarose gel due to the difference in the length of DNA after BstZ17I treatment because the amplification products from IR24 DNA having a BstZ17I recognition sequence (GTATAC) are cleaved with BstZ17I while the amplification products from Nipponbare DNA are not cleaved with BstZ17I for the lack of the BstZ17I recognition sequence.

(10) Development of PCR Marker B40936 MseI

Development of all the following PCR markers (10)-(12) relates to a study of the base sequences corresponding to further downstream regions (3') of base 76363 at the 3' end of SEQ ID NO:1.

The following primer pair was designed for the base sequence of the BAC clone described above (Accession No. AC068923):

```
                                    (SEQ ID NO: 31)
5'-tacgacgccatttcactccattgc-3'
and
                                    (SEQ ID NO: 32)
5'-catttctctatgggcgttgctctg-3'.
```

PCR was routinely performed using this primer pair in combination with total DNAs of MS-FR Koshihikari (genotype of the Rf-1 locus: Rf-1 Rf-1) and Koshihikari as templates. The resulting amplification products of about 1300 bp were electrophoresed on an agarose gel and then purified by QIAEXII (QIAGEN). Analysis of the base sequence of the purified DNA by a DNA sequencer 377 (ABI) showed several polymorphisms.

One of them can be detected by PCR amplification of a region surrounding said position using the following primer pair:

```
B40936 MseI F:
                                  (SEQ ID NO: 33)
5'-acctgtaggtatggcaccttcaacac-3'
and

B40936 MseI R:
                                  (SEQ ID NO: 34)
5'-ccaaggaacgaagttcaaatgtatgg-3'.
```

The amplification products can be visualized by electrophoresis on an agarose gel after treatment with MseI. Thus, the change can be detected as a difference in mobility in the agarose gel due to the difference in the length of DNA after MseI treatment because the amplification products from MS-FR Koshihikari (Rf-1 Rf-1) DNA having an MseI recognition sequence (TTAA) are cleaved with MseI while the amplification products from Koshihikari DNA are not cleaved with MseI for the lack of the MseI recognition sequence.

This marker was developed by applying the dCAPS method.

(11) Development of PCR Marker B19839 MwoI

The following primer pair was designed for the base sequence of the BAC clone described above (Accession No. AC068923):

```
                                  (SEQ ID NO: 35)
5'-tgatgtgtttgggcatccctttcg-3'
and

                                  (SEQ ID NO: 36)
5'-gagataggggacgacagacacgac-3'.
```

PCR was routinely performed using this primer pair in combination with total DNAs of MS-FR Koshihikari (genotype of the Rf-1 locus: Rf-1 Rf-1) and Koshihikari as templates. The resulting amplification products of about 1200 bp were electrophoresed on an agarose gel and then purified by QIAEXII (QIAGEN). Analysis of the base sequence of the purified DNA by a DNA sequencer 377 (ABI) showed several polymorphisms.

One of them can be detected by PCR amplification of a region surrounding said position using the following primer pair:

```
B19839 MwoI F:
                                  (SEQ ID NO: 37)
5'-tcctatggctgtttagaaactgcaca-3'
and

B19839 MwoI R:
                                  (SEQ ID NO: 38)
5'-caagttcaaacataactggcgttg-3'.
```

The amplification products can be visualized by electrophoresis on an agarose gel after treatment with MwoI. Thus, the change can be detected as a difference in mobility in the agarose gel due to the difference in the length of DNA after MwoI treatment because the amplification products from Koshihikari DNA having an MwoI recognition sequence (GCNNNNNNNGC) are cleaved with MwoI while the amplification products from MS-FR Koshihikari (Rf-1 Rf-1) DNA are not cleaved with MwoI for the lack of the MwoI recognition sequence.

This marker was developed by applying the dCAPS method.

(12) Development of PCR Marker B2387 BfaI

The following primer pair was designed for the base sequence of the BAC clone described above (Accession No. AC068923):

```
                                  (SEQ ID NO: 39)
5'-cactgtcctgtaagtgtgctgtgc-3'
and

                                  (SEQ ID NO: 40)
5'-caagcgtgtgataaaatgtgacgc-3'.
```

PCR was routinely performed using this primer pair in combination with total DNAs of MS-FR Koshihikari (genotype of the Rf-1 locus: Rf-1 Rf-1) and Koshihikari as templates. The resulting amplification products of about 1300 bp were electrophoresed on an agarose gel and then purified by QIAEXII (QIAGEN). Analysis of the base sequence of the purified DNA by a DNA sequencer 377 (ABI) showed several polymorphisms.

One of them can be detected by PCR amplification of a region surrounding said position using the following primer pair:

```
B2387 BfaI F:
                                  (SEQ ID NO: 41)
5'-tgcctactgccattactatgtgac-3'
and

B2387 BfaI R:
                                  (SEQ ID NO: 42)
5'-acatactaccgtaaatggtctctg-3'.
```

The amplification products can be visualized by electrophoresis on an agarose gel after treatment with BfaI. Thus, the change can be detected as a difference in mobility in the agarose gel due to the difference in the length of DNA after BfaI treatment because the amplification products from Koshihikari DNA having an BfaI recognition sequence (CTAG) are cleaved with BfaI while the amplification products from MS-FR Koshihikari (Rf-1 Rf-1) DNA are not cleaved with BfaI for the lack of the BfaI recognition sequence.

(13) Segregation Analysis

Two recombinants between the Rf-1 and S12564 Tsp509I loci (RS1 and RS2) and 8 recombinants between the Rf-1 and C1361 MwoI loci (RC1 to RC8) obtained in Reference example 1 were genotyped at the 12 DNA marker loci developed in (1) to (12) above. The results are shown in Table 1 along with the genotypes of each recombinant at the S12564 Tsp509I and C1361 MwoI loci.

[Table 1]

TABLE 1

Genotypes of recombinants proximal to the Rf-1 locus at various marker loci

| Locus | RS1 | RS2 | RC1 | RC2 | RC3 | RC4 | RC5 | RC6 | RC7 | RC8 |
|---|---|---|---|---|---|---|---|---|---|---|
| S12564 Tsp509I | J | J | H | H | H | H | H | H | H | H |
| P4497 MboI | J | J | H | H | H | H | H | H | H | H |
| P9453 BslI | H | H | H | H | H | H | H | H | H | H |
| P23945 MboI | H | H | H | H | H | H | H | H | H | H |
| P41030 TaqI | H | H | H | H | H | H | H | H | H | H |
| P45177 BstUI | H | H | H | H | H | H | H | H | H | H |
| B60304 MspI | H | H | H | H | H | H | H | H | H | H |
| B59066 BsaJI | H | H | H | H | H | H | H | H | H | H |
| B56691 XbaI | H | H | H | H | H | H | H | J | H | H |
| B53627 BstZ17I | H | H | H | H | H | H | H | J | H | H |
| B40936 MseI | H | H | H | H | H | H | H | J | H | H |
| B19839 MwoI | H | H | H | H | H | J | H | J | H | H |
| B2387 BfaI | H | H | H | H | H | J | H | J | H | J |
| C1361 MwoI | H | H | J | J | J | J | J | J | J | J |

J: Homozygous for Koshihikari
H: Heterozygous for Koshihikari/MS-FR Koshihikari

Figure 3:
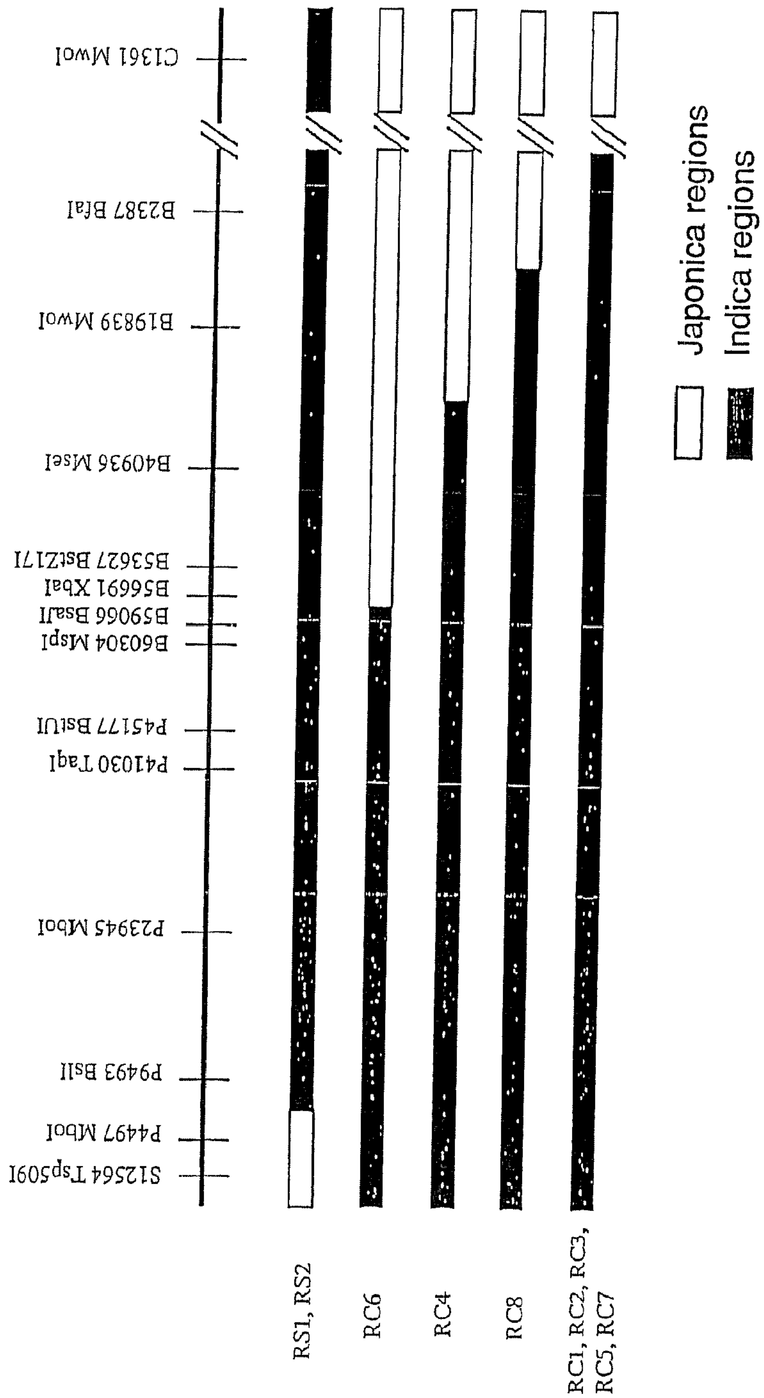
FIG. 3 shows the chromosomal organization of recombinant pollens proximal to the Rf-1 locus (all fertile) as mapped in close proximity to the Rf-1 locus based on the genotypes at the marker loci of 10 individuals (RS1, RS2, RC1-8) generated from the pollens. White bars represent japonica regions and black bars represent indica regions.
Figure 4:
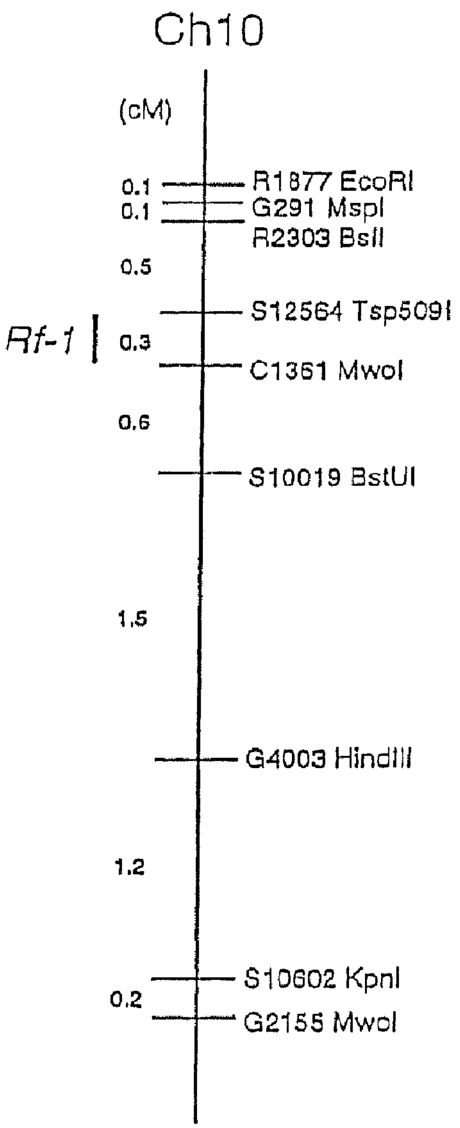
FIG. 4 is a gene map in which the locus of Rf-1 gene on chromosome 10 of rice is positioned on a linkage map in relation to various markers; the values of map distance were calculated from the segregation data from 1042 F1 individuals.

Table 1 shows that all the recombinants have an indica-derived Rf-1 chromosomal region between P9493 BslI and 59066 BsaJI. This result showed that recombinant pollens having the chromosomal organization as shown in FIG. 3 have pollen fertility, i.e. the Rf-1 gene is functional in these pollens. This means that a sequence determining the presence of the function of the Rf-1 gene is included in the indica region common to these recombinant pollens, i.e. in a region from the P4497 MboI to B56691 XbaI loci (about 65 kb) as estimated at maximum.

Reference Example 4

Complementation Assay for A 15.7 Kb Fragment from XSG16

(1)
(Materials and Methods)

The λ phage clone XSG16 (FIGS. 1 and 5) was partially digested with NotI and electrophoresed on an agarose gel. The separated 15.7 kb fragment (including bases 38538-54123 of SEQ ID NO:1) was purified by QIAEXII (QIAGEN).

On the other hand, an intermediate vector pSB200 having a hygromycin-resistant gene cassette was prepared on the basis of pSB11 (Komari et al., supra.). Specifically, a nopaline synthase terminator (Tnos) was first fused to a ubiquitin promoter and a ubiquitin intron (Pubi-ubiI). A hygromycin-resistant gene (HYG(R)) was inserted between ubiI and Tnos of the resulting Pubi-ubiI-Tnos complex to give an assembly of Pubi-ubiI-HYG(R)-Tnos. This assembly was fused to a HindIII/EcoRI fragment of pSB11 to give pKY205. Linker sites for adding restriction enzyme sites NotI, NspV, EcoRV, KpnI, SacI, EcoRI were inserted into the Hind III site upstream of Pubi of this pKY205 to give pSB200 having a hygromycin-resistant gene cassette.

After the plasmid vector pSB200 was completely digested with NotI, DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The two fragments prepared above, i.e. the 15.7 kb fragment from XSG16 and the vector fragment were subjected to a ligation reaction using DNA Ligation Kit Ver. 1 (TAKARA). After the reaction, DNA was recovered by ethanol precipitation. The recovered DNA was dissolved in pure water (prepared by a Millipore system) and then mixed with *E. coli* DH5a cells, and the mixture was electroporated. After electroporation, the solution was cultured with shaking in LB medium (37° C., 1 hr) and then plated on an LB plate containing spectinomycin and warmed (37° C., 16 hr). Plasmids were isolated from 24 of the resulting colonies. Their restriction enzyme fragment length patterns and boundary base sequences were analyzed to select desired *E. coli* cells transformed with recombinant plasmids.

The *E. coli* cells selected above were used for triparental mating with the *Agrobacterium tumefaciens* strain LBA4404/pSB1 (Komari et al., 1996) and the helper *E. coli* strain HB101/pRK2013 (Ditta et al., 1980) according to the method of Ditta et al. (1980). Plasmids were isolated from 6 of the colonies formed on an AB plate containing spectinomycin and their restriction enzyme fragment length patterns were analyzed to select desired *Agrobacterium cells.*

The *Agrobacterium* cells selected above were used to transform MS Koshihikari (having BT cytoplasm and a nucleus gene substantially identical to Koshihikari) according to the method of Hiei et al. (1994). Necessary immature seeds of MS Koshihikari for transformation can be prepared by pollinating MS Koshihikari with Koshihikari.

Transformed plants were transferred to a greenhouse under long-day conditions after acclimation. 48 individuals grown to a stage suitable for transplantation were transplanted into 1/5000a Wagner pots (4 individuals/pot), and transferred into a greenhouse under short-day conditions 3-4 weeks after transplantation. About one month after heading, seed fertility was tested on standing plants.

(Results and Discussion)

Figure 6:
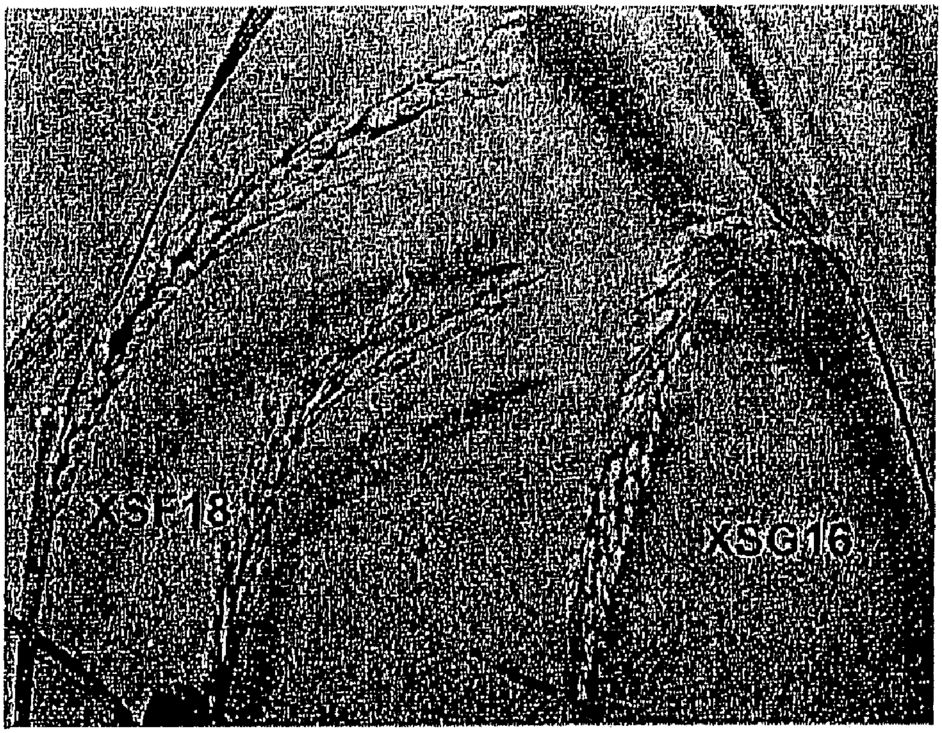
FIG. 6 shows the results of complementation assays using a 15.7 kb fragment from XSG16 (Reference example 4) and a 16.2 kb fragment from XSF18 (comprising bases 21065-33946 and 38592-41921 of SEQ ID NO:1). The plant transformed with the 15.7 kb fragment from XSG16 has restored fertility as proved by ears bowing.

Of the 47 transformed individuals, at least 37 individuals clearly restored fertility (FIG. 6). This indicates that 15586 bases (bases 38538-54123 of SEQ ID NO:1) derived from rice (IR24) in the 15.7 kb insert fragment include the full-length Rf-1 gene.

(2) Complementation Assay for an Internal 11.4 kb Fragment in XSG16
(Materials and Methods)

The λ phage clone XSG16 was completely digested with AlwNI and BsiWI and then DNA was recovered by ethanol precipitation. The recovered DNA was dissolved in TE solution and then blunted by DNA Blunting Kit (TAKARA). The reaction solution was electrophoresed on an agarose gel to separate a 11.4 kb fragment, which was purified by QIAEXII (QIAGEN).

The plasmid vector pSB11 (Komari et al. Plant Journal, 1996) was completely digested with SmaI and then DNA was recovered by ethanol precipitation. The recovered DNA was dissolved in TE solution and then dephosphorylated by CIAP (TAKARA). The reaction solution was electrophoresed on an agarose gel, and then a vector fragment was purified from the gel using QIAEXII (QIAGEN).

The two fragments prepared above were subjected to a ligation reaction using DNA Ligation Kit Ver. 1 (TAKARA). After the reaction, DNA was recovered by ethanol precipitation. The recovered DNA was dissolved in pure water (prepared by a Millipore system) and then mixed with *E. coli* DH5α cells, and the mixture was electroporated. After electroporation, the solution was cultured with shaking in LB medium (37° C., 1 hr) and then plated on an LB plate containing spectinomycin and warmed (37° C., 16 hr). Plasmids were isolated from 14 of the resulting colonies, and their restriction enzyme fragment length patterns and boundary base sequences were analyzed to select desired *E. coli* cells.

The *E. coli* cells selected above were used for triparental mating with the *Agrobacterium tumefaciens* strain LBA4404/pSB4U (Takakura et al., Japanese Patent Application No. 2001-269982 (WO02/019803 A1)) and the helper *E. coli* strain HB101/pRK2013 (Ditta et al., 1980) according to the method of Ditta et al. (1980). Plasmids were isolated from 12 of the colonies formed on an AB plate containing spectinomycin and their restriction enzyme fragment length patterns were analyzed to select desired *Agrobacterium cells.*

The *Agrobacterium* cells selected above were used to transform MS Koshihikari (having BT cytoplasm and a nucleus gene substantially identical to Koshihikari) according to the method of Hiei et al. (1994). Necessary immature seeds of MS Koshihikari for transformation can be prepared by pollinating MS Koshihikari with Koshihikari.

Transformed plants were transferred to a greenhouse under long-day conditions after acclimation. 120 individuals grown to a stage suitable for transplantation were transplanted into 1/5000a Wagner pots (4 individuals/pot), and transferred into a greenhouse under short-day conditions about one month after transplantation. About one month after heading, one typical ear was sampled from each plant to evaluate seed fertility (the percentage of fertile paddies to total paddies).

(Results and Discussion)

Of the 120 transformed individuals, 59 individuals showed seed fertility of 10% or more, among which 19 individuals showed seed fertility of 70% or more. This indicates that the 11.4 kb insert fragment (bases 42357-53743 of SEQ ID NO:1) contains an essential Rf-1 gene region for expressing a fertility restoring function.

(3) Complementation Assay for an Internal 6.8 Kb Fragment in XSG16

(Materials and Methods)

The λ phage clone XSG16 was completely digested with HpaI and AlwNI and electrophoresed on an agarose gel. The separated 6.8 kb fragment was purified by QIAEXII (QIAGEN).

The subsequent procedures including the preparation of the plasmid vector pSB11 were performed according to the method in (2) above.

(Results and Discussion)

Of the 120 transformed individuals, 67 individuals showed seed fertility of 10% or more, among which 26 individuals showed seed fertility of 70% or more. This indicates that the 6.8 kb insert fragment (bases 42132-48883 of SEQ ID NO:1) contains an essential Rf-1 gene region for expressing a fertility restoring function.

Figure 5:
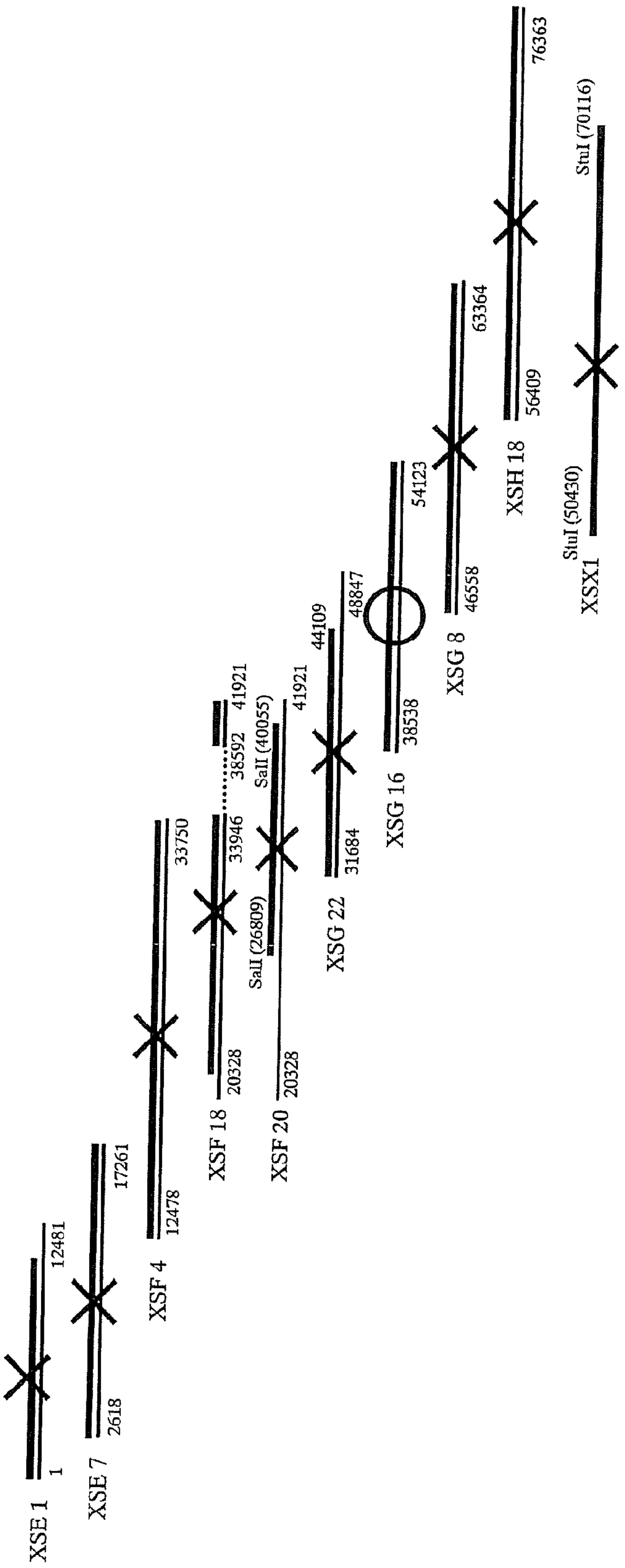
FIG. 5 shows fragments from 10 genomic clones used for the identification of the Rf-1 region by complementation assays. Lambda clones obtained by chromosomal walking (thin lines) were used for complementation assays of the chromosomal regions shown by bold lines. XSF18 was found to contain a deletion shown by dotted line.

Other fragments derived from Asominori shown in FIGS. 1 and 5, i.e., XSE1, XSE7, XSF4, XSF4, XSF18, XSF20, XSG22, XSG8, XSH18 and XSX1 were also subjected to complementation assay in a similar manner. However, none of them had a fertility restoring function.

Reference Example 5

Preparation of cDNA Library

Firstly, IL216, a line wherein the Rf-1 is introduced into Koshihikari via backcrossing (the genotype, Rf-1/Rf-1), was prepared. The IL216 was grown in a greenhouse by a conventional method, and young panicles were sampled during the growth stage wherein the length between auricles is −5-5 cm. Total RNA was extracted by the SDS-phenol method (Watanabe, A. and Price, C. A. (1982) Translation of mRNAs for subunits of chloroplast coupling factor 1 in spinach. Proceedings of the National Academy of Sciences of the U.S.A., 79, 6304-6308), and the poly $(A)^+$ RNA was purified using QuickPrep mRNA Purification Kit(Amersham Pharmacia Biotech).

The purified poly $(A)^+$ RNA was provided to prepare a cDNA library by ZAP-cDNA Synthesis Kit (Stratagene). The titer of the prepared library (1 ml) was calculated to be 16,000,000 pfu/ml, and was determined to be sufficiently large.

Reference Example 6

Screening of the cDNA Library (1) Preparation of the Screening Primers

PCR was performed by using the following two types of primes:

```
Sense primer
                                    (SEQ ID NO: 50)
5'-tctcattctctccacgccctgctc-3'

Antisense primer
                                    (SEQ ID NO: 51)
5'-acggcggagcaattcgtcgaacac-3'
```

and XSG16, a genomic clone of IR24, as a template. SEQ ID NOS:50 and 51 correspond to the bases 43733-43756 and the bases 44038-44015 of SEQ ID NO:1, respectively.

After the electrophoresis, the amplification product of about 300 bp was recovered from the agarose gel by QIAEX II Gel Extraction Kit (QIAGEN). The recovered fragment was $^{32}P$-labeled by Rediprime II DNA labelling system (Amersham Pharmacia Biotech) (The fragment is hereunder referred to as "Probe P").

Further, PCR was performed by using the following two types of primes:

```
Sense primer
5'-agtgtgtggcatggtgcatttccg-3'    (SEQ ID NO: 52)

Antisense primer
5'-ctctacaggatacacggtgtaagg-3'    (SEQ ID NO: 53)
```

and XSG16, a genomic clone of IR24, as a template. SEQ ID NOS:52 and 53 correspond to the bases 48306-48329 and the bases 50226-50203 of SEQ ID NO:1, respectively. After the electrophoresis, the amplification product of about 1900 bp was recovered from the agarose gel. The recovered fragment was $^{32}P$-labeled by the method mentioned above (The fragment is hereunder refers to as "Probe Q").

(2) Screening of the cDNA Library

The cDNA library prepared in Reference example 5 was provided to prepare 70 of agar medium wherein about 15000 plaques appeared. Plaque lift was performed twice for each agar medium, and the plaques were transferred to Hybond-$N^+$ (Amersham Pharmacia Biotech). One membrane was used for hybridization with Probe P, and the other membrane was used for hybridization with Probe Q. The whole steps were performed according to the manufacture's instructions.

Probes were added to a hybridization solution containing 250 mM $Na_2HPO_4$, 1 mM EDTA and 7% SDS, and hybridization was performed at 65° C. for 16 hours. Washing was performed twice with a solution containing 1×SSC and 0.1% SDS, at 65° C. for 15 minutes, and then twice with a solution containing 0.1×SSC and 0.1% SDS, at 65° C. for 15 minutes. After the washing, the membranes were analyzed with FUJIX BAS 1000 (Fuji Photo Films).

As a result, 8 plaques which showed positive for both Probe P and Probe Q were identified. Therefore, those plaques were isolated, subcloned into pBluescript according to the instructions of the manufacture (Stratagene). Among 8 clones, the terminal base sequences of 6 clones were identical to that of XSG16. The entire base sequences of the 6 clones were determined, and the results are shown in SEQ ID NOS:43-74 in the sequence listing.

All of the sequences, SEQ ID NOS:43-74 are presumed to encode a protein having the amino acids 1-791 of SEQ ID NO:49. Specifically, all and each of the 215-2587 of SEQ ID NO:43, the bases 213-2585 of SEQ ID NO:44, the bases 218-2590 of SEQ ID NO:45, the bases 208-2580 of SEQ ID NO:46, the bases 149-2521 of SEQ ID NO:47 and the bases 225-2597 of SEQ ID NO:48 encodes a protein having amino acids 1-791 of SEQ ID NO:49. The above base sequences correspond to the bases 43907-46279 of SEQ ID NO:1.

The amino acid sequence of SEQ ID NO:49 was compared with the presumed amino acid sequence of the corn fertility restorer gene (Rf2), and the N-terminal 7 amino acid residues (Met-Ala-Arg-Arg-Ala-Ala-Ser) in both amino acid sequences were concurred. These 7 amino acid residues are considered to be a portion of a targeting signal to mitochondria (Liu et al., 2001). Based on the above facts, the cDNAs isolated on this occasion are considered to contain the full coding region of the Rf-1 gene. No homology between the amino acid sequences of the rice Rf-1 and the corn Rf2 can be found except for the above region. It is presumed that the mechanisms by which the gene products of the Rf-1 and the Rf2 can restore fertility after being transferred to mitochondria are distinct from each other.

Figure 7:
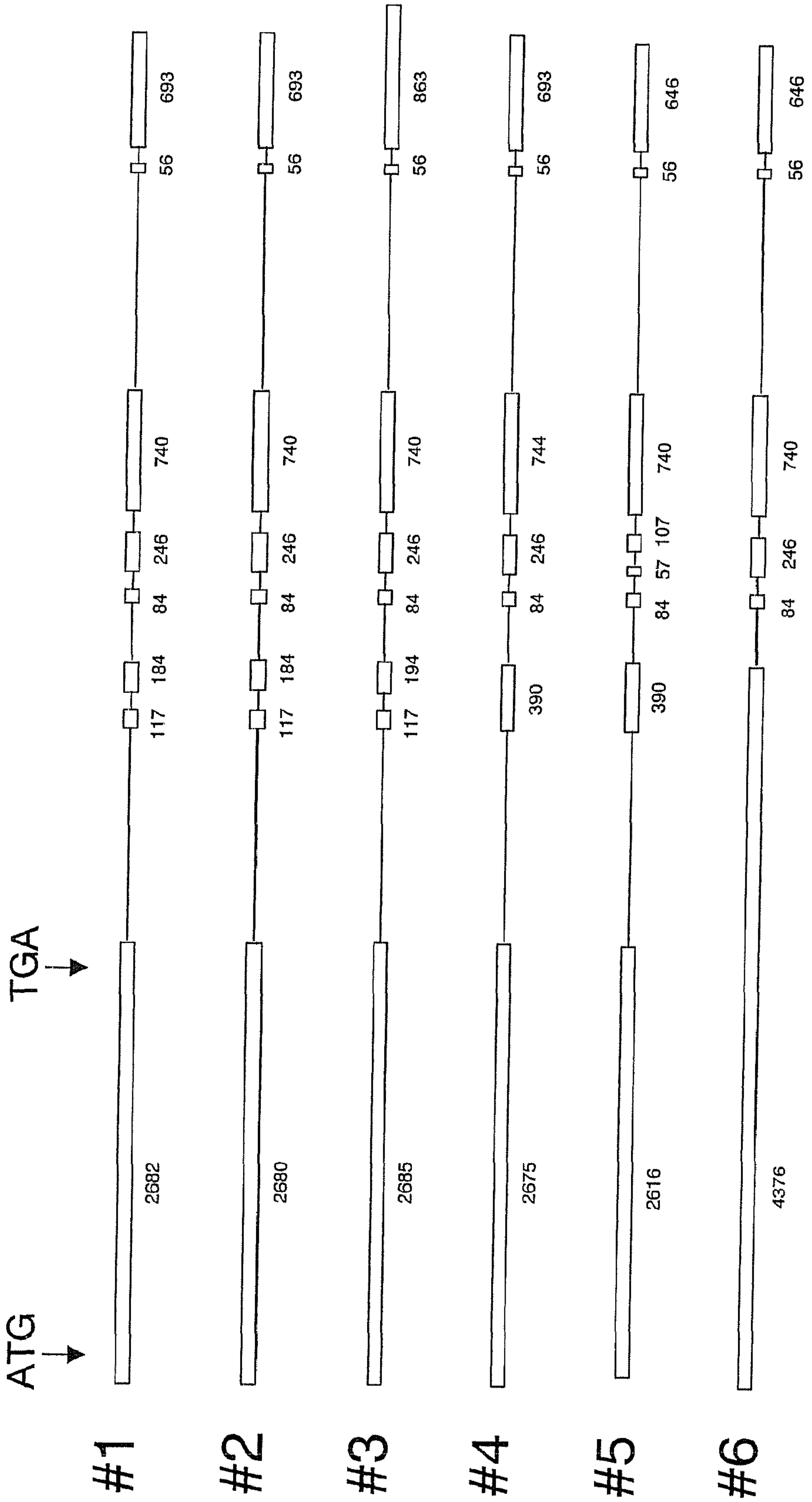
FIG. 7 is a schematic of the Rf-1 gene structure. The white rods and black lines respectively indicate exon regions and intron regions. The number of base pairs for the exon regions are shown.

In addition, the sequences of cDNAs isolated on this occasion were compared with the genome sequence of IR24 (SEQ ID NO:1), and the structures of exons and introns of the Rf-1 gene were clarified (FIG. 7). As a result, it was shown that various transcription products wherein the splicing forms and the poly A addition positions are different, are present in a plant body. There is no intron in the coding region of the Rf-1 gene.

Reference Example 7

Complementation Assay

A complementation assay was performed by using a 4.2 kb fragment containing the promoter region and the presumed translation region of the Rf-1 gene. The 4.2 kb fragment is in a plasmid containing the 6.8 kb genome derive from IR24 which proved to have fertility restorer function in Reference example 4(3).

Firstly, the plasmid described in Reference example 4(3) was treated with EcoRI, and was subjected to electrophoresis with agarose gel. The 4.2 kb fragment containing the promoter region and the presumed translation region of the Rf-1 (corresponding to the bases 42132-46318 in SEQ ID NO:1) was separated, recovered from the gal using QIAEXII (QIAGEN). The 4.2 kb fragment was subjected to ligation reaction using DNA Ligation Kit Ver. 1 (TAKARA) together with pBluescript II SK (−) which has been treated with EcoRI and then with CIAP (TAKARA). After the reaction, the DNA was recovered by ethanol precipitation.

The recovered DNA was dissolved in pure water (prepared by a Millipore system) and then mixed with *E. coli* DH5a cells, and the mixture was electroporated. After electroporation, the solution was cultured by shaking in LB medium (37° C., 1 hr) and then plated on an LB plate containing ampicillin and warmed (37° C., 16 hr). Plasmids were isolated from 12 of the resulting colonies, and their restriction enzyme fragment length patterns and boundary base sequences were analyzed to select desired *E. coli* cells. Then, plasmids isolated from the selected *E. coli* were treated with BamHI and SalI, and electrophoresed on an agarose gel. The 4.2 kb fragment containing the promoter region and the presumed translation region of Rf-1 was separated, and recovered from the gel using QIAEXII (QIAGEN).

On the other hand, TnosJH0072 (an intermediate vector comprising the nos terminator and a cassette of the ampicillin resistant gene) was treated with BamHI and SalI, and electrophored on an agarose gel. The 3.0 kb fragment containing the nos terminator and the ampicillin-resistant gene was separated, and was recovered from the gel using QIAEXII (QIAGEN).

The 4.2 kb fragment containing the promoter region and the presumed translation region of Rf-1, and the fragment derived from TnosJH0072 were subjected to ligation reaction, and to electroporation by the methods discussed above. The reactant was spread on LB plates containing ampicillin, and incubated (37° C., 16 hr). Plasmids were isolated from 12 of the resulting colonies, and their restriction enzyme fragment length patterns and boundary base sequences were analyzed to select desired *E. coli* cells.

Further, plasmids isolated from the selected *E. coli* were treated with SgfI, and electrophoresed on an agarose gel. The 4.2 kb fragment containing the promoter region and the presumed translation region of Rf-1 was separated, and recovered from the gel using QIAEXII (QIAGEN). The 4.2 kb fragment and pSB200Pac (an intermediate vector comprising a cassette of the hygromycin-resistant gene) which has been treated with PacI and then with CIAP (TAKARA) were subjected to ligation reaction, and to electroporation by the methods discussed above. The reactant was spread on LB plates containing spectinomycin, and incubated (37° C., 16 hr). Plasmids were isolated from 16 of the resulting colonies, and their restriction enzyme fragment length patterns and boundary base sequences were analyzed to select desired *E. coli* cells.

As a result of the above steps, *E. coli* cells were obtained wherein the chimera gene of the fragment containing the promoter region of the Rf-1 and the presumed translation region of the Rf-1 attached with the nos terminator has been inserted within an intermediate vector. The *E. coli* cells were used for triparental mating with the *Agrobacterium tumefaciens* strain LBA4404/pSB1 (Komari et al., 1996) and the helper *E. coli* strain HB101/pRK2013 (Ditta et al., 1980) according to the method of Ditta et al. (1980). Plasmids were isolated from 6 of the colonies formed on an AB plate containing spectinomycin and their restriction enzyme fragment length patterns were analyzed to select desired *Agrobacterium cells.*

The *Agrobacterium* cells selected above were used to transform MS Koshihikari (having BT cytoplasm and a nucleus gene substantially identical to Koshihikari) according to the method of Hiei et al. (1994). Necessary immature seeds of MS Koshihikari for transformation were prepared by pollinating MS Koshihikari with Koshihikari.

Transformed plants were transferred to a greenhouse under long-day conditions after acclimation. 32 individuals grown to a stage suitable for transplantation were transplanted into 1/5000a Wagner pots (4 individuals/pot), and transferred into a greenhouse under short-day conditions 3-4 weeks after transplantation. About one month after heading, seed fertility was tested on standing plants. As a result, 28 individuals among the 32 transformed individuals restored fertility.

By the above procedures, it has been experimentally demonstrated that the function of the Rf-1 gene can be furnished by expressing the presumed translation region.

Reference Example 8

Isolation of cDNA

In Reference example 6, the cDNA library derived from IL216 young panicles was screened with Probe P and Probe Q. Plaques which are positive for both probes were isolated and analyzed, and 6 cDNA were isolated. In this reference example, similar screening was performed with Probe P and Probe R as mentioned below, and six additional cDNAs were isolated. Details are as follows.

Firstly, PCR was performed by using the following two types of primes:

```
Sense primer
5'-cagttgggttgaaacctaatactg-3'    (SEQ ID NO: 60)

Antisense primer
5'-cactaaaccgttagacgagaaagc-3'    (SEQ ID NO: 61)
```

and a genomic clone of IR24, XSG16 as a template. SEQ ID NOS:60 and 61 correspond to the bases 45522-45545 and the bases 45955-45932 of SEQ ID NO:1, respectively.

After the electrophoresis, the amplification product of about 430 bp was recovered from the agarose gel by QIAEX II (QIAGEN). The recovered fragment was $^{32}$P-labeled by Rediprime II DNA labelling system (Amersham Pharmacia Biotech) (hereinafter referred as "Probe R", FIG. 8).

The cDNA library derived from IR24 young panicles was provided to prepare 20 of agar medium wherein about 15000 plaques appeared. Plaque lift was performed twice for each agar medium, and the plaques were transferred to Hybond-N$^+$ (Amersham Pharmacia Biotech). One membrane was used for hybridization with Probe P of Reference example 6, and the other membrane was used for hybridization with Probe R. All of the steps were performed according to the manufacture's instructions. As a result, 12 plaques were identified which proved to be positive for both Probe P and Probe R.

Accordingly, those plaques were isolated, and subcloned into pBluescript according to the instructions of the manufacture (Staratagene). The terminal base sequences of the cones were determined. Among 12 clones, the terminal base sequences of 6 clones were identical to that of XSG16, and thus the entire base sequences of those 6 clones were determined (#7-#12). The results were shown in SEQ ID NOS:54-85.

All of the sequences, SEQ ID NOS:54-85 are presumed to encode a protein having the amino acids 1-791 of SEQ ID NO:49. Specifically, all and each of the 229-2601 of SEQ ID NO:54, the bases 175-2547 of SEQ ID NO:55, the bases 227-2599 of SEQ ID NO:56, the bases 220-2592 of SEQ ID NO:57, the bases 174-2546 of SEQ ID NO:58 and the bases 90-2462 of SEQ ID NO:59 encodes a protein having amino acids 1-791 of SEQ ID NO:49. The above base sequences correspond to the bases 43907-46279 of SEQ ID NO:1.

Figure 8:
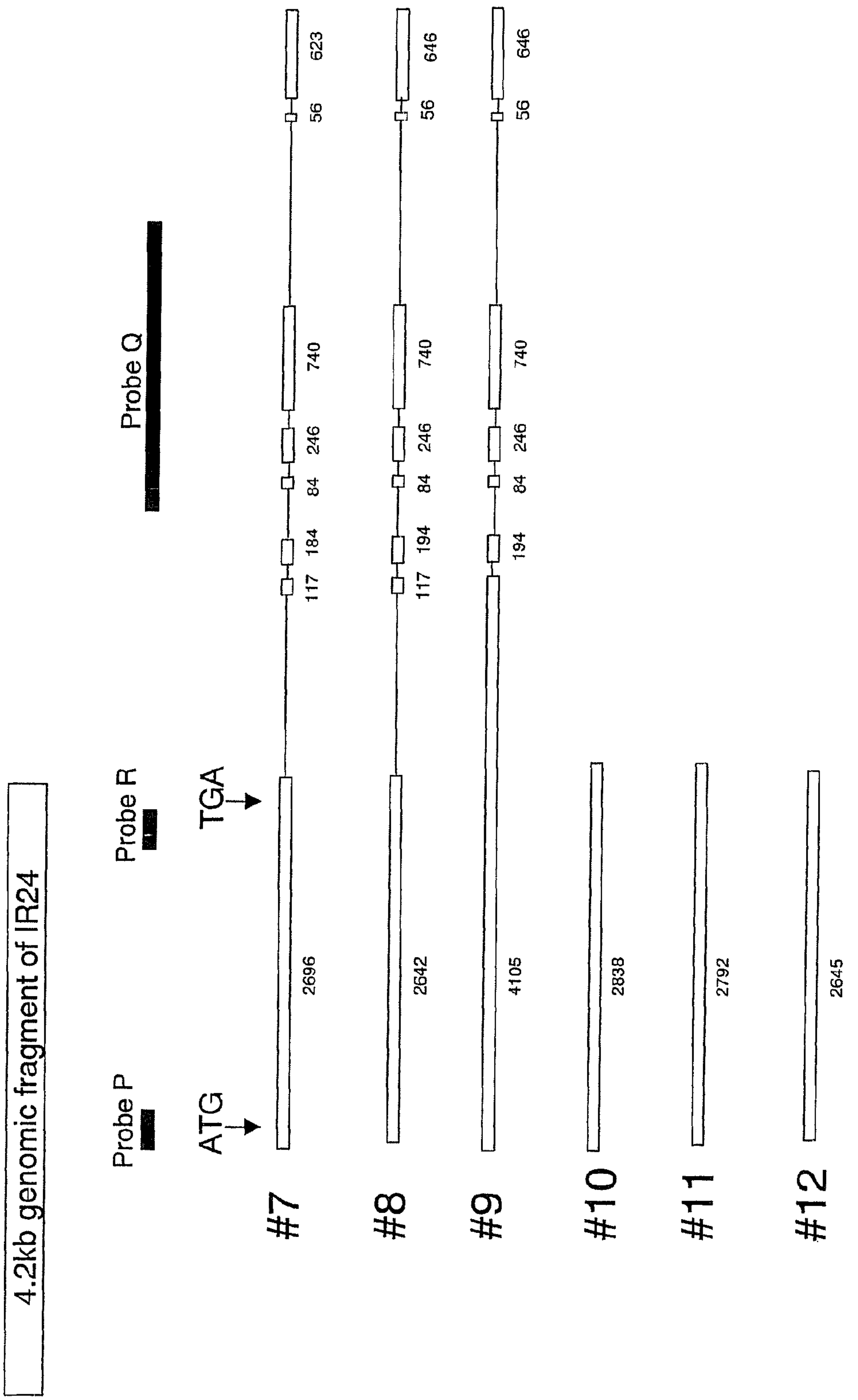
FIG. 8 is a schematic showing the relative positions of IR24 genome fragments on which a complementation assay was performed, the probes used in cDNA library screening, and the putative Rf-1 gene from the isolated cDNA. The white rods and black lines on the Rf-1 gene respectively indicate exon regions and intron regions. The number of base pairs for the exon regions are shown.

The sequences of cDNAs isolated on this occasion were compared with the genome sequence of IR24 (SEQ ID NO:1), and the structures of exons and introns were clarified (FIG. 8). Among the cDNAs isolated on this occasion, there are three cDNAs which do not have any exons irrelevant to the presumed translation region, and consist of a single exon (#10-#12, SEA ID NOS: 57-59).

Example 1

Selection of Single-Copy Insertion Transformant (Materials and Methods)

The present inventors discovered that, in Reference example 4(1), when a 15.6 kb fragment from the genomic clone XSG16 of IR24 is inserted into MS Koshihikari (which has BT cytoplasm and substantially the same nuclear genes as Koshihikari), seed fertility is restored in primary transformants ($T_0$ generation).

Twelve plants were selected from among the primary transformants ($T_0$ generation) in which fertility had been restored, and total DNA was extracted from green leaves on the selected plants by the SDS-phenol method (Komari et al., 1989). The DNA was completely digested with SacI and submitted to agarose electrophoresis, then transferred to Hybond-N$^+$ (Amersham Pharmacia Biotech) in accordance with the manufacturer's manual and furnished to Southern analysis.

The probe used for Southern analysis was created as follows. First, using two different primers:

```
5'-attgagggttgaacaatgatgggc-3'    (SEQ ID NO: 62)
```

(corresponding to bases 49244 to 49267 of SEQ ID NO:1) and

```
5'-ctctacaggatacacggtgtaagg-3'    (SEQ ID NO: 63)
```

(corresponding to bases 50226 to 50203 of SEQ ID NO:1), the PCR was carried out using the above-mentioned genomic clone XSG16 as the template. Following electrophoresis, an approximately 980 bp amplification product was recovered from the agarose gel with the QIAEX II Gel Extraction Kit (QIAGEN). The recovered fragment was $^{32}$P-labeled using the Rediprime II DNA labeling system (Amersham Pharmacia Biotech).

Hybridization was carried out at 65° C. for 16 hours by adding the probe to a hybridization solution containing 250 mM $Na_2HPO_4$, 1 mM EDTA and 7% SDS. The membrane was washed twice at 65° C. for 15 minutes each time with a solution containing 1×SSC and 0.1% SDS, then washed twice at 65° C. for 15 minutes each time with a solution containing 0.1×SSC and 0.1% SDS. The washed membrane was then analyzed using FUJIX BAS1000 (Fuji Photo Film). Other test methods were carried out while referring to the above-referenced laboratory manual (Sambrook et al., 2001).

Some of the individuals that were found from the results of SacI digestion to be single-copy transformants were EcoRV digested, then subjected to Southern analysis in the same way as described above.

(Results and Discussion)

As a result of SacI digestion and Southern analysis on 12 individuals, in addition to the approximately 12 kb band corresponding to the intrinsic rf-1 gene, bands of various sizes were observed. Because the number of bands in the respective individuals is believed to reflect the number of inserted copies in that individual, the seven individuals in which only one band other than the approximately 12 kb band was observed were treated as candidate single-copy insertion transformants.

Six of these candidate single-copy transformants were selected and subjected to EcoRV digestion and Southern analysis. As a result, in each individual, one band was observed in addition to an approximately 15 kb band corresponding to the intrinsic rf-1 gene. The foregoing results showed that these six individuals were single-copy insertion transformants.

Example 2

Selection of Individuals Homozygous for Insertion Gene (Materials and Method)

Four individuals (16T0-6, 16T0-26, 16T0-34, 16T0-35) of the six that were shown in Example 1 to be single-copy insertion transformants were inbred, and six $T_1$ individuals for each line were cultivated. The total DNA was extracted by the method described in Example 1 and subjected to EcoRV digestion and Southern analysis.

(Results and Discussion)

One individual homozygous for the inserted gene was selected from each line (16T1-6, 16T1-26, 16T1-34, 16T1-35) by comparing within each line the intensities of the approximately 15 kb band corresponding to the intrinsic rf-1 gene and the band corresponding to the inserted gene. The pollen fertilities of these four individuals were examined by iodine-potassium iodide staining, whereupon all were found to be close to 100%, indicating that the genotypes of the insertion loci inferred from the Southern analysis results were correct.

Example 3

Identification of Chromosomal Sites of Inserted Genes (1) Identification of Insertion Site in 16T0-6

(Materials and Method)

The DNA of 16T0-6 used in Example 1 was completely digested with PstI, following which amplification of the insertion site was carried out using the LA PCR in vitro Cloning Kit (TAKARA) in accordance with the manufacturer's manual. In the first PCR, Nos F1:

```
5'-agattgaatcctgttgccggtcttgcgatg-3' (SEQ ID NO: 64)
```

was used as the specific primer. The PCR conditions were 2 minutes of treatment at 94° C., followed by 30 cycles, each consisting of 1 minute of thermal denaturation at 94° C., 1 minute of annealing at 58° C. and 2 minutes of elongation reaction at 72° C., then 2 minutes of treatment at 72° C. at the end.

The second PCR was carried out with 1 μL of a 200-fold dilution of the first PCT solution as the template and using Nos F2:

```
5'-tcatctatgttactagatccgatgataagc-3' (SEQ ID NO: 65)
```

as the specific primer. The PCR conditions were the same as in the first PCR. The second PCR solution was furnished to agarose gel electrophoresis, following which the amplified fragments were recovered from the agarose gel by QIAEX II Gel Extraction Kit (QIAGEN) and the base sequence was analyzed.

(Results and Discussion)

The second PCR solution was submitted to agarose gel electrophoresis, and approximately 500 bp fragments were recovered. The end base sequences of the recovered fragments were determined, and a BLAST search (Altschul et al., 1990) was performed on the Genbank public database. As a result, the base sequence was found to match the complementary strand sequence of the genomic clone (Accession NO: AP004007) on chromosome 6 on Nihonbare.

Figure 9:
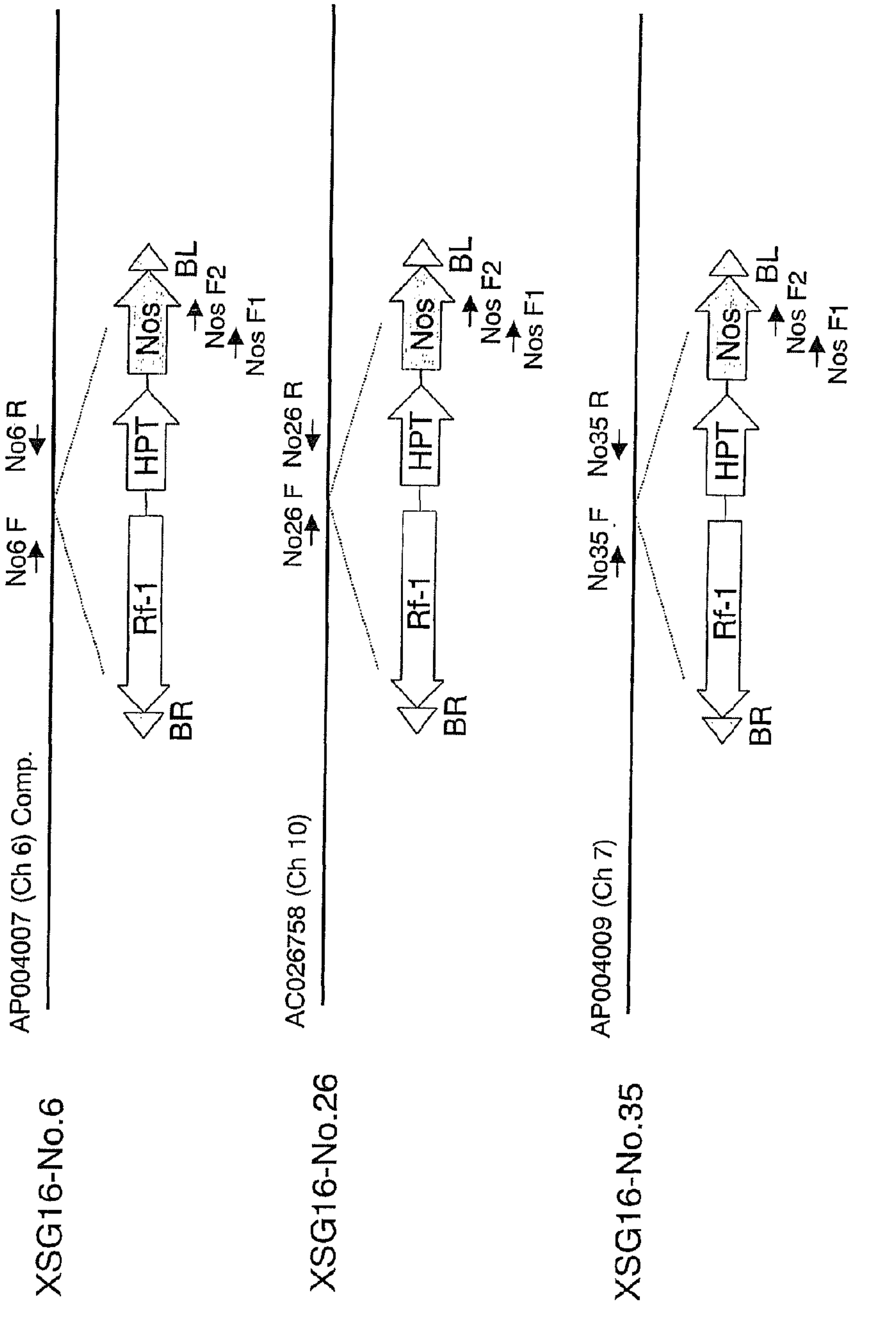
FIG. 9 is a schematic showing the position of primers used for verifying the site of Rf-1 insertion. Nos: nopaline synthase terminator (Tnos); HPT: hygromycin-resistant gene; BR: right border; BL: left border.
Figure 10:
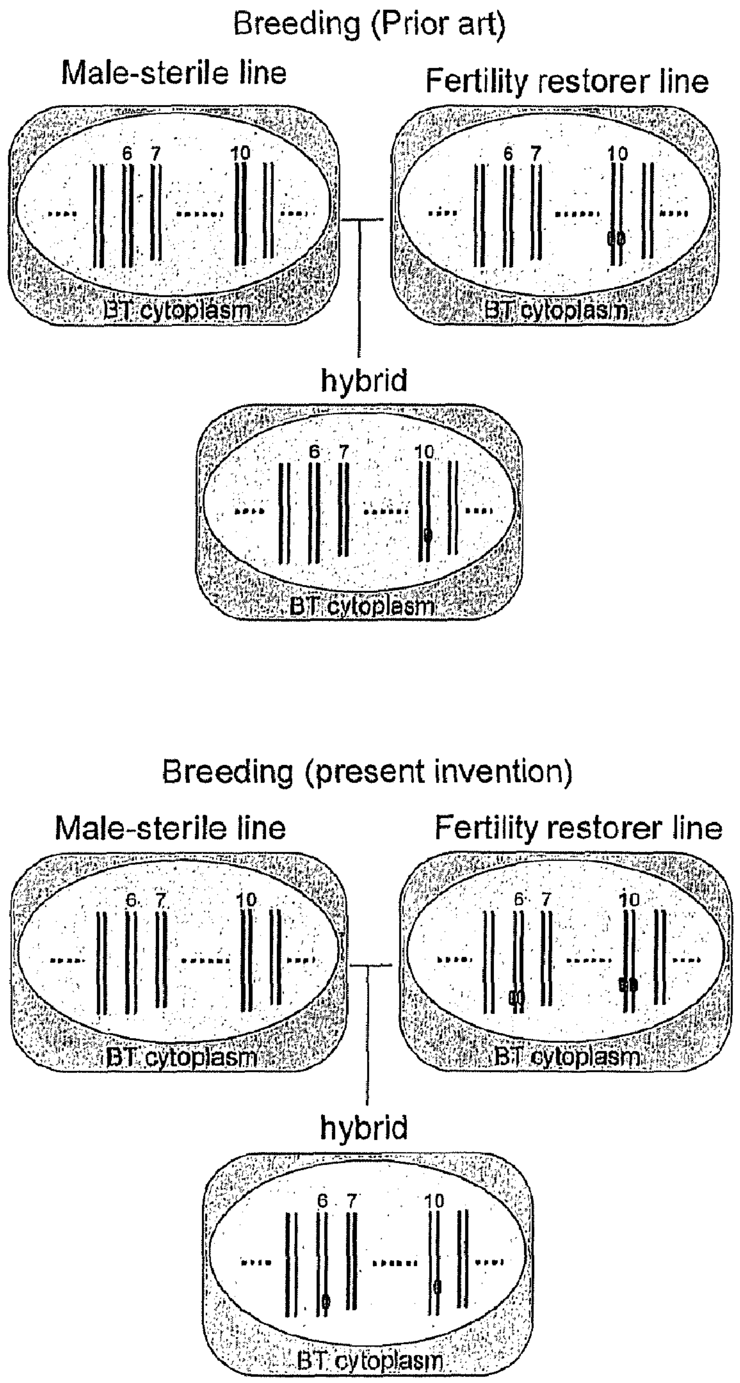
FIG. 10 is a schematic showing examples of methods for creating hybrid plants according to the invention and according to the prior art.

Hence, the two following primers were designed for the positions shown in FIG. 9 with respect to the complementary strand sequence of AP004007:

```
5'-acttcaactagcaccctctctcacct-3',    (SEQ ID NO: 66)
and
No6 R:
5'-tctgctggttgaacatggtgtgatag-3'.    (SEQ ID NO: 67)
```

Using these primers, the PCR was carried out with the complete DNAs of Koshihikari and 16T1-6 (an individual homozygous for the inserted gene) described in Example 2 as the templates. The PCR conditions were 2 minutes of treatment at 94° C., followed by 35 cycles, each consisting of 30 seconds of thermal denaturation at 94° C., 30 seconds of annealing at 58° C. and 30 seconds of elongation reaction at 72° C., then 2 minutes of treatment at 72° C. at the end. On submitting the PCR solution to agarose gel electrophoresis, the results showed that fragments of the expected size (210 bp) were amplified from the Koshihikari DNA. However, as expected, the product of interest here was not amplified from 16T1-6.

In addition, the PCR was carried out under the foregoing conditions with a primer combination of NosF2 and No6R and using the total DNAs of Koshihikari and 16T1-6 as the templates. As a result, fragments of the expected size (234 bp) were amplified from 16T1-6. However, as expected, the product of interest was not amplified from Koshihikari.

The above results show that the insertion site of the inserted gene in 16T0-6 is a site which corresponds with AP004007 on chromosome 6.

(2) Identification of Insertion Site in 16T0-26

(Materials and Method)

The 16T0-26 DNA used in Example 1 was completely digested with PstI, following which the insertion site was amplified by the method described in (1) above, and the base sequence was analyzed. GC Buffer (I) shipped with TaKaRa LA Taq (TAKARA) was used as the PCR buffer.

(Results and Discussion)

The second PCR solution was submitted to agarose gel electrophoresis, and approximately 1700 bp fragments were recovered. The end base sequences of the recovered fragments were determined, and a BLAST search (Altschul et al., 1990) was performed on the Genbank public database. As a result, the sequence was found to match the sequence of the genomic clone (Accession NO: AC026758) of chromosome 10 on Nihonbare.

The two following primers were thus designed for the positions shown in FIG. 9 on the sequence of AC026758:

```
No26 F:
5'-cccccccctctcctct-3',          (SEQ ID NO: 68)
and

No26 R:
5'-tcccaccaaagggcattcctctcatc-3'.  (SEQ ID NO: 69)
```

Using these primers, the PCR was carried out with the complete DNAs of Koshihikari and 16T1-26 (an individual homozygous for the inserted gene) described in Example 2 as the templates. The PCR conditions were 2 minutes of treatment at 94° C., followed by 35 cycles, each consisting of 30 seconds of thermal denaturation at 94° C., 30 seconds of annealing at 58° C. and 30 seconds of elongation reaction at 72° C., then 2 minutes of treatment at 72° C. at the end. On submitting the PCR solution to agarose gel electrophoresis, the results showed that fragments of the expected size (246 bp) were amplified from the Koshihikari DNA. However, as expected, the product of interest here was not amplified from 16T1-26.

In addition, the PCR was carried out under the foregoing conditions with a primer combination of Nos F2 and No26 R and using the complete DNAs of Koshihikari and 16T1-26 as the templates. As a result, fragments of the expected size (352 bp) were amplified from 16T1-26. However, as expected, the product of interest was not amplified from Koshihikari.

The above results show that the insertion site of the inserted gene in 16T0-26 is a site which corresponds with AC026758 of chromosome 10.

(3) Identification of Insertion Site in 16T0-34

(Materials and Method)

The 16T0-34 DNA used in Example 1 was completely digested with BamHI, following which the insertion site was amplified by the method described in (1) above, and the base sequence was analyzed.

(Results and Discussion)

The second PCR solution was submitted to agarose gel electrophoresis, and approximately 1700 bp fragments were recovered. The end base sequences of the recovered fragments were determined, and a BLAST search (Altschul et al., 1990) was performed on the Genbank public database. As a result, as of Sep. 9, 2002, clones having the aforementioned sequences had not been found.

(4) Identification of Insertion Site in 16T0-35

(Materials and Method)

The 16T0-35 DNA used in Example 1 was completely digested with PstI, following which the insertion site was amplified by the method described in (1) above, and the base sequence was analyzed.

(Results and Discussion)

The second PCR solution was submitted to agarose gel electrophoresis, and approximately 500 bp fragments were recovered. The end base sequences of the recovered fragments were determined, and a BLAST search (Altschul et al., 1990) was performed on the Genbank public database. As a result, the sequence was found to match the sequence of the genomic clone (Accession NO: AP004009) on chromosome 7 on Nihonbare.

Hence, the two following primers were designed for the positions shown in FIG. 9 on the sequence of AP004009:

```
No35 F:
5'-ggctagggtttggggaaatgggcg-3',    (SEQ ID NO: 70)
and

No35 R:
5'-cgtcatcatcttctcccaaaacagcc-3'.  (SEQ ID NO: 71)
```

Using these primers, the PCR was carried out with the complete DNAs of Koshihikari and 16T1-35 (an individual homozygous for the inserted gene) described in Example 2 as the templates. The PCR conditions were 2 minutes of treatment at 94° C., followed by 35 cycles, each consisting of 30 seconds of thermal denaturation at 94° C., 30 seconds of annealing at 58° C. and 30 seconds of elongation reaction at 72° C., then 2 minutes of treatment at 72° C. at the end. On submitting the PCR solution to agarose gel electrophoresis, the results showed that fragments of the expected size (235 bp) were amplified from the Koshihikari DNA. However, as expected, the product of interest was not amplified from 16T1-35.

In addition, the PCR was carried out under the foregoing conditions with a primer combination of Nos F2 and No35 R and using the complete DNAs of Koshihikari and 16T1-35 as the templates. As a result, fragments of the expected size (177 bp) were amplified from 16T1-35. However, as expected, the product of interest was not amplified from Koshihikari.

The above results show that the insertion site of the inserted gene in 16T0-35 is a site which corresponds with AP004009 of chromosome 7.

Example 4

Pollen Fertility Study by Iodine-Potassium Iodide Staining of Cumulative Rf-1 Gene Line (Materials and Methods)

The following plant materials were furnished for testing.

1) MS Koshihikari
2) Koshihikari
3) FR Koshihikari (a line established by inserting the Rf-1 gene into Koshihikari by continuous back-crossing)
4) MS Koshihikari×FR Koshihikari
5) self-fertile $F_1$ plants (16T2-6, 16T2-26, 16T2-34, 16T2-35) of lines 16T1-6, 16T1-26, 16T1-34 and 16T1-35
6) MS Koshihikari×16T1-6, MS Koshihikari×16T1-26, MS Koshihikari×16T1-34, MS Koshihikari×16T1-35
7) FR Koshihikari×16T1-6, FR Koshihikari×16T1-26, FR Koshihikari×16T1-34, FR Koshihikari×16T1-35
8) 3-loci Rf-1 heterozygote
9) 4-loci Rf-1 heterozygote The 3-loci Rf-1 heterozygote and 4-loci Rf-1 heterozygote of 8) and 9) were created as described below. The 3-loci Rf-1 heterozygote was created by extracting the DNA from 39 plants obtained by the following cross: (FR Koshihikari×16T1−6)×(FR Koshihikari×16T1-35), and estimating the Rf-1 locus genotype, the 16T1-6 insertion locus genotype (chromosome 6) and the 16T1-35 insertion locus genotype (chromosome 7) of each individual as described below using DNA markers. The Rf-1 locus was estimated from the genotype of the S12564 Tsp509I and C1361 MwoI loci in accordance with Komori et al. (2002). In the case of the 16T1-6 insertion locus, if a 234 bp fragment was amplified when the PCR was carried out using the primers Nos F2 and No6 R described in Example 3, the genotype of this locus was regarded as heterozygous. Similarly, in the case of the 16T1-35 insertion locus, if a 177 bp fragment was amplified when the PCR was carried out using the primers Nos F2 and No35 R described in Example 3, the genotype of this locus was regarded as heterozygous. As a result of marker assays, three individuals of the population obtained from this cross were inferred to be heterozygous for the Rf-1 locus, the 16T1-6 insertion locus and the 16T1-35 insertion locus.

To create a 4-loci Rf-1 heterozygote, the Rf-1 locus genotype, the 16T1-6 insertion locus genotype, the 16T1-35 insertion locus genotype and the 16T1-34 insertion locus genotype were estimated for 62 plants obtained by the following cross: (16T1−34×16T1−6)×(FR Koshihikari×16T1-35). In the case of the 16T1-34 insertion locus, the PCR was carried out using as the primers Nos F2 and No34 R described in Example 3:

```
5'-cctttatacctccccacttcttatcc-3'.   (SEQ ID NO: 72)
```

The PCR conditions were 2 minutes of treatment at 94° C., followed by 35 cycles, each consisting of 30 seconds of thermal denaturation at 94° C., 30 seconds of annealing at 58° C. and 30 seconds of elongation reaction at 72° C., then 2 minutes of treatment at 72° C. at the end. The PCR solution was then submitted to agarose gel electrophoresis. If 245 bp fragments were amplified, the genotype of this locus was regarded as heterozygous. As a result of marker assays, five individuals of the population obtained from this cross were inferred to be heterozygous for the Rf-1 locus, the 16T1-6 insertion locus, the 16T1-35 insertion locus and the 16T1-34 insertion locus.

Four unopened glumous flowers after heading were collected per plant from two plants of each of the above varieties and lines 1) to 9). The anther was removed from each flower, lightly ground in an iodine-potassium iodide solution, then examined under a microscope. Pollens that elicited a deep blue color from the iodine-starch reaction were regarded as fertile pollen, and other pollens were regarded as infertile pollens. At least 200 pollens were examined for each glumous flower.

(Results and Discussion)

The pollen fertility of each glumous flower was computed. Table 2 shows the results obtained from calculations of the average pollen fertility and standard deviation for eight glumous flowers of each variety and line.

[Table 2]

TABLE 2

Result of Pollen Fertility Study by Iodine-Potassium Iodide Staining

| Variety • Line | average pollen fertility (%) | standard deviation |
|---|---|---|
| MS Koshihikari | 0.00 | 0.00 |
| Koshihikari | 97.24 | 1.12 |
| FR Koshihikari | 95.71 | 1.71 |
| MS Koshihikari × FR Koshihikari | 50.17 | 2.38 |
| 16T1-6 | 95.12 | 2.79 |
| 16T1-26 | 93.66 | 1.61 |
| 16T1-34 | 94.08 | 2.06 |
| 16T1-35 | 95.20 | 1.20 |
| MS Koshihikari × 16T1-6 | 51.92 | 4.03 |
| MS Koshihikari × 16T1-26 | 53.27 | 4.37 |
| MS Koshihikari × 16T1-34 | 49.65 | 2.81 |
| MS Koshihikari × 16T1-35 | 51.20 | 4.19 |

TABLE 2-continued

Result of Pollen Fertility Study by Iodine-Potassium Iodide Staining

| Variety • Line | average pollen fertility (%) | standard deviation |
|---|---|---|
| 2-loci Rf-1 hetero (FR Koshihikari × 16T1-6) | 74.34 | 3.78 |
| 2-loci Rf-1 hetero (FR Koshihikari × 16T1-26) | 91.71 | 3.04 |
| 2-loci Rf-1 hetero (FR Koshihikari × 16T1-34) | 70.41 | 5.18 |
| 2-loci Rf-1 hetero (FR Koshihikari × 16T1-35) | 75.69 | 4.72 |
| 3-loci Rf-1 hetero | 86.28 | 2.01 |
| 4-loci Rf-1 hetero | 92.23 | 1.73 |

The theoretical pollen fertilities of 1) MS Koshihikari, 2) Koshihikari, 3) FR Koshihikari and 4) MS Koshihikari×FR Koshihikari are respectively 0%, 100%, 100% and 50%. Pollen fertilities close to these theoretical values were observed.

The lines in 5) (16T2-6, 16T2-26, 16T2-34, and 16T2-35) exhibited the same degree of pollen fertility as FR Koshihikari, and the crossed lines in 6) (MS Koshihikari×16T1-6, MS Koshihikari×16T1-26, MS Koshihikari×16T1-34, and MS Koshihikari×16T1-35) exhibited the same degree of pollen fertility as MS Koshihikari×FR Koshihikari. The implication of these results is that each of the Rf-1 genes introduced by genetic engineering techniques functions in the same way as an intrinsic Rf-1 gene.

The crossed lines in 7) (FR Koshihikari×16T1-6, and FR Koshihikari×16T1-35) had pollen fertilities of respectively 74% and 76%. The intrinsic Rf-1 gene carried by FR Koshihikari is located on chromosome 10, whereas the inserted Rf-1 genes carried by 16T1-6 and 16T1-35 are located on chromosomes 6 and 7, respectively, as noted in Example 3. Therefore, in $F_1$ plants, pollen having both the intrinsic Rf-1 gene and the inserted Rf-1 gene, pollen having only the intrinsic Rf-1 gene, pollen having only the inserted Rf-1 gene, and pollen having neither Rf-1 gene should segregate in a ratio therebetween of 1:1:1:1. Given that the pollen fertilities of these $F_1$ plants is about 75%, pollen having one or more Rf-1 gene was assumed to be fertile.

The pollen fertility of FR Koshihikari crossed with 16T1-34 was 70%, which is close to the expected value of 75% when the intrinsic Rf-1 and the inserted Rf-1 are independent. The position of the inserted Rf-1 gene carried by 16T1-34 has not been identified, although these results indicate at the very least that it is a locus which is not strongly linked to the intrinsic Rf-1 locus on chromosome 10.

The pollen fertility of FR Koshihikari crossed with 16T1-26 was 92%. As mentioned in Example 3, the inserted Rf-1 gene carried by 16T1-26 is located inside AC026758 on chromosome 10; AC026758 corresponds to the RFLP marker locus C797. On the other hand, the intrinsic Rf-1 gene carried by FR Koshihikari is closely linked with the RFLP marker locus S12564 on chromosome 10 (Komori et al., 2002). According to a RFLP linkage map (Harushima et al., 1998), the map distance between C797 and S12564 is about 20 cM. In cases where the frequency of recombination between both markers is about 20%, the theoretical pollen fertility of FR Koshihikari×16T1-26 is calculated to be about 90%. The observed pollen fertility is close to this theoretical value.

The 3-loci Rf-1 heterozygote in 8) carries the Rf-1 gene on chromosomes 6, 7 and 10, and so each Rf-1 gene is inherited independently. Therefore, in these individuals, pollen carrying three, two, one and no Rf-1 gene are expected to segregate in a ratio of 1:3:3:1. These plants had a pollen fertility of approximately 87.5%, indicating that the pollens having one or more Rf-1 gene were fertile. It was thus assumed that pollen containing three Rf-1 genes develops normally.

The 16T1-34 insertion locus has not been identified in the 4-loci Rf-1 heterozygote in 9), and so it is unclear whether each Rf-1 gene is inherited independently. However, the pollen fertility observed was very close to the theoretical pollen fertility of 93.75% when it is assumed that each Rf-1 gene is independently inherited and that pollen carrying one or more Rf-1 gene is fertile. It was assumed from this that pollen carrying four Rf-1 genes develops normally.

Example 5

Pollen Germination Tests on Cumulative Rf-1 Gene Lines (Materials and Method)

The following plant materials were furnished for testing.

1) Koshihikari

2) MS Koshihikari×FR Koshihikari

3) FR Koshihikari×16T1-6, FR Koshihikari×16T1-35

Four glumous flowers during flowering were selected per plant from two plants for each of the above varieties and lines. The anther in each flower was snipped off with tweezers, and placed pollens directly on a pollen germination medium. In accordance with an earlier report (Kariya, 1989), an agar medium composed of 1% agar, 20% sucrose and 20 ppm $H_3BO_3$ was used as the pollen germination medium. Pollen in which the elongation of pollen tubes was observable under a microscope after at least 20 minutes had elapsed was regarded as fertile pollen. At least 200 pollens were examined for each flower.

(Results and Discussion)

The germination rate was computed for each glumous flower. Table 3 shows the results obtained from calculations of the average germination rate and standard deviation for eight glumous flowers of each variety and line.

[Table 3]

TABLE 3

Result of Pollen Germination Rate Tests

| Variety • Line | average germination rate (%) | standard deviation |
|---|---|---|
| Koshihikari | 92.85 | 1.40 |
| MS Koshihikari × FR Koshihikari | 38.98 | 8.16 |
| FR Koshihikari × 16T1-6 | 58.25 | 9.20 |
| FR Koshihikari × 16T1-35 | 65.91 | 6.07 |

The germination rates for Koshihikari and MS Koshihikari×FR Koshihikari were respectively 93% and 39%. The germination rates for FR Koshihikari×16T1-6 and FR Koshihikari×16T1-35 were respectively 58% and 66%; while not as high as the germination rate for Koshihikari, these were significantly higher than the germination rate for MS Koshihikari×FR Koshihikari.

When considered together with the pollen fertility test results obtained by iodine-potassium iodide staining, those lines that are heterozygous for the Rf-1 gene at multiple gene loci had an increased proportion of starch-storing pollen (i.e., an increased proportion of normal development) compared with ordinary hybrids (heterozygous for Rf-1 at one locus). As a result, the proportion of pollen that actually germinates also presumably increases.

Example 6

Establishment of a 2-Loci Rf-1 Homozygous Fertile Restorer Line and a 3-Loci Rf-1 Homozygous Fertility Restorer Line A 2-loci Rf-1 homozygous fertility restorer line was established as follows. DNA was extracted from 24 $F_2$ plants obtained by crossing FR Koshihikari with 16T1-6, and the genotypes at the Rf-1 locus and the 16T1-6 insertion locus (chromosome 6) were estimated for each individual. The Rf-1 locus was estimated from the genotypes of the S12564 Tsp509I locus and the C1361 MwoI locus, in accordance with Komori et al. (2002). As for the insertion locus in the 16T1-6 line, if a 210 bp fragment was not amplified when the PCR was carried out using the primers No6 F and No6 R described in Example 3, the genotype of that locus was regarded as homozygous for the introduced gene. Based on the marker assays, one of the plants studied was presumed to be homozygous for the fertility restorer gene at both the Rf-1 locus and the 16T1-6 insertion locus.

A 3-loci Rf-1 homozygous fertility restorer line was established as follows. DNA was extracted from 39 plants obtained by carrying out the following cross: (FR Koshihikari×16T1-6)×(FR Koshihikari×16T1-35), and the Rf-1 locus, 16T1-6 insertion locus (chromosome 6) and 16T1-35 insertion locus (chromosome 7) in each individual were estimated by means of DNA markers as described below. The Rf-1 locus was estimated from the genotypes of the S12564 Tsp509I locus and the C1361 MwoI locus, in accordance with Komori et al. (2002). In the case of the insertion locus in the 16T1-6 line, if a 234 bp fragment was amplified when the PCR was carried out using the primers No6 F2 and No6 R described in Example 3, the genotype of that locus was regarded as heterozygous. Similarly, if a 177 bp fragment was amplified when the PCR was carried out using the primers Nos F2 and No35 R described in Example 3, the genotype of the insertion locus in 16T1-35 was regarded as heterozygous. Based on marker assays, one individual from among the population obtained by this cross was presumed to be homozygous for the Rf-1 gene at the Rf-1 locus and heterozygous for the Rf-1 genes at both the insertion locus in 16T1-6 and the insertion locus in 16T1-35.

This one individual was self-fertilized and DNA was extracted from 24 offspring in the $F_2$ generation, following which the 16T1-6 insertion locus and 16T1-35 insertion locus of each offspring were estimated. The genotype of the 16T1-6 insertion locus was regarded as homozygous if a 210 bp fragment was not amplified when the PCR was carried out using the primers No6 F and No6 R as described above. The genotype of the 16T1-35 insertion locus was taken to be homozygous if a 235 bp fragment was not amplified when the PCR was carried out using the primers No35 F and No35 R described in Example 3. Based on marker assays, two individuals from among those studied were presumed to be homozygous for the fertility restorer gene at both the 16T1-6 insertion locus and the 16T1-35 insertion locus. Because these individuals were also Rf-1 homozygous at the Rf-1 locus, they were Rf-1 homozygous at a total of three loci.

Example 7

Cold Hardiness Test (Materials and Methods)

Koshihikari, the $F_1$ plants obtained from MS Koshihikari crossed with FR Koshihikari, and $F_1$ plants obtained from FR Koshihikari crossed with 16T1-35 (described in Example 4) were furnished for testing. After being grown by a conventional method up to the transplantation stage, four plants of each variety and line were transplanted to 1/5000 are Wagner pots (1 plant per pot). Following transplantation, the plants were cultivated in an air-conditioned chamber set to 12 hours of lighted conditions (24° C.) and 12 hours of darkness (19° C.). After ripening, ten panicles from each plant were collected and the seed fertility (proportion of all the caryopses that have ripened) for each panicle was determined. The average seed fertility for the ten panicles was treated as the seed fertility for that plant.

(Results and Discussion)

The average seed fertility of four plants was about 95% in Koshihikari, and about 57% in the $F_1$ generation of MS Koshihikari×FR Koshihikari. Because the $F_1$ generation of MS Koshihikari×FR Koshihikari had a lower seed fertility than Koshihikari, a comparison between cold-hardy cultivars and lines was thought to be possible under the low-temperature conditions used at this time. Also, the average seed fertility among four $F_1$ plants obtained by crossing FR Koshihikari with 16T1-35 was about 76%, which, although not as high as for Koshihikari, is nonetheless higher than for the $F_1$ plants obtained by crossing MS Koshihikari with FR Koshihikari. In a test conducted on the difference in the population ratio, the difference in seed fertility between $F_1$ plants obtained by crossing MS Koshihikari with FR Koshihikari (3,276 out of 5,808 caryopses ripened) and $F_1$ plants obtained by crossing FR Koshihikari with 16T1-35 (4,587 out of 5,900 caryopses ripened) had a significance level of 1%. These results mean that, compared with prior-art hybrids, hybrids which are heterozygous for the Rf-1 gene at a plurality of loci retain a high seed fertility even under low temperature conditions. Hence, it is likely that the cold hardiness of hybrid varieties can be enhanced by using a fertility restorer line which is homozygous for the Rf-1 gene at a plurality of loci.

The invention claimed is:

1. A hybrid plant having two or more copies of a gametic fertility restorer gene at two or more gene loci which do not have a complete linkage relationship, wherein the hybrid plant is rice and the gametic fertility restorer gene is the rice restorer gene for BT-type male sterility.

2. The hybrid plant according to claim 1, which has two to four copies of the gametic fertility restorer gene at two to four gene loci which do not have a complete linkage relationship.

3. The hybrid plant according to claim 1, wherein multiple copies of the gametic fertility restorer gene are located on distinct chromosomes.

4. The hybrid plant according to claim 1, wherein the rice restorer gene for BT-type male sterility is a nucleic acid which encodes the amino acid sequence of SEQ ID NO: 49, or an amino acid sequence which is at least 70% identical to the amino acid sequence of SEQ ID NO: 49, and which functions to restore fertility.

5. A method for producing the hybrid plant of claim 1, comprising introducing a gametic fertility restorer gene by genetic engineering and placing two or more copies of the gametic fertility restorer gene at two or more gene loci which do not have a complete linkage relationship.

6. The method for producing the hybrid plant according to claim 5, which comprises:

1) introducing a gametic fertility restorer gene by genetic engineering to produce a plant of fertility restoring line containing multiple copies of the gametic fertility restorer gene homozygously at two or more loci; and
2) crossing the plant of fertility restoring line produced by the step of 1) with a plant of sterility line.

7. A plant of fertility restoring line containing a gametic fertility restorer gene homozygously at two or more loci, wherein the plant is rice and the gametic fertility restorer gene is the rice restorer gene for BT-type male sterility.

8. The hybrid plant according to claim 1, having higher seed fertility under a low temperature condition compared to an individual that has only one copy of the gametic fertility restorer gene at a single locus, and wherein the gametic restorer gene is heterozygous at that locus.

* * * * *